US011412353B2

(12) United States Patent
Williams et al.

(10) Patent No.: US 11,412,353 B2
(45) Date of Patent: *Aug. 9, 2022

(54) SYSTEMS AND METHODS FOR MONITORING FOR AND PREEMPTING THE RISK OF A FUTURE OCCURRENCE OF A QUARANTINE VIOLATION

(71) Applicant: Conquer Your Addiction LLC, Kirkwood, MO (US)

(72) Inventors: David H. Williams, Kirkwood, MO (US); Adam H. Williams, Kirkwood, MO (US)

(73) Assignee: Conquer Your Addiction LLC, Kirwood, MO (US)

(*) Notice: Subject to any disclaimer, the term of this patent is extended or adjusted under 35 U.S.C. 154(b) by 58 days.

This patent is subject to a terminal disclaimer.

(21) Appl. No.: 17/104,136

(22) Filed: Nov. 25, 2020

(65) Prior Publication Data
US 2021/0084451 A1    Mar. 18, 2021

Related U.S. Application Data

(63) Continuation-in-part of application No. 16/654,708, filed on Oct. 16, 2019, now Pat. No. 10,853,897,
(Continued)

(51) Int. Cl.
*H04W 4/02* (2018.01)
*H04W 4/029* (2018.01)
(Continued)

(52) U.S. Cl.
CPC ............ *H04W 4/029* (2018.02); *A61B 5/165* (2013.01); *G06Q 50/265* (2013.01); *H04W 4/021* (2013.01)

(58) Field of Classification Search
CPC ...... H04W 4/029; H04W 4/021; A61B 5/165; G06Q 50/265
See application file for complete search history.

(56) References Cited

U.S. PATENT DOCUMENTS

| 5,601,598 A | 2/1997 | Fisher |
| 5,722,418 A | 3/1998 | Bro |

(Continued)

FOREIGN PATENT DOCUMENTS

| JP | 5867847 B2 | 2/2016 |
| JP | 5877528 B2 | 3/2016 |

(Continued)

OTHER PUBLICATIONS

Ayyar, Ranjani, One Heart on YuppTV, Chennai girl makes it to Forbes list with tool to combat addictions, https://timesofindia.indiatimes/city/chennai/chennai-girl-makes-it-to-forbes-list-with . . . , Nov. 16, 2017, 42 pages.

(Continued)

*Primary Examiner* — Dai Phuong
(74) *Attorney, Agent, or Firm* — Harness, Dickey & Pierce, P.L.C.; Anthony Fussner

(57) ABSTRACT

The present disclosure generally relates to systems and methods for monitoring for and preempting the risk of a future occurrence of a quarantine violation, such as by using behaviors and/or actions (e.g., pre-identified behaviors, preemptive actions, etch determined via one or more different devices, sensors, sensor arrays, and/or communications networks (e.g., the Internet of Things (IOT), social networks, etc.).

19 Claims, 35 Drawing Sheets

Related U.S. Application Data which is a continuation-in-part of application No. 16/516,822, filed on Jul. 19, 2019, now Pat. No. 10,497,242, which is a continuation-in-part of application No. 15/840,762, filed on Dec. 13, 2017, now Pat. No. 10,477,342.

(60) Provisional application No. 62/701,252, filed on Jul. 20, 2018, provisional application No. 62/480,206, filed on Mar. 31, 2017, provisional application No. 62/435,042, filed on Dec. 15, 2016, provisional application No. 62/746,330, filed on Oct. 16, 2018, provisional application No. 63/011,949, filed on Apr. 17, 2020.

(51) Int. Cl.
  *G06Q 50/26* (2012.01)
  *A61B 5/16* (2006.01)
  *H04W 4/021* (2018.01)

(56) References Cited

U.S. PATENT DOCUMENTS

| | | | |
|---|---|---|---|
| 5,980,447 A | 11/1999 | Trudeau | |
| 6,039,688 A | 3/2000 | Douglas et al. | |
| 6,425,764 B1 | 7/2002 | Lamson | |
| 6,437,696 B1 | 8/2002 | Lemelson et al. | |
| 6,639,516 B1 | 10/2003 | Copley | |
| 7,219,368 B2 | 5/2007 | Juels et al. | |
| 7,343,365 B2 | 3/2008 | Farnham et al. | |
| 7,633,076 B2 | 12/2009 | Huppi et al. | |
| 7,908,645 B2 | 3/2011 | Varghese et al. | |
| 8,301,767 B1* | 10/2012 | Davis | H04L 63/102 709/224 |
| 8,798,593 B2 | 8/2014 | Haney | |
| 8,862,393 B2 | 10/2014 | Zhou et al. | |
| 9,017,078 B2 | 4/2015 | Gross | |
| 9,104,788 B2 | 8/2015 | Friedman et al. | |
| 9,288,196 B2 | 3/2016 | Shuster | |
| 9,341,050 B2 | 5/2016 | Al-Buraik | |
| 9,917,824 B2 | 3/2018 | Britt | |
| 10,114,351 B2 | 10/2018 | Fadell et al. | |
| 10,218,844 B1 | 2/2019 | Edwards et al. | |
| 10,477,342 B2 | 11/2019 | Williams | |
| 10,497,242 B2 | 12/2019 | Williams | |
| 10,853,897 B2 | 12/2020 | Williams | |
| 2005/0068169 A1 | 3/2005 | Copley et al. | |
| 2006/0004680 A1 | 1/2006 | Robarts et al. | |
| 2008/0146193 A1 | 6/2008 | Bentley et al. | |
| 2009/0099985 A1 | 4/2009 | Tesauro et al. | |
| 2009/0265326 A1 | 10/2009 | Lehrman et al. | |
| 2010/0076968 A1 | 3/2010 | Boyns et al. | |
| 2010/0125563 A1 | 5/2010 | Nair et al. | |
| 2010/0227629 A1 | 9/2010 | Cook et al. | |
| 2011/0022540 A1 | 1/2011 | Stern et al. | |
| 2012/0083911 A1 | 4/2012 | Louboutin et al. | |
| 2012/0135756 A1 | 5/2012 | Rosso et al. | |
| 2012/0268269 A1 | 10/2012 | Doyle | |
| 2012/0308970 A1 | 12/2012 | Gillespie et al. | |
| 2013/0145441 A1 | 6/2013 | Mujumdar et al. | |
| 2013/0216989 A1 | 8/2013 | Cuthbert | |
| 2014/0094192 A1 | 4/2014 | Annett | |
| 2014/0142729 A1 | 5/2014 | Lobb et al. | |
| 2014/0192325 A1 | 7/2014 | Klin et al. | |
| 2014/0248904 A1* | 9/2014 | Meredith | G01S 5/0252 455/456.1 |
| 2014/0278212 A1 | 9/2014 | Torgersrud et al. | |
| 2014/0331278 A1 | 11/2014 | Tkachev | |
| 2015/0009028 A1 | 1/2015 | Gehrke et al. | |
| 2015/0065822 A1 | 3/2015 | Blenkush | |
| 2015/0230086 A1 | 8/2015 | Bentley et al. | |
| 2015/0367230 A1 | 12/2015 | Bradford et al. | |
| 2016/0019382 A1 | 1/2016 | Chan et al. | |
| 2016/0066864 A1 | 3/2016 | Frieder et al. | |
| 2016/0140353 A1 | 5/2016 | Biswas et al. | |
| 2016/0140404 A1 | 5/2016 | Rosen | |
| 2016/0260135 A1 | 9/2016 | Zomet et al. | |
| 2016/0330601 A1 | 11/2016 | Srivastava | |
| 2016/0381502 A1 | 12/2016 | Kern, Jr. et al. | |
| 2017/0020442 A1 | 1/2017 | Flitsch et al. | |
| 2017/0134832 A1 | 5/2017 | Briggs et al. | |
| 2017/0276489 A1 | 9/2017 | Breed | |
| 2017/0365182 A1 | 12/2017 | Lavi et al. | |
| 2018/0103341 A1 | 4/2018 | Moiyallah, Jr. et al. | |
| 2018/0140241 A1 | 5/2018 | Hamalainen et al. | |
| 2018/0173866 A1 | 6/2018 | Williams | |
| 2018/0176727 A1 | 6/2018 | Williams | |
| 2018/0240544 A1 | 8/2018 | Lo et al. | |
| 2020/0160223 A1 | 5/2020 | McGavran et al. | |
| 2021/0035675 A1* | 2/2021 | Shantharam | G10L 15/26 |
| 2021/0112064 A1* | 4/2021 | Losseva | H04L 63/102 |
| 2021/0391089 A1* | 12/2021 | Eswara | G06V 20/52 |
| 2022/0086649 A1* | 3/2022 | Korenwaitz | H04W 12/088 |

FOREIGN PATENT DOCUMENTS

| | | |
|---|---|---|
| KR | 100692803 B1 | 3/2007 |
| KR | 101581772 B1 | 1/2016 |
| KR | 1020160046690 A | 4/2016 |
| WO | WO-2015171702 A1 | 11/2015 |
| WO | WO-2016178617 A1 | 11/2016 |
| WO | WO-2018112047 A2 | 6/2018 |
| WO | WO-2018112048 A1 | 6/2018 |

OTHER PUBLICATIONS

Campbell, Discovering addiction: The science and politics of substance abuse research, 2007, Abstract, 2 pages.

Carise et al., Development a National Addiction Treatment Information System: An Introduction to the Drug Evaluation Network System; Journal of Substance Abuse Treatment; 1999: Abstract; 2 pages.

Cartreine, PhD., et al., A Roadmap to Computer-Based Psychotherapy in the United States, Copyright 2010 President and Fellows of Harvard College; 16 pages.

Conquer Your Alcoholism, conqueryouraddiction.com, accessed Dec. 7, 2017 3 pages.

D. H. Williams, How to Conquer Your Alcoholism—Made Simple! The Practical Way to Get and STAY Sober; paperback—Aug. 3, 2017; 259 pages; 1 page attached.

D. H. Williams, How To Conquer your Alcoholism: A Complete and Useable Program and Reference Guide to Getting & Staying Sober; Jan. 16, 2015; 654 pages; (1 page attached).

Dackis, et al., Neurobiology of addiction: treatment and public policy ramifications; Nature Neuroscience vol. 8, No. 11, Nov. 2005; 1 page.

DiClemente, Ph.D., et al., Readiness and Stages of Change in Addiction Treatment, *The American Journal on Addictions.* Coypright 2004; 13: 103-119.

Final Office Action from U.S. Appl. No. 15/840,762, filed Dec. 13, 2017 which claims priority to the same parent applications as the instant application, dated Jan. 4, 2019, 35 pages.

Fussel, Sidney; The Next Data Mine is Your Bedroom, Nov. 17, 2018, 6 pages.

Gainsbury, A systematic Review of Internet-based therapy for the Treatment of Addictions, Southern Cross University, 2011, vol. 31, No. 3, pp. 490-498.

Gotham, Diffusion of mental health and substance abuse treatments; development, dissimentation, and implementation; 2004; absract; 1 page.

Gravenhorst et al., Mobile Phones as Medical Devices in Mental Disorder Treatment: an Overview; Personal and Ubiquitous Computing, 2015, abstract: 2 pages.

Gustafson et al., An E-Health Solution for People with Alcohol Problems; ARCR/Alcohol Research Current review; 2011; 33(4): pp. 327-337.

Gustafson, Ph.D., et al., Explicating an Evidence-Based, Theoretically Informed, Mobile Technology-Based System to Improve Out-

(56) References Cited

OTHER PUBLICATIONS comes for People in Recovery for Alcohol Dependence; NIH Public access, Author Manuscript, Subst Use Misuse. 2011; 46(1):96-111. doi:10.3109/10826084.2011.521413.
Heron et al., Ecological Momentary Interventions: Incorporating Mobile Technology In to PSychosocial and Health Behavnior Treatments; HHS Public Access; Author Manuscript;Published online 2009; Br J Health Psychol. Feb. 2010: 15(Pt 1): 22 pages.
International Search Report and Written Opinion for PCT/US2017/066134 filed Dec. 13, 2017 which claims priority to the same parent application as the instant application, dated Mar. 29, 2018, 11 pages.
International Search Report and Written Opinion for PCT/US2017/066136 filed Dec. 13, 2017 which claims priority to the same parent application as the instant application, dated Apr. 9, 2018, 15 pages.
Kaplan et al., Bringing the Laboratory and Clinic to the Community: mobile technologies for health promotion and disease prevention; Annual Review of Psychology; 2013; abstract, 2 pages.
Kelly, Laura; Teen suicide rate suddenly arises with heavy use of smartphones, social media, The Washington Times—Tuesday, Nov. 14, 2017; https://www.washingtontimes.com/news/2017/nov/14/teen-suicides-rise-with-smartphone; 4 pages.
Lee et al., The SAMS: Smartphone addicion mangement System and Verification; Journal of Medical Systems; 2014, abstract; 2 pages.
Luxton et al., mHealth for Mental Health: Integrating Smartphone Technology in Behavioral Healthcare, Professional Psychology: Research and Practice, 2011, vol. 42, No. 6. pp. 505-512.
McClure et al., Utilization of Communication Technology by Patients Enrolled in Substance Abuse Treatment, NIH Public Access, Author Manuscript, Drug Alcohol Depend. Apr. 1, 2013: 129(1-2): 145-150 doi:10.1016/j.drugalcdep.2012.10.003.
McKay et al., Conceptual, methodological, and analytical issues in the study of relapse, Copyright 2005, www.sciencedirect.com, 19 pages.
McLellan, et al., Reconsidering the evaluation of addiction treatment: from retrospective follow-up to concurrent recovery monitoring; Copyright 2005 Society for the Study of Addiction; Addiction, 100, 447-458.
Nonfinal Office Action for U.S. Appl. No. 15/840,775, filed Dec. 13, 2017 which claims priority to the same parent application as the instant application as the instant application, dated Aug. 7, 2018, 22 pages.
Stacy et al., Implicit Cognition and Addiction: A Tool for Explaining Paradoxical Behavior; HHS Public access, Author Manuscript, Ann. Rev. Clin. Psychol. 2010: 6: 22 pages.
The Conquer Quiz, Test for Alcoholism, conqueryouraddiction.com, accessed Dec. 7, 2017, 2 pages.
US nonfinal Office Action for U.S. Appl. No. 16/516,822, filed Jul. 19, 2019 which claims priority to the instant application, dated Aug. 21, 2019, 44 pages.
Notice of Allowance from U.S. Appl. No. 15/840,762, filed Dec. 13, 2017 which claims priority to the same parent application as the instant application, dated Sep. 23, 2019, 13 pages.
Notice of Allowance for U.S. Appl. No. 16/516,822 which is the parent application to the instant application, dated Oct. 17, 2019, 11 pages.
Luxton et al., Health for Mental Health: Integrating Smartphone Technology in Behavioral Healthcare, Professional Psychology: Research and Practice, 2011, vol. 42, No. 6. pp. 505-512.
Final Office Action for U.S. Appl. No. 16/700,561 which names the same inventor but is not related through a priority claim; dated Oct. 8, 2020; 55 pages.
Final Office Action from U.S. Appl. No. 15/840,762, filed Dec. 13, 2017 which is the parent application to the instant application, dated Jan. 4, 2019, 35 pages.
Blockchain—Wikipedia; https://en.wikipediaorg/wiki/Blockchain; Feb. 28, 2020; 19 pages.
Proof-of-Work, Explained; https://cointelegraph.com; 2013-2020; 6 pages.
USPTO Final Office Action for U.S. Appl. No. 16/70601, filed Dec. 2, 2019 that claims priority to the same parent application as the instant application; dated Apr. 8, 2021; 20 pages.
USPTO Final Office Action for U.S. Appl. No. 16/700,601, filed Dec. 2, 2019 that claims priority to the same parent application as the instant application; dated Mar. 23, 2022; 34 pages.

\* cited by examiner

- ASSESS TRIGGER/RELAPSE RISK
- LEARN/MODIFY RISK ALGORITHMS

| DETERMINE/PREDICT TRIGGER RELAPSE RISK | ☐ - REPRESENTS MAJOR STEP, PROCESS, OR OPERATION |
|---|---|

| ADDICT #243 TRIGGERS | RISK PRIORITY/ SEVERITY (H/M/L, 1-10) (10 HIGHEST) | LOCATION/CONTEXT ELEMENTS/SENSORS MONITORED/ANALYZED | RISK FORMULA; RISK ACTION CLASSIFICATION |
|---|---|---|---|
| BOREDOM | RP = HIGH (RP SCORE=9) | A. ADDICT STAYS IN ONE PLACE MORE THAN X HOURS (EXCEPT SLEEP HOURS) = A=X-2; ZERO LOWEST VALUE) B. LOW BLOOD PRESSURE (BELOW 100/70 (YES/NO = 1/0) C. BOREDOM BUTTON PUSHED = 10) | RISK = RP/5*(A +(B*2)+C) RISK CLASS: >=6 THEN TRIGGER BASED; <6 THEN RESOURCE-BASED |
| DEPRESSION | MED (5-) | A. SENSOR 1 VALUE B. SENSOR 2 VALUE C. DEPRESSION BUTTON PUSHED =10 | RISK = A +(B*2)+C/RP RISK CLASS: TRIGGER-BASED (DEFAULT) |
| INSOMNIA | LOW (3) | A. UNUSUAL NIGHT-TIME MOVEMENT B. HIGH RESTLESS SLEEP SCORES (E.G. VIA SLEEP NUMBER BED) | RISK = A +(B*3) – RP RISK CLASS: ACTION CATEGORY BASED |
| YELLING/ CONFLICT | MED (6) | A. LOUD NOISES DETECTED B. DISTRESS DETECTED (ELEVATED BLOOD PRESSURE RAPID RISE IN SKIN TEMPERATURE) | RISK = A +(B*4) + RP RISK CLASS: INTERFACE-BASED |

NOTE/LEGEND

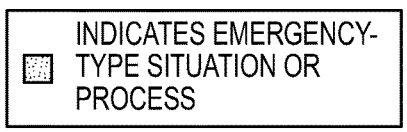 INDICATES EMERGENCY-TYPE SITUATION OR PROCESS

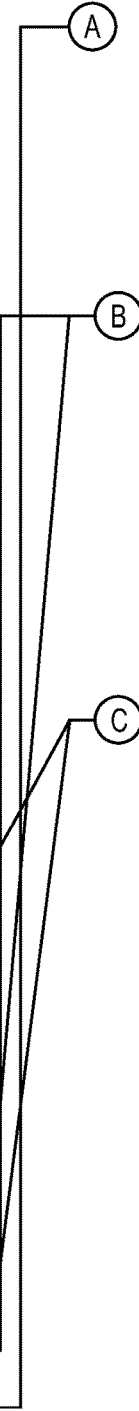

MODIFY FREQUENCY AND SCOPE OF MONITORING

FIG. 5

- IDENTIFY/REFINE POSSIBLE ACTION(S)
- IDENTIFY/REFINE POSSIBLE RESOURCE(S)
- IDENTIFY/REFINE POSSIBLE INTERFACE(S)

RESOURCE-BASED ACTION PARAMETERS, W/ SUPPORTED ACTIONS & INTERFACE REQS

| SUPPORT RESOURCE | LOGISTICAL CONSTRAINTS, PREFERENCES | SUPPORTED ACTION(S) (PREFERRED SEQUENCE) | INTERFACE REQUIREMENTS / PREFERRED INTERFACE (S) |
|---|---|---|---|
| SPONSOR 1 | NO WEEKENDS | 1. LIVE, FACE-TO-FACE VISITS WITHIN 30 MINUTES OF CURRENT LOCATION | • FACE-TO-FACE<br>• HOLOGRAM<br>• PHONE CALL |
| MEDICAL PROFESSIONAL 3 (DR. D) | • AFTER 5PM<br>• TRIGGER(S):ANXIETY, DISORDER ONLY<br>• RELAPSE RISK >=8 | 1. PROTOCOLS A, D | 1. PHONE CALL ONLY |
| MOTHER | NONE | 1. FACE-TO-FACE MEETING<br>2. LIVE VIDEO/CALL<br>2. SEND MOM "MEDITATION MESSAGE" (VIA BEST "HUMAN" I/F, E.G. HOLOGRAM VOICE SYNTHESIS, VIDEO MESSAGE ETC.) | 1. LIVE VISIT<br>2. HOLOGRAM<br>3. SKYPE<br>4. PHONE CALL<br>4. VIDEO-BASED I/F IF LIVE NOT POSSIBLE |
| PROBATION OFFICER | ONLY IF RELAPSE IS EMERGENCY AND MEETS CONDITIONS OF PROBATION | 1. AUTO GENERATE CALL CONNECTING PROBATION OFFICER TO ADDICT CONTROLLER OFFICER<br>2. EVALUATE FURTHER OPTIONS UNDER PROTOCOLS E, F, G | 1. ANY |
| BOWLING @BRUNSWICK LANES (5 LOCATIONS) | MONDAY-SATURDAY 9AM – 11PM, SUNDAY 10AM-6 PM | 1. PROMPT FOR ANY HOBBY USAGE REQUIREMENT IN BAD WEATHER, OR BOREDOM IN GENERAL.<br>2. BRUNSWICK LOCATION B GOOD FOR SPORTS VIEWING-RELATED ACTIONS | 1. IN PERSON<br>2. USE WII VIDEO GAME AS A OPTION IF NO SUPPORT PERSONS AVAILABLE |
| SOCIAL MEDIA C | ALL MEMBERS OF GROUP C HAVE BEEN THROUGH PRIVACY PROTOCOL TRAINING AND VETTING | 1. PROMPT POSTS FROM ADDICT TO GROUP X FOR IDENTIFIED TRIGGER(S)<br>2. GENERATE AUTOMATED POSTS REQUESTING HELP; ROUTE RESPONSES TO ADDICT | POSTS AUTOMATICALLY DELETED AFTER 5 MINUTES |

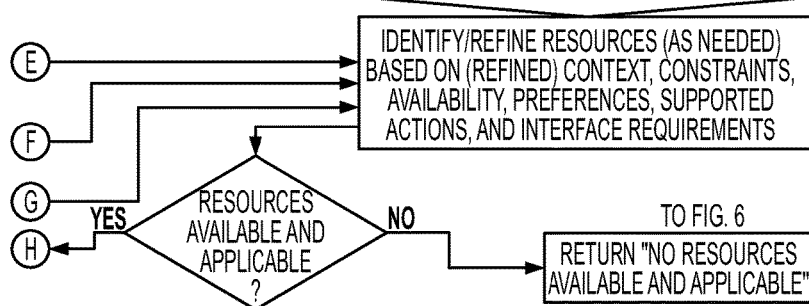

FIG. 7 (Cont.)

POSSIBLE ACTION – ADDICTION COMMUNITY MEETING
MEETING CRITERIA

| PERSON | SEVERITY THRESHOLD | MEETING CONTEXT CONSTRAINTS/LIMITATIONS | LOCATION LIMITATION |
|---|---|---|---|
| ADDICT 1 | HIGH (IMMEDIATE OR TRENDING) | 1. WOMEN-ONLY<br>2. ANXIETY, DEPRESSION-THEMED MEETINGS PREFERRED<br>3. AFTER 5 PM WEEKDAYS<br>4. PARTICULARLY INTERESTED IN ANXIETY-DEPRESSION DUAL TRIGGER MEETINGS | < 5 MILES CURRENT |
| SUPPORT PERSON 5 | MEDIUM OR ABOVE (IMMEDIATE OR TRENDING) | 1. CLOSED MEETINGS<br>2. HATES COFFEE | < 15 MILES CURRENT OR WITHIN 30 MINUTES |
| ADDICT 26 | MEDIUM OR ABOVE (IMMEDIATE ONLY) | 1. ONLY WHEN OUT-OF-TOWN (OUTSIDE OF HOME/WORK GEOFENCE)<br>2. OPEN, CLOSED MEETINGS | <10 MILES WITHIN 2 HOURS |
| ADDICT 62 | ANYTIME | 1. WHEN DRIVING<br>2. WHEN SPOUSE NOT NEARBY | BETWEEN 20 AND 50 MILES FROM HOME |

FLASH MEETING POTENTIAL SITES (COMMUNITY MEETING DB)

| POTENTIAL MEETING SITE | DESCRIPTION | CONSTRAINTS/ LIMITATIONS | COORDINATOR |
|---|---|---|---|
| X1, Y1 | STARBUCKS, CORNER OF LINDBERGH AND WALLEY STREETS | 1. STARBUCKS HOURS (LINK)(<br>2. NO MORE THAN 4 PEOPLE<br>3. COFFEE-DRINKERS PREFERRED | ADDICT 53 (LINK) |
| X3, Y3 | MISSOURI BAPTIST CHURCH (WEBSTER GROVES) | 1. ANYTIME EXCEPT SUNDAY<br>2. PROVIDE KEY CODE TO NEAREST INDIVIDUAL; CYCLE CODE AFTER MEETING (LINK) | MEDICAL PROFESSIONAL 5 (LINK) |
| X7, Y7, Z7 | 123 MAIN STREET, CITY HALL BUILDING, FLOOR 3, ROOM 312 | 1. PUBLIC ACCESS HOURS (LINK)<br>2. SECURITY GUARD NEEDS 30 MINUTE LEAD TIME (LINK) | FACILITY MANAGER'S OFFICE (LINK) |
| VIRTUAL 9 | ANYTIME | 1. NONE | TRIGGERMEETING.COM COORDINATORS |

FIG. 7A

LOCATION/CONTEXT-BASED PRIVACY AND SECURITY

LOCATION/CONTEXT-BASED VERIFICATION QUESTION EXAMPLES

- WHERE HAVE YOU BEEN IN THE LAST (WEEK, MONTH, YEAR, ETC.)?
- WHERE HAVE YOU BEEN WITH YOUR YOUNGEST DAUGHTER (TIMEFRAME)?
- WHERE HAVE YOU NOT BEEN IN THE LAST MONTH?
- PLEASE SELECT YOUR VACATION-RELATED IMAGES (TIMEFRAME OPTIONAL)?
- PLEASE SELECT IMAGES* THAT ARE FAMILY ACTIVITY-RELATED.
- PLEASE SELECT IMAGES OF LOCATION(S) WHERE YOU CURRENTLY RESIDE.
- PLEASE SELECT IMAGES OF LOCATION(S) WHERE YOU HAVE NEVER BEEN
- PLEASE SELECT VACATION IMAGES BETWEEN X AND Y DATES
- PLEASE SELECT PICTURES OF YOUR FIRST DAUGHTER'S WEDDING LOCALES (CHURCH, RECEPTION, HONEYMOON)

LOCATION/CONTEXT-BASED VERIFICATION ANSWER EXAMPLES

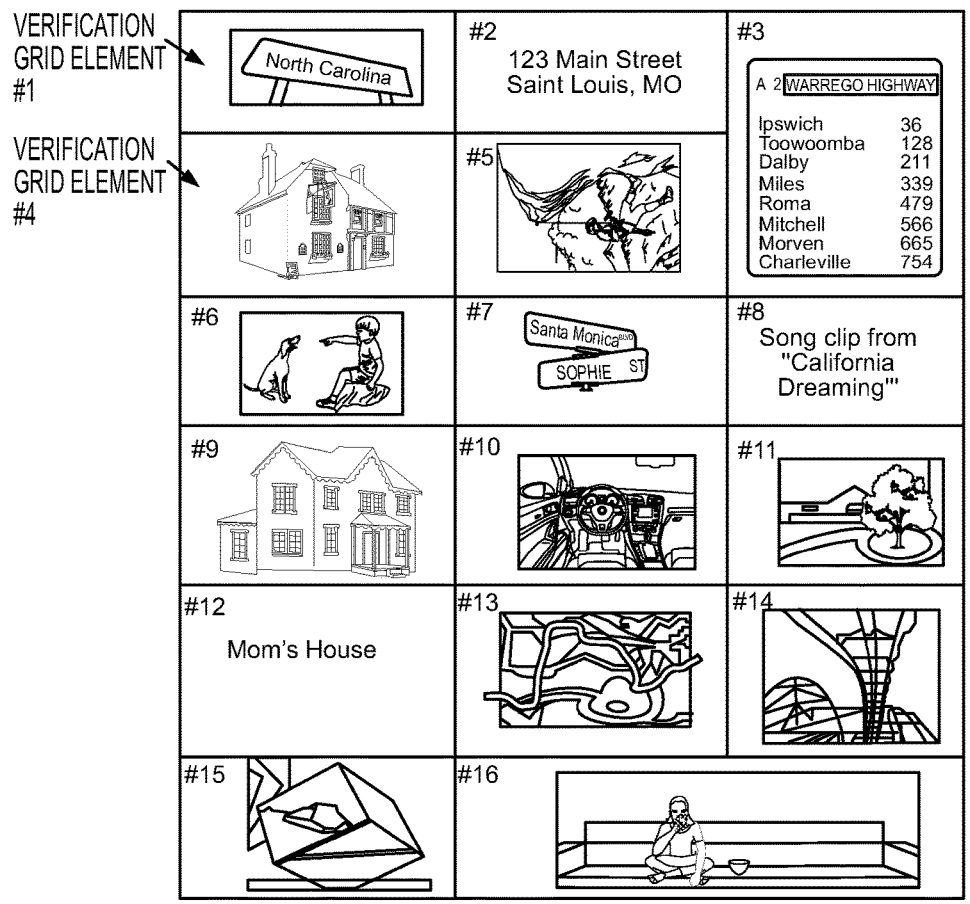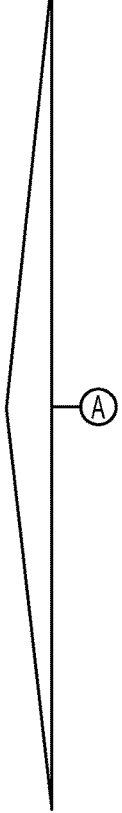

FIG. 11

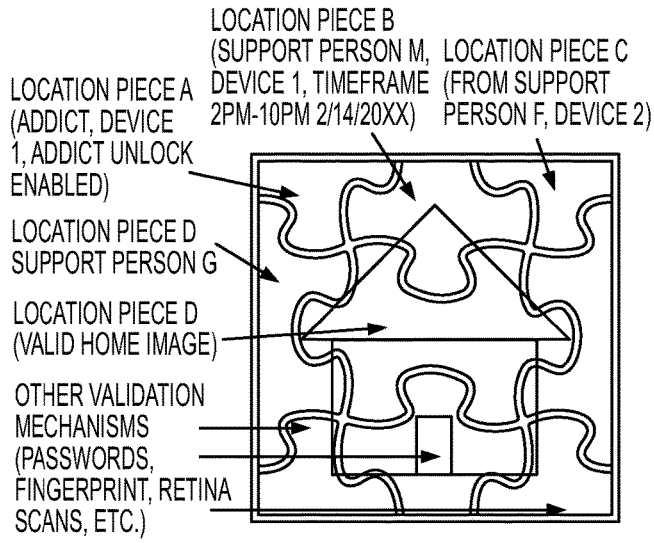

| | JIGSAW PUZZLE LOCATION/CONTEXT-BASED SECURITY |
|---|---|

LOCATION/CONTEXT-BASED P/S MEMORY PROFILE

PRIORITY 1: HISTORICAL VACATION IMAGES (< 1 YEAR OLD; HAWAII, SKIING PREFERRED)

PR #2: ROAD SIGNS (NEAR MOTHER'S HOUSE) (NO TIME LIMIT)

PR #3 SONGS WITH LOCATIONS IN THEM (E.G. CALIFORNIA DREAMING, SWEET HOME ALABAMA, ETC.)

NO IMAGES FROM NORTH/SOUTH DAKOTA, BROTHER'S WEDDING

LOCATION PIECE A (ADDICT, DEVICE 1, ADDICT UNLOCK ENABLED)

LOCATION PIECE B (SUPPORT PERSON M, DEVICE 1, TIMEFRAME 2PM-10PM 2/14/20XX)

LOCATION PIECE C (FROM SUPPORT PERSON F, DEVICE 2)

LOCATION PIECE D SUPPORT PERSON G

LOCATION PIECE D (VALID HOME IMAGE)

OTHER VALIDATION MECHANISMS (PASSWORDS, FINGERPRINT, RETINA SCANS, ETC.)

| GRID # | SOURCE (DEVICE, PROCESS, ETC.) |
|---|---|
| #1 | GEOFENCE EXCEPTION DATA FROM CAR 1/DEVICE B |
| #2 | LAT/LONG TO ADDRESS TRANSLATION OF IMAGE #4 |
| #3 | ALGORITHMIC DERIVATION AND GRAPHICAL IMAGE CREATION FROM LAT/LONG CENTERPOINT OF VACATION X (ALL DEVICES) |
| #4 | PICTURE OF MOM'S HOUSE (DEVICE A) |
| #5 | VACATION PHOTO (FROM PERSON C HELMET CAM) |
| #6 | PICTURE OF PET (WHO DIED IN 2002) AT HOME XYZ |
| #7 | GRAPHICAL/AUGMENTED REALITY SIMULATION DERIVED FROM DRIVERLESS CAR C LOCATION OR IMAGE CAPTURE |
| #8 | AUDIO CLIP INDICATING VISIT TO CALIFORNIA IN TIMEFRAME P (MOBILE SOCIAL NETWORKING POST FROM FRIEND E) |
| #9 | RANDOM LOCATION SAMPLE OF RETAIL "VISITS", WITH ADDRESS MATCHED WITH STORE NAME AND IMAGE PULLED FROM INTERNET |
| #10 | IMAGE TAKEN FROM CHILD DEVICE B, OR CAR SYSTEM A |
| #11 | SATELLITE IMAGE FROM GOOGLE MAPS OF HOMESTEAD A |
| #12 | COLLOQUIAL NAME OF MOM'S HOUSE (MANUALLY INPUT, TAGGED FROM PICTURE IN #4 OR FROM IMPORTED FROM FAMILYMAP APP (SEE RIGHT) |
| #13 | DELIBERATE DISTORTION/OBSTRUCTION OF CURRENT HOMESTEAD |
| #14 | 3D IMAGE OF SIX-FLAGS ROLLERCOASTER RIDE (3D DEVICE D) |
| #15 | A REVOLVING 3D IMAGE WITH DIFFERENT LOCATIONS (COMPOSITE) |
| #16 | VIDEO OF ME WATCHING TV IN LIVING ROOM (TV DEVICE 1) |

TIMEFRAME EXAMPLES
- SINCE D (DATE AND /OR TIME)
- LAST 24 HOURS
- LAST WEEK/MO/YR
- SINCE MOVE TO MOST RECENT ADDRESS
- BETWEEN X & Y
- NOT SINCE D OR BETWEEN X & Y

3RD PARTY APP IMPORT (AT&T FAMILYMAP EX.)

FIG. 11 (Cont.)

SYSTEMS AND METHODS FOR MONITORING FOR AND PREEMPTING THE RISK OF A FUTURE OCCURRENCE OF A QUARANTINE VIOLATION

CROSS-REFERENCE TO RELATED APPLICATIONS

This application claims the benefit and priority of U.S. Provisional Patent Application No. 63/011,949 filed Apr. 17, 2020.

This application is a continuation-in-part of allowed U.S. patent application Ser. No. 16/654,708 filed Oct. 16, 2019 (published as US2020/0051189 on Feb. 13, 2020 and issuing as U.S. Pat. No. 10,853,897 on Dec. 1, 2020).

U.S. patent application Ser. No. 16/654,708 claims the benefit and priority of U.S. Provisional Patent Application No. 62/746,330 filed Oct. 16, 2018. U.S. patent application Ser. No. 16/654,708 is a continuation-in-part of U.S. patent application Ser. No. 16/516,822 filed Jul. 19, 2019 (now U.S. Pat. No. 10,497,242 issued on Dec. 3, 2019).

U.S. patent application Ser. No. 16/654,708 is also a continuation-in-part of U.S. patent application Ser. No. 15/840,762 filed Dec. 13, 2017 (now U.S. Pat. No. 10,477,342 issued on Nov. 12, 2019).

U.S. patent application Ser. No. 16/516,822 claims the benefit and priority of U.S. Provisional Patent Application No. 62/701,252 filed Jul. 20, 2018. U.S. patent application Ser. No. 16/516,822 is a continuation-in-part of U.S. patent application Ser. No. 15/840,762 filed Dec. 13, 2017 (now U.S. Pat. No. 10,477,342 issued on Nov. 12, 2019).

U.S. patent application Ser. No. 15/840,762 claims the benefit and priority of U.S. Provisional Patent Application No. 62/435,042 filed Dec. 15, 2016 and U.S. Provisional Patent Application No. 62/480,206 filed Mar. 31, 2017.

The entire disclosures of the above applications are incorporated herein by reference.

FIELD

The present disclosure generally relates to systems and methods for monitoring for and preempting the risk of a future occurrence of a quarantine violation, such as by using behaviors and/or actions (e.g., pre-identified behaviors, preemptive actions, etch determined via one or more different devices, sensors, sensor arrays, and/or communications networks (e.g., the Internet of Things (IOT), social networks, etc.).

BACKGROUND

This section provides background information related to the present disclosure which is not necessarily prior art.

There has been a recent explosion in awareness regarding historical and current sexual harassment as evident by the ongoing falls from power or travails of prominent celebrities, politicians, government officials, businessmen, etc. While the widespread movement and the disgrace of various individuals may be justified, the broader ramifications, side effects, and "unintended consequences" on society and interpersonal behaviors and dynamics have also become apparent. One of these side effects is in "dating"—the seeking of and "executing" of potential romantic and/or sexual relationships. There have been numerous news stories where a person apparently said "Yes" to an invitation to a sexual encounter at some point (often early) in a relationship—at least a "Yes" as interpreted by the other person—that once concluded (attempted or completed), the person has changed their view on what happened, why, or both with assertions, e.g., "took advantage of me when I was drunk", etc.

Previously, such a "defense" may have been waved off on the alleged grounds that "the person knew what they were doing" or "as long as the person was conscious then what is the problem?". More recently, the slightest hint that one person took advantage of another person in some way during a sexual (or even non-sexual dating) encounter may be treated harshly by society and increasingly so by law enforcement. In such situations, the accused party has heretofore had very little defense beyond "he said, she said" and with the "accuser said" typically receiving more weight than before. Even in situations where the accused has been cleared (e.g., college campus tribunals where the weight of evidence is less than criminal court, etch, the accusation— often fueled by social media—may never really go away and may follow the cleared accused person like a tattooed Scarlet Letter.

DRAWINGS

The drawings described herein are for illustrative purposes only of selected embodiments and not all possible implementations, and are not intended to limit the scope of the present disclosure.

FIG. 1 is a diagram of an example system for determining location and context of an addict, a support network, and other information and aspects of an addict's personal and professional life for addiction treatment purposes, including relapse prevention and containment. This diagram includes various example networks and technologies that may be used for collecting and analyzing the addict's location and context. Also shown are example data sources and analytical engines that may be needed to process such data and to identify and implement actions to preempt, prevent, and/or contain any relapse.

FIG. 2 describes an example Addict Monitor/Controller (AMC) device that may be used to collect, process, and disseminate context and addiction trigger-related data from and about an addict via various sensors and other data collection mechanisms, and to interface with/to the addict and 3rd party mechanisms. The device may also provide mechanisms to provide feedback to the addict and assist in the implementation of relapse-related preventative and containment actions.

FIG. 2a provides examples of distributed sensor deployment, data collection options, localized sensors, and localized networks that may be used in exemplary embodiments.

FIG. 2b provides examples of internet of things (IoT) addict-related sensors, devices, and networks that may be used in exemplary embodiments.

FIG. 3 depicts example steps for monitoring an addict's triggers, and in the course of doing so assessing/predicting the addict's risk of relapse. FIG. 3 also describes identifying possible resources that could help the addict, and the actions that could be taken to prevent, preempt or contain a relapse. FIG. 3 also describes an example process for selecting such resources and actions.

FIG. 4 depicts an example system and example process for determining the location/context of an addict as well as the location/context of support resources using a variety of sensors and other information sources.

FIG. 5 describes an example system and example process for assessing an addict's trigger/relapse risk.

FIG. 5 also describes how such algorithms could be made self-learning to better assess an addict's relapse risk.

FIG. 5A depicts an example embodiment of a method for managing damage control and recovering from a relapse situation.

FIG. 5B provides examples of risk, support areas maps, and map mashups.

Figure 7:
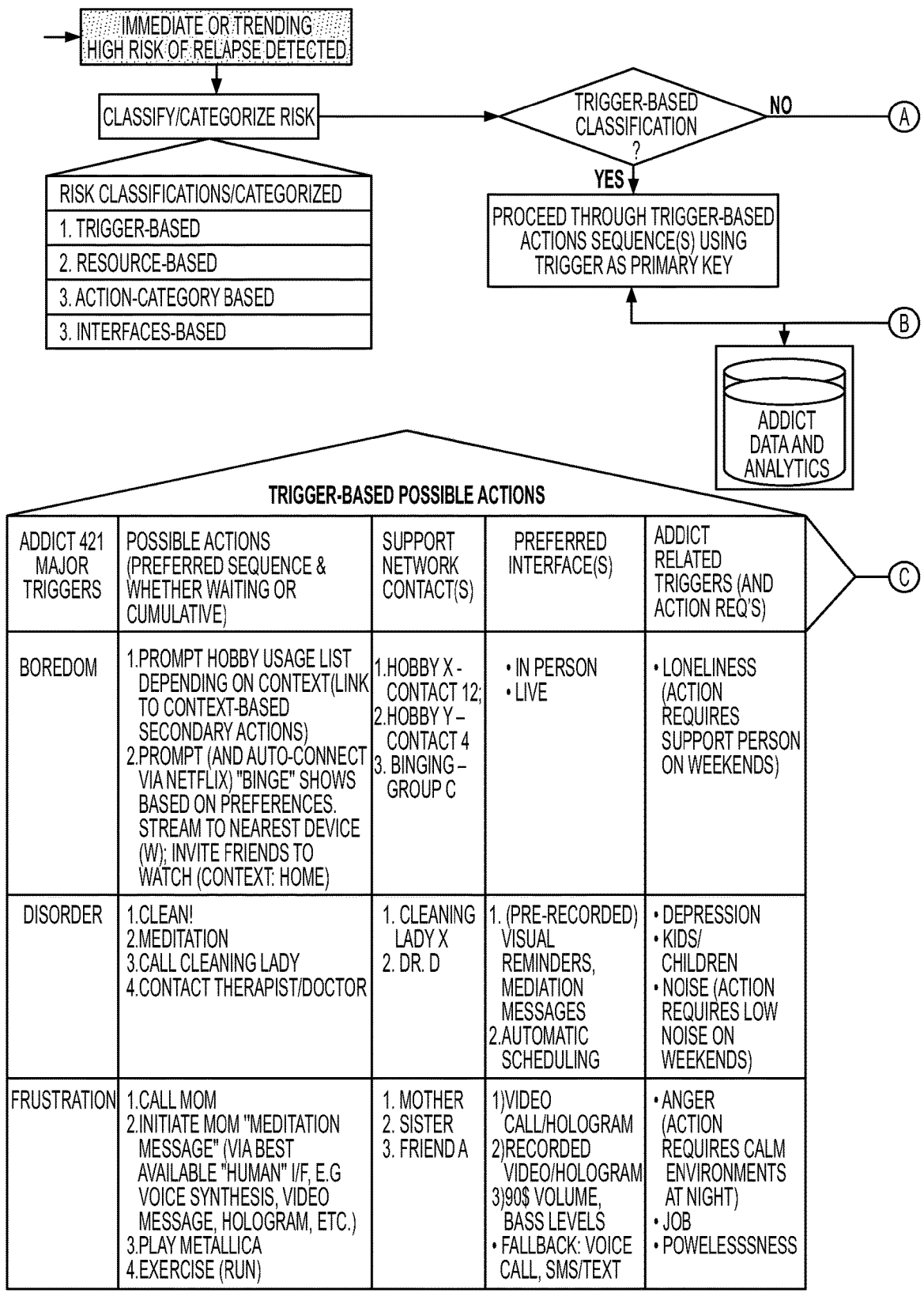
Figure 7:
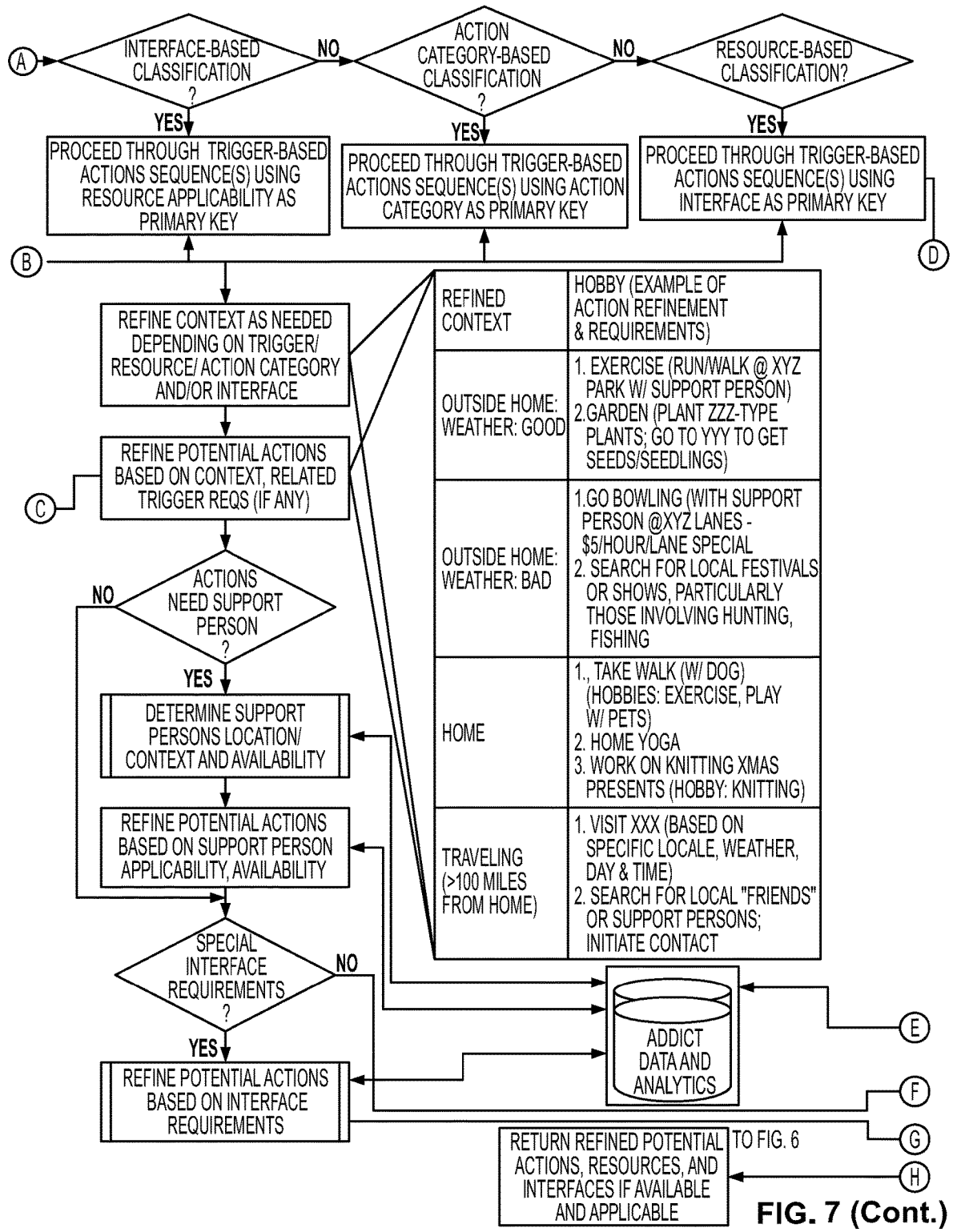

FIG. 7 describes example ways to identify/determine and select the best actions and resources when relapse risk is high.

Figure 7A:
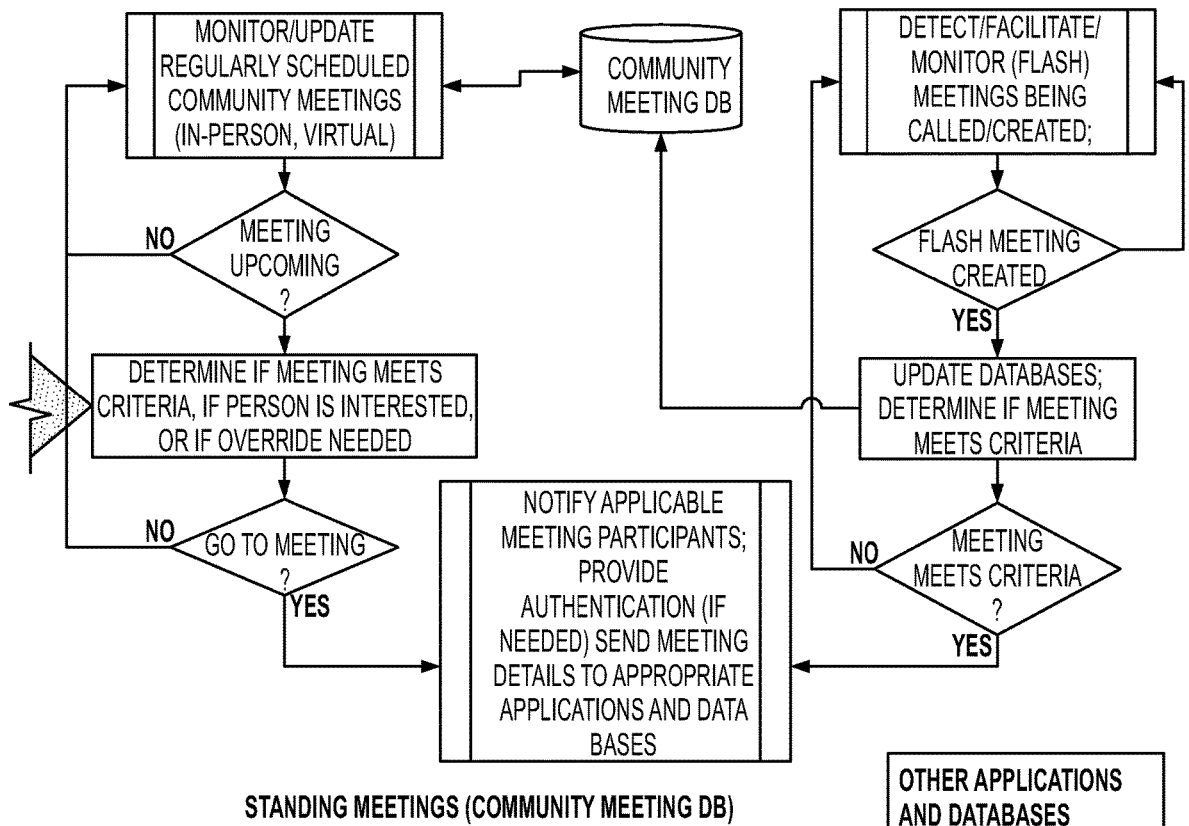

FIG. 7A describes an example of an action-determining sub process-specifically, ways to utilize regularly scheduled addict community meetings or spontaneous, unscheduled, flash addict community meetings.

Figure 8:
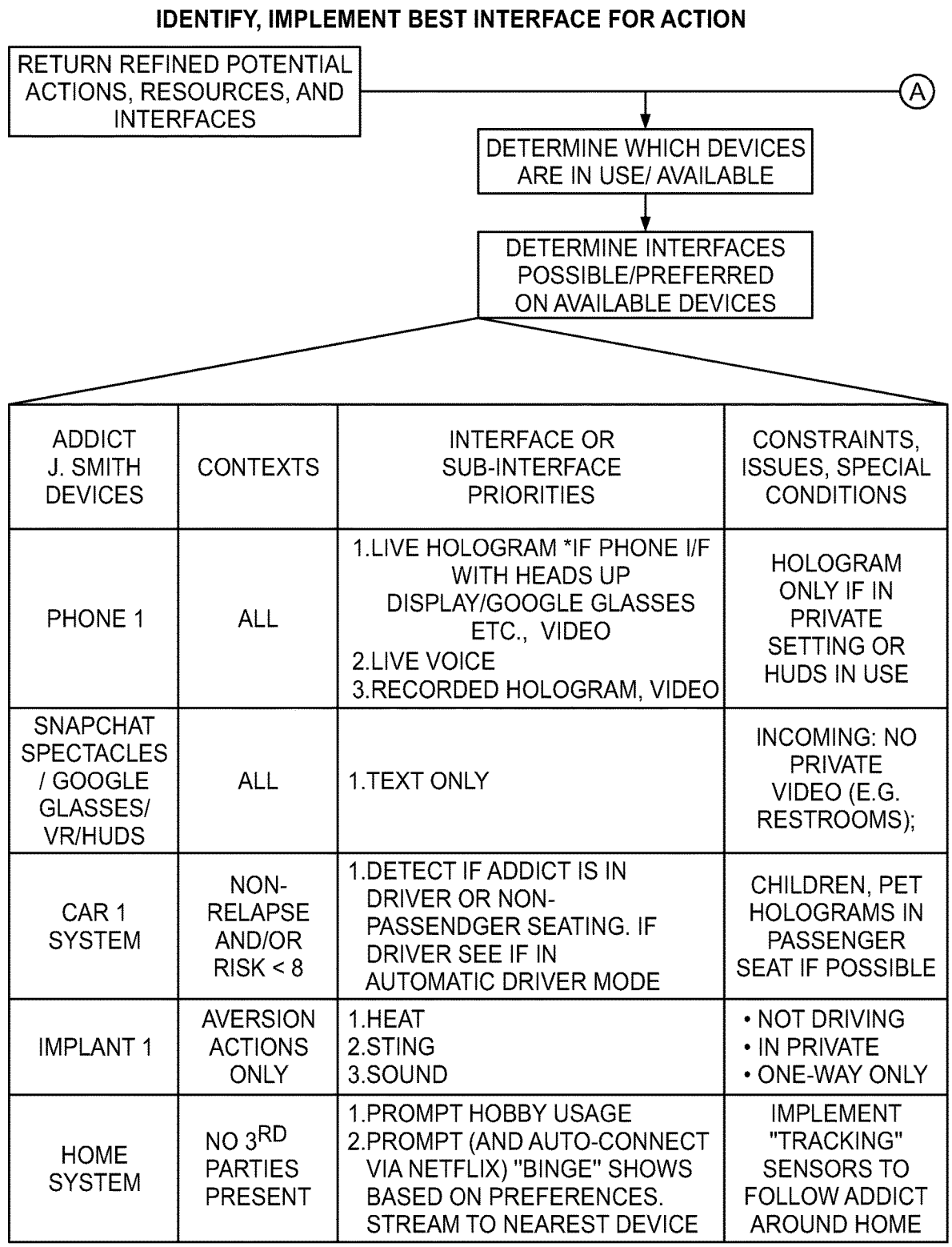
Figure 8:
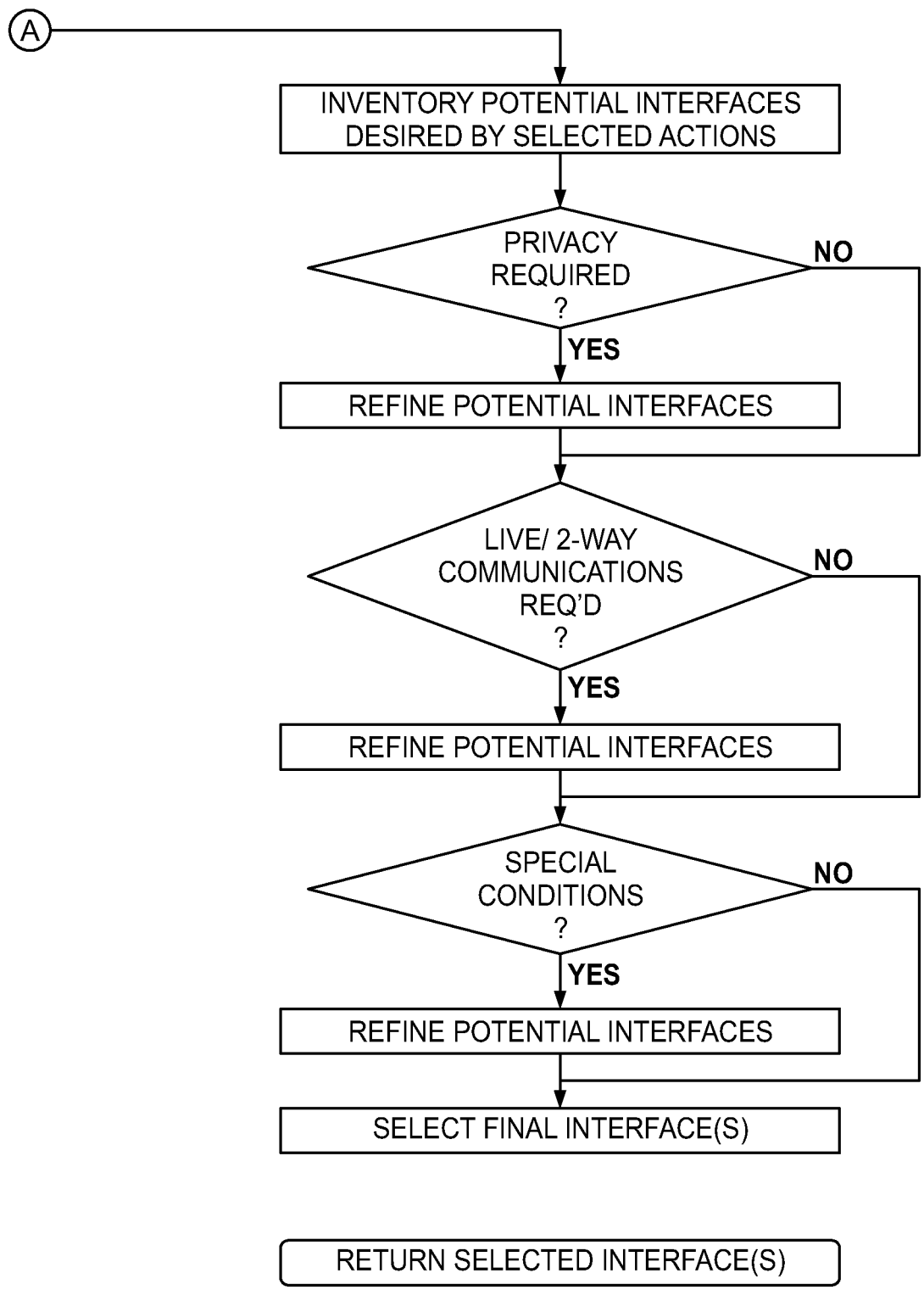

FIG. 8 describes example ways to select the best interfaced) for interacting with an addict, including implementing relapse prevention actions.

Figure 9:
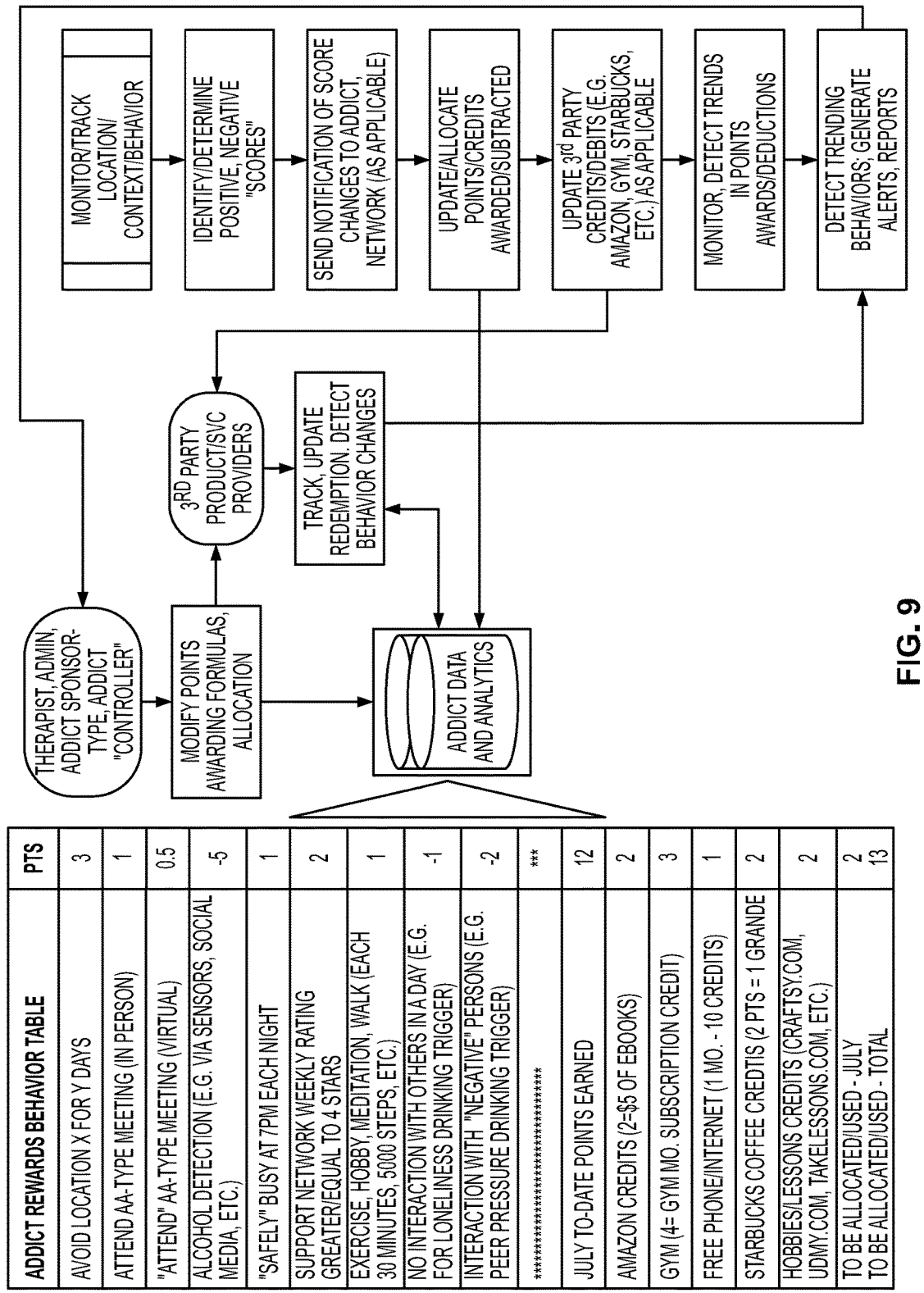

FIG. 9 describes an example addict rewards/demerits system based on an addict's behaviors and actions, which may include rewarding (or punishing) an addict based on behavior via tracking and data analytics and various reward mechanisms.

Figure 10:
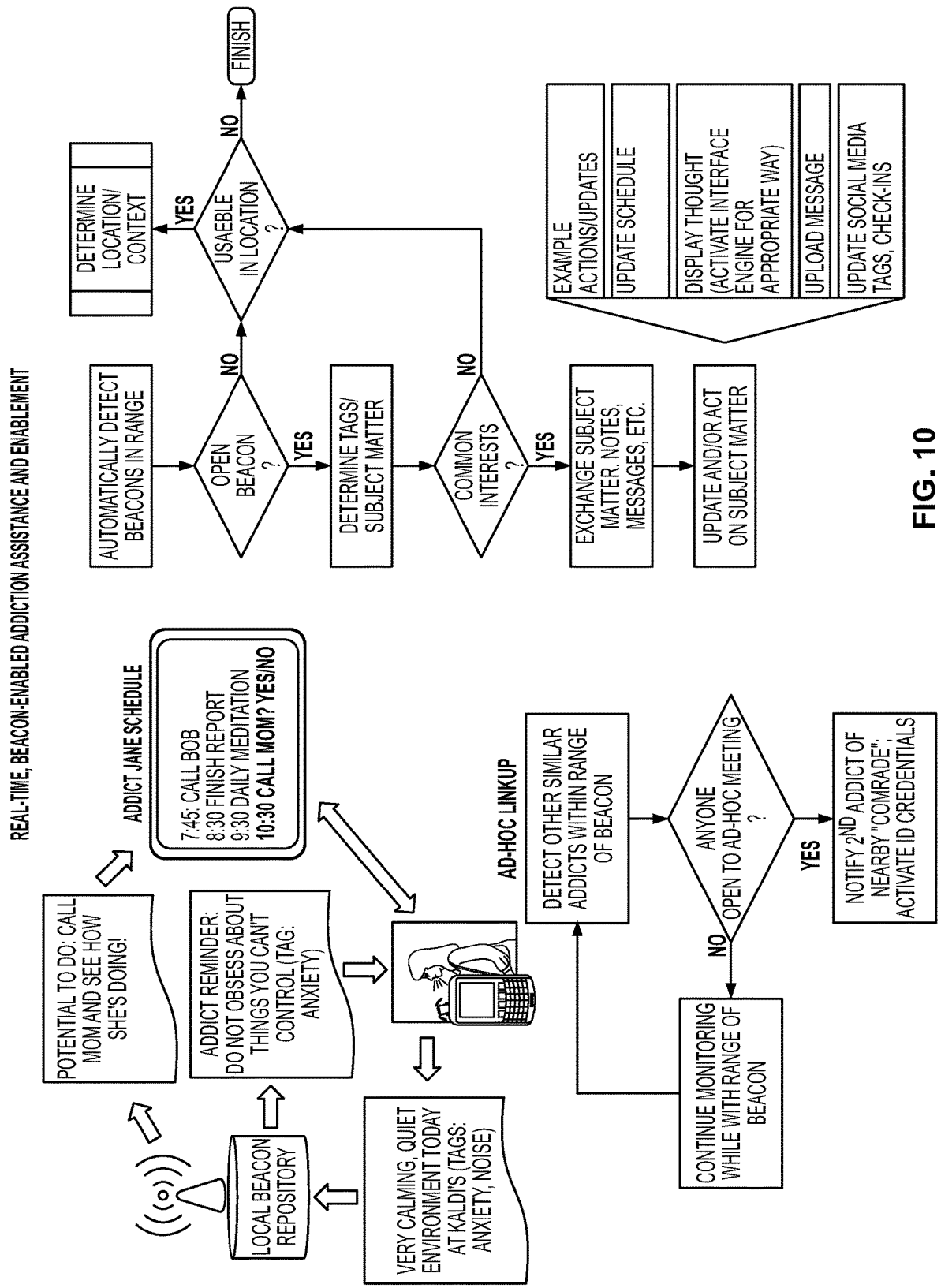

FIG. 10 describes example ways in which addicts can receive and transmit sobriety ideas in public and private places via beacons. FIG. 10 also illustrates example ways in which Real-Time Location System (RTLS) technologies can be used to enable ad hoc, spontaneous, unscheduled, or flash addict meetings between people with similar addiction issues.

FIG. 11 thru 14 describe examples of using location and/or context information to provide privacy and security for data collected in various implementations of the present disclosure.

Figure 15:
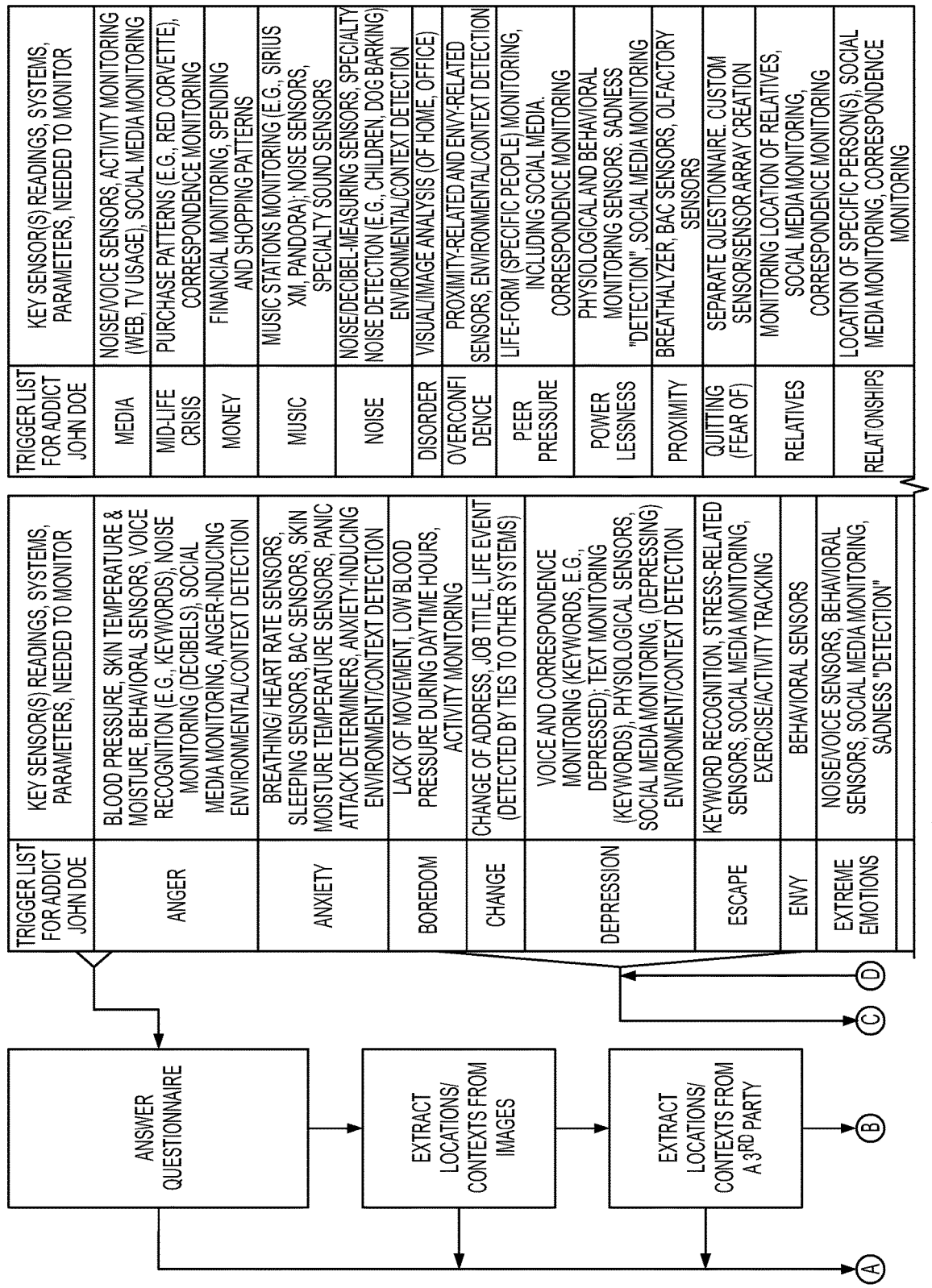
Figure 15:
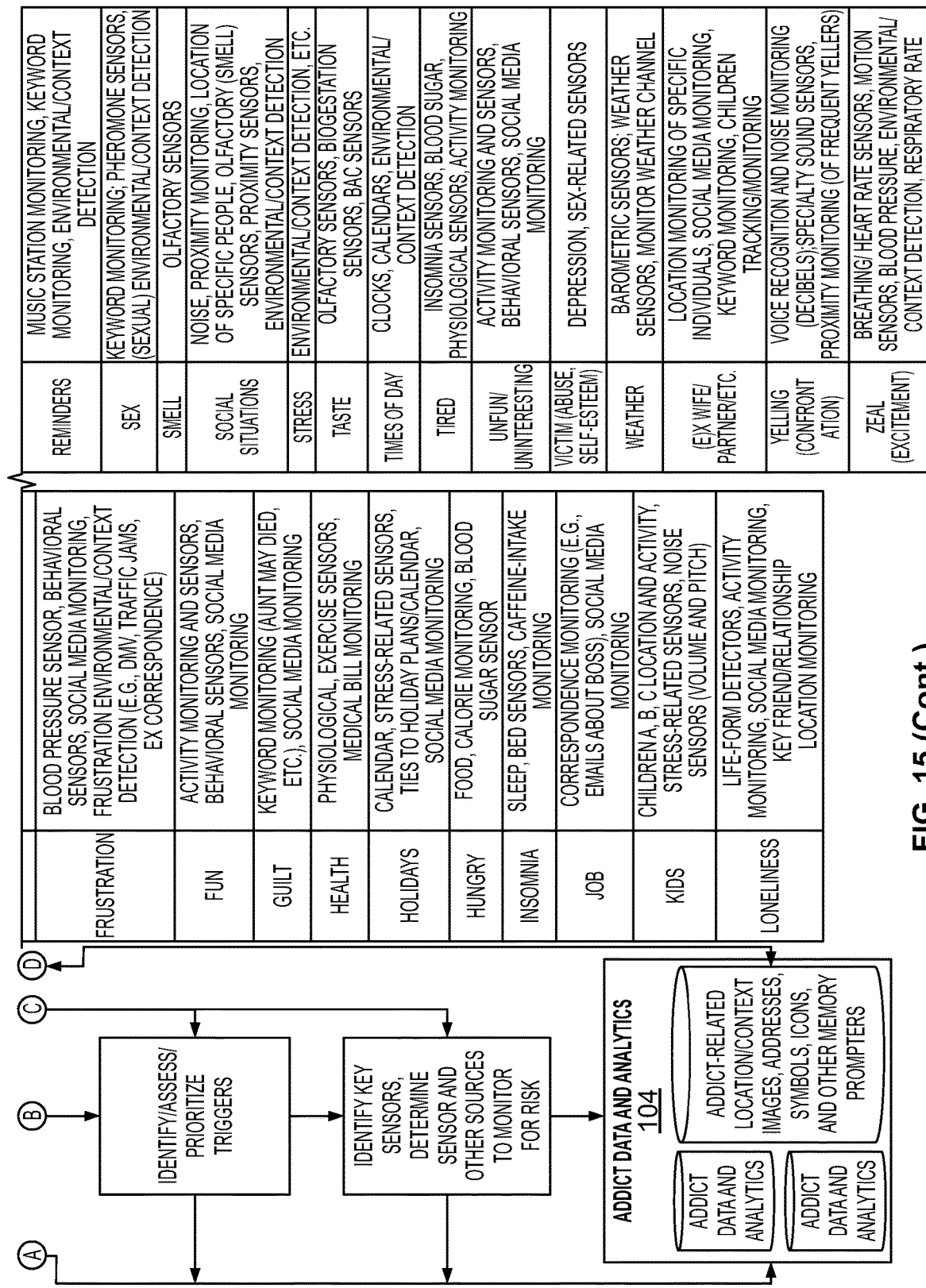

FIG. 15 depicts an example embodiment of a method for monitoring for a risk of a pre-identified behavior (e.g., pre-identified addict-related undesirable behavior, etc.). FIG. 15 also includes example triggers, priorities, and initial risk assessment/detection sensors.

DETAILED DESCRIPTION

Example embodiments will now be described more fully with reference to the accompanying drawings.

Addiction to substances, such as alcohol and drugs, and activities, such as gambling, are a major scourge of society. Addictions can come in many forms, but generally can be put into two categories: 1) addiction to a substance, such as drugs, alcohol, or food, or 2) addiction to an activity, such as gambling, sex, or shopping. The human impact of an addiction can vary greatly in terms of physical toll on the mind and body as well as everyday life-damage such as destruction of families and job loss. Common life-ruining addictions include those involving alcohol, prescription and non-prescription drugs, cigarettes/nicotine, and gambling. Less common but very serious addictions involve overindulging in sex, eating, and avoidance/lack of food (e.g., anorexia or bulimia). Other addictions typically (but not always) can be considered relatively minor or annoying such as shopping, exercise, work, sports viewing, beauty enhancement/plastic surgery, videogames, or even surfing the Internet or constant use of smartphones, to name a partial list.

The term addiction has many definitions, but in general it refers to a person or persons who cannot, or will not, stop using or doing something that is potentially harmful to them and/or others around them. While addiction often conjures images of drunks or drug addicts roaming the streets, in reality addiction impacts all walks of life, from professionals to blue-collar workers to athletes to celebrities to stay-at-home parents, even to children. Many addicts live otherwise useful, functional lives, that can be greatly improved if their addiction is effectively treated.

Various types of addiction treatments, programs, and other methods for addressing addiction have been around for many decades. Examples include: 12-Step Programs such as Alcoholics Anonymous (AA), Acupuncture, Aversion Therapy (multiple forms). Behavioral Self-Control Training, Cognitive Therapy, Going Cold Turkey, Community Reinforcement, Diet-based Programs, Drug-based Treatments (multiple forms). Exercise-based programs. Hypnosis, Interventions, Meditation, Motivational programs. Nutrition-based programs. Rehabilitation (Inpatient and Outpatient)/Hospitalization stays. Religious-based programs, Self-Change Manuals/Guides, (Traditional) Psychotherapy (multiple forms). Spiritual Immersion, and Work/Treatment programs to name some of the more commonly-known approaches.

Sometimes addiction treatments such as those mentioned above work. But very often addiction treatments do not work, at least not for long. While there are many reasons why an addiction treatment might not work, one common reason is that most treatments are most effective when they are actively being implemented, such as when a person is actively in residence in a treatment facility, attending an AA meeting, or in a therapy session. Put another way, one of the vulnerabilities of these and many of the above approaches is that their effectiveness is closely tied to their immediacy, both in terms of physicality to the addict (for treatments that have a personal counseling and/or physical location element) and in time-how fresh the teachings of the program are in the mind of the addict, not to mention how long the addict is willing to actively participate in treatment or treatment-related activities. This is particularly true for many of the most common treatments, such as rehab facility stays (inpatient or outpatient), therapy sessions, or alcoholism-related community meetings. Once the addict leaves those (usually physical, but increasingly virtual or augmented) places where the treatment takes place, the lessons or motivations from those treatments become weaker or start to fade, while at the same time opportunities and temptations to partake in the addiction increase.

Another issue with the above treatments is that many surprisingly place little emphasis on the triggers that may cause or set off one's addiction—particularly in understanding what situations, circumstances, or mindsets (broadly, triggers) make or drive the addict to want to use the substance and/or activity in question. Triggers are what very often drives the desire to use. By way of background, triggers may be situations, circumstances, activities, events, and mental thought processes and frames-of-mind that tempt or cause an addict to want to use a substance or engage in an activity. Without such detailed knowledge of the triggers of addiction, such treatments often focus on symptoms, or controlling such triggers after they occur. In any event, even in treatment programs where understanding of addiction triggers are emphasized, such emphasis is usually focused on general understanding of the triggers, not in dealing with them on a practical, day-to-day, hour-by-hour basis of every-day life.

As the addict gets farther away from the treatment program—physically and/or in time—the lessons from those programs naturally start to fade, becoming less effective, and, in turn, making the addict more susceptible to relapse. Thus, it is desired to find ways of keeping treatment lessons fresh in the mind of the addict, or alternatively refreshing them in a way to actively deter an addict from relapsing. It is also unfortunately true that even the best-intentioned addict cannot see all the possible situations that might tempt or trigger the addict to relapse in time to avoid such triggers, or at least mitigate them—the addict may find himself in a high-risk environment before realizing it. After recognizing the above, the inventor hereof has further recognized a need for a way to use technology to provide treatment reinforcement when the addict is away from the place of primary treatment(s), while simultaneously protecting the addict from the temptations/addiction triggers of their addiction.

As mentioned earlier, some, but not all of the treatment programs above include education about addiction triggers. Such triggers include situations, circumstances, activities, events, and mental thought processes and frame-of-minds that tempt or cause an addict to want to use a substance or engage in an activity known or identified to be detrimental to the addict and/or others. Examples of triggers include but are not limited to: Anger, Anxiety, Boredom, Change, Children, Conflict, Depression, Disorder, Embarrassment, Escape, Envy, Excitement, Fun, Frustration, Guilt, Health issues. Holidays Hunger, Insomnia, Job stress. Loneliness, Mid-life Crises, Money worries. Noise, Overconfidence, Pain, Peer Pressure, feeling Powerful or Powerless, Proximity (to the substance). Fear of Quitting (the substance or activity). Relationship issues. Relatives, Reminders, Sex, Shopping Situations, Social Situations, Special Occasions, Stress, Taste and Smell, Times of Day, being Tired, being Unfun, being a Victim (or crime, abuse), ex-spouses/partners. Yelling, even Season or Weather changes or Music. There are potentially hundreds of possible addiction triggers, and many thousands of trigger combinations.

It is when an addict's most vulnerable triggers become active or are present that the addict is most vulnerable to relapse. Thus, if boredom is a major trigger for an addict, it is imperative to keep the addict from becoming bored, or failing that, to respond to, and correct a bored addict before the temptation to use a substance or engage in an addictive activity becomes too strong and relapse occurs. Determining an addict's triggers and proscribing actions and activities to deal with those triggers without relapsing is anticipated to become a more common and important part of many addiction treatments, and is at the core of various exemplary embodiments of the present disclosure. In particular, various exemplary embodiments disclosed herein focus significant attention on understanding an addict's triggers and, in particular, using an array of sensors and other information to anticipate and/or detect triggers that are active, present, or in danger of becoming active or present, particularly by using location and context to a) anticipate, predict, and/or preempt an addict's triggers from becoming active or present, b) prevent a relapse when triggers do become active by initiating one or more actions, activities, and/or contacts with an addict's support network, and/or c) contain or manage a relapse if and when its occurs.

Surprisingly, there is relatively little application of technology in addiction treatment in the prior art, less that incorporates location, and practically nothing that utilizes context. For example, location technology has been used to aid patient recovery, but this was focused on physical rehabilitation of ambulatory (hospital) patients, not addiction recovery nor patient monitoring outside a hospital environment. Location technology has also been used as a small part of an Internet addiction treatment, which focuses primarily on understanding the amount and type of internet activity that is taking place (e.g., games, certain types of websites, etc.). This latter example also utilized the concept of support groups, but not in a manner that emphases location or context of the addict or the support group.

Exemplary embodiments of addiction treatment systems and methods are disclosed herein. One example embodiment of a system includes a plurality of user devices, sensors, and other technology to: determine, through one or more communications networks, the location of an addict and the context of the addict at the location; evaluate a risk of relapse by the addict in relation to the location and/or the context; facilitate one or more actions and/or activities to mitigate the risk, if any, and/or react to a relapse, if any, by the addict. By way of example, the context may include a situation, environment, and/or state of mind of the addict at the location. The context may include why the addict is at the location, who the addict is with at the location, what the addict is doing at the location, when (day/time) the addict is at the location, and/or how the addict got to the location, etc.

One example embodiment of a method of treating an addict for an addiction includes determining, through one or more communications networks, the location of an addict and the context of the addict at the location, where the context includes a situation, environment, and/or state of mind of the addict; evaluating a risk of relapse by the addict in relation to the location and/or the context; and facilitating one or more actions and/or activities to mitigate the risk, if any, and/or react to a relapse, if any, by the addict. This may be done primarily by determining the location and context of the addict and assessing that data relative to the addict's addiction triggers.

In various exemplary embodiments, a plurality of user devices, sensors, and/or other technologies are provided to protect privacy and security of information collected as disclosed herein. In some exemplary embodiments, experience-based data, including but not limited to location and/or context data, may be used to condition access to protected information. Access to the protected information may be permitted to a permittee based on recognition by the permittee of the experience-based data.

The distinction between location and context and its importance should be noted. The location of a person is often (not always) part of determining a person's broader context. With respect to exemplary embodiments of the present disclosure, depending on the circumstances of an individual, the location of the person may be most important; in other circumstances, the broader context may be more important. For example, if the methods and/or apparatus described in the present disclosure determine that the best course of action may be to attend a nearby AA (Alcoholics Anonymous) meeting, the specific circumstances of that person at that time may dictate that the addict should attend the nearby AA meeting. In another exemplary embodiment, the methods/apparatus of the present disclosure may determine that for the addict's current situation and addiction inducing trigger level (e.g., anxiety trigger, etch, the addict should meet a certain person in the addict's support network who also has the same or similar issues (e.g., anxiety and alcoholism etch issues at an (e.g., anxiety-related, etch meeting that is quite a bit farther away than the addict's current location. Here, the context of the addict is more important than just the addict's location.

In various embodiments of the present disclosure, addicts can be helped to detect and deal with the triggers that initiate or enhance the craving to indulge in their addiction. There generally are many such triggers, including but not limited to: Anger, Anxiety, Boredom, Change, Conflict, Depression, Disorder, Envy (desire to) Escape, Excitement, Extreme Emotions, Fear, Frustration, Guilt, Health problems. Holidays, Hunger, Insomnia, Job issues, Kids/Children, Loneliness, Media (TV, Radio, the Internet) marketing, Mid-Life Crisis, Money problems. Music, Noise, Overconfidence, Peer Pressure, Power, Powerlessness, Proximity (to an addictive substance), (fear of) Quitting, Relationships, Relatives, Reminders, Sex, (change of) Seasons, Smell, Social Situations, Stress, Taste, Times of Day, (being) Tired, (feeling) Not Fun or Unhappy, (feeling) Victimized, Weather, Yelling, and Zeal (high energy). Many addicts are especially vulnerable to relapsing when faced with one or more of these triggers. Some of these triggers have a location dimension to them, most notably proximity to an addiction substance or activity, and many more have a location element in the actions or solutions for dealing with those triggers (and/or high-risk for relapse situations) without relapse. For example, a response to the detection of the Boredom trigger may require the addict to go to a certain place to do a certain activity. Loneliness would involve visiting with or visit by a member of the addict's support network. Noise could require going to a quiet place to meditate, such as a church or library, or to retreat to a serene program on a virtual reality device. This kind of information could be captured in a data profile (e.g., an addict profile including actions to take in relation to the addict, etch stored in a database or similar data store.

The present disclosure includes various exemplary embodiments of systems and methods that utilize the location and context of an addict and other resources to a) preempt trigger and/or high risk relapse situations, b) prevent relapse in high risk situations, and/or c) respond to, manage, and recovery from a relapse when they do occur. Various embodiments include collecting, aggregating, and analyzing addict- and addiction-related data specific to that addict's condition, vulnerabilities, motivations, and usage triggers. Such data/information can be collected from a wide variety of sensors and other data sources, including but not limited to: personal devices such as smartphones, tablets, computers, PDAs, wearables (data collection devices worn on the person, such as Fitbit, etch, implants, Google Glass, etc.; nearby sensors or devices such as security/video cameras, smart devices (such as smart home-related sensors, etch, crowdsourcing data collection applications of nearby users, building/store/office Wi-Fi networks, location-sensitive beacons, etc.; and/or extended data collection mechanisms such as road traffic sensors, public video cameras or billboard displays, weather data collection sensors, law enforce men t/security-related devices, etc.

Various system and method embodiments according to the present disclosure make use of trigger-based sensor networks and trigger-based support networks that may be tuned or modified so as to collect data potentially related to one or more particular addiction triggers, such as Anger, Frustration, Noise, Social Situations, Stress, Yelling, etc. Such data solely or in combination can identify various high risk (of addiction usage) contexts or relapse situations, circumstances, events, and/or possible mental frame-of-mind/ thought processes that often have to be managed to allow the addict the ability to successfully deal with such situations without succumbing to the addiction(s). This managing of such situations may include providing, recommending, and/ or injecting actions, activities, resources, recommendations, directions, and/or elements of control into the addict's life on either an ad-hoc, occasional, periodic, and/or (near) continuous manner to help the addict to refrain from their addiction. Management of such situations can be done via a variety of analysis, assessment, and prediction engines and algorithms that anticipate or predict the impact of certain situations, contexts, circumstances, or events on an addict's behavior and overall sobriety and devise and quickly put in place a course of action to minimize the addict's risk of relapse, or failing that, minimizing any resultant harm and damage. Such a course of action may be predominately location-based, meaning using location information as a key part of the course of action, but the present disclosure is not limited to location-based information; key information may well include non-location based elements, particularly the use of sensors that can provide valuable input into understanding the current context of the addict, and actions that may have little or nothing to do with an addict's location (such as the addict calling a family member to discuss his Frustration, for example).

While various aspects of exemplary embodiments of the present disclosure are targeted at the treatment of addiction, actual addiction is not always involved. As noted before, exemplary embodiments of the present disclosure can be used for the prevention of addiction, dealing with possible or actual use or misuse of substances and/or activities that can potential be harmful to individuals or groups, or indeed unrelated to any addiction or substance/activity use/misuse at all. In order to utilize and receive the benefits of exemplary embodiments of the present disclosure, a person does not necessarily have to be an addict with an addiction to a substance and/or activity. For example, a person may want to cut back on drinking, for example, even if not physically addicted thereto or even if the person does not drink often. Treatment may refer to any assistance provided in various exemplary embodiments to help an addict and/or others in dealing with the addiction (as described broadly herein) in some form or fashion, and/or for informational purposes. Sober may refer to non-usage of the addiction substance/ activity. Relapse may refer to usage of the addiction substance/activity.

Exemplary embodiments of the present disclosure may also be applicable to persons and/or situations in a pre-addiction situation or scenario where the substances/activities are merely abused, that is, done more or more often than might be considered acceptable, healthy, or desirable. Thus, various embodiments of the present disclosure may be applicable in relation to persons who may be considered high-risk, such as the children of alcoholics, though no symptoms of addiction exist. Various embodiments of the present disclosure further may be applicable in relation to situations and/or scenarios where person(s) are neither addicted nor considered abuser(s) nor high-risk; rather, they and/or others would like to reduce the usage of a substance or activity to achieve some real or perceived benefit. The above situations/scenarios and other applicable contexts may be generally included under the term addiction, and a person suffering from addiction, abuse, or the general desire to reduce/stop doing some substance and/or activity may also be referred to as an addict. Also, an addiction or addict is not limited to just one substance or activity; many addicts concurrently or serially suffer from more than one addiction (sometimes referred to as dual diagnosis, though it can actually be 2 or more addictions). Various embodiments of the present disclosure can be equally applicable to such persons with multiple addictions, either concurrent or consecutive.

In addition, a distinct set of exemplary embodiments related to prisoner and particularly parolee tracking and monitoring is enabled by the present disclosure. Such tracking and monitoring is currently done by a GPS bracelet attached to the person's ankle or other body part, with their movements then monitored via GPS readings. In situations where GPS does not work or work well, particularly in a building or other structure or environment where GPS does not work, cell tower triangulation is employed to provide a rough calculation. Both have limitations: GPS with it primary use cases of being tracked outdoors, and the inaccuracies associated with cell tower triangulation for indoor situations.

Because of these limitations, GPS bracelets in effect determine the type of prisoner/parolee tracking that can be done, limiting the person to a particular area or building. It cannot get more "micro" than that and/or cannot granularly track the person's location and activities in an indoor environment, which is, however, possible with exemplary embodiments of the present disclosure. For example, a parolee could be confined to house arrest in a multi-unit apartment or motel due to the enhanced ability to track a person's movements indoors. In addition, activities can be monitored or controlled, such as a person on parole for a DUI (Driving Under The Influence) being prohibited from drinking. The sensors associated with the present disclosure as well as risk calculation algorithms could be used to detect high risk situations where the parolee is about to violate parole, generating various alarms. If the parolee followed through and drank, then exemplary embodiments of the present disclosure would provide the evidence needed to revoke parole.

Context may generally refer to an addict's situation, environment, and/or state-of-mind (e.g., as determined by biometric data, etch particularly as it relates to a potential substance abuse relapse. Traditionally in mobile systems, a person's physical location can form a key cornerstone of that person's context—and indeed may be all that is needed to determine the person's overall context in many instances. For example, if an alcoholic has stopped at a bar on his way home from work, it typically takes no additional data to infer a high-risk relapse situation and state-of-mind. However, other or additional sensors may be used to confirm and/or refine a person's context. For instance, a light sensor on an addict's device may indicate that the person is still outdoors (perhaps debating himself in the parking lot). A breathalyzer sensor could indicate a relapse—that the situation has moved from needing a prevention set of actions to a set of damage control and safety actions. Thus, an addict's location may be considered the entirety of the context (stopped at a bar), part of the context (not yet in the bar), or perhaps even not a key part of the context (e.g. the person is drinking or is drunk, having left the bar, etc.). However, for many if not most embodiments, physical location plays at least a partial role in determining a person's overall context; in addition, the location of support resources very often plays a key role in if and/or how such resources may be employed.

In various exemplary embodiments of the present disclosure, systems and methods are provided for preempting, anticipating, and/or detecting high risk addiction relapse situations and determining and implementing actions and activities to prevent a relapse from occurring, or in the case of actual relapse minimizing the associated damage and returning the addict to sobriety as soon as possible. Various mechanisms are provided for determining and utilizing an addict's context-particularly location—in assessing their risk of relapse, and utilize that context as well as the relative locations and contexts of other resources to determine and implement relapse preventative actions. In various exemplary embodiments of the present disclosure, location/context-based mechanisms are provided to minimize or contain the consequences in the event that a relapse occurs, as well as mechanisms to preempt and prevent high risk situations from occurring At a more granular level, an example communications network includes a plurality of heterogeneous, differing, or different types of sensing devices configured to monitor the location and/or context of an addict; and a plurality of heterogeneous, differing, or different types of interface devices each configured to engage in interaction with the addict, with a support person for the addict, and/or with a third party in the event that the network detects a relationship between the monitored location and/or context and a trigger predetermined in the network for the addict as being related to relapse; wherein the interaction is selected based on the trigger and the monitored location and/or context.

The example communications network may include one or more server, client, cloud, peer-to-peer, and/or other devices configured to develop and/or update a profile of the addict based on monitoring data from the sensing devices and/or the interaction engaged in by one or more of the interface devices.

In the above example communications network, one or more of the sensing devices may be configured to detect and/or determine the relationship between the trigger and the monitored location and/or context.

In the above example communications network, the sensing devices may be located in, on, and/or near the addict, and/or elsewhere relevant to a current and/or future location/con text of the addict.

In various aspects of the present disclosure, a network-implemented method of providing support for an addict includes monitoring the location and/or context of the addict, the monitoring performed by one or more sensing devices; detecting a relationship between the monitored location and/or context and a trigger predetermined in the network for the addict as being related to relapse; and based on the detected relationship, one or more of a plurality of interface devices of the network interacting with the addict, with a support person for the addict, and/or with a third party.

The foregoing example method may include, based on the monitoring, the detecting, the determining, and/or the interacting, developing and/or updating a profile of the addict, the profile including actions to take in relation to the addict.

In the foregoing example method, one of the sensing devices may be configured to send the monitored location and/or context and/or the detected relationship to one or more other devices of the network.

In the foregoing example method, the sensing devices may be one or more of the following: located in, on, and/or in the vicinity of the addict, mobile, and stationary.

Figure 1:
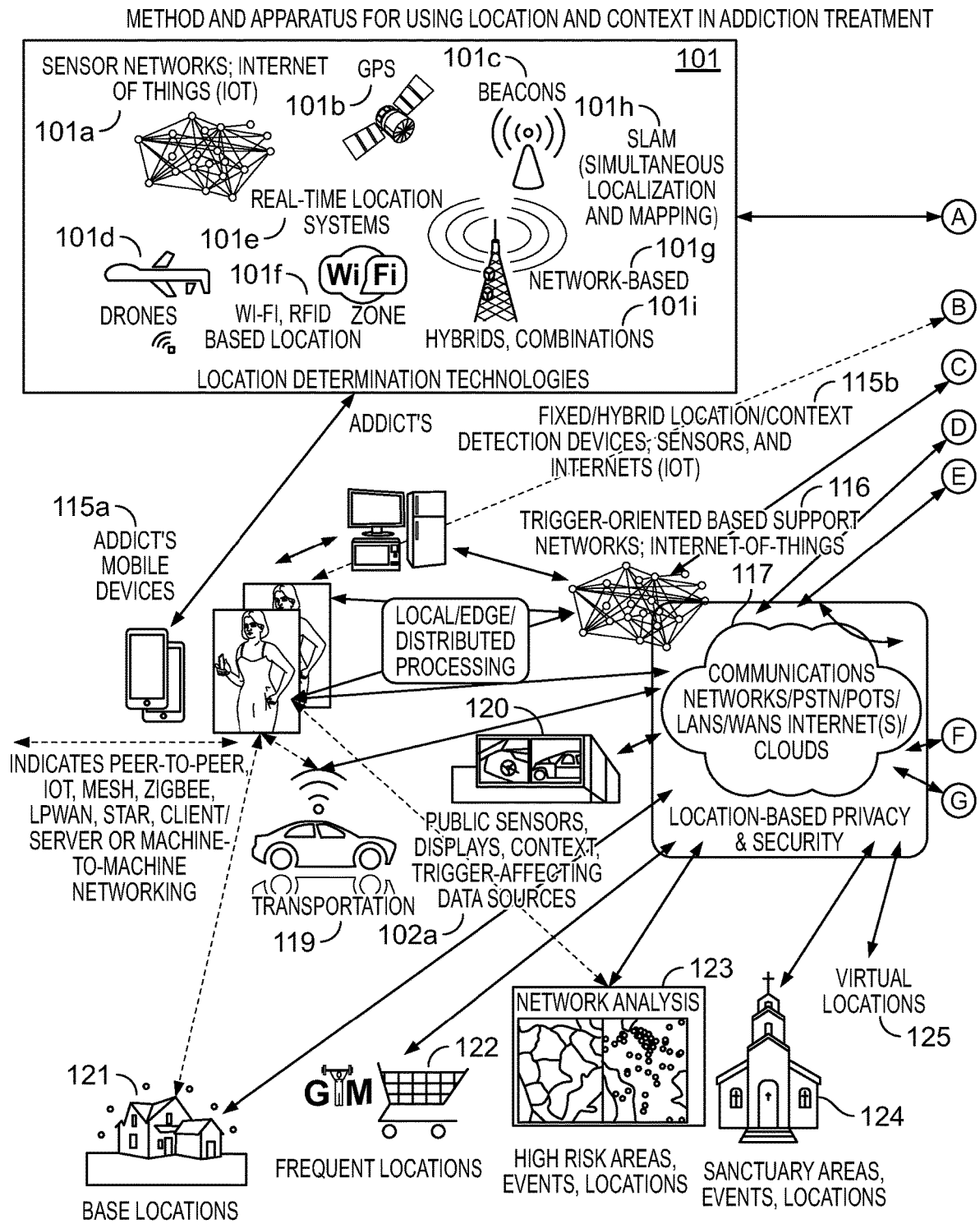
Figure 1:
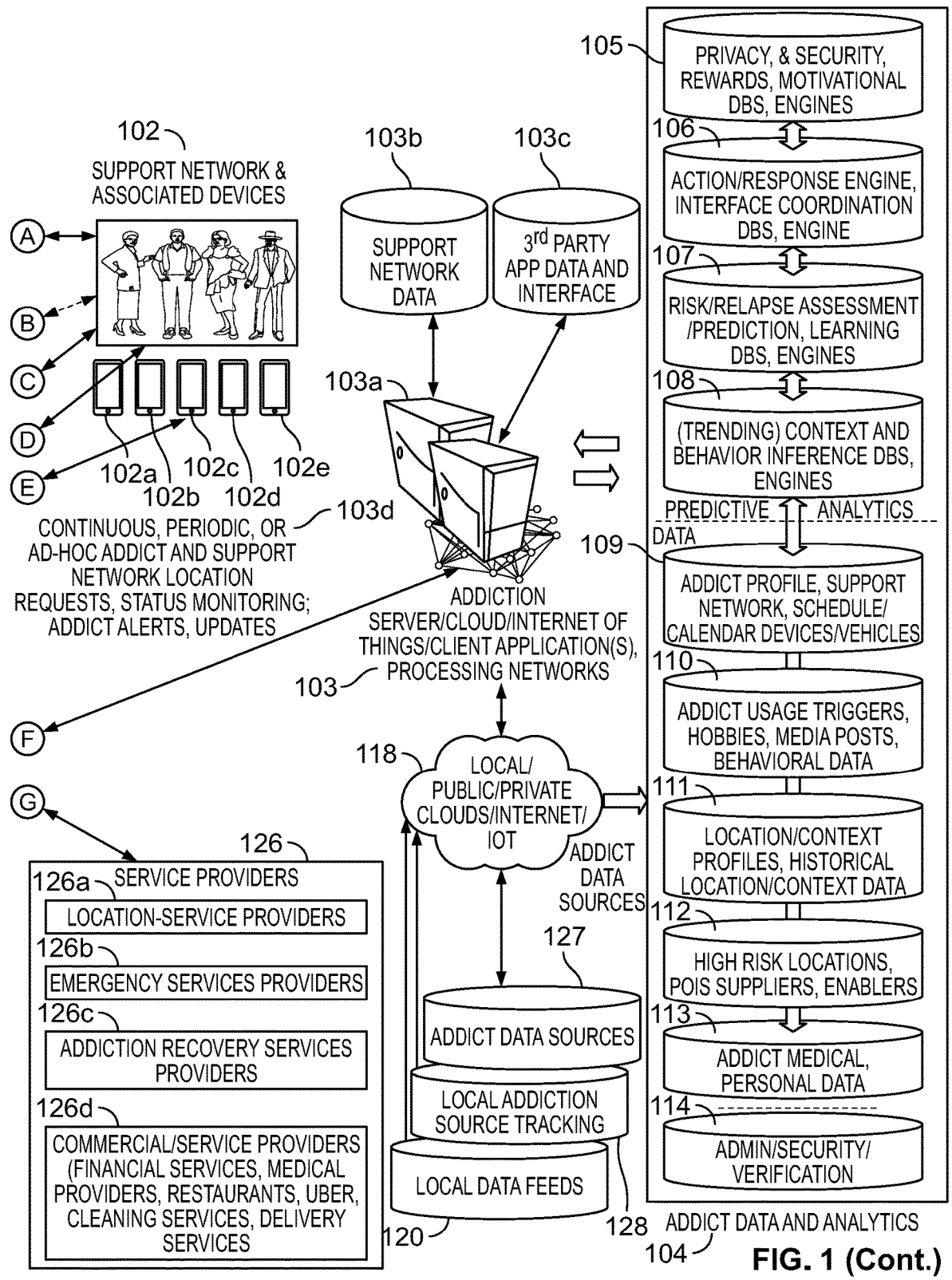

FIG. 1 is a high-level summary diagram that shows an addict with associated devices, sensors, wearable/embedded tags, and other locatable technology. FIG. 1 also shows an exemplary scope of potential people, resources, assets, locations, applications, and data that may be helpful and/or important in helping the addict become and stay sober. Associated devices generally refers to any technology that may be directly or indirectly associated with the addict for collecting data on or about the addict and/or for disseminating data or actions to or about the addict. Thus, an addict does not have to be in physical contact with a device for a given exemplary embodiment to work. For example, an associated device could be the use of a drone to shadow an addict's movements, location, and behavior and reporting that information back to analytical engine(s) of the given embodiment. The scope of potential resources is not limited to those listed in FIG. 1 as other resources may be used in other exemplary embodiments.

FIG. 1 illustrates various example embodiments 100 of the present disclosure including the use of an addict's support network 102. A support network is generally considered people who have some knowledge of and/or influence about the addict's problems and are prepared to help. The support network 102 of people may include medical professionals. Mends, family members, therapists, co-workers, spouses/partners, social workers, advocates, pastors, priests, rehab/treatment centers, emergency responders, lawyers, courts, parole officers, social/business networks, family support networks, specialized social media (Addiction, Trigger-Focused) support, other websites, internet/cloud help, addiction community members, other addicts (using, recovering) or anyone who might be aware of the addict's situation and in a position (including physical location) to assist the addict in some form if the need arises (e.g., a support person, etc.).

Various example embodiments of the present disclosure provide for continuous, periodic, ad-hoc, and/or as-needed monitoring 103d of the support person's location and/or status for potentially helping one or more addict's, such as but not limited to Busy, Work, Available, In Emergency, Please Find Someone For Me To Help (e.g. assist anyone, not just the persons listed as approved assisters), and/or schedule/calendar for one or more of those support persons and associated respective statuses. This monitoring could be initiated by the Addiction Server, by the support person's device(s) 102a, 102b, 102c, 102d, 102e, cloud-based services, and/or 3rd party applications that already make use of location and/or status monitoring.

While FIG. 1 shows a variety of networking and communications technologies, systems, and architectures, such as wireless communications, client-server, peer-to-peer, and cloud computing, the present disclosure is not limited to these. For example, an architecture may be deployed that deploys disclosed functionality for a very limited area for a select type of receiver/person for a limited period of time, such as spontaneous, unscheduled, or flash (short-notice) drinking trigger meeting (a kind of specialized Alcoholics Anonymous meeting). Some or all of these attendees might have a specially issued RFID-type (printable, downloadable, or temporarily/specialty activated) tag, and/or beacon-based network that allows them access to the meeting and interfaces with other personal technology that enables them to enjoy benefits from the meeting, such as personalized holographic presentations to their personal visor, specialized drug doses, or just validation of their identity. Addiction FOB or dongle-type devices might also be used that serve as the interface means between such meeting technology and other personal technology such as a wearables or implantable, or the Addiction Monitor/Controller device 200 shown in FIG. 2.

FIG. 1 also discloses an example Addiction Server/Cloud/Internet of Things/Client Application(s) and Processing Networks 103 (server 103a) that can be a key hub for communications with a variety of people 102, resources, assets, applications, and data sources that may have relevance to the addict. As shown, the data sources may include a database 103b of support network data (e.g., location, availability/schedule, specialties, privacy requirements or regulations, etch and a database 103c of third party app data and interfaces (e.g., social medial, local search, navigation, etch and affinity programs. The data sources may also include data sources accessible over a network 118 (e.g., local network, public network, private network, internet, IOT, etch such as a database 127 of addict data (e.g., medical, professional, public records, media, etch, a database 128 of local addiction data (e.g., police reports, trends, etch and a database 129 of local data feeds (e.g., events, traffic, news, weather, camera feeds, etc.). Additional data sources may include addict data sources including addict data and analytics 104, including predictive analytics data, etc. The addict data and analytics 104 may include privacy, security, rewards, motivational database(s) and engine(s) 105, action/response engine, interface coordination database(s) and engine(s) 106, risk/relapse assessment/prediction, learning database(s) and engine(s) 107, (trending) context and behavior inference database(s) and engine(s) 108, addict profile, support network, schedule/calendar, devices/vehicles 109, addict usage triggers, hobbies, media posts, behavioral data 110, location/context profiles, historical location/context data 111, high risk locations, places of interests (POIs) suppliers, enablers 112, addict medical, personal data 113, and administration, security, and verification 114.

The server 103a also serves as the primary analytical engine for developing and processing algorithms for profiling an addict's behavior, tendencies, risks, and probabilities of relapse for a wide range of possible situations, and for determining a variety of actions to, for, or on behalf of the addict to avoid relapse and/or improve the addict's overall treatment. Included in potential actions are monitoring the location of the addict and the addict's support network for scenarios where one or more support persons may be dispatched to the addict's location, or vice versa.

Such server functionality can be physically and/or logically configured in many forms. It can be centralized in one or more servers. It can be partitioned in a centralized manner such that functionality is split among different servers, such as one server being a communications network front-end for communicating with various addicts, devices, sensors, and other networks, while another server or set of servers does the analysis of the data. It can also be architected in distributed manner such that some or all of the functionality is performed on addict and/or support network devices. It can be architected such that some or all of the functionality is done in the Cloud via various forms of cloud computing. Regardless of physical and/or logical distribution of functionality, it may be described as or referred to as a server unless otherwise indicated.

The server serves as a monitoring, assessing, and controlling function of, for, and/or on behalf of the addict. This could include providing a variety of alerts to various resources that the addict is in a high-risk situation or area. This control could further extend to actions such as disabling the addict's car, informing the addict's addiction sponsor or community members, or alerting family or law enforcement about dangerous situations. Indeed, one example embodiment of the present disclosure provides a form of involuntary monitoring and action coordination, not unlike GPS ankle bracelet monitoring, where an addict on parole for addiction-related offenses (e.g. DUIs, etch may have their devices (and even attached sensors such as Blood Alcohol Content sensors) monitored to detect the presence of offending substances, and implementing actions to mitigate the risk to the community and the addict themselves.

Another aspect of exemplary embodiments of the present disclosure is the use of multiple location determination technologies or sources 101 to determine locations of addicts and other persons/places/things. These technologies or sources 101 include, but are not limited to, sensor networks (e.g., Internet of Things (IOT) 101*a*, etch, GPS/Assisted GPS 101*b*, cell tower identification 101*g*, cell tower triangulation (TDOA, AFLT), beacons 101*c*, Radio Frequency fingerprinting, Real-Time Location Services (RTLS) 101*c*, WiFi based location systems 101*f*, Radio Frequency Identification (RFID) based location systems and similar systems, drones 101*d*, crowdsourcing, hybrids 101*i*, simultaneous localization and mapping (SLAM) 101*h*, and/or combinations of these or other location determination systems. These location determination systems may be on, worn or carried by, used by, embedded in, or nearby the addict or addiction-related resource sufficiently to determine approximate location.

Not all aspects of the present disclosure need to be centralized in the addiction server. The addict's local device(s) 115*a* may also have functionality as disclosed herein, both for Peer-to-Peer, IoT, Mesh, ZigBce, LPWAN, Star, Client/Server, and/or machine-to-machine (M2M) networking, situations and in circumstances where the addiction server or other parts of the present disclosure are not operating or accessible. An example of this functionality is in the device on/in/around the addict detecting a high-risk situation and the addict attempting to enter and drive a car in an underground garage (thereby preventing a GPS locate). The addict's device would automatically connect with the vehicle's transportation system 119 (e.g., personal vehicle, friend or colleague's vehicle, transportation service like Uber, airlines, public transportions, etch to inform or provide an alert of a high-risk situation and proceeding to disable the car. Indeed, many, even all of the server's functions could conceivably be done in one or more of the addict's device(s) or in other computing/data processing architectures such as cloud computing; a centralized server is a convenient/logical way to represent many of the present disclosure's functions, but not inherently necessary to its overall functionality. For example, the risk/prediction engine part of the server could easily be resident on the addict's device(s) (client). Indeed, in one exemplary embodiment, many or even all functions could be resident and/or controlled on the client.

Similarly, not all devices that can be used are depicted in FIG. 1. Devices 115*a* that can be associated with the addict include but are not limited to portable devices such as mobile phones/smartphones, tablets, laptops, other portable or mobile devices, etc.; wearable devices and tags on or in clothing, jewelry, shoes, watches, etc.; mobile payment devices/wallets, etc.; embedded sensors, tags, chips or other electronics dial can be implanted or ingested (e.g., ingestibles or implantables, etch in an addict, augmented reality and heads-up-displays (e.g. Google Glass, etch and virtual reality-enabling systems. Fixed or mobile/fixed hybrid devices 115*b* such as desktop computers and smart home connected devices that can also be associated with the identity and/or location addict are also part of aspects of some exemplary embodiments of the present disclosure. For example. FIG. 1 shows additional examples of smart home connected devices 115*b* including a TV, refrigerator, and microwave. As more and more devices become smart, the smart device will have the ability to capture data that will help determine a person's location/context through onboard or connected data capture devices such as video, audio, and/or other sensors. Combined with the device's known location (or ability to determine the device's location), and the connectivity associated with communicating to and from these devices (also known as the Internet of Things or IoT), these devices/networks may provide new key sources of personal context information.

FIG. 1 also discloses a variety of location and categories useful in a wide variety of embodiments, not limited to the addict, support resources, or even enforcement resources. One key concept can be to utilize these varieties of location types and categories in a variety of ways in supporting the above resources. These include, but are not limited to:

Base Locations 121 including common locations for the addict, such as home, work, school, or church, etc.;

Frequent Locations 122 including locations frequented often by the addict, such as homes of friends or family, stores, restaurants, malls, gym, hobbies, etc.;

High Risk Areas, Events, Locations 123, such as liquor stores, casinos, concerts, drug-dealing areas that could pose a temptation for the addict, bad peers, trigger activating situations, etc.

Sanctuary Areas, Events, Locations 124 where an addict might feel safe and have a very low temptation to use, such as AA meetings, churches, key/safe friends and family members, dry public areas or events;

Virtual Locations 125 including online forums, such as Face book, Twitter, Women for Sobriety, therapy sites/sessions. Virtual Reality Locations, addiction communities where an addict can involve him or herself safely (without using) in an online activity. This includes the use of virtual and/or augmented reality to put oneself in a different (safer) location, context, and/or frame-of-mind.

While location is most often a key distinguishing characteristic, context can also be important, particularly for support network members. Just having a support person nearby in time of trouble is not enough, the person needs to be available, interested, and in a position (e.g. situation/context) that he/she can break away from whatever they are doing to help the addict. Thus context-determining sensors and other mechanisms can be important not only to the addict but the support network as well.

Put another way. Base Locations are where the addict is frequently, such as Home, Work, or School. Frequent Locations are where the addict frequently visits such as family and friends, the addict's gym, frequently visited stores or restaurants, and various hobby locations such as a bowling alky. High-Risk Locations are another element used in various embodiments, to track possible high-risk areas for the addict with both fixed locations (such as liquor stores, casinos) and varying locations (such as recent drug-activity areas). Opposite these high-risk locations would be Sanctuary Locations, where the addict will presumably be especially safe from high-risk situations, such as an AA meeting or church service. The use of Virtual Locations is also disclosed, used when an addict is logged into and/or viewing a service like Facebook or Twitter or is using Virtual Reality devices such that the addict is on those applications and can be contacted or otherwise influenced by those applications.

These location categories have a wide range of uses. They can be an integral part of action determination when relapse risk is high, by finding the closest Sanctuary Location, for example, and arranging for a nearby support person to meet the addict there, including providing each of them directions via their navigation application based on their current location. High-risk locations of course are to be avoided, but can this can be done in many ways. They can be omitted from navigation applications (de-augmented) to prevent temptations. Geo-fences can be setup around them such that when the addict enters one automatic alerts are sent to nearby support persons to give them a heads up to possibly prepare for an interception. Indeed geo-fences can play an important role in various embodiments, e.g., in risk prediction (e.g. if a high-risk location geo-fence is violated then risk score goes up by 20%, etch, support resource identification (alert people within 10 miles of the addict when X occurs), and context setting (e.g. locations with walking distance of home-half a mile—are considered safe/home location), etc. If an addict is within 1000 feet/5 minutes of a park, then a walking/running excursion can be added to a list of potential actions. And so on. Virtual locations can also have a wide range of uses, e.g. special Reddit groups, as could quasi virtual/physical locations such as safe zones for Anxiety sufferers within the broadcasting distance of a coffee-shop beacon, that provides for virtual or physical meetings of sufferers only within range of the beacon.

Figure 2:
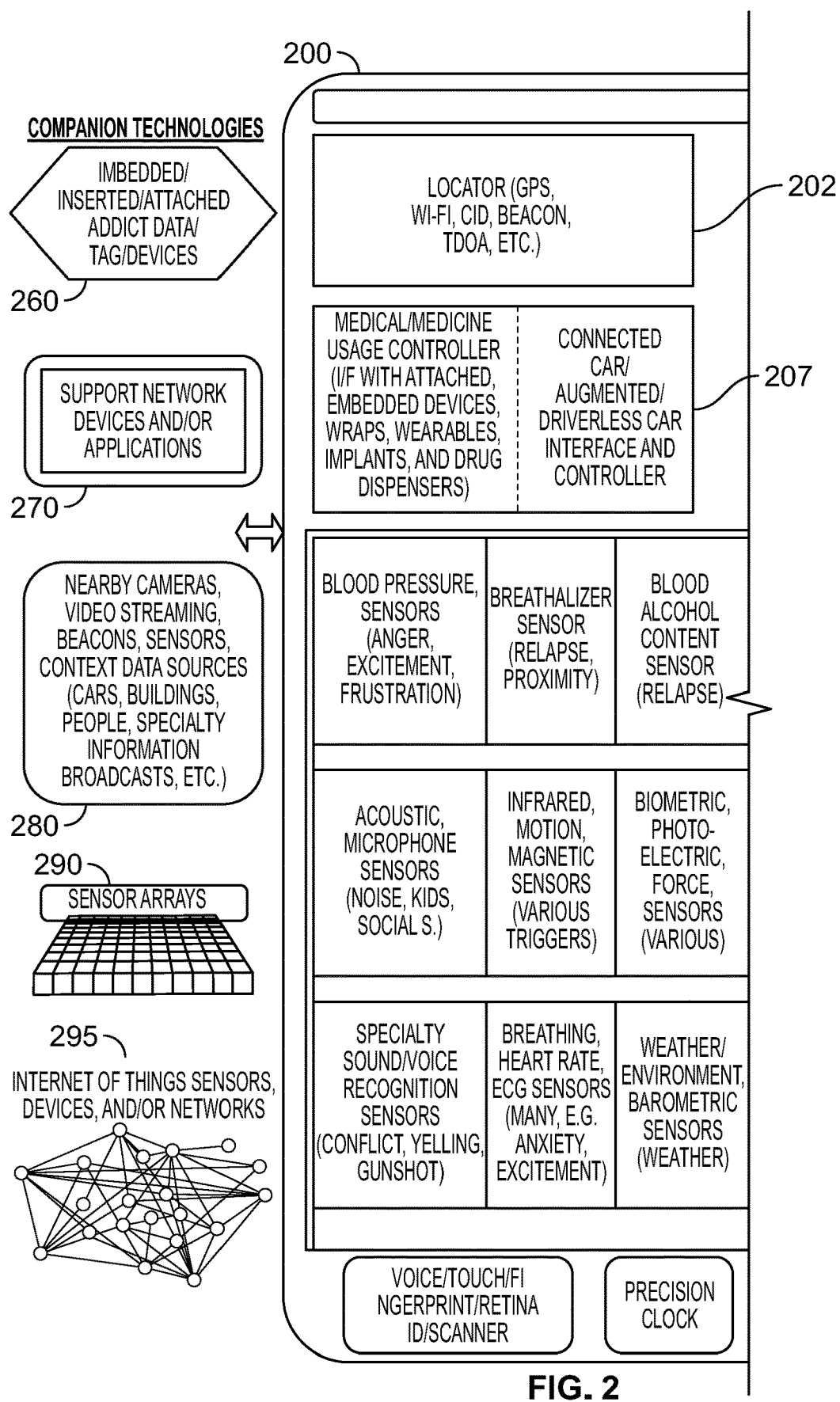
Figure 2:
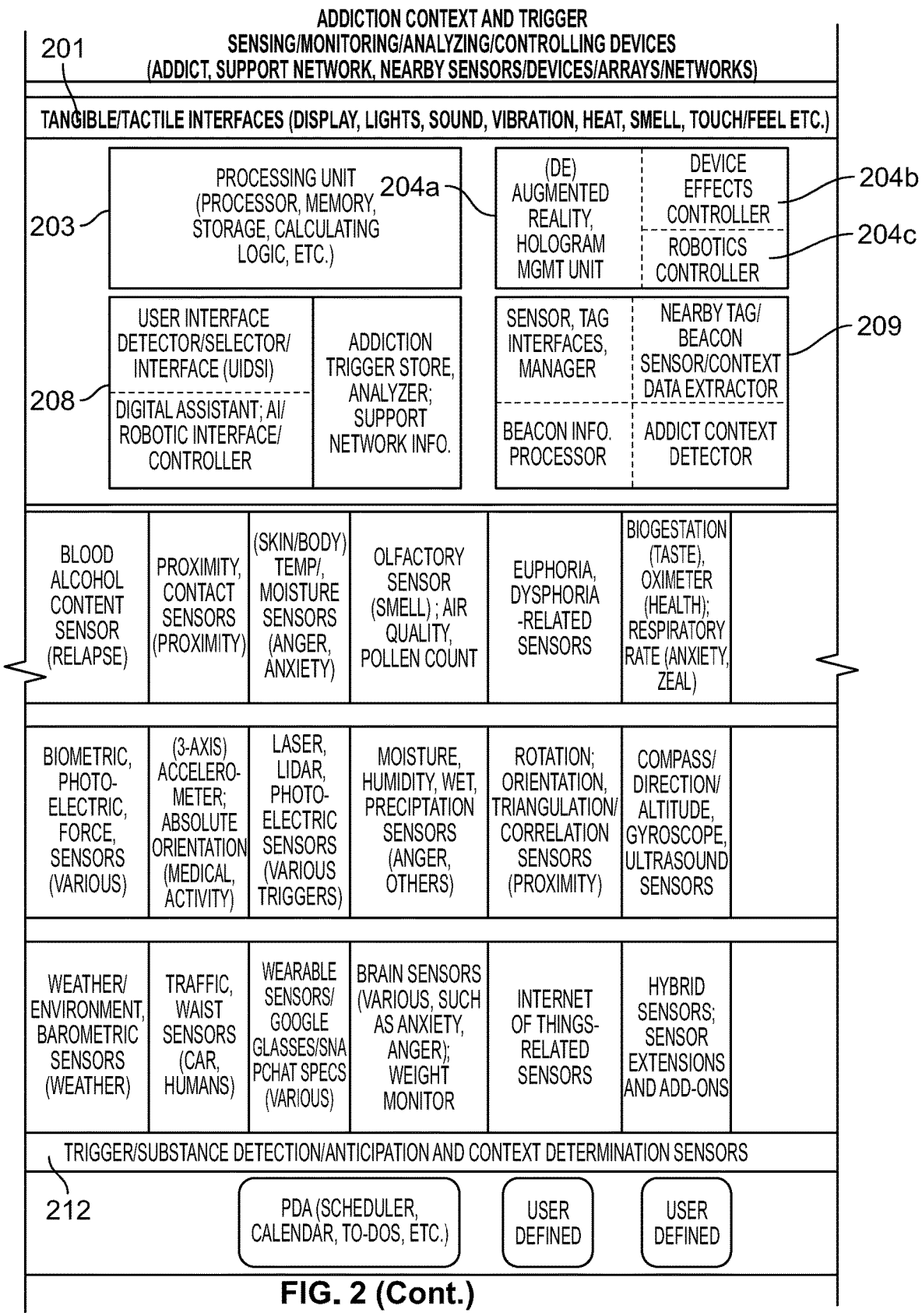
Figure 2:
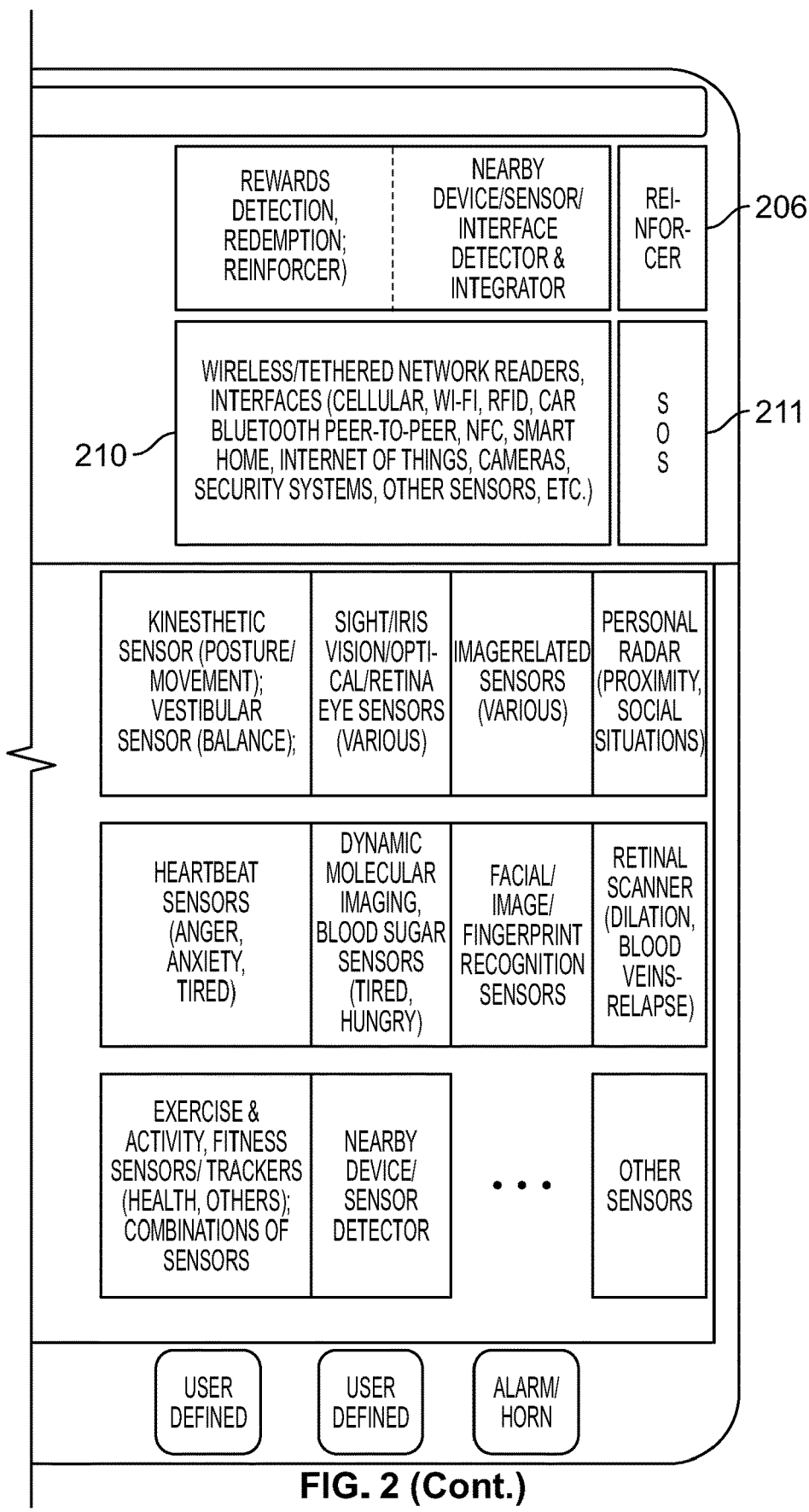

In various embodiments, a variety of sensors, devices, and mechanism, may be used to determine the location and particularly the context of the addict. FIG. 2, for example, describes a device 200 an addict might have on their person (e.g., a smartphone, etch, wear (e.g. in the form of a watch), have implanted, or otherwise be on or near an addict. This device 200 could contain a variety of sensors 212, such as sensors that detect and capture sounds, images, video, or body conditions, for example. FIG. 2 provides a detailed (but not exhaustive) list of such sensors 212, including Blood Pressure sensors. Breathalyzers, Blood Alcohol Content sensors, Environmental/Weather sensors. Skin Temperature sensors. Olfactory (smell) sensors, Bio/gestation sensors. Vestibular sensors. Kinesthetic sensors, and Sight/Vision/Optical sensors to name a few. Other sensors may also be used including sensors for Water Quality/Pressure, Chemical/Gas/Fire/Smoke/CO2/Flood, Level, Gyroscope, (Passive) Infrared, Eddy current, contact. Ultrasonic, Images, Alarm, Doppler, Fiber Optic, Occupancy, Reed, Touch Switch, Magnetic, Inductive, Microwave, Radiation, Parking, etc.

The use of these various sensors can be to aid in the detection and/or determination of the addict's context, e.g., what the addict is experiencing, feeling, even thinking, etc. Even further, to the extent possible individually or in combination with other sensors and/or data, the goal of such sensor use can be to detect/determine what triggers) the addict may be experiencing, and to what degree, in order to gauge the risk of relapse and factors involved in the potential relapse, and to identify and set in movement a course of actions that will preempt or prevent an addict's environment from deteriorating to the point of relapse.

FIG. 2 discloses one such device(s) 200 that can sense, monitor, and/or control aspects of an addict's context. The device 200 includes an array of capabilities, including sensors for detecting or anticipating addiction trigger conditions (e.g., contexts, situations, circumstances, environments, and/or state of mind(s) that may cause the addict to relapse or use substances or activities related to his/her addiction, etch; mechanisms for interfacing with the addict including tangible/tactile Interfaces 201 (Display, Lights, Sound, Vibration, Heat, Smell, etc.). For example, a Smell Interface could generate the smell of fresh pine trees or pine tar in response to high risk associated with the Escape trigger being detected (helping remind the addict of good times he has had when hiking in the Rocky Mountains). The wide variety of interfaces is premised that dissemination of information to/from an addict needs to be in the most effective means possible at any given time or context, which can vary from day-to-day or hour-to-hour. In addition to traditional interfaces such as sound or vibration interfaces, some exemplary embodiments of the present disclosure include the ability to project (or interface to a projector) 2 or 3 dimensional images, video, GIFs, or real-time holographic projections that the addict can converse with. It also includes the ability to augment reality (insertion of images not actually present), and even (de) augmenting reality, such as the elimination of addiction triggers/temptations such as liquor stores from the addict's vision.

FIG. 2 depicts a partial list of a variety of sensors that can be used to determine the addict's context. These sensors can be used individually, in combination, and/or with other information about the addict, environment, situation, circumstance to determine the addict's context, as well as determine if there are any triggers being activated or in the process of doing so. Simple examples include using acoustic sensors to detect the volumes and type of sounds in an addict's vicinity, to potentially identify triggers such as Noise (e.g., too high or low volume, etc.). Children (e.g., detecting high-pitched voices and/or multiple children, etch, or Social Situations (e.g., multiple voices in the background, etc.).

The addict's device 200 shown in FIG. 2 may be configured to serve as a local controller of information of, in, and around the addict. Towards that end it is, to the extent possible, self-reliant and contained in how it collects, processes, and disseminates data-based and physically-based actions. To begin with, it provides a set of tangible/tactile interfaces for interacting with the addict, under the assumption that having good preventative actions is only part of the battle-such actions must be presented in a manner acceptable/receptive by the addict. Very often this is dependent on the context of the addict; for example, at night an addict may be most receptive to audio-based messages, while in the day he or she may be most receptive to visual-based actions. In public places the addict may not want either, but instead be physically pulsed/shocked/vibrated/or heated to remind them they are increasing their risk of relapse for example (one addiction reality is that many relapses are not deliberate, meaning they are a culmination of smaller, even innocent-seeming behaviors that rapidly culminate in a relapse situation before the addict was even aware they were in danger. Small shocks or other physical cues can help wake up the addict early in the process and stop the danger before it starts to build out-of-control).

The device 200 in FIG. 2 has a variety of capabilities to be self-sufficient and help monitor/manage/control the addict. The device 200 has a Locator Unit 202 that has or interfaces to a variety of location determination technologies (e.g., GPS, Wi-Fi, CID, Beacon, TDOA, etc.). The device 200 has at least one CPU 203 and associated memory, storage, and calculating circuitry, hardware and software, to do data collection, analysis, and decision making. The device 200 has specialty processing and display/interfacing capabilities for managing such capabilities as virtual reality, (de)augmentation, holograms 204a, device effects controller 204b, and robotics 204c. The device 200 has a mechanism 210 for detecting and interfacing with other nearby devices to extend its sensor/data collection capabilities (for example, tapping into a nearby security camera to see the addict's surrounding environment). The device 200 has an onboard medical controller 207 that can interface/integrate with attached and/or embedded devices or physical wraps, wearables, implants, and/or drug dispensers, in order to—if needed—suddenly inject or offer for immediate consumption an addiction treatment drug. The device 200 has a User Interface detector 208 that can tie into nearby systems if such systems are deemed advantageous for delivering a message (for example, broadcasting the message over a car's stereo system while it is playing a song (e.g. interrupting the song), instead of ineffectually playing on the addict's phone). The device 200 has a digital assistant and/or interface to a digital assistant for managing the addict's day-to-day, hour-to-hour schedule. The device has a self-contained module for storing and managing the addict's triggers (particularly useful if the addict is cut off from the broader system). The device has an onboard manager for all the myriad of sensors and tags on or nearby the addict so such data can be analyzed locally. Similarly, the device has a beacon interface/manager 209c to transmit/receive information from local beacons. More broadly, the device 200 has the capability of determining context locally, particularly in its ability 210 to tie into local networking connections such as Wi-Fi, RFID, RTLS, Bluetooth, peer-to-peer, Internet of Things, mesh/ZigBee, security systems, and other local-oriented networks. As shown in FIG. 2, the device 200 may be configured for connection and communication with companion technologies, such as imbedded/inserted/attached addict data/tag/devices 260, support network devices and/or applications 270, nearby cameras, video streaming, beacons, sensors, context data sources 280 (e.g., cars, buildings, people, specialty information broadcasts, etch, sensor arrays 290, Internet of Things (IoT) sensors, devices, and/or networks 295 (also shown in FIG. 2b), etc.

Other capabilities include an SOS button 211 or similar mechanism that the addict can push/activate when he or she is feeling particularly vulnerable to relapse, which will in turn activate other portions, aspects or features disclosed herein. The device 200 also includes mechanisms for causing various levels of physical pain or discomfort (called a reinforcer 206) and/or pleasure, such as a sharp stinging sensation or warm/caressing sensation, that can be used to reinforce or dissuade certain behaviors, with the intention of preventing such behaviors and/or associating addiction-related behaviors or contexts with the pain or discomfort. The device also has a variety of identity verification/privacy protection mechanisms for protecting and if need be disabling the device and preventing anyone from accessing the data on the device. There are also user-controllable/definable capabilities on the device, either programmable or insertable such as SIM-like add-on sensors.

The above does assume an all-in-one device for such capabilities. Such capabilities could be spread across multiple devices on and/or near the addict. Example of these device extensions are specialized addiction-related wearable and implantable devices that focus extensively or exclusively on detecting and reporting certain addiction-related conditions, not unlike today's Fitbit, such as bracelets that do double duty as a fashion accessory and blood pressure and skin temperature monitor. These readings could be prompted by and/or received by the Addict Monitor/Controller (AMC) shown in FIG. 2, or the extended device could do self-contained monitoring of those conditions and alert the AMC when they reach an concerning level. Smartphones with embedded alcohol detection sensors is another example. These addiction-specialty devices could continually monitor addiction-related conditions which could then send alerts and data (including location data) to the addiction server when conditions warrant. Such device extensions could include permanent devices not unlike today's parolee GPS monitoring ankle bracelets. A similar form could allow such actions as court-ordered alcohol use monitoring for DUI (Driving Under the Influence) offenders, or even voluntary usage by persons committed to beating their addiction but needing extra external discipline to achieve it.

In fact, the use in Parolee Tracking and Monitoring Systems is an exemplary embodiment of the present disclosure in at least two respects. The first addresses the limitation that current GPS-based ankle bracelets have in tracking and monitoring parolees and other prisoners, and that is its limited effectiveness inside a building. GPS does not work well inside buildings or in other contexts where there are obstructions between the bracelet and the GPS satellites, such as trees or metal containers, etc. Exemplary embodiments may utilize a variety of location-determination technologies and methods to monitor the location of the parolee. It then goes further to monitor the behavior of the parolee.

Of course, the devices and associated sensors and capabilities are only effective if they are actually powered on. It is an unfortunate fact of addiction life that many don't want to become sober, or at least feel they can be so without any outside help. In any event, it is assumed there will be the temptation to tamper with/otherwise disable such monitoring devices, and includes the ability to determine which addict-related devices are active (powered on and in the proximity of the addict) and which are the primary one(s) in use at an given place and time, via monitoring of usage as well as determining which device(s) are in the best position/proximity to monitor the addict's behavior, risks, and actions. This is important as well in general context determination, as people are trending towards having multiple devices, only some of which are actively on or near the person at any given time. In particular, it may be important to determine the primary device when determining what the best interface is for communicating with an addict at any given time.

The above capabilities can be packaged in a variety of form factors, ranging from being worn on the wrist or neck to glasses form to even implants. Form factors include but are not limited to: wrist/ankle devices, wearables, implantables (devices implanted/embedded in the skin/body), clothes, accessories, wallet, Google glasses. Snap spectacles, heads up display, augmented reality displays, inserts (e.g. ear), FOBs, key chains, are some of the form factors, Siri personal assistants (Built-In, Included, Add-on), smartphones, tablets, laptops, personal digital assistants, etc. The capabilities shown in FIG. 2 do not have to all be in one device, but can be spread across many different devices-even ones with no physical contact with the addict (such as security cameras, local RTLS beacons, etc.).

Figure 2A:
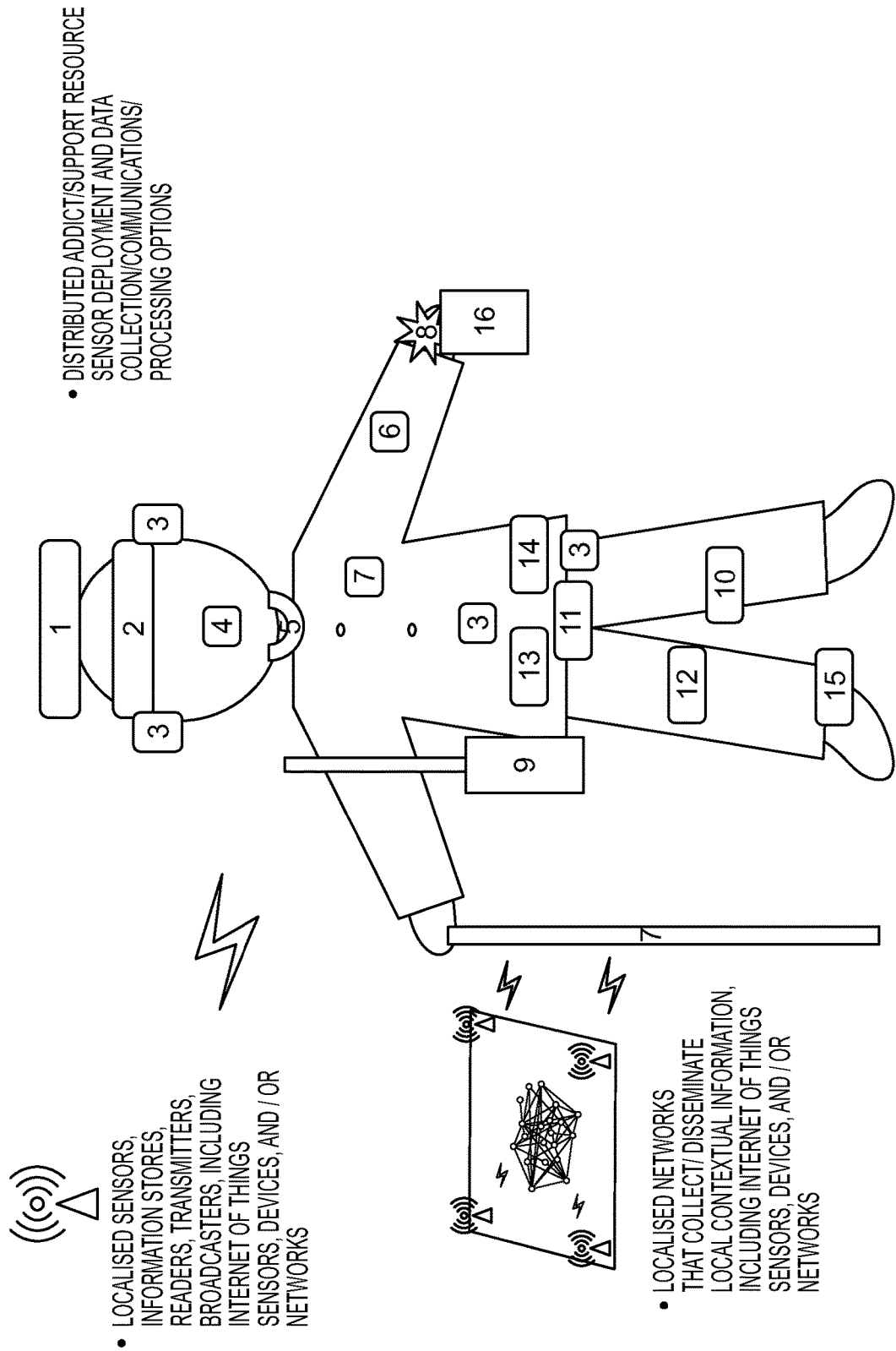

FIG. 2a provides examples of distributed sensor deployment, data collection options, localized sensors, and localized networks that may be used in exemplary embodiments. Form factor/sensor placement 1 may include a hat or headband. Form factor/sensor placement 2 may include glasses or a visor. Form factor/sensor placement 3 may include earplugs, earpieces, earrings, etc. Form factor/sensor placement 4 may include implants/inserts (e.g., teeth crown, pacemaker, ID chip, medicine deployment, etc.). Form factor/sensor placement 5 may include a necklace, piercings, nose rings, tattoos, etc. Form factor/sensor placement 6 may include a shirt, blouse, jacket, coat, etc. Form factor/sensor placement 7 may include accessories (e.g., pens, pocket protector, umbrella, cane, tools, touchpoints such as buttons and light switches, etc.). Form factor/sensor placement 8 may include a ring, bracelet, jewelry, etc. Form factor/sensor placement 9 may include a purse, briefcase, etc. Form factor/sensor placement 10 may include one or more sewn-in sensors, etc. Form factor/sensor placement 11 may include a zipper, belt, buttons, etc. Form factor/sensor placement 12 may include pants, a skirt, etc. Form factor/sensor placement 13 may include underwear (e.g., a bra, etc.). Form factor/sensor placement 4 may include a wallet including payment methods, etc. Form factor/sensor placement 15 may include shoes (e.g., a heel of a shoe, etc.). Form factor/sensor placement 16 may include a smartphone, tablet, laptop, PDA, FOB, key chains, etc. Included in the form factor/sensor placement may be the deployment/use of Artificial Intelligence (AI) assistants/Digital Personal Assistants such as Apple Siri, Amazon Alexa, etc. Sensors may be included/attached in such assistants. Conversely, AI assistance functionality may be embedded/attached to a variety of sensors and/or sensor form factors.

Also shown in FIG. 2a are localized Sensors, information stores, readers, transmitters, broadcasters (e.g., individual rooms, nearby persons, environmental sensors, etch, Internet of Things (IoT) sensors, devices, and/or networks. FIG. 2a further shows localized networks that may collect/disseminate local contextual information (e.g., multiple rooms, malls, campuses, stores, schools, office buildings, etch, Internet of Things (IoT) sensors, devices, and/or networks.

Figure 2B:
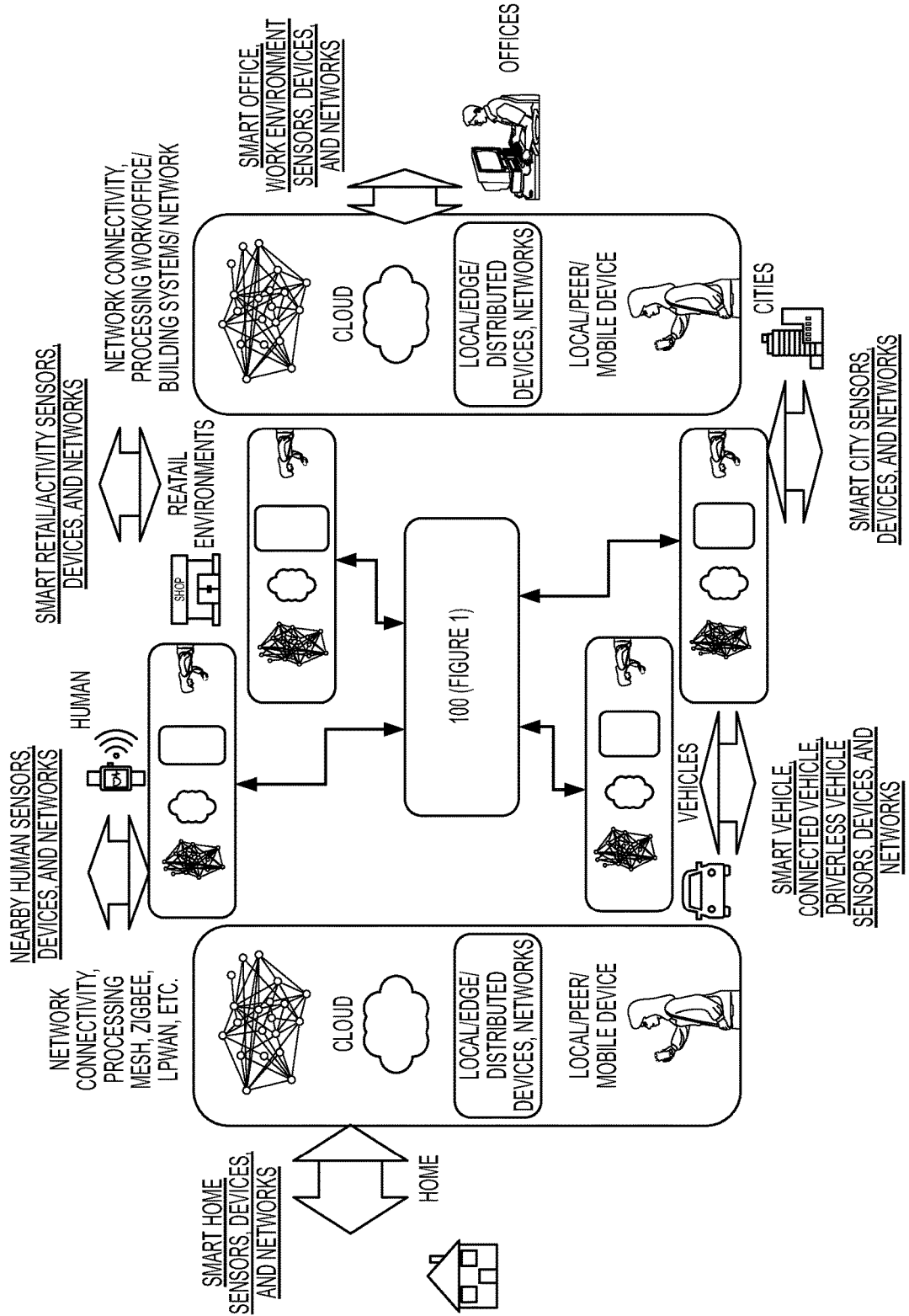

FIG. 2b provides examples of internet of things (IoT) addict-related sensors, devices, and networks 295 that may be used in exemplary embodiments. As shown, the IoT addict-related sensors, devices, and networks 295 may include smart home sensors, devices, and networks, such as home controllers, window/door, garage doors, HVAC, lighting, kitchen, security systems, appliances, computers and media, furniture, furnishings, media, landscaping, TV, decorations, rooms, pets, traps, fireplaces, etc.

The IoT addict-related sensors, devices, and networks 295 may include smart vehicle, connected vehicle, driverless vehicle sensors, devices, and networks, such as cars, trucks, aircraft, trains, boats, RVs/rec vehicles, etc. addict/support resources are using, in, within, or near—sensors, devices, and networks that provide location/context usage of such vehicles and directly or by inference usage and mindset of addict and/or support resources and activities to help detect, anticipate, prevent or mitigate high relapse risk situations, such as deactivating manual driving capabilities and activating driverless capabilities (e.g. for drunk drivers, etc.).

The IoT addict-related sensors, devices, and networks 295 may include nearby human sensors, devices, and networks, such as nearby (to the addict and/or support resource) person(s), devices, networks and sensors—including proximity and/or access to person(s) et al. and contextual data on, in or near that person as well as groups of persons and activities to help detect, anticipate, prevent or mitigate high relapse risk situations.

The IoT addict-related sensors, devices, and networks 295 may include smart retail/activity sensors, devices, and networks, such as restaurants, stores, banks/ATMs, arenas, gas stations, gym, parking, amusement, hospital, gym, etc.—places persons (addict and/or support resources) might shop or otherwise spend time in, including indicators of items being considered, purchased, and/or used (e.g. liquor, etch and activities to help detect, anticipate, prevent or mitigate high relapse risk situations.

The IoT addict-related sensors, devices, and networks 295 may include smart office, work environment sensors, devices, and networks, such as temperature, entry/exit, security, work-activity related, stress (mental or physical)-related, productivity-related, co-worker, office/work area-related (e.g., conference room lighting, temp, A/C & Heating, Vending, Smoking machines, energy savings, bathroom, security cameras, lights, etc.).

The IoT addict-related sensors, devices, and networks 295 may include smart city sensors, devices, and networks, such as public spaces and infrastructure with associated sensors, devices, and/or networks (e.g., that addict/support resources, etch including parking, meters, advertising, police, first responders, etch that are in proximity of, connected to, and/or associated with that provide location/contextual information about addict, support resources, and activities to help detect, anticipate, prevent or mitigate high relapse risk situations.

Some exemplary embodiments of the present disclosure may include or involve the collection of large volumes of addict-related data, which is to be handled in terms of volume of data as well as the protection and security of that data and in particular the identity of the addict. The security and privacy of this data is protected in various embodiments, as the potential for abuse is huge given that in some instances an addict's location and context may be tracked nearly 24/7 at times. In addition, the social and professional stigma of addiction remains huge in our society, and many-even most-addicts greatly prefer their affliction remain private. Accordingly, a variety of systems and methods are provided for addressing such considerations, including but not limited to limiting the length of time data is stored, physically distributing the data among different databases including having location/super localized, context-specific, and/or trigger-specific data stores, invitation-only data access methods, time-limited networking, and encrypting and/or anonymizing such data so it is very difficult if not impossible to link addiction-related data to a specific addict identity. Such protections may include unusual protection mechanisms such as location selective availability coding (deliberately introducing errors into location calculations) or "nuclear football" keys where the codes for unlocking/decrypting data change daily and/or under physical protection (e.g. not stored where it can be hacked online).

Figure 3:
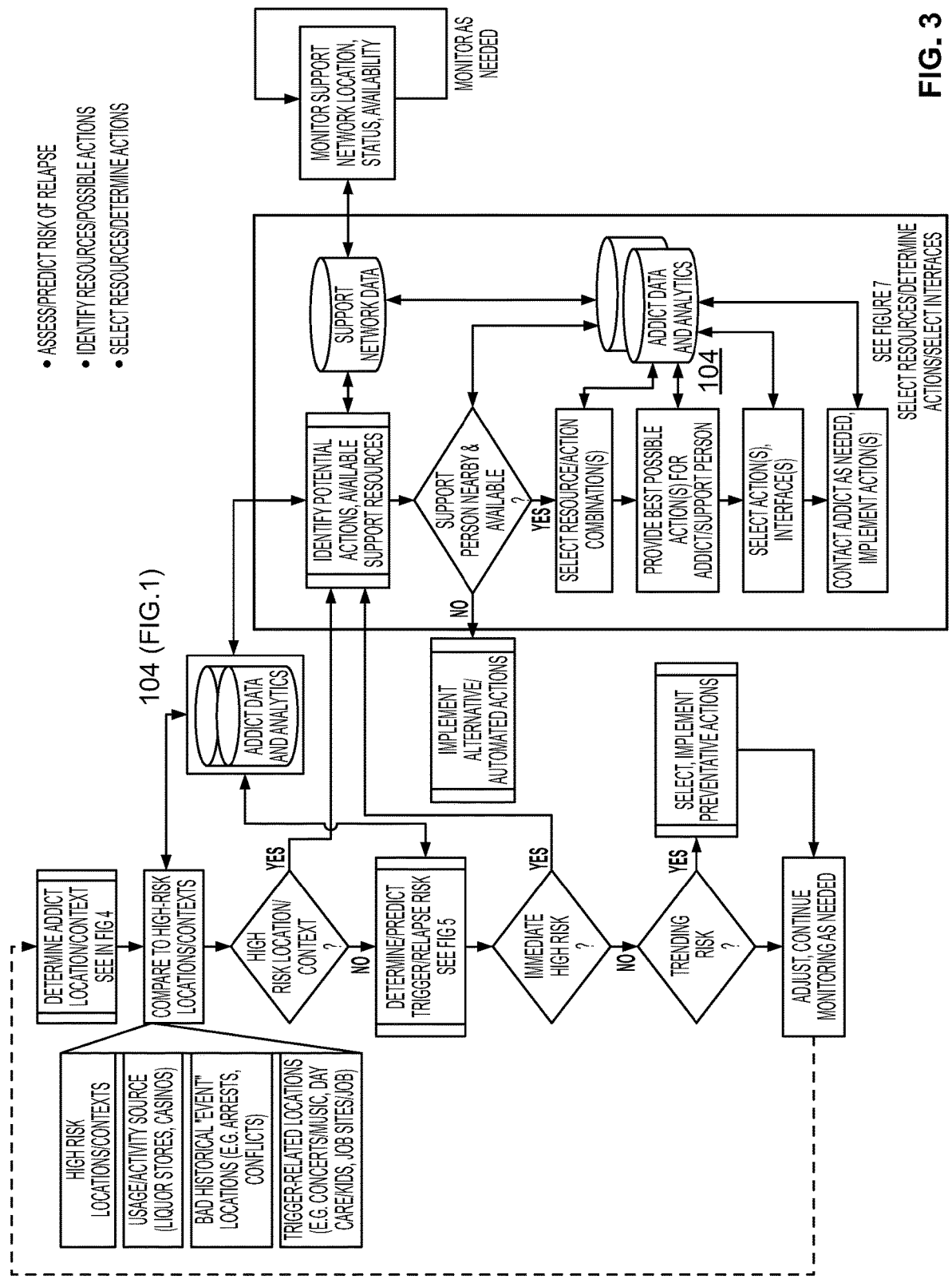

In various embodiments, a learning engine is provided that utilizes artificial intelligence and other learning algorithms and methods to learn from an addict's behavior and to refine various systems, algorithms, and processes, such as an addict's likelihood of relapse, effectiveness of actions taken, and types and frequency of data collected. FIG. 3 depicts an example process for assessing an addict's risk of relapse and determining potential actions and support resources, with FIG. 5 providing more detail on how such an assessment could occur, and how the assessment algorithm may be modified as more data points about the addict's behavior become available.

By way of an example relating to an addict's Anger trigger, an initial approach to detecting an Anger condition may initially be based solely on blood pressure (e.g. a spike in blood pressure is indicative of anger). However, learning mechanisms disclosed herein may find that for a particular addict the correlation between a spike in blood pressure and an anger condition is low. Instead, the mechanism may determine that the addict's anger is immediately preceded in a rapid rise in skin temperature, and is exacerbated when loud noises (e.g. yelling, etch is in the immediate vicinity. Thus, the addict's anger-related sensor readings will change from monitoring blood pressure to monitoring skin temperature and noise levels.

Indeed, various embodiments provide leveraging of numerous data sets about, related-to, or of potential value to the addict, and the use of data analytics, algorithms, and analysis engines to aggregate, compile, assess, analyze, synthesize, and otherwise bring together disparate pieces of information (many location-related) that can be used in the addict's treatment. Data/data sets can include but are not limited to information regarding the addict's medical history, personal profile (e.g., friends, hobbies, etch, schedule/calendar information, historical data (often location-based) that describes past actions and behaviors, key enablers (people/places/things that can aggravate the addiction), key usage triggers, and sources of addiction (e.g. liquor stores, drug dealers)/Points of Interest (e.g. bars, casinos) that the addict has been known to frequent and/or has demonstrated vulnerability to in the past. Such information could be obtained in many ways, including but not limited to directly from: the addict (e.g. questionnaires, etch, the addict's support network, friends and family, medical data, historical behavioral data, public records, news media, social media, school records, etc. The communications links used to obtain this information can include, but are not limited to, the Internet, wireless and wireline networks, cloud sources, crowd sources, peer-to-peer networking, sensor networks, machine-to-machine networking, smart homes/neighborhoods, and electrical-grid based networks.

Such data sets and other information may be analyzed on multiple levels using analytics that include but are not limited to a Usage Trigger, Potential Response Analyzer, Risk Prediction Algorithms, and an Action/Coordination Engine (many of these concepts are illustrated in FIG. 1 in the Addict Data and Analytics, and used implicitly or explicitly in many of the Figures). The Usage Trigger and Potential Response Analyzer takes as inputs the addict's usage triggers (defined by techniques such as questionnaires or psycho-therapy), and the addict's personal profile and schedule/calendar, as well as historical information about the addict's movements, actions, behaviors, and hobbies, to develop a risk assessment and prediction algorithms about the addict's vulnerabilities to future potential addiction-related situations and develop a series of potential responses. Risk Prediction Algorithms utilize information about the addict's current situation/location/context, addiction triggers, and historical behavioral data to develop a risk score, rating, or level (score) for the addict. If the risk assessment score reaches or exceeds a threshold, and/or falls within a certain range, the Action Coordination Engine will develop an action or course of action that will then be launched, such as contacting members of the addict's support network, rearranging the addict's navigation (away from high risk locations), or disabling the addict's vehicle and arranging for alternative transportation, as a few examples.

In various embodiments, an action/coordinating engine (based on the Addiction Server, one or more of the Addict's devices, via a cloud, or some combination) is provided to coordinate various actions on behalf of or in the interest of the addict. This action/coordination engine (action engine), the use of which is illustrated in several drawings in particular FIGS. 6, 6A, 7, and 7A), is responsible for identifying, determining, and/or managing a variety of actions that the addict, the addict's support network, or others can take on behalf of the addict, usually in response the detection of a relapse risk or actual relapse situation. Such actions could be automatic in nature, such as the engine directing the addict to move to a sanctuary location for example, such as a nearby AA meeting getting ready to start, in response to a high risk alert generated in various embodiments. An action could be more of a coordination function, such as coordinating a meeting between the addict and a nearby addict sport person at a nearby meeting in an hour, action could include interfacing with the meeting place (e.g. restaurant) reservation system, as well as identifying nearby available parking, and providing instructions to the addict's and the support person's cars to activate the self-parking application once in range. This is an example of communicating/coordinating with a variety of third-party applications and services that will make the action(s) go as smoothly and hassle/aggravation-free as possible, as a key to resolving high-relapse risk situation without relapse is often to the addict in as a tranquil, trouble-free mindset as possible.

Other actions include obtaining alternative transportation for the addict, modifying navigation applications to avoid areas where addictions can be enabled (such as liquor stores for an alcoholic), and/or posting on social media that the addict is in a high risk situation. Note not all actions may be reactive, or reactive only to only high-risk or in-progress relapse situations. The action engine may manage the selection and communications of daily morning motivation messages to the addict, or perform an alert reminder function to one of the addict's support persons reminding him do to his weekly Friday call to the addict.

An often underappreciated and overlooked aspect of successful addiction treatment is the use of rewards mechanisms associated with good or desirable behavior. While addiction outsiders often take the attitude that avoiding the destructive aspects of addiction should be motivation enough for an addict to get and stay sober, the reality is that for many addicts that is not enough. Indeed, the destructive aspects of addiction get progressively less of concern to many addicts the longer they are addicted. However, the prospect of a reward for good behavior (not relapsing) can have a very stimulating/powerful effect on some addicts—thus, various embodiments provide a method and apparatus for detecting/determining good behavior and rewarding such behavior. For example, as shown in FIG. 9, a rewards mechanism is provided under the presumption that many addicts' need a positive-enforcement mechanism as a deterrent to relapse. For example, engaging in good behavior such as avoiding trigger aggravating locations and contexts earns points, as does attending (in person or virtually) addiction community meetings. The points accumulate, and can periodically be redeemed for (usually) addiction-related goods and services, such as passes to (non-alcohol serving) movie theaters or deep discount coupons for safe hobbies such as gym memberships or sewing supplies. In contrast, risky behaviors such as visiting with bad friends (friends that very actively drink for example) could results in points being deducted.

More broadly, various embodiments include rewards for behavior that inhibits or prevents addiction usage/relapse (e.g. good behavior), and/or behavior that specifically avoids relapse or the possibility of relapse (e.g. bad behavior). While ideally the addict will be self-motivating in his/her desire to get sober, the reality is that many if not most addicts need some sort of external motivation and reinforcement—both positive and negative—to get and particularly stay sober. Thus, a sobriety rewards program can be an integral part of various embodiments. For example, the addict may accrue reward points when he or she spends time in a new (good) hobby, or exercises for at least 30 minutes a day. Similarly, points may be earned if the addict does not go near vulnerable locations such as high drug areas, bad Mends, or liquor stores for at least 30 days. An example embodiment would detect and track these good behaviors through functionality disclosed herein and/or data obtained from interfacing with other applications and devices used by the addict or his/her support network. Rewards could be in many forms, such as points redeemable for goods and services, discounts on using an embodiment of the present disclosure or related applications, free tickets to an event (presumably but not necessarily safe events), or even direct cash credits to their bank account or mobile pay account. Note a further feature of the present disclosure may be to detect/prevent the use of any financial transaction for the purchase of substances negatively related to the addict's addiction. Thus purchases from liquor stores would be detected and rejected via interfaces with the addict's financial accounts and transaction enablers, e.g. credit/debit cards, mobile pay and bank accounts, etc. Similarly credits could be posted to these accounts. Credits could be selectively posted for good behaviors, such as paying for new hobbies, free Uber rides, etc. Similarly, bad (or not good) behavior could result in points/financial deductions from the addict. In one example embodiment, a reward engine would determine the applicability and value of such behaviors, track such additions/deductions, and coordinate with addict-related third party accounts.

Not all motivation-enhancers will be rewards-oriented; some need to be encouragement-oriented. This would include words-of-encouragement, testimonials, thoughts-for-the-day, and other types of motivation or self-esteem building messages. Thus, various embodiments provide ways of detecting when such messages would be particularly timely, selecting appropriate messages, and delivering them to the addict at the appropriate time, context, and using the best method for encouraging the addict to get on/stay on the path to sobriety. For example, an embodiment of the present disclosure may determine that the addict is susceptible to the Time of Day trigger, when he/she particularly desires drinking at 5 pm every day. Starting at 4:30, motivational messages and testimonials may be sent every 15 minutes, such as "life is short—make the most of it!" This could be sent using any number of methods, including text, MMS, email, (pre-recorded) phone call, internet/(private) social media, and other methods. The embodiment could also automatically create rotating schedule reminders to (random or previously selected) various members of the addict's support network so that those members could connect real-time with the addict to offer words of encouragement during these vulnerable times-of-day.

Sometimes actions require more than a positive reinforcement-orientation, meaning a more urgent, aggressive approach may be needed. One such scenario could involve the detecting of the addict relapsing while at a bar, and having driven himself there. The addiction server will have monitored the addict's smartphone for example, showing that both it and the addict's car have been following the same path and has stopped at a local bar. Sensors on the addict's clothing will have detected the presence of alcohol, and other sensors noting a risk in blood pressure and blood alcohol content. Such data may cause the Risk/Prediction engine to generate a very high alert—addict has been drinking. If no addict support person is in the immediate vicinity to come get the addict, the action engine may elevate the urgency and send signals to the addict's vehicle that disables it (an alternative would be putting it into self-driving mode if such option was available). Concurrent with disabling the call would be requesting an Uber/taxi ride dispatched to the bar, with an alert to the addict that such a ride has been arranged for, with the details showing on the addict's smartphone screen. To make it clear that the addict needs to get into the taxi, the action engine may also inform the addict that one of his support network will be meeting the taxi at his home in 30 minutes, and he is expected to show at that time. Since this meeting would be considered a penalty meeting, the addict will lose points from his sobriety program if he is not punctual.

Numerous communications methods to/from the addict and other resources are used in various embodiments of the present disclosure. These can include (but are not limited to) text/SMS/MMS, voice calls, email, social media, video, peer-to-peer and machine-to-machine communications, instant messaging, voice messaging/mail, 3rd party applications, heads-up-displays (such as Google Glass), hologram projections, and other applicable voice and data methods and mediums. For example, the server may alert via text someone in the addict's support network that the addict is nearby and should be contacted because of a detection of a high-risk situation. The support person may send the addict an MMS with an uplifting message, and also send an invite to the addict via a 3rd party application to meet him at a local restaurant at a certain time. The addict could respond with an instant message thanking the support person, and accept the invitation via the 3rd party app along with a note that the addict will be approximately 15 minutes late. The support acknowledges this via a return text, but hits an option on his device to instruct the addiction server to increase the location monitoring of the addict to detect if he/she takes a relapse-type action (such as stopping at a liquor store). These real-time updates may be transmitted to the support person in the support person's car system display/voice system or augmented reality sunglasses on the way to the restaurant so he/she knows exactly what the addict has been doing since the original alert was issued.

As introduced above, a key element present in many embodiments of the present disclosure is the use of location technology such as mobile devices and associated GPS or other location determination technology to track or monitor the location of the addict. The addict's location can be continually, periodically, occasionally, or on an ad-hoc basis compared to numerous other individuals and/or data sources to provide location-related assistance to the addict in continuing his treatment or in avoiding succumbing to the temptation of his or her addiction.

Another feature or aspect of the present disclosure is the use of unaugmented reality technology. Instead of inserting objects into an addict's environment (such as a Pokémon character), instead an exemplary embodiment includes performing a continuous, real-time or otherwise timely monitoring of the addict's environment, detecting threatening objects such as advertisements for alcohol, and blanking out or otherwise hiding or obstructing the addict's ability to perceive such threatening objects. This could range from removing such objects from a navigation screen (such as liquor stores) to actual blanking or replacing said object within a Google Glass or Snapchat Spectacles or other Virtual Reality interface.

Another feature or aspect of the present disclosure is the development and use of risk scores of relapse or other adverse treatment situation. Such scores could be in the form of a number (like credit scores), a high/medium/low designation, color schemes (e.g. Red, Yellow, Green, etch, and other scoring and/or range classifications (scores). Such risk scores could be for a variety of risk types: general risks, situation-specific, location-related, and/or date/time or date/time-range specific risks, among others. An embodiment would develop these risk assessments/scores using data/data sets but not limited to the addict's medical history, personal profile (friends, hobbies, etch, schedule/calendar information, historical behavior data (often location-based) that describes past actions and behaviors, key enablers (people/places/things that can aggravate the addiction), key usage triggers as described above, and sources of addiction (e.g. liquor stores, drug dealers)/Points of Interest (e.g. bars, casinos) that the addict has been known to frequent and/or has demonstrated vulnerability to in the past.

Such scores would be developed/calculated continuously, periodically, ad-hoc, or on-demand, as well as when certain individual conditions are detected by various devices and/or combination of conditions, as well as device-independent conditions. An example of a device-independent condition would if it were detected by external data sources that the addict was facing a heavy traffic jam on his usual route home at the usual time. Knowing from his trigger profile that this situation could activate the Anger trigger (e.g. road rage), the Risk Assessment Engine would calculate a high risk score. This score, in turn, may be used in various other aspects of the present disclosure.

Taken together, various implementations of the present disclosure could monitor the location of people in an addict's support network—such as social workers or their sponsor in an addiction treatment program—to have them alerted and ready to stand by to assist the addict if the addict appears to be heading into a difficult situation, such as physically meeting an alcoholic if they appear to be in danger of entering a bar. To detect this kind of scenario, the addict's location may be compared to other data sources of potentially dangerous locations such as bars or liquor stores (for alcohol addiction), known drug-trafficking areas (for drug addiction), casinos (gambling addiction), shopping malls (shopping addiction), and so on. If it appears that the addict is possibly going to enter a dangerous situation or area, the nearest person (to either the addict or the place in question) in their support network can be alerted to intervene.

In various exemplary embodiments, integration and coordination are provided with the addict's medical and psychological status and prognosis. Medical and psychologist/psychiatrists can embrace various embodiments as providing ways to monitor real-time the progress of their addiction patients, as well as provide near real-time/real-time adjustments to medications. For example, an embodiment, in monitoring addict with an embedded naltrexone dispenser, may start detecting high-risk behavior. The example embodiment could inform the addict's psychiatrist of this behavior, who then may decide that the medicine will need to be increased in dosage. The embodiment would interface to the service/application controlling the embedded naltrexone, e.g., either remote or attached/embedded with the dispenser, increasing the dosage, all potentially in real or near-real time, or as otherwise directed by the addict's medical professionals.

More broadly, this may entail obtaining or otherwise receiving access to an addict's treatment records, providing updates to those records, and interacting with rehabilitation, therapy, and/or medical providers. It may also entail acquiring access to pharmaceutical/drug treatment prescription information, and being able to administer through the addict's controller device real-time modifications to drugs administered through the controller.

Such an embodiment could also be used by rehab professionals, in monitoring compliance of addicts under active treatment, during those periods where the addict is in a halfway house or similar situation, where the addict is no longer being closely monitored by rehab personnel but it is desired to see if the addict can manage by oneself in a somewhat controlled situation. The example embodiment may monitor the addicts attached/embedded devices as well as other behavior to detect out-of-desired norm conditions or positive ("good") behavior which will then provide additional data towards release of the addict from treatment.

Some exemplary embodiments of the present disclosure include the use of crowd sourcing in generating and disseminating addiction-coping ideas and actions. For example, in FIG. 10 an addict enters a room where an "open" beacon is placed as part of a real-time location services (RTLS) network. In addition to providing location help, the beacon also serves as a repository for addiction-related ideas only for those people who are "tuned" to that beacon, such as a special ID and/or application that enables a one or two-way communication between the addict and the beacon. This could be, for example, only for alcoholics, only for addicts with the Anxiety trigger, and only accessible if the addict is in physical communications range with the beacon. The addict could download ideas for dealing with Anxiety for example, including specific ideas relevant for that specific location. Alternatively, the addict could upload uplifting messages such as praising the locale for its calming environment. It could even be used to identify and connect addicts with similar triggers that are in range of the beacon at that time, thus allowing ad hoc, spontaneous, unscheduled, or flash interactions not otherwise possible or likely. In effect, this would enable very specialized, private ad-hoc meetings or linkups between two or more addicts suffering from similar issues, in a safe, public yet private, anonymized environment As noted before, helping the addict avoid relapse into their addiction is not necessarily voluntary. Several of the embodiments of the present disclosure are predicated on providing help to the addict without their advanced knowledge and/or permission. In various embodiments, no assumptions are made regarding the legality of such assistance, but it is presumed that the embodiment includes acquiring permissions from/for the addict, either directly or via parental/court-ordered ones on behalf of the addict.

One example embodiment of an involuntary use is tracking of the mobile device(s) of an alcohol-related court offender. An extension of GPS device tracking for parolees, the embodiment could continually track the movements of a court-ordered person who is required to attend AA meetings and/or stay away from any alcohol establishments. The embodiment would correlate the person's movements and report back to the court or parole officer to confirm adherence to the court order, or alternatively provide proof of violation of the order. In extreme cases, an embodiment could be configured to report directly to the local police any situation where addict impairment is detected, along with necessary information to apprehend the addict, e.g. location of the addict/vehicle.

Various embodiments provide insertion, to the extent possible and appropriate, of inspirations, testimonials, motivational messages, and other positive (or deterring) information into an addict's daily life. What messages/information this would include would depend on the addict's location and/or context, in order to maximize their appropriateness and effect. A common theme throughout many of the embodiments is the use of these kinds of messages. The "delivery" of such can come in many forms-again geared to maximizing the ability for the addict to pay attention to and assimilate such messages-through the appropriate interfaces as well as third party applications such as social media, twitter. Face book, snapchat, etc.

Various embodiments of the present disclosure provide monitoring of an addict's physical and mental condition through the use of sensors, such as wearable ones of even medical sensors embedded in the addict's body. These sensors can be monitored to detect conditions of particular danger or vulnerability to the addict, such as a spike in blood pressure that could be indicative of the addict becoming angry. If this trigger is detected, a message could be sent to the nearest person in the support network to alert them and have them contact the addict to arrange a calming meeting. Alternatively, if there is no one nearby, an embodiment could then interface with other medical delivery systems attached or embedded in the addict to deliver a tranquilizer or dose of a craving-inhibiting drug or other medical treatment. Similar actions could be taken with implants, prosthetics, or other artificial body/brain parts.

Various embodiments of the present disclosure provide minimizing of the extent of and damage from a relapse of the addiction. This could include the detection (such as via sensors, mobile device, or support network) that the addict has relapsed. This relapse once detected may set off a chain of events such as locking or disabling the addict's personal or work transportation if he/she gets within 100 feet of it; to automatically call a taxi or Uber-type service if the addict is in need of transportation (facilitated by accessing the addict's schedule and relapse contingency management instructions); to alert as appropriate portions of the addict's support network; alert family that the addict has "used" and is under-the-influence (for substance addiction); if appropriate automatically lock-out the addict from certain houses/buildings if the addict comes within a certain range; to alert school officials if the relapsed addict is detected with a certain distance of their children's schools; even to alert law enforcement (and his lawyers) if a breach of a restraining order is imminent.

Indeed, there are many transportation-related embodiments related to the present disclosure. As numerous studies show that a high percentage of violent crimes (and of course other crimes such as drunk-driving) occur under the influence of alcohol or other substances, there would be many scenarios under which transportation would play a key role if impairment of the addict is detected or suspected. These could include involvement of the addict's friends or family (e.g. automatic programing of a driverless car to take the addict to their house), ex-girlfriends/spouses (preventing driving to their location(s), addict's support networks (routing those persons to the addict), even law enforcement (routing law enforcement to the addict's location).

As the above scenarios illustrate, the civil liberties, privacy, and/or security of an addict are considerations to be taken into account in various embodiments. Accordingly, in various embodiments, a privacy engine is provided that determines the conditions under which the addict's location/context can or cannot be disclosed or used. In most situations, the privacy engine may be under the control of and/or entail the acquisition of the approval of the addict. For example, the addict may "pre-approve" an embodiment in which a car is disabled or re-programmed in the event that usage is suspected. Many addicts who admit they have an addiction and are trying to become sober will agree to such conditions. They may recognize that that kind of monitoring and control mechanisms would serve as effective deterrents. In various embodiments, a privacy engine may prevent override of previous deterrence approvals in contexts where the privacy engine detects usage/abuse. But similar to parolee GPS ankle bracelets, the addict may not have control over the privacy engine in some exemplary embodiments. Instead, it may be under the control of a parole officer, medical professional, or other responsible party (for the latter, for example, the addict may sign power of control over to a trusted family member).

In various embodiments, various differing privacy levels and other control mechanisms may be provided through multiple administration/authorization levels. For example, an addict may have one level of access, and an administrator can have a second, higher-level of access to control/override the addict's choices. There may also be additional levels of admin/control such that someone such as parole officer or medical professional may manage multiple addict's profiles with the same user login information. Although the typical control over any one user's privacy may be controlled by only one individual at a time, it is conceivable that multiple persons may have concurrent control, such as a parole officer and a medical professional.

There may also be the opportunity to anonymize people involved in various embodiments. Not only may there be times when an addict desires to be anonymous, even to people within his or her support network, but a support network person may want to be anonymous to the addict. An example of the latter for example may be when there is no one available in the addict's known network to talk to at a vulnerable time—particularly if a relapse is in progress and no one in the addict's known network is available. In one example embodiment, an addict may connect, as a backup, to a general or on-call addiction support person that may provide someone to talk to, or even arrange to meet if they are close together.

In various embodiments, obstacles may be introduced to obtaining the addiction substance or pursuing the addiction activity. One example is in using the information from one or more of the scenarios in combination with the proximity of the addict to transportation sources, such as the addict's car. In situations where the addict has relapsed, various embodiment components may automatically interface with transportation systems within the addict's reach and/or control to disable them or modify them, for example switching on a driverless car feature (and preventing manual driving).

In various embodiments, interfaces are provided that are ways of interacting with the addict. One common and unfortunately generally applicable characterization of addicts is the tendency to be lazy. It is more accurate to say that because of the effects (or after-effects) of their abuse (particularly substance abuse) they have low levels of energy, motivation, and attention span. In various embodiments, interfacing—i.e., receiving input from but particularly providing output to—the addict can be very effective when appropriately provided. Thus, a wide variety of interfaces may be provided, the deployment of which is often context-dependent, and appropriately simple and intuitive for the addict to use, with minimal actions required on part of the addict.

The use of Siri and other types of personal assistants are anticipated and included as possible interfaces. For example, if it the addict is determined to be at high risk of a relapse while home alone, a program could be initiated that talks to the addict to ask the addict what is bothering the addict (if the trigger is Loneliness for example and no human support person is available), or to suggest a call to mom if a trigger response to do so is high on the response list. The use of such interfaces could even be adjusted to use the type of voice (e.g., male, female, English, Australian accent, etch that has been determined to be appropriate in the past. The use of the addict's children's voices could also be used, as a reinforcer or defense to not to drink otherwise the children will be harmed in some way.

The types of interfaces anticipated to be used are wide, varied and utilizing a diversity of technologies. They may range from, e.g. variations of smartphone interfaces (e.g., touchscreen, high quality video/sound, etch to others such as augmented reality, personal robotics, etc. The goal of using such interfaces in all cases is the same: to have a significant effect on the addict, which in turn may be provided by an interface appropriate for that addict in a particular context.

The use of augmented reality and robotics can be beneficial in addiction treatment. With Augmented Reality, particular contexts/situations may be modified to both see things that are not there, but not see things that are there, or see different things (also referred to as de-augmented reality). For example, for alcoholics who see a spike in their desire to drink when they see a liquor store, their Google Glasses or equivalent may be programmed to block out all words and images of alcohol as they drive by. An alternative may be to replace the words and images with something benign, such as words and images about a charity, or even replace them with disgusting words and images along site symbols of alcohol in order to associate such disgusting words and images (such as someone vomiting) with the concept of alcohol.

As discussed before, interfaces with third party applications may be provided in various embodiments. For example, interfaces with social media applications can identify friends who are nearby as candidates for transactional support needs (e.g. serve as support network substitutes if no other resources are nearby). Navigation applications can be modified to exclude the location of liquor stores or casinos. Communicating with support resources via Snapchat, WhatsApp, Twitter, or Facebook can be used depending on the best/most convenient way of interfacing with an addict and/or their support networks. A filter and program can be applied to online grocery applications that may prevent alcohol purchases from being made. This type of prevention may be extended such that if an alcoholic nears a local bar, an interface may be established with the bar's systems that download a Do-No-Serve notice to the bar owner along with facial recognition information.

In various embodiments, a wide variety of interfaces may be provided to interact with the addict, support network, and third parties. Such interfaces include but are not limited to: Direct manipulation interface (e.g. augmented/virtual reality). Graphical user interfaces, Web-based user interfaces Touchscreens, Command line interfaces (e.g., command string input). Touch user interfaces Hardware interfaces (e.g. knobs, buttons) Attentive user interfaces (e.g., that determine when to interrupt a person). Batch interfaces. Conversational interfaces. Conversational interface agents (e.g. animated person, robot, dancing paper clip). Crossing-based interfaces (e.g., crossing boundaries versus pointing). Gesture interfaces (e.g. hand gestures, etch Holographic user interfaces. Intelligent user interfaces (e.g., human to machine and vice versa). Motion tracking interfaces. Multi-screen interfaces. Non-command user interfaces (e.g., infer user attention). Object-oriented user interfaces (e.g., to manipulate simulated objects). Reflexive user interfaces (e.g., achieves system changes). Search interface. Tangible user interfaces (e.g., touch). Task-focused interfaces (e.g., focused on tasks, not files). Text-based user interfaces. Voice user interfaces. Natural-language interfaces. Zero-input (e.g., sensor-based) interfaces Zooming (e.g., varying-levels of scale) user interfaces. Various mechanisms may be provided for selecting/modifying the interfaces based on the user's context. Such mechanisms are part of the User Interface Detector/Selector/Interface (UIDSI) unit in the Addict Monitor/Controller (AMC) 200 shown in FIG. 2.

In various embodiments, robots and robotics may be used. A robot could be used, for example, to serve as an addiction monitor, controller, and/or enforcer. A robot, sensing or being instructed that a high-relapse risk situation is developing, might literally grab the addict by the hand and lead them to a different (safe) destination.

In various embodiments, scheduling and to-do lists of the addict are utilized, as well as the addict's support network. For the support network, integrating with any scheduling program that they use (such as Outlook) can assist in determining their availability (and in some instances location) when an addict risk situation occurs. For the addict, an embodiment may make a dynamic scheduling adjustment and/or add or delete to-do items if in so doing so reduces the risk of relapse for a particular situation. For example, various sensors and other information may indicate that the addict's anxiety levels are rising in the morning. A schedule may have some high probably high anxiety-inducing appointments in the afternoon, for example a meeting with an ex-spouse and their lawyers that afternoon. Various embodiment algorithms may determine that such a meeting is too high risk, and prompt (say via a speech, Siri-like interface) the addict to determine if the meeting should be rescheduled, and do so if the answer is yes (in some embodiments it may even be done automatically).

Consistent with simple and intuitive philosophy of the interfaces, an Addict Monitor/Con trailer (AMC) 200 (FIG. 2) may have a variety of form factors. Such form factors may include, e.g., being part of a mobile phone, tablet, PDA, or laptop: part or fully of Tablet/Laptop/PDA, implants, wearables, wrist devices, or any number of form factors. Note also that while the functionality described for the Addict Monitor/Controller is anticipated to be done on the device, it is not necessary, and could be done on a server, in the cloud, via peer-to-peer, or some other processing mechanism.

The variety and diversity of interfaces and the ability to detect/select them—including specialized interfaces within the Monitor/Con trailer and interfacing to other third party devices via their interfaces—are effective for 1) determining the context, 2) receiving input from the addict in the ways most convenient to the addict, 3) providing information/output to the addict in the ways most receptive to the addict, and/or 4) providing the most effective deterrent(s) to prevent (or inhibit) a relapse from occurring.

For determining context, an addict user interface detector/selector (UIDSI) on the addict monitor/controller (AMC) may utilize sensors on the AMC to detect context-related data. A simple example is using an optical sensor to detect the addict's light environment, helping to indicate if the addict is inside or out, in a lighted environment or dark. Readings (like loud music) from the audio sensor may be used, e.g., to confirm/modify a conclusion (supported by data from the Locator) that the addict has entered a Rave (an impromptu party with large amounts of substances to abuse) and is in a high-risk context.

Various embodiments may include the linking and coordinating of ad-hoc, spontaneous, unscheduled, or flash meetings between two or more addicts—who may or may not know each other—who either are a) generally open to idea of meeting; b) would like to meet a certain time and/or place; and/or c) are concurrent/coincidently sharing similar trigger risk profiles and where a potential solution for a high risk situation is their meeting, preferably in a sanctuary location.

Various embodiments utilize physical locations as part of their risk identification and/or resulting actions/solutions or coordination efforts. However, many if not most of such embodiments may also use virtual locations as part of their description. For example, if an addict is posting on or in a chat room online (in a situation where their physical location is not relevant, determinable, or near anyone else), and making comments indicating a relapse/usage mindset, a risk assessment engine through a social media monitoring module could detect these comments and generate an alert to the addict's support network. In turn, those members of the support network who were also on that social media site at the same time (or could quickly log on to it) could then join the addict at that virtual location to interact live with the addict, to talk about their risk situation and/or active triggers. In this sense, the physical location of the addict and the appropriate support network person is not nearly as relevant as is their presence at/on the same virtual location on the Internet that enables them to interact real-time.

Figure 5:
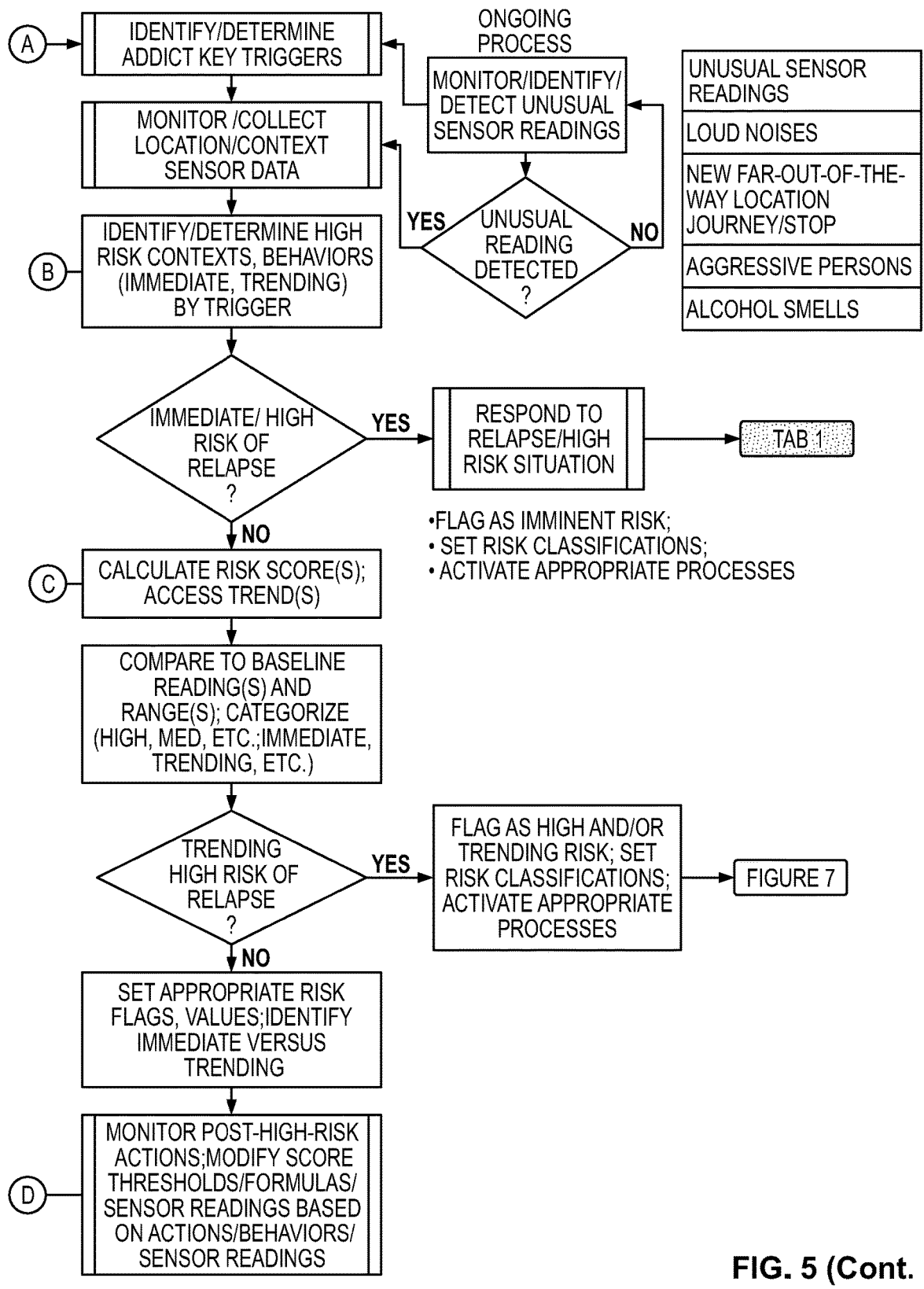
Figure 5A:
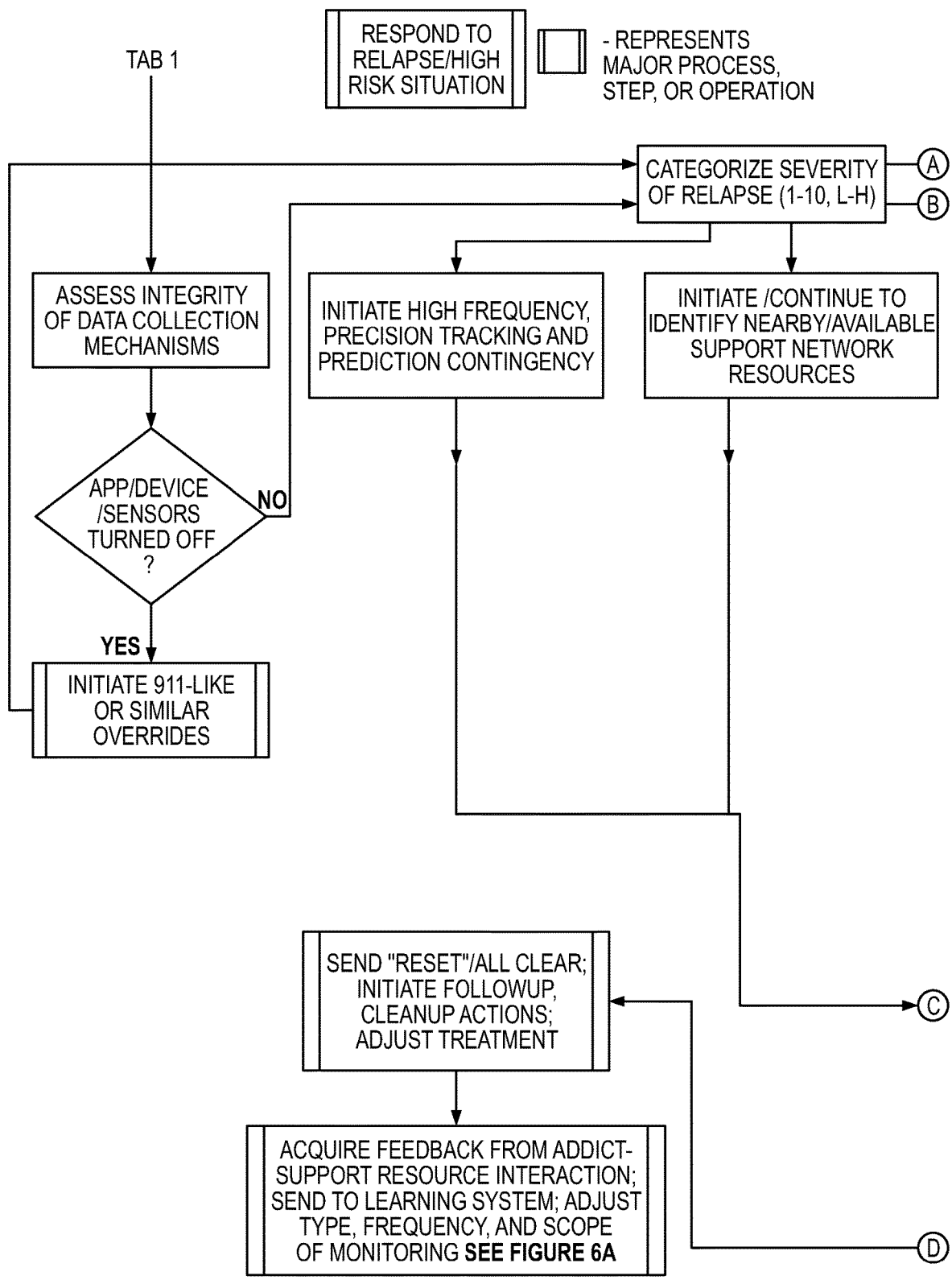
Figure 5A:
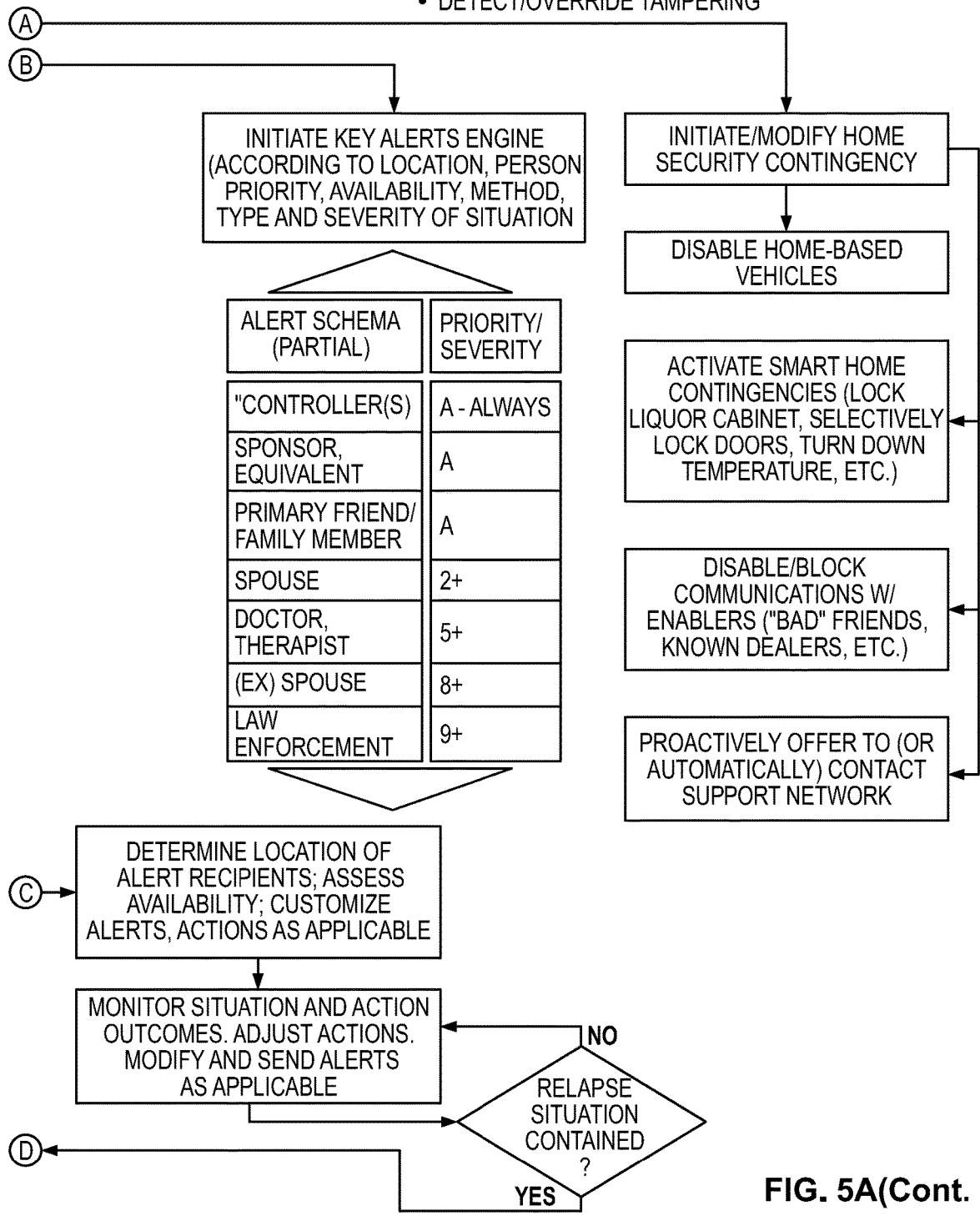
Figure 5B:
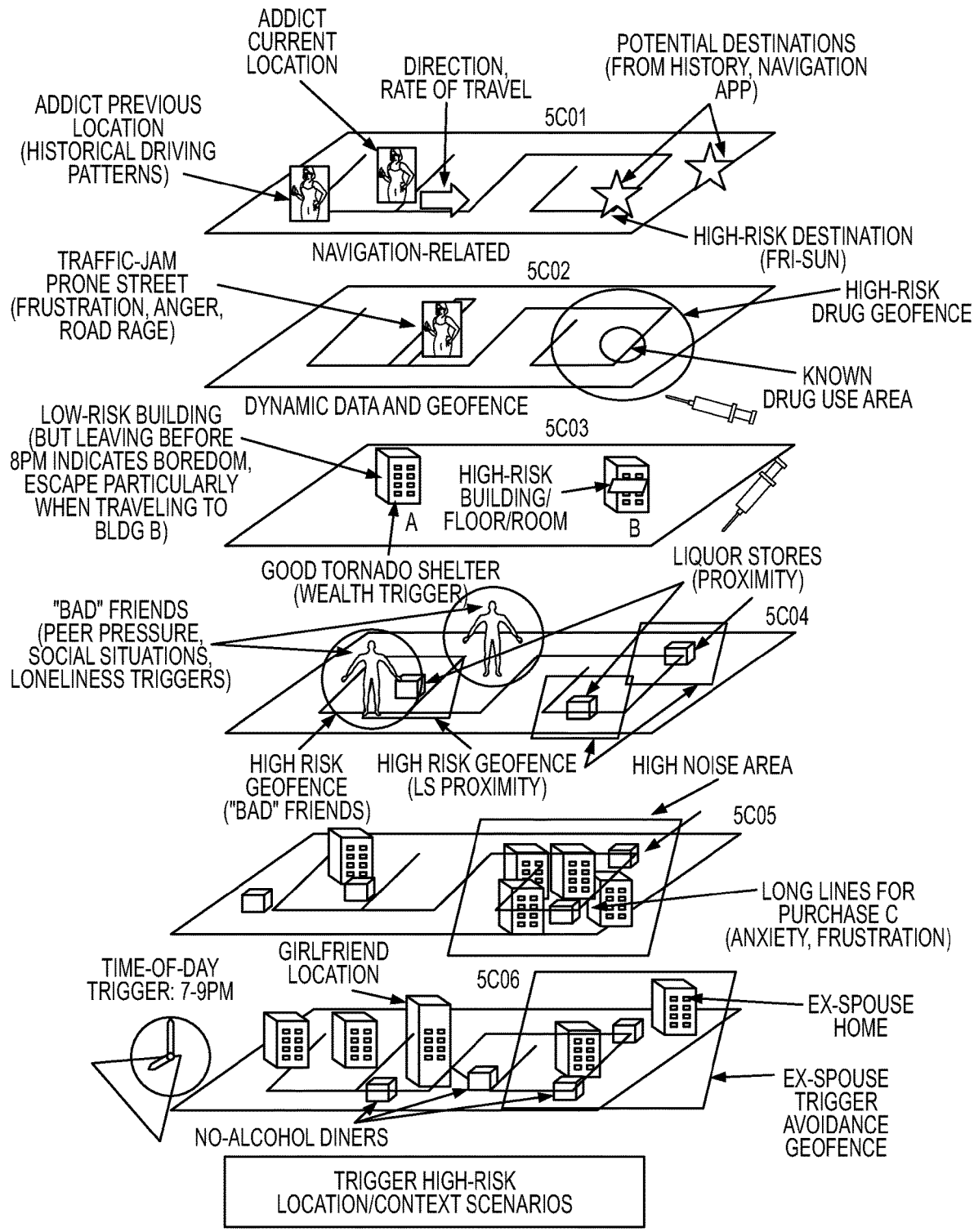
Figure 5B:
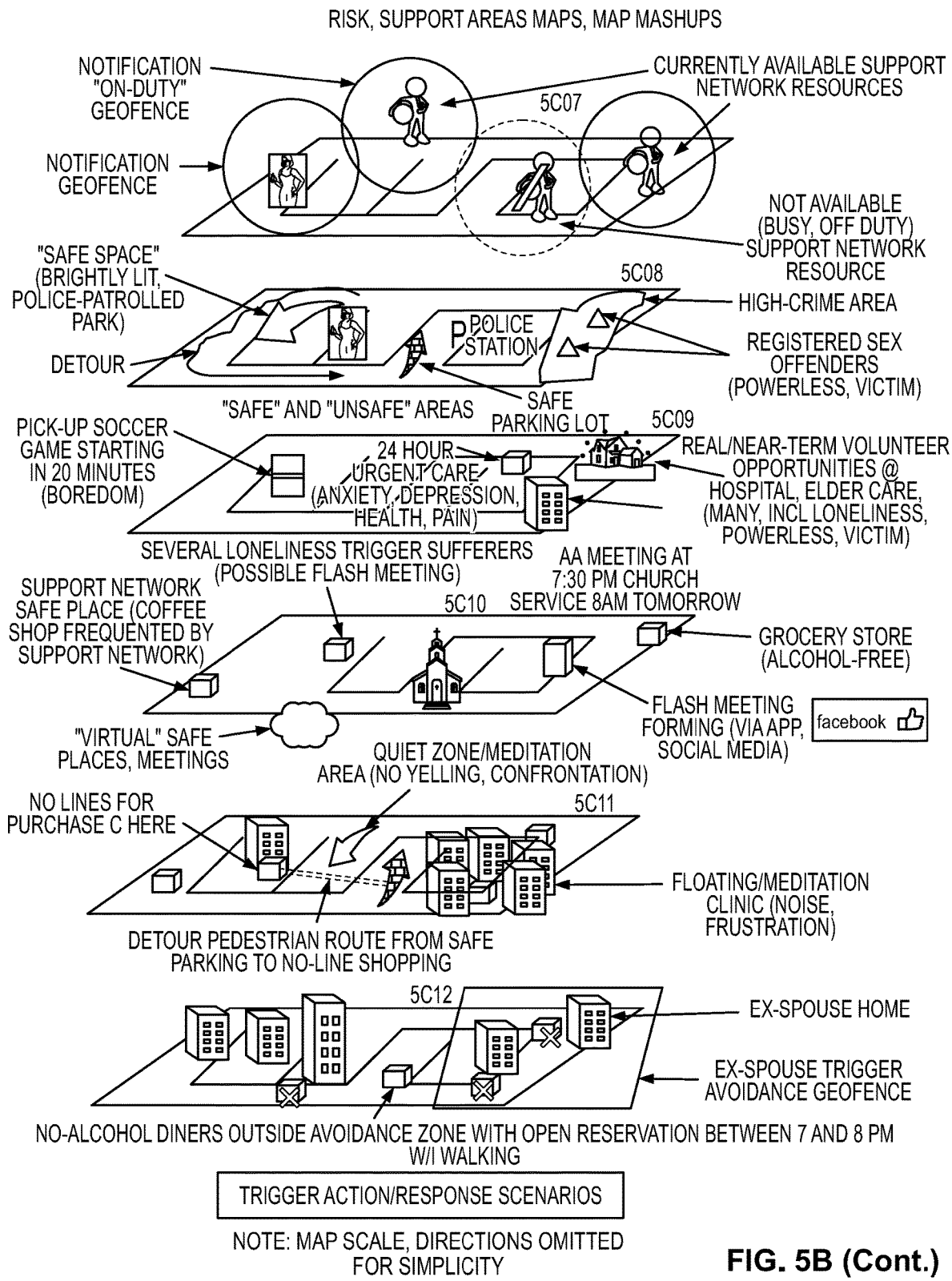
Figure 6:
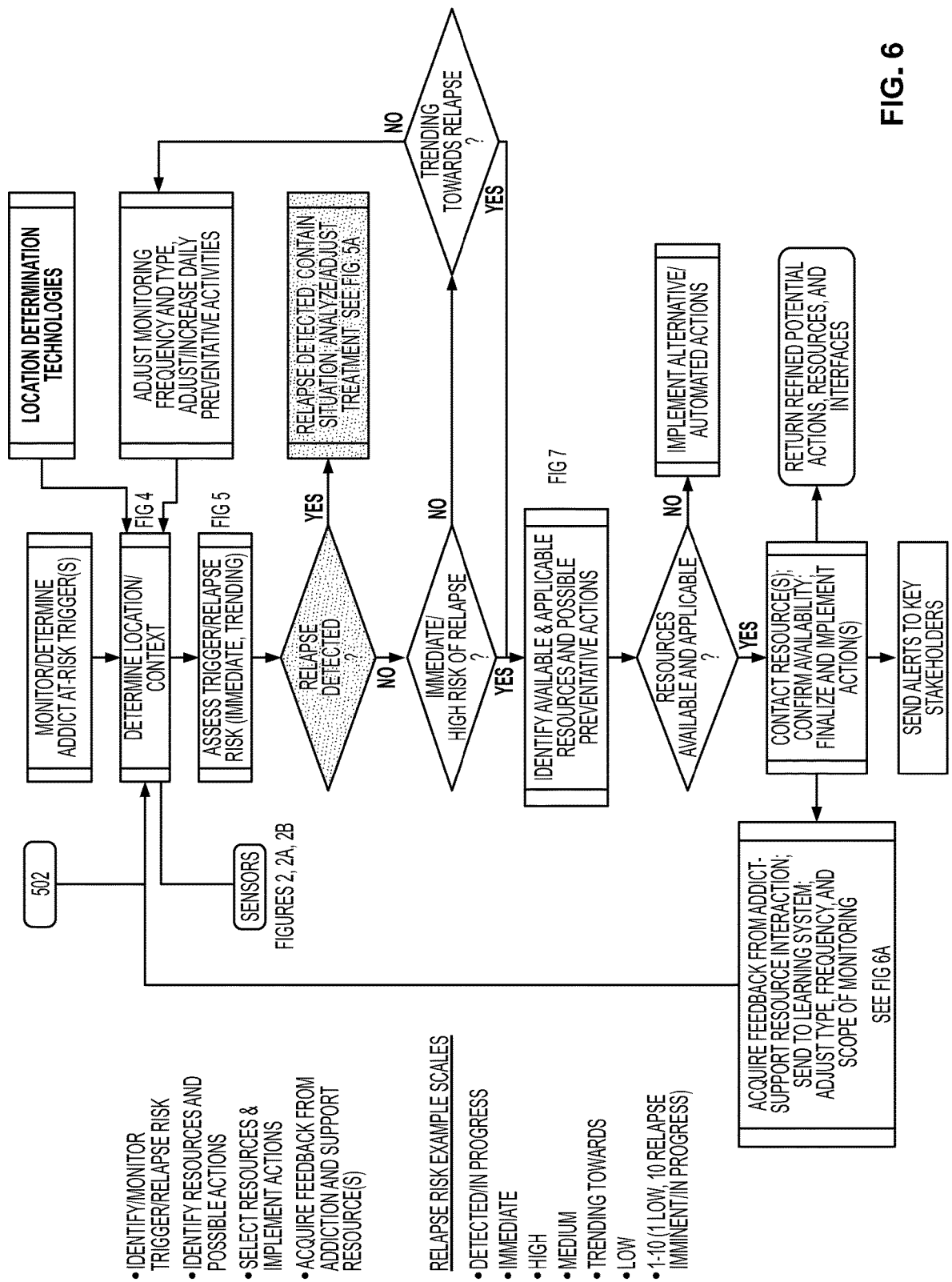
FIG. 6 depicts example ways to identify/monitor trigger/relapse risk and identifying, selecting, and implementing support resources and actions.
Figure 6A:
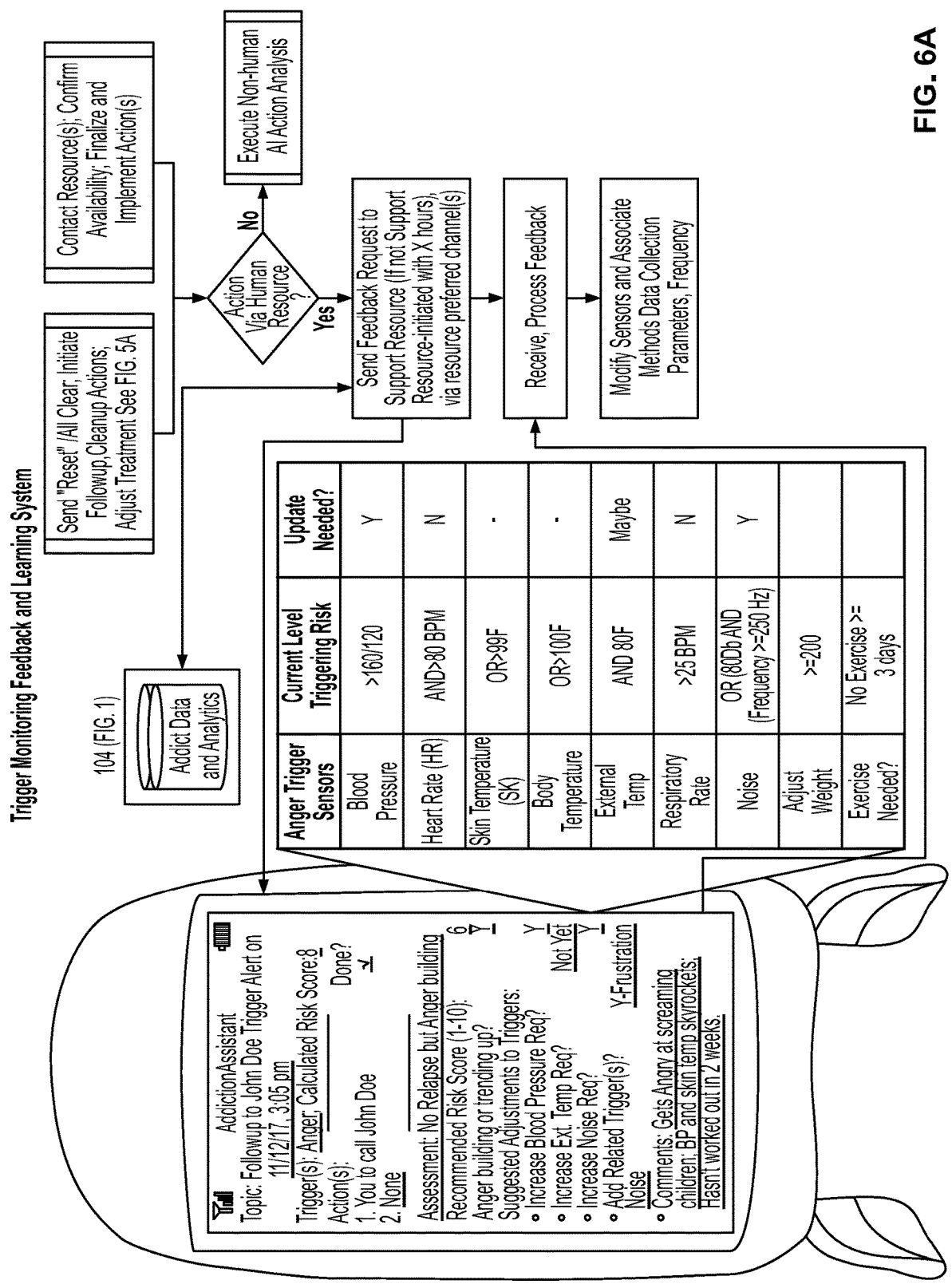
FIG. 6A depicts an exemplary embodiment of a trigger monitoring feedback and learning system.

Various embodiments utilize algorithms that assess and determine the potential of a relapse of the addiction(s) in question. Such algorithms may be based on many factors, including, e.g., addict's profile, behavior/context history, triggers, medical data, the current or trending context of the user, etc. As shown in FIG. 5, such information could be utilized in a set of prediction algorithms and/or scoring formulas geared to determining a current or trending degree of risk.

Various embodiments utilize the concept of trending context of the addict. Various embodiments may attempt to anticipate/predict the addict's context at some point(s) in the future—10 minutes, 1 hour, 3 hours, etc.—in order to identify high-risk situations and proscribe some sort of preventive actions. A simple example is detecting the travel of the addict on a route for which a highly likely/only conceivable destination is a prohibited or forbidden destination, such as a liquor store, gambling establishment, known drug-dealing area, etc., or related forbidden areas such as an ex-wife's house under a court order of protection.

The above trending context example is also an example of various embodiments' integration with other applications. In the above example, the prediction of the addict's destination of a liquor store, gambling den, or drug haven may be made very simple if the addict programs the destination into his/her GPS navigation application. An interface may be provided by one embodiment that would automatically (subject to privacy and/or administration limitations discussed earlier) transmit the destination/route information from the navigation application to the embodiment, allowing confirmation of the addict's destination.

Various embodiments provide integration with third party applications, systems, and processes, e.g., as relating to dealing with high risk or actual relapse situations. For example, in situations where it is deemed too risky for an addict to drive a car, an embodiment may automatically scan through alternatives to get the addict home or to help, without them endangering themselves or others by getting behind the wheel. This could include automatically integrating with an Uber or Lyft application to obtain a ride, or interacting with the addict's car to alternatively disable it, make it switch to self-driving mode (and not allow manual driving at all), or only switch on if the addict was a passenger. Such third party integration could be extended even further, for example, extending to home security applications (e.g., sending an alert to an ex-spouse's house under a restraining order to inform that the ex-spouse has been drinking and take appropriate precautions). It could even extend, e.g., to automatically informing law enforcement if such restraining order geo-fences have been violated.

While the above embodiments emphasize anticipation and prevention of relapse, there are also many embodiments of the present disclosure that address minimizing damage if usage of the addiction occurs. In one example embodiment, alternative transportation mechanisms are leveraged when a risk of the addict traveling while impaired is considered high. Beyond and including communicating with the addict's personal vehicle(s) and interfacing with the appropriate systems to prevent the addict from driving the vehicle, the example embodiment may also interface with systems such as Uber or Lyft to automatically request ride services when it detects that the addict is in need of such transportation. It may also interface with driverless cars or cars with that option. For example, if the addict's personal vehicle has a driverless option, the example embodiment may automatically switch the car into that mode to prevent the addict from taking control. An alternative may be to completely disable the addict's car, or any other car the addict attempts to drive (such as those with embedded breathalyzers or similar driver condition monitoring/car interfacing technologies).

Other transportation-related embodiments include, but are not limited to, communicating with rental car companies if an embodiment detects impairment; airlines to prevent drinks from being served to the addict. It also includes alerting key parties (such as spouses) when the (possibly impaired) addict is on the way to home, and activate if desired various security measures when the addict is with a certain distance of the home or other location (such as children schools) so that measures such as automatically locking the home, calling security/police, family etc. can be taken before the addict arrives at the location.

Another example embodiment of the present disclosure provides interfacing with the increasingly personalized digital media world. Digital signs/signage may be capable of communicating with personal devices to detect information about the owner in order to tailor advertising to the owner's specific needs, preferences, and desires. Other signage looks to market to common denominators with beer commercials and the like-causing distress in some alcoholics. One example embodiment may interface with public digital signage, e.g., to prevent alcoholism-related signs from appearing while the alcoholic is in the viewing vicinity, or alternatively causing uplifting, trigger-soothing related ads or messages to be displayed. The signage for use by interfaces could be coordinated, e.g., by the Addiction Server or by an application on one of the addict's devices with access to the Action Coordination Engine.

Various embodiments may address the privacy of the addict and others via a privacy engine 117 to both protect the addict's privacy—to the extent possible and/or desirable—as well as the privacy of others involved in implementing such embodiments, such as friends and service providers. As the transportation embodiment above illustrates, implementing restraints on an addict in terms of utilizing third party services and/or informing third parties of an addict's risk situation can involve privacy concerns and legal considerations. In various embodiments, a privacy engine 117 may address such matters while still providing functionality as disclosed herein. The privacy engine 117 may interact with various embodiments such as the Action Coordination engine to ensure that privacy concerns are appropriately addressed in the selection and implementation of any course of action.

One example embodiment includes sending alerts to persons in an addict's support network when the addict is near, nearing, and/or stopped at a Point of Interest—POI—(e.g. liquor store, casino, shopping mall, etch and/or known geographical area (e.g. drug dealing areas and sites) that may provide a temptation to the addict or indeed is the intended destination of the addict. Selection of recipients of such alerts may be based on any number of parameters such as their location (e.g., proximity to the addict), time of day, day of week, etc. The triggering of such alerts could incorporate the use of geo-fences to initiate the application(s) and/or trigger various types of functionality when the addict enters or leaves the geo-fence. This could help the addict in knowing he/she is being monitored (e.g. is being systematically supported by his/her personal, semi-anonymous, and/or anonymous safety network(s), etch and/or causing members of the network to actively intervene to help stop/prevent/advise/console the relapse or repetition of the addiction event. This could include generating alerts when the addict is near/nearing, and/or stopped by a person of interest, e.g. a known bad influence on the addict (e.g., see FIG. 1, etch, etc.

Another embodiment includes providing alternative routes for navigation applications (and/or data to navigation applications that can provide alternative routes) that modify directions to avoid these kinds of proximity to the points of interests (POIs) or areas described above and other functionality described below (e.g., see FIG. 1, etc.).

Another example embodiment includes providing information/alerts to addiction means entities such as casinos and liquor stores when the location of the addict is in their proximity, so as to enable on-site activities such as refusal of service or counseling to the addict. Various embodiments may provide information to credit/debit card companies to temporarily disable the cards to prevent purchases or cash advances, and/or disable the usage of other electronic or computerized payment mechanisms such as mobile wallet technologies. Various embodiments may provide capabilities to block individual transactions when a part of that transaction includes addiction-enabling products or services. For example, grocery stores in many states allow the sale of beer, wine, and even liquor. It would be very undesirable to block a grocery store transaction by the addict just because the place he was shopping in sold alcoholic beverages in addition to many other non-alcoholic items. Various embodiments may provide a capability to tie the store's check out mechanisms (e.g. bar code scanners and the like) to the mobile payment system as well as to the data profile of the addict (see below) to detect when an addict (in this case an alcoholic) attempts to buy alcohol. An alert may be sent to the mobile payment system or perhaps directly to the grocery store's check-out system to deny the transaction. The addict would perhaps be given the opportunity to remove the alcohol from the checkout process and continue the checkout without the alcohol being included to avoid embarrassment and the like.

Another feature or aspect in some exemplary embodiments of the present disclosure includes providing an addict with a panic button or hot-key or equivalent on the addict's device(s) that could trigger some predefined functionality described herein. Such activated functionality could also be based on the location, medical state, and/or other condition of the addict, or even randomly selected.

Various exemplary embodiments may provide ability for an addict to post blogs on addiction websites describing his/her state of mind and/or other pieces of context, including location, that could help the addict in unburdening themselves and/or cause other addicts to post response blogs and/or contact the addict directly to support the addict. Various embodiments may provide linkages to book/article passages or video footage showing the author(s)/actors in addiction situations and/or describing the impact of their addiction and/or showing them in embarrassing situations and the like. Various embodiments may provide various media reminders of public figures who have seriously damaged themselves in some fashion, such as high profile actors or sports figures who seriously impacted their careers by behavior that seriously damaged their public profile and in turn their careers and finances.

Another feature or aspect in some exemplary embodiments of the present disclosure includes providing predictive analysis of potential relapse based on the addict's historical data, such as travel patterns and health data such as blood pressure, and linking them to real-time data (e.g. current location and directions; blood pressure monitors on or in the person), to anticipate and evaluate the potential for a relapse, and to initiate preventative measures, such as some of the types of alerts above or alternatives below, or even triggering a release of blood pressure medicine or other types of medicine that would be deemed appropriate in the circumstances, such as Campral or Naltrexone (e.g. alcohol containing medications, etc.). These medicines' administration could be, e.g., in the form of alerts to the addict to take it urgently or as a reminder to a periodic schedule, or even triggering the release of the appropriate dosage via implants in the addict, or even more exotic methods such as being shot with the medicine from a drone following the addict, or providing a supercharged vibrate on the mobile device that could serve as a sort of wake up call, or more benign mechanisms to the addict like changing their ring tone to the addicts favorite (or least favorite song), or launching a song on their iPod that reminds them of good/bad childhood experiences. Alerts could be sent, in various embodiments, to appropriate physicians and/or as updates to the addict's medical records. Various embodiments may provide capabilities such as functionality during the addict's sleeping period to subconsciously reinforce the addict's resolve to fight the addiction, such as special programs broadcast next to the addict's bed.

Another feature or aspect in some exemplary embodiments of the present disclosure includes providing linkages to sensors such as in-vehicle breathalyzers that can activate alerts and other functionality disclosed herein. Various embodiments may provide capabilities such as addiction-trained dogs that detect the presence/usage of the means of addiction/relapse and take preventative action such as hiding the means (a kind of reverse application of the dog getting a beer for his master). Various embodiments may provide capabilities such as affixing RFID tags on addiction means (e.g. alcohol) that trigger alerts and other disclosed functionality if the tags are moved.

Another feature or aspect in some exemplary embodiments of the present disclosure includes providing location-based alternatives via the addict's mobile device to the addict to help either passively or actively in dealing with the addiction in general and/or relapses in particular. Such alternatives include:

Alerting the addict when he/she is in the proximity of their support structure, such being near an active or soon-to-start AA meeting or other support groups that meets the needs/preferences of the addict (example: a women-only meeting), or near a member of his support network such as a sponsor, family member, or friend; linking to navigation functionality to provide the addict with directions to the support person or structure; automatically calling the nearest support person or type of support person (e.g. family member, etc.).

Providing location-based suggestions for other alternative activities by linking with a personal preference database, such as a nearby teen/youth center, church, movie theatre with a movie/movie type he likes that will start soon, bingo, a bowling alley, book store, coffee shop, and other types of alternative activities based on a database of preferences, such as self-esteem boosting activities which may include volunteering/community service. Other alternatives may include errand-running based on location, such as going to the grocery store or picking up the dry cleaning. These could be done in general while the addict's device is on and/or based on other parameters such as only during a certain day or time or geographical location, on a periodic basis, or randomly.

Providing location-based advertisements for key products and services based in whole or in part on preferences and/or templates for resisting temptation, such as bakery or coffee coupons of nearby establishments (in this example, sugar and/or coffee being considered an effective alternative to alcohol). Could include special sales for that addict only and/or for a limited time (e.g. 2 hours, etch on those products and services.

Another feature or aspect in some exemplary embodiments of the present disclosure includes detecting that the addict, having been located at his/her residence for a certain period of time, leaves that residence in a way or timeframe that triggers an alert to said social network or legal/public authorities. Said alert may preferably have the effect of either: 1) deterring the addict from said action (presupposing that the reason for the leaving of the residence is to indulge in the addiction); and/or 2) providing a public safety service.

Another feature or aspect in some exemplary embodiments of the present disclosure includes providing linkages with databases storing images of photos, videos, text messages, legal transgressions (proven or otherwise), and other testimonial type data that can be used to remind the addict of the consequences of their addiction, and/or be communicated to their social safety network and/or other entities, particularly in the prospect of harm or inconvenience to other individuals and/or property is deemed possible. These linkages could be of a personal nature, or of an external nature, such as DUI car crashes having nothing to do personally with the addict but serving as stark reminders to the addict of the potential consequences of their actions. These images and/or messages could be automatically sent to the addict's device and displayed in the most effect manner to gain the addict's attention.

Another feature or aspect in some exemplary embodiments of the present disclosure includes providing linkages to/reminders of loss of marriage, deteriorated connections with children, family, and friends, loss of job(s), embarrassing behavior, situations or events caused by the addict's addiction, negative financial impacts like lost opportunities or assets, and other personally negative situations experienced by the addict. Reminders could be in any form, such as photos, videos, text, testimonials, etc., and rendered to the addict via display, text, audio, 3D, 4D+, heads-up display, etc.

Another feature or aspect in some exemplary embodiments of the present disclosure includes providing linkages to medical databases that show the effect of addictions of various parts of the body, such as liver, stomach, colon, nose, and other effects such as blood clots, diabetes, etc. This information could/would be transmitted to the addict's device in various methods, e.g. voice, text, photos, video, or other methods such as heads-up-display, direct neural-to-the-brain and/or other body connections (e.g. implants or other methods of directly internally communicating with the addict, and other methods). This may include being able to display, text, and/or provide verbal reminders to the addict and/or others in the addict's network. This may also include the potential for notifications/linkages to other interested parties, such as the addict's doctors, therapists, etc.

Another feature or aspect in some exemplary embodiments of the present disclosure includes providing linkages to legal and other public records indicating personal or of an external nature of the effects of the addiction, such as DUIs, restraining orders, and the like. This may include being able to display, text, and/or provide verbal reminders to the addict and/or others in the addict's network, particularly to those in close proximity to the addict. This may also include potential for notifications/linkages with public and private safety personnel and systems in close proximity to the addict.

Another exemplary embodiment of the present disclosure includes the development and presentation via various types of user interfaces of location-based information about the above in the form of news, alerts, other presentations, etc. This presentation may be motivational and/or dissituational in nature to reinforce the need for the addict to abstain from their addiction. For example, a newsfeed could pop up as a banner ad on the addict Jane Doe's phone or Google Glass as she was nearing a liquor store on 5 th and Elm Street saying "News Flash: Jane Doe laughs at the temptation of Joe's Liquor at 5 th & Elm!—World Rejoices!" This would have the dual effect of a) reminding Jane she is being watched or monitored, and b) providing real-time reinforcement and praise for resisting that particularly temptation.

Another feature or aspect in some exemplary embodiments of the present disclosure includes the creation of an anonymous and/or semi-anonymous social networks, allowing users (helpers for the addiction that meet certain parameters including location proximity to the addict) to flag themselves as available to help (perhaps after achieving some sort of training) in the event that no one is available in the addict's personal social network, or as a supplement or substitute. These networks can be crowd-sourced from the community at large. The primary goal would be to empowering the addict to know that someone is just an action away if the addict needs help. The helper could choose to appear anonymously or not, as could the addict.

Another feature or aspect in some exemplary embodiments of the present disclosure includes detecting, monitoring, and/or preventing purchases and/or usage of addiction-related materials. This may include providing periodic, continuous, or random reporting of such purchases and/or purchase attempts to other interested parties on a specific, semi-anonymous, or anonymous basis.

Another feature or aspect in some exemplary embodiments of the present disclosure includes providing incentive programs and frameworks that rewards the addict for positive behavior, such as coupons for free dinner for two if the addict's behavior reached a certain positive threshold, such as not stopping at a liquor store for 30 days consecutively (verified by the application). This would entail a historical tracking/counter/points type system within the addict's application profile. This would entail methods and technologies such as periodic intensive tracking of the addict for an amount of time, such as a week or a month (or moderate tracking as a regular ongoing part of the application), and awarding points (redeemable for prizes) based on verifying going to a certain number of meetings or NOT stopping at a liquor store. This framework also has a lot of applicability for others involved. There can be support quests, where say a child has to write a letter to their estranged parent (a real letter) and if so they get X number of points, which are redeemable for products or services appropriate to that person's demographic, such as an ice cream coupon for children 10-15, or iTunes credit for persons 10-25, with appropriate controls to prevent abuse. Another aspect of incentives is a behavior-based pricing model. This could entail raising the monthly cost of the service to the addict when the addict exhibits bad or undesirable behavior (e.g., relapsing, etch, then lowering the price and/or providing refunds when the addict exhibits good or desirable behavior over a certain period of time.

Another feature or aspect in some exemplary embodiments of the present disclosure includes providing a user interface (UI) platform to the above functionality that minimizes or reduces the actions that the addict has to take for the functionality to activate. Indeed, by using capabilities that the user does not have to provide any action to activate the functionality, particularly the use of the addict's location, various embodiments may provide ways that reduce/eliminate any reluctance on part of the addict to use the functionality. Various embodiments may provide the ability to customize the user interface for the addict to maximize the convenience and usability of the functionality based on the user's profile. For example, the UI for an alcoholic may be much different than that for a prescription drug addict which in turn may be much different than the UI for a shopaholic. They could vary by many parameters, such as gender or location (e.g. text to voice conversion could be done in a western, southern, or northeastern dialect depending on the home location of the addict, etc.). The sensors used for detecting high risk situations may be much different; means of communicating messages may be much different. Various embodiments may provide the ability to modify/customize the user interface based on multiple parameters, particularly location. Other accessory type modifications to a UI based on location also may be provided. For example, if an embodiment detects that an addict (or in this case also includes non-addicts) is in a movie theater, it may automatically switch the device to vibrate, and provide a capability that inverts the display of any messages, e.g. instead of a bright background with messages in dark colors, the background would switch to a dark one with the messages in a lighter color, thereby greatly diminishing the impact on the dark movie theater environment. This capability could be enabled by various technologies tracking the movement and location of the person (addiction not a requirement in this kind of use case), and other technologies such as detecting payment for the product or service and using the nature of that transaction (e.g. buying a movie ticket, etch to automatically modify the behavior/user interface of the device. The device could then be instructed to revert to its former configuration when the user/device is detected to be leaving the theater.

Another feature or aspect in some exemplary embodiments of the present disclosure includes providing an initial setup capability that minimizes actions and time by the addict to setup his/her profile to take advantage of the functionality described herein. A pre-populated profile templates may initially be used based, e.g., on a few parameters such as addiction(s), gender, age, key medical conditions such as depression, medication taken, home/work locations, key hobbies/leisure activities, key addiction triggers, and/or (for some addictions) ethnicity, etc. In addition, various embodiments may provide the addict with a number of options for setting up his/her support network. These could include manual input of individuals/groups (generally undesirable), accessing/downloading individual/group information from other applications such as Face book/social networking apps, phone and/or email address books, local AA meeting participants, etc. The addict would then need to confirm each individual (using voice or computerized confirmation) before they would be active in the addict's profile database, plus other parameters such as type of support (e.g. alert 24 hours/day, only certain circumstances such as only when the addict is out of town, etc.). These individuals may need to be sent confirmation messages, depending on circumstances (e.g. wanting to send alerts to that user) and/or the addict's preferences, asking permission to be included in the addict's support structure. Other parameters such as allowing the use of anonymous support individuals/entities would be requested. This initial information would then be used to provide the initial profile template for the addict. This information would include flagging of location-related/addiction-related POIs, such as liquor stores within a 50-mile radius of the addict's home/work or movie theatres within a 10-mile radius. It would include key directional information such as the various routes between home and work, which could then be used to provide alternative routes to avoid addiction tempting locations/POIs and triggers and/or provide convenient access to alternative activities, plus other data.

Another feature or aspect in some exemplary embodiments of the present disclosure includes providing an ongoing profile modification capability, which could be done by one or more means or ways: manually and incrementally, such as when the addict is calling, texting, or emailing a person asking the addict if he/she would like to add them to their support structure. Various embodiments may also provide or have a learning capability, such as detecting changes in behavior or condition of the addict (e.g., changed driving patterns or elevated blood pressure, etch, correlating the changes in the addict's behavior or condition to relapse risk factors and then modifying the activation/prioritization/type of functionality described herein. Various embodiments may include suggestions by others in the addict's support network, such as recommending a good restaurant frequented by other addicts, a new bridge game being setup, a club at the addict's high school that might be helpful to the addict, etc.

Another feature or aspect in some exemplary embodiments of the present disclosure includes providing linkages to, usage of, and combination of a wide variety of databases, including but not limited to: street/navigation databases; POI databases: satellite map databases: addiction group databases, such as AA meeting types, times, and locations: event databases (e.g., ballgames, concerts, etch; rehab facility databases: self-help databases such as WebMD; weather databases; public safety databases (e.g. police stations, sex offender databases, etch; geographical/terrain databases: highly specialized databases such as databases that show hot fishing or surfing locations: plus a host of individual databases such as local theater databases/listings describing the locations, showings, and times of a movie theatre chain's location in the vicinity of the addict's home or work. This may include linkages to products and services in the addict's area that could help deal with triggers particular to the addict. This may include sign-up databases for addicts in a certain area who want to be part of a local, regional, national, and/or international (even special) support network on a personal, semi-anonymously, or anonymous basis either offering to be part of a support structure, seeking the support of a support structure, or both. These databases could be public, private, or both. Various embodiments may provide new and unique value both in the application/usage of the databases, and also in combining/integrating them in new and unique ways.

FIG. 15 depicts an example embodiment of a method for monitoring for a risk of a pre-identified behavior (e.g., pre-identified addict-related undesirable behavior, etc.). FIG. 15 also includes example triggers, priorities, and initial risk assessment/detection sensors. As shown in FIG. 15, a first step may include providing a questionnaire (e.g., on paper, online, video, etc.). Questions on the question may be designed to obtain not just facts but to also elicit an emotional response from the person (e.g., addict, etch answering the questionnaire. The questionnaire may be used to determine the priority/impact/severity of each drinking trigger listed as well as any other ones that might apply. A high ranking for a trigger may indicate that the person often drinks or wants to drink when this trigger occurs, whereas a low ranking for a trigger may indicate that the trigger never causes the person to drink or want to drink.

Continuing with FIG. 15, location(s)/context(s) for the addict may be extracted, such as from computers, phones, social media (including location and time stamp), etc. Location(s)/context(s) for the addict may be extracted from a third party, such as location, context-rich and/or image/photo-intensive applications, e.g. navigation, etc. After extraction of location(s)/context(s) for the addict, the method may include identifying, assessing, and prioritizing triggers, and identifying key sensors, determining sensor and other sources (e.g., key readings, values, levels, ranges, yes-no parameters, etch to monitor for risk. The method may also include accessing and/or using addict data sources including addict data and analytics 104 (FIG. 1), including predictive analytics data, etc. The various possible triggers shown in FIG. 15 are not necessarily independent from each other as there may be relationships between the triggers.

Another feature or aspect in some exemplary embodiments of the present disclosure includes providing the ability to anonymize the addict's identity for some or all of the above functionality, particularly (but not exclusively) for functionality that goes outside of the addict's support network, such as providing moment of value mobile coupons discussed above that would shield the addict's identity from the company providing the coupons.

More broadly, the protection of addict (and their support network) privacy is one aspect of the present disclosure. The personal data collection mechanisms described in the present disclosure can conceivably be used to track a person's movements 24/7. To prevent inappropriate use of data, the present disclosure provides new systems, methods, mechanisms, and techniques particular to how and where the data is collected, and who, how, when, and why it is used.

The present disclosure describes exemplary embodiments of new systems/methods/techniques to use location and/or context information-based security as a way to protect location and/or context information. An important premise is that such personalized location/context-based images and other prompting mechanisms are readily familiar in some way to the user without the need of memorization. At the same time, such images/mechanisms would be very hard to hack or recognizable by (ro)bots since the ability to recognize them is rooted in the user's experience—not in any sort of logical or algorithmic mechanism. Such security keys, passwords, or other security-related elements and mechanisms could be used in protecting the broader collection of location/context information. Besides the ability to protect the voluminous addict behavior data, such location-based security could be used as part of financial account password verification or reset processes, or even an extra layer of security to prevent individual household appliance or device hacking or access such as preventing fake off hacking of TVs, etc. that could become more vulnerable as the Internet of Things becomes more prevalent.

One of the important premises of the location-based privacy and security components, embodiments, and examples is that location and context, presented in a user friendly manner, requires little memorization of the image, unlike say an alphanumeric password. They are readily identifiable by the user once presented to them in some recognizable fashion. In particular, location/context can take advantage of the concept in human memory of recognition versus recall. Recognition refers to our ability to recognize an event or piece of information as being familiar, triggered or prompted from external piece of information or input. Recall designates the retrieval of a piece of information from memory without any external prompting or input. Today's passwords requiring number, letters, capital letters, and punctuation signs are examples of account/data/database keys or passwords that rely in total or significantly on a person's recall ability. Nearly all memory experts acknowledge that recognition is far easier for most humans than recall. Location-based privacy and security takes advantage of recognition, which besides being easier for a given person it much harder for others that have not experienced the piece of data recognized by the user, hence it being much harder to hack, guess, or otherwise deduce, particularly if constrained in some way, such as a time limit, etc.

FIGS. 11, 12, 13, and 14 describe examples of location/context-based elements and embodiments of protecting/verifying valid users and/or access to this information. Broadly, the capabilities illustrated by these diagrams and associated disclosure and embodiments may be referred to as location-based security and/or location-based privacy, using some form of image(s) as key(s) to locking/unlocking/securing a broader set of information, such as account information and/or location/context data collected for purposes of preventing or dealing with an addiction risk or relapse. The images are not limited to only visual/graphical items, such as photographies as the images may also or instead be visual, audio, graphical, video-based, photographic, textual, alphanumeric, and/or other types of passwords depending on the user interface. The images could be in the form of sensor readings, which often have unique values depending on the sensor. The images could be multi-dimensional, such as two-dimensional (2D), three-dimensional (3D), four-dimensional (4D), or beyond if, e.g., including time/time-lapse/time-projecting images. The images may be static (e.g. still pictures), dynamic (e.g. videos, etch, past or present, based in memory or live streaming. Or, the images may also be combinations/hybrids of the above. In whatever form in various embodiments, the location-based security/privacy images are location and/or context-based, experienced by or known to the user and/or person(s) authorized to have access to the broader information.

Location/context images can be obtained, derived, or computed from numerous sources. FIGS. 1 and 2 show a variety of location/context data collection devices, networks, sensors, and other mechanisms and sources. FIG. 11 further describes several example sources and associated types of data along with examples. FIG. 11 also describes examples of questions that can be used to prompt for passwords/keys and/or access to/resets/verifications of changes/access to key information. FIG. 11 provides an example of a user memory profile that can help tailor questions/potential answers to how that person best remembers/recognizes images. Images may be a general term that is inclusive of all forms of Q & A methods and user interfaces. Questions can be tailored based on user interfaces employed, e.g., text, photo, graphics, audio. Virtual/Augmented Reality, etc.

Figure 12:
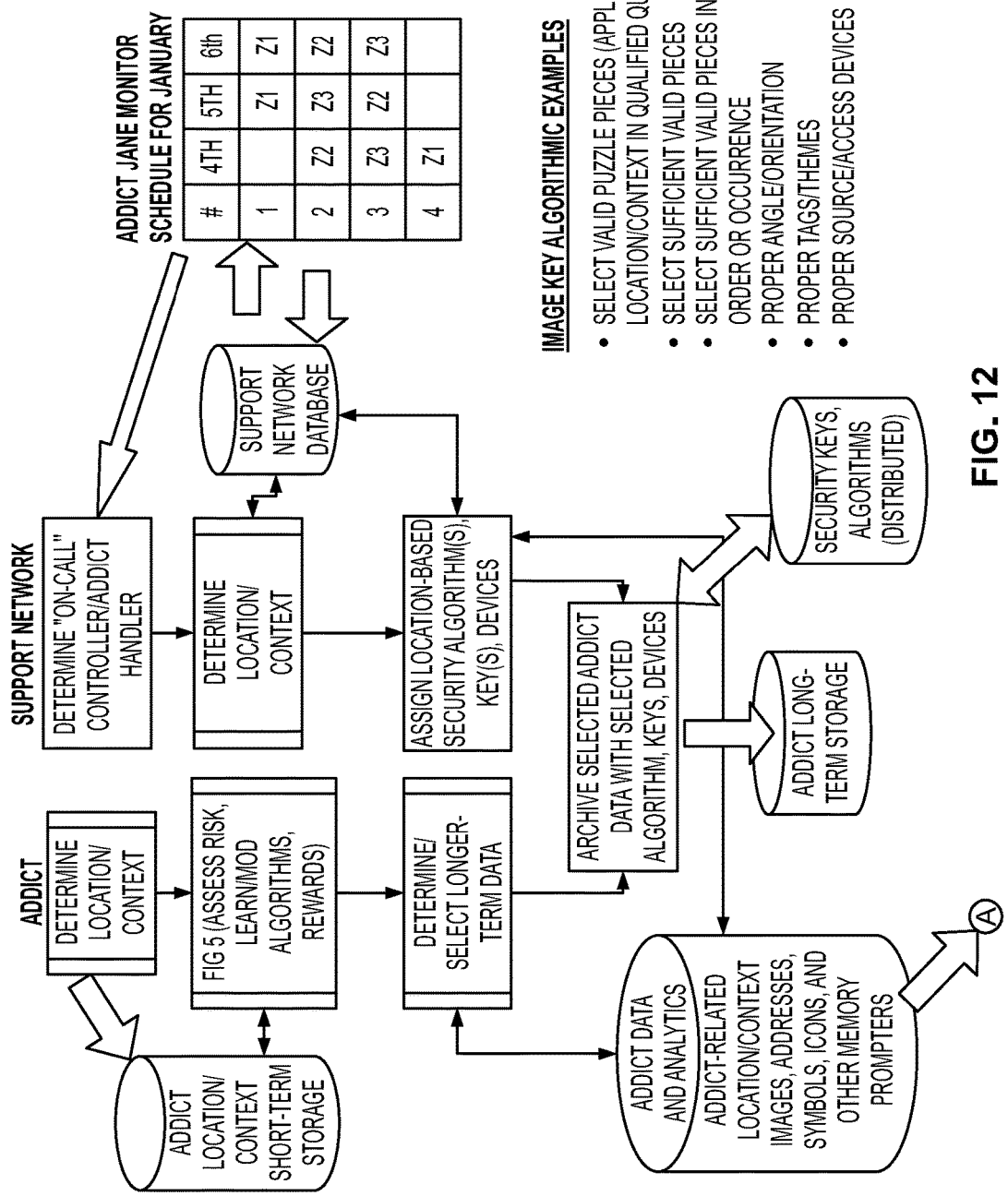
Figure 12:
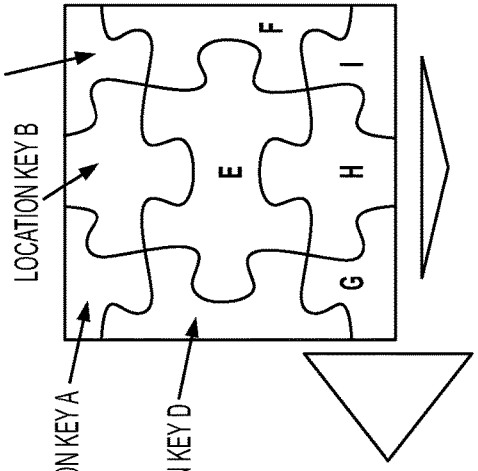
Figure 13:
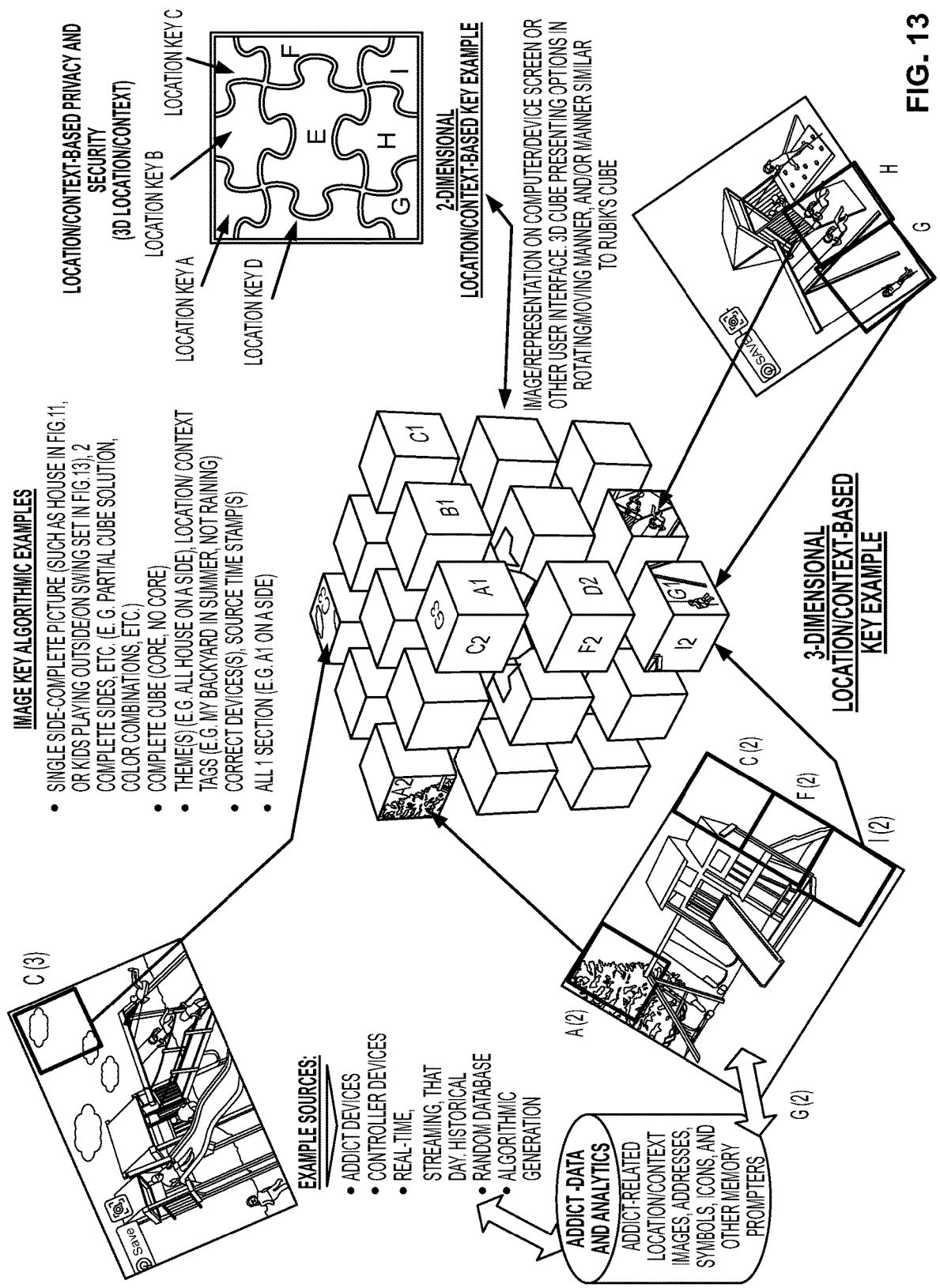
Figure 14:
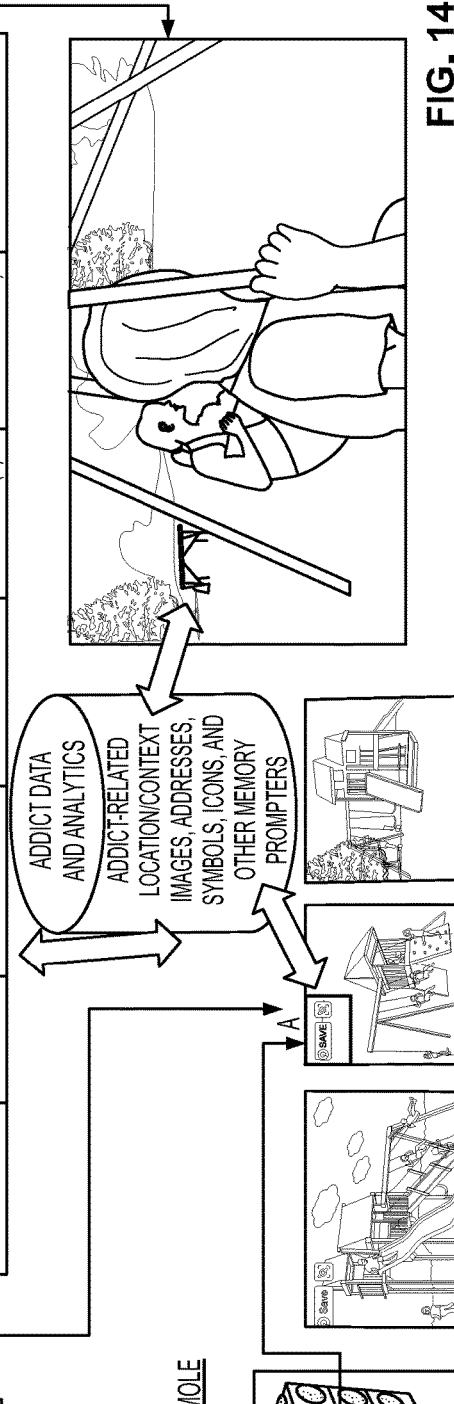

FIG. 12 provides more detail in terms of a method of how such keys might be obtained and used; examples of such keys; and algorithm examples for generating/developing/answering verification questions. FIG. 13 takes the two-dimensional oriented algorithms and examples of FIG. 12 to three dimensions, showing how 3D images (e.g., Rubik's-cube type shape, etch could be used to introduce more sophistication into location/context-based security. FIG. 14 shows a variety of 3D form factors and breaks out in more detail, data elements that would be captured and associated with image keys in order to provide more algorithmic and verification options.

For the figures, it is important to note the parts that devices/sensors/networks play in sourcing images, providing access to images, and in algorithmic processing of such images. A 2D photograph taken by a low-resolution smart phone of a backyard swing set has similarities with and distinct differences from a 3D image capture or video of that same swing set taken by a 3D heads-up-display camera with multi-media sound. The device, beyond capturing the time, place, and image of the location/context, also adds certain contextual elements to the image. In turn, those elements may play an important role in the ability of the user to recognize the image later when it is presented during a verification/password acceptance Q & A process.

One of the embodiments illustrated in FIG. 11 is the concept of a multiple-key or jigsaw puzzle-based key or password for location/con text-based security. The jigsaw puzzle based information lock includes multiple keys to be correctly assembled in the correct order/sequence in order to provide access to any data.

For example, the overall key is that a picture of a house must be assembled. This house has been broken up into 9 separate images with 9 separate associated location/con text-based keys. Each of the 9 keys were created and assigned during a particular time during which certain controllers or monitors were on-call for a particular addict.

The Location-Based Verification Examples sections of FIG. 11 describes some of these either as Verification Grid Element # or Grid #. In various embodiments, data produced and used as described in the present disclosure could be location/context images as actually experienced or seen by the device/user, or they could be representations of a location/concept. Example of questions or limitations on verification answers are also shown in FIG. 11, such as "Where you have been in the last (week, month, year, etc.)?" The use of multiple devices and/or perspectives of the same image (such as a house, daughter, etch would make it much more difficult for a (ro)bot and/or hacker to replicate through algorithms, analysis, or even guessing, whereas for the user it would take very little effort to recall/recognize the correct images. In the location/privacy-related examples and embodiments disclosed herein, a user may refer to a person or entity trying to gain access/validation to an account, database, data set, or other piece of information. Or, for example, a user may refer to a person and/or an entity generating such data/in formation. A user can be a human, computerized entity, and/or anyone or anything that has valid permission to access the information involved.

In addition, there are potentially more persons/entities involved in location/context privacy and security than just users. Certainly data can be generated/sourced from a wide variety of mechanisms/methods/sources. In addition, control over this data does not necessarily have to be by the (primary) user or account holder. Indeed, in addiction-related embodiments in particular, different data sets can be controlled by someone other than the key user (e.g. addict, etc.). One embodiment of such in location-based security is the use of an addict monitor or controller. Such an entity can be a human (or even artificial entity) that is responsible for monitoring the addict over a certain time period. The idea is to maximize or at least increase the probability that if a relapse were to happen, there would be a person on-call that would be at least generally aware of what the addict was doing, or at least have no uncertainty that if a high-risk/relapse situation were to occur that they are #1 on the list of support persons to respond. This entity may be a human or an artificial intelligence entity that has the responsibility of being at the top of the addict support hierarchy during a given time period if the addict were to encounter a high-risk situation during that time. The general purpose of such controllers is multi-faceted: to distribute security of addict information across different entities as a general security precaution: make it progressively more difficult for hacker to access the data; and, in the case of addiction-related data provide security control to entities that are (almost literally) more sober than the actual user.

A side aspect of the controller function is that the controller's location/context would be sampled or otherwise tracked periodically for the time-period when they are on-duty. This location/context information, besides being used in identifying/locating support person if needed, could also be used to create a location/context-based password for the addict's location/context—based on the controller's location/context—during the period of time the controller was on-duty.

While the location-based security and privacy elements and embodiments described in the present disclosure are primarily intended to protect information gathered in relation to getting/keeping an addict sober, its use is not limited to such addiction-related purposes. For example, one set of embodiments of this location-based security and privacy disclosure is in using recent and/or historical location/context information as a password reset verification mechanism, to prove that a user is not a robot, and/or to verify financial transaction. In one of its simplest forms, such verification would consist of a system (or person) asking where a person was on a certain date and/or certain time. Note that this query and response mechanism could be done using any of the user interface forms described elsewhere in the present disclosure.

Below is a variety of embodiments and examples that illustrate location-based security and privacy concepts applicable to many types of situations, verification environments, and protections/access to financial, addiction-related, or other types of sensitive data. Most (but not all) such example data protection/access mechanisms have some sort of qualifiers to limit the scope of a location/con text-related question or statement.

For example. Grid answers to the question could "Select the location & activities you were doing on Jul. 26, 20XX." Note that the specificity of the question/statement can be tailored to the User's Location/Context-based Privacy and Security (P/S) Memory Profile, so that questions/statements are not limited too narrowly (or broadly) for recognition purposes:

As an easy example. Grid #4 could be an image of the user's mother's house-a location and associated context (where they live currently, as it looked before after a remodel last year)—easily identifiable to the user but less so to others and unlikely to be the current image in a readily accessible databases (e.g. Zillow, Google Maps, etc.). Such images could also be taken from angles (such as the backyard) that are generally not accessible on those kinds of databases, particularly since such databases do not generally have linkages to specifically identified family members and associated belongings. Additional security could be added that requires the user to identify how the image was captured (in this case from User's Device A). It may be that a user may have many devices (particularly for an Internet of Things user), but only takes pictures from 1 or 2 devices. This fact might be known only to the valid user.

Grid #5 shows a vacation picture of the user's son on vacation in Location X doing Activity/Context of mountain climbing, taken with a Helmet Cam—also easily identifiable to the user but much less so to others. This verification question statement could be further qualified by asking for example images that "were on vacation", "shows 1 of your children", "shows mountain climbing" or "ocean", "an activity you did 20 years ago", etc.—knowledge likely known only to the user, as would the device used, which could be further obscured by using a nickname for the Helmet Cam, such as "3rd Eye" or "Gorgon".

Grid #1, shows a picture of a "North Carolina" street sign. The image may or may not have been "seen" by the user's device; rather, it is representative of whether the user had (or had not) been in North Carolina on (or around) the 7/26/XX time frame. Such an image could be generated from the raw data of a navigation app (such as the user's car #1—Device B onboard navigation system), combined with a geo-fence around the state of North Carolina that generated a database reading when the user crossed the state boundary on 7/26/XX.

Grid #2 shows a textual representation of an address visited on 7/26/XX, such as the street address of the user's mother's house in Grid #4, derived from that image's latitude/longitude through a latitude/longitude to address converter program.

Grid #3 shows an algorithmic derivative and associated graphical image that was created from the latitude/longitude centerpoint of all activity on a certain date. So in this case, the actual location/context of the user is not displayed, and used in an indirect manner, but the user could easily associate that they were a) indeed traveling overseas, b) it was in Australia, and c) it was on business (a hacker might assume it was for vacation, which in this case would be incorrect).

Grid #6 shows am image that has multiple images of past context, in this case a picture of an dining room in a former home with a now deceased pet. This could alternatively be a possible answer to questions about playing with pets in old homes contexts.

Grid #7 is an algorithmic representation of a crossroads that the user passed in a certain timeframe. Alternatively, it could be a subtle representation of a location/context, such as taking a trip with my cousin Sophie to Santa Monica Calif.

Grid #8 illustrates how an image is not necessarily photo/video/visual/graphical in nature. In this case, it is an audio clip of "California Dreaming" by the Mamas and Papas as a way of indicating a location or geo-fence, based on location information taken in this case from a mobile social networking post from Friend "e". This illustrates how images do not have to be directly sourced by or even known to a user—the key is to be recognizable to the user/person trying to access the account/data.

Grid #9 is an image pulled at random from a sample of retail visit locations, with the address matched with the store name and image (source: Internet). This could be in response to a question of where the user did NOT shop in the last week for example, or something even more subtle in response to a question of "select store(s) in a retail strip mall where you've shopped the last week", assuming the person knows that there is such a store right next to a frequent shopping destination he or she went to, even if they did not go to that specific store during the timeframe in question.

Grid #10 illustrates an image taken from an indirect source (in this case for example a child in the backseat of a car). The driver may not have known such an image was being captured, but enough detail about the driver (user) and his context is shown that he would be able to recognize key location/context questions (such as what car was this picture taken from, or what state was the car in at the time of this picture?).

Grid #11 is another example of an externally sourced image—a satellite image of a house from Google Satellite. Such images could be asked in a verification process regarding valid family member homes. It is likely only a user that is very familiar with such homesteads could quickly identify such homes, making more difficult for a bot to answer correctly.

Grid #12 shows how colloquial references to a location can be used as a verification mechanism. In this case, like Grid #'s 2 and #4, it is intended to represent the user's mother's home. This colloquial/textual representation could be used as a stand-alone answer to a verification question or be paired with other images such as asking the user to select all images related to a family member. In addition, a family tracking application such as AT&T Familymap can be used to extract colloquial names and locations of key places, such as "Mom's House", "Kids School", etc. These terms can then be paired/matched to actual or derived images of those locations, and some or all of the results presented as options in the Verification Process.

Grid #13 shows how the quality of an image (or lack thereof) can be used as a verification mechanism, under the premise that a poorer quality image will be more difficult to analyze by a bot or other hacking mechanism. Grid #13 is actually a much poorer version of the image of the user's mother's house in Grid #4. While still recognizable to the user, the image is likely to just appear as a bunch of squiggly lines to a bot or non-authorized user. Quality variations could be done in numerous different ways, including changing image fill/lines colors or solidarity (e.g. dashes instead of lines), color to black and white, pixel density, and/or circus mirror-type distortions.

Grid #14 shows a three-dimensional image of a roller coaster ride, illustrating how 3D images (including dynamic images such as video) can be used as both as a type of source data (e.g. requiring 3D-capable data capturing mechanisms) but also images where the person/entity trying to access the data has to have the correct devices to appropriately view/select the image. In some cases for example access to images could only be practically possible through viewing through 3D glasses—in effect prohibiting bots or automated/computerized mechanisms from being able to process such images.

Grid #15 extends the 3D concepts of Grid #14 even further by portraying possible verification images in a dynamic, 3D manner, such as a rotating Rubik's cube type presentation where images are not only presented in 3D but also done in a temporary, rotating manner that requires very fast decision making. This concept is elaborated on further in FIGS. 13 and 14, where solving Rubik's cube type images is required to verify an account and/or gain access to the account/data and where different portions of the cube are sources/controlled by different users/sources involved in the data collection and/or usage process.

Grid #16 illustrates the potential role and sourcing (and security and privacy concerns) associated with smart homes and the Internet of Things (IoT), as common household items such as TVs evolve beyond being dumb or one-way communications mechanisms to being able to collect, store, and transmit location/context and other data about a user (TV viewer). The image in Grid #16 is a possible example of a picture/video that could be taken of a TV viewer by the TV itself. As shown also in FIG. 1, IoT may play a major role in collecting location/contextual data (particularly activity/behavioral data) in places/situations not historically available to such data collection. This type of household data has the potential for being particularly sensitive, and as such needs the extra protections offered by the location-based privacy and security mechanisms, systems, and methods described herein.

To successfully use the protections and security described by this location-based privacy and security, there needs to be ways of verifying, authorizing, or otherwise providing access to the very large (and often very sensitive) volumes of data collected. At its simplest, a location-based key (or password) needs to be matched to the correct image/answer in order to proceed further. There are numerous ways of matching two images to see if they are the same. Many have to do with the degree of uniqueness, e.g. do the two images share the same unusual representation or pattern—sometimes done on a pixel-by-pixel basis.

For exemplary embodiments of the present disclosure, doing exact matches are fairly straightforward, as the images being offered as a verification/password matching option may often be the exact image stored in a reference database, with few if any technical differences. Where degree of uniqueness comes into play is when certain location/contextual elements are the focus of the verification question or password sequence, such as requesting all images that show children-at-play in my backyard during summer of 20XX. In those cases, the possible images not only may not be an exact duplicate of a baseline/reference image, there may not be a baseline/reference image, and/or the possible correct images may seem very different to the typical viewer. In these cases, it can be subset(s) of the images that would be important—those portions of the image that determine key location/context elements, such as "children", "at play" and "summer 2000." In those cases, a person may designate the important elements, or a matching algorithm may pick out key elements, such as the presence of a swing set to be the proxy for "play", "children" being anyone under 5 feet tall (this needing a reference height), or "Summer 2000" showing trees and grass in full bloom, with a date stamp of June, July, August, or September 2000 as part of the image metadata. A statistical probability technique may also apply, such that any match with more than a 90% probability would be considered sufficient.

A new way of dealing with the variances/uncertainties of matching/verifying images that are not technically/digitally the same yet have sufficiently matching elements is location/context fingerprinting, described in the present disclosure. As background, in the wireless field, there is a concept called Radio Frequency (RF) Fingerprinting. This is a generally a location-determination method where surrounding cellular or Wi-Fi signals at a given point are measured (such as measuring signal strength, or time-differences), and those measurements stamped with a GPS location—constituting a fingerprint of that location. When a user of such a system later reports a variety of signal measurements, they can be compared to the fingerprint database, and if they match a fingerprint in the database, then that user is reported to be at the corresponding location.

A new variant of that concept is disclosed here. For example, a verification database may have many hundreds or thousands of images of a location and/or context—some drawn from/known to a user and others not. In a verification process, the verification engine could offer several images, and request the user to select the 3 that all have the same location or context in common. The common element could be any number of things—same location (home) or context (playing with my children), same location at the same point in time (summer last year), etc. It could even be which images were taken from the same (user) device—e.g. matching based on source device and/or metadata attached to the image versus the image itself. All of these examples would be relatively easy for the user to remember, and remember quickly; a hacker would have a difficult, even impossible job in deducing the correct answers. Like a physical fingerprint is only on the user's physical person, these location/context fingerprints are available only in the user's brain. A simple example of a location-based fingerprint is to have a front, side, and top image of the same object or situation that the user then has to recognize. For example, while such images of a house are readily available from various sources (e.g. Google Earth, Zillow), such different perspectives of the same object would look very different to someone without a vested interest in the property (e.g. the owner), and thus it would likely only be an owner/resident that could quickly pick out 3 such images from a collection of several, for example.

The above is another instance of the importance and effectiveness of location/con text-based privacy and security in protecting against robots or hots seeking to compromise data/system security. For example, when asked to verify whether or not a person is a robot, many such existing techniques display several photos and ask the user to select those that display portions of street signs or store fronts. If the user correctly selects all frames, then they are allowed to proceed with the transaction. As an enhancement, the present disclosure could provide images of locations personal to the user. For example, a variety of storefront images could be presented to the user, and the user asked to select which ones they have been to within, say, the last 24 hours. These transactions could be selected according to a procedure, algorithm, or even randomly from the locations collected from the user during that time period. This kind of verification would deter a sophisticated robot as the validation process would be based on the user's personal experiences and not a robot's general image recognition capability. Similarly several street signs with a real or systemically-overlaid image of a street or road could be displayed, and ask the user to select which streets/roads the user has traveled in the last week. The system could provide as much granularity as needed in selecting the roads, whereas a "week" could be very specifically 7 days, or generally several days, depending on how good the user's memory is (and which is described in their memory profile discussed shortly).

Such a query could be structured to include locations/streets/roads that the system knows definitively has not been to during the proscribed time period. This could create by a simple geo-fence-type algorithm that encapsulates a user's movements in a particularly geographical designation, such as town, city, zip code, county, or state for example, within a certain time period, and then providing other selection options clearly outside those areas during that time. A simple illustration could ask the person "have you been to O'Fallon, Illinois recently?" The system's data store would know if the user has ever been there, but such answer is not part of public record such as asking where you've lived in the past or even the model of car that you have owned. The verification is based on the user's personally experienced location/context-information unlikely to be available in other databases that are accessible by hackers.

The selection of the location transaction to base a query on could be done in a variety of ways. The selection of the preferred method could be established beforehand in user profiles, for example, giving the user choices to select locations for verification purposes based on day (e.g. Saturday), time (only in the afternoon), time period (within the last day, week, or month), historical only (only last year's locations), geography (only Missouri locations), and/or context (e.g. locations when I had been on vacation and/or clearly engaged in leisure activities). This allows the user to be prompted with locations that they are most likely to remember, yet with little or no obviousness to a hacker.

Indeed, the above could be used not just for verification or reset purposes, but as an application/system password or key itself. Every time a person logs onto Application B for example, instead of being asked for an alphanumeric-based password, it could be shown as several images—individual or parts of images, e.g., as shown in the jigsaw or Rubik's cube puzzles in FIGS. 11 and 13. Images are not limited solely to visual/graphical items. The images may be visual, audio, alphanumeric, or other types of passwords depending on the user interface, but are nonetheless referred to as images for convenience. In whatever form, the images are location and/or context-based and/or personally experienced by or known to the user. Several images could be displayed to the user, and the user may be asked to select the one(s) they've experienced at or during a selected time period. Or a time period could be displayed with images all experienced or known to the user, then the user may be asked to select the correct time-period from a list of options. An incorrect selection would be replaced by new options with a new answer that is based on the user's location/context experience or knowledge.

The user interface used in the verification/password selection process can do more besides providing a large variety of image and image-type selections—it can also enable new types of verification methods. For example, a 3D touch-type screen could enable choosing the correct images as they are raised or elevated in the view screen, and the user can touch/press those images that are correct/in the correct sequence, in a kind of virtual whack-a-mole mechanism. This concept is illustrated in FIG. 14. An example embodiment of this concept is that the user is presented with a static or rotating image (or cube) that has one or more pictures being enhanced (e.g., popped-up, etch every few seconds. The person trying to gain access to the data/account/system would only have, for example, 2-3 seconds to select (virtually whack) the valid option(s)—validity being dependent on the verification/authorization question or statement, such as "select all images showing your kids playing in your backyard in summer 20XX." This is an example of a question that would be relatively easy for a valid user to answer because the user could readily recognize the user's own children, own backyard, and even season/year (if, for example, the user's backyard was a landscaping mess up to Spring of that year, and a new swing set replaced the old swing set the winter of 20XX). Conversely, this would be very difficult if not impossible for a bot or other hacking-type algorithm to discern the correct answers).

To provide further protection, the location data used could be selected randomly from the historical data store both in time and/or place. A live, real-time, or near-live/real-time (e.g. only a few seconds, minutes, hours-old, etch stream or recording could also be used, requiring the user to relatively instantaneously or instantly recognize images not seen or recorded anywhere else because they are happening now or just happened.

In exemplary embodiments associated with addiction, there are additional location-based security embodiments above and beyond (or particularly tailored) to addiction-related issues and/or data sensitivity. For example, one or more specific persons may be provided with control of a location-key that is based on some personal information of the addict and/or support person(s). This key could be relatively static, changing relatively infrequently, or dynamic, changing perhaps every day or even hour. The premise is that much—even most—of an addict's data will go unused, or used very infrequently—thus it is not necessary to have a commonly-known, even easily accessible password or equivalent. Because exemplary embodiments of the present disclosure are generally is centered around the prevention of re lapse s/usage of substance or activity, if during a given period of time there has been no usage-related activity, there is little reason to retain that information once key addict location/context/behavior information (such as rewards-eligible behavior calculations) has been extracted. Once the data has been fully used, it can then be erased in a Snapchat-like manner, or archived with a location-based password or key, or pointer to who has the password or key. Or, portions of the data could be randomly selected (or selected based on the user's memory profile) and stored for future verification/location-based security purposes. Depending on the addict, addict-situation, controller or controller-situation, or other factors such as court-orders or law enforcement requirements, knowledge of and/or access to location/context-related keys could be bypassed (or enhanced) to make it easier (or more difficult) for an addict's location/context data to be readily accessed. In certain circumstances, the addict's consent could be an absolute requirement for anyone to access the data—in other circumstances (e.g. court orders) the addict's consent might not be required at all.

The duration or longevity of location/con text-related data, particularly addiction-related data, is also significant. As indicated in the process flow in FIG. 12, not all location/context data would be stored indefinitely. To the contrary, once the utility of an addict's location/context data has been fully utilized—either in detecting and/or preventing and/or dealing with a high risk/relapse situation, or learning/adjusting/modifying applicable learning mechanisms, as well as rewards, there may not be any reason to (continue to) store the data and thus can be deleted in Snapchat-type fashion. On the other hand, if there is a longer-term reason to store such data (court orders, a desire by the addict to journal addiction recovery, etch, then location/con text-based privacy and security measures would be put in place.

If location/context data for an addict is indeed archived, in general it should not be easy to retrieve and be extension very difficult for non-authorized persons or programs to access. Location-based security, with different pieces of historical data protected by different location-based security mechanisms and passwords known to different persons, would achieve this high level of protection. To resurrect a 24 hour period for example may require location-based passwords from several different people—an electronic version of old-style bank lock-boxes that require multiple keys to be inserted at the same time to open the box. Instead, to retrieve the location data from Feb. 18, 20XX for addict A, it may require location-based passwords from the three different addict controllers that were on-duty that day, as well as the addict themselves, to reassemble/reconstruct that day.

Images used in a visual matching scheme such as in FIG. 11 need not be ones actually taken in photo form by a user or otherwise captured in a graphical form. For example, if the user had been detected at being at the intersection of Santa Monica Blvd and Sophie Street within an acceptable time frame (according to the user's memory profile), a street sign could be generated showing an street intersection sign image. Such images could even be generated using even more abstract mechanisms, such as a mileage street sign showing how far to certain locations could be derived by a visited location, then displayed in visual form. For example, if a person was in Disney World in Orlando, Fla. 2 months ago, and their profile allows for vacation locations within the last year to be used, a street sign could be shown that says 204 miles to Miami, 74 miles to Tampa, etc.—those being the mileages between Orlando and those cities. Thus, an image-based location key could be generated just using a visited location or latitude/longitude.

The image selection process for the above embodiments can be simplistic or very difficult. On the simplistic end, for example, only one of several images could be valid. On the difficult end, several could be valid, but they must be selected in order of oldest to newest (or vice versa). The latter, for example, could be images (pictures, addresses, etch of previous home locations, pets (that were only alive at a certain property), etc. that only the user is likely to readily know in the proper sequence, yet not require little additional effort by the user to actually remember. Thus, it would be possible to create a very complex password or verification sequence, yet easy for the user to understand, and nearly impossible for an outside party to know, at least without extensive research. A time or other context-based limit to provide the answers could be included in the verification algorithm to prevent such research from successfully taking place.

Another exemplary embodiment or variation of the present disclosure uses 3 dimensional, jigsaw-type verification. As seen in FIGS. 12, 13, and 14, a location or context can be divided into numerous pieces, then scrambled similar to a (2D or 3D) jigsaw puzzle, requiring the entire puzzle to be solved, only certain pieces of it solved, or solved for a particular type of solution, theme, and/or in a given time-sequence for example. The general philosophy behind such puzzle approaches is that it becomes progressively (even exponentially) more difficult for a human/entity not-familiar with the locations/contexts involved to solve the puzzle, while being only incrementally more difficult for those humans/entities who are familiar with the locations/contexts involved.

That said, it is possible to use location-based concepts in the generation of a traditional password. For example, if the first 9 images in FIG. 11 were offered as possible answers to a verification question/statement, and there were only two correct images out of the 9, with each frame being assigned a value from 1 to 9, then a point score could be calculated based on the values assigned to each image. A simple example would be if the two correct images had a value of 3 and 7, respectively, the resulting key/password could be thirty-seven (concatenation of the values) or twenty-one (the multiple). That traditional password adding potential capitalization and/or numbers, such as "Thirtyseven37", could then be used by the various addiction (or other verification) analytical systems in accessing active data.

The various exemplary embodiments described above may provide an extremely sophisticated capability that establishes and systemically enforces privacy policies to support a balance of functionality and privacy. There are at least two main types of privacy policy scenarios that may be established and enforced. The first is where the addict voluntarily signs up for functionality as disclosed herein. For such a scenario and associated policy, many of the more severe elements of such functionality may be made optional, such as disabling payment mechanisms, etc. A second scenario is an involuntary sign up of an addict by other parties with the legal right, such as by parents of minors, via judicial judgments, etc. In such cases, the functionality to be activated may be decided by those parties with or without the addict's consent or even without their knowledge (if deemed legal). Various exemplary embodiments may support and in some cases require the coordination and integration of privacy and/or security policies and systems by a host of parties: application(s) as disclosed herein: financial entities: support group entities (e.g. AA, etch, public safety and law enforcement entities: education entities (e.g. for teens, etch; retail/wholesale chains and individual stores, service areas (e.g. movie theaters, etch and services: individuals, and the like.

Various exemplary embodiments may provide functionality specific to a given demographic. One example of this is for teenagers. Teenagers, and especially teenage addicts—regardless of their addiction (though usually drugs or alcohol)—can have triggers and influences in their lives that are particularly distinct from other demographic categories: high school angst, peer pressure, parental pressure, academic pressure, sexuality issues, not to mention that most of the mechanisms for enabling the addiction to begin with are illegal. Also, many addicts in that age demographic have not reached the conclusion that they are an addict, let alone think they need help. They also are much more likely to be technically savvy, which can be a double-edged sword. On the one hand, they would likely be loath to give up/not use those devices/mechanisms that various embodiments may utilize (e.g. teenagers in this day and age are almost tethered at the hip with their cell phone, with one of the most often used disciplinary methods used by parents is taking away their cell phone privileges). On the other hand, teenagers are one of if not the most inventive demographic in getting around technical issues and constraints on their activities. It is anticipated that teenagers may represent a significant percentage of involuntary users of various embodiments. Accordingly, in an example embodiment, social networks may be used in detecting true friends (non-addicts or non-enablers) with those who are technically friends in an addict's network but are recognized by the addict, his family, and/or other entities (e.g., judicial system, etch to be a negative influence on the addict. For example, permission may be given by these friends (particularly the negative type) to transfer, copy, or otherwise apply that permission for the addict to track the friend to the application of the example embodiment. Thus, the negative friend's location could be used in the example embodiment to help the addict stay away from that so-called friend. This could be done with or without the addict's and/or the friend's permission, e.g. supporting the voluntary and involuntary privacy scenarios described above.

Unlike smoking where addiction may occur relatively immediately, alcoholism generally takes much longer and is much more nuanced in its progression, hence alcoholics may have very long periods of denial. In exemplary embodiments disclosed herein, sensors and other mechanisms may be utilized for alcoholism testing for a person consciously or not and/or with or without the person's consent.

In various exemplary embodiments of the present disclosure, various functionalities described herein may be integrated as a whole or in part, e.g., into one or more methods, mechanisms, and/or applications. While any individual element above could be implemented individually, it is anticipated that much of the value of embodiments of the present disclosure is in the integration of the above, in whole or in part, to accommodate the wide range of addiction enablers and alternatives, and the various technology platforms that could be involved. Such integration may include other applications such as family finders, social networking applications, weather monitoring, navigation applications, Facebook, Groupon, etc. Various embodiments can provide ways in which to make the most of the moment of value, e.g. at times and/or in context where an addict is in significant danger of relapsing.

That said, many features/aspects of the present disclosure are also anticipated to be of applicability to non-addicts or partially addict-related scenarios, such as persons with common medical conditions, sports enthusiasts, dating websites, law enforcement (e.g. additional functionality/flexibility beyond just GPS bracelets, providing other flexibility to the judicial system such providing innovative options to judges in DUI cases to revoke their parole if they are found to have stopped at a liquor store, etch, medical applications, insurance applications, employee verification, medical alerts, amber alerts, suicide prevention, etc. For example, blood alcohol sensors may indicate a relapse by an alcoholic. Any one or more triggers as disclosed herein may also or instead be used to identify an increasing suicide risk and be monitored accordingly.

All of the above covers one or more addictions: a substantial portion of the addict community has more than one addiction. Also, it covers addictions that may be replaced by others, such as replacing alcohol with caffeine and/or sugar.

Exemplary embodiments are disclosed of systems and methods of using location, context, and/or one or more communication networks for monitoring for, preempting, and/or mitigating pre-identified behavior. For example, exemplary embodiments disclosed herein may include involuntarily, automatically, and/or wirelessly monitoring/mitigating undesirable behavior (e.g., addiction related undesirable behavior, etch of a person (e.g., an addict, a parolee, a user of a system, etc.). In an exemplary embodiment, a system generally includes a plurality of devices and/or sensors configured to determine, through one or more communications networks, a location of a person and/or a context of the person at the location; predict and evaluate a risk of a pre-identified behavior by the person in relation to the location and/or the context; and facilitate one or more actions and/or activities to mitigate the risk of the pre-identified behavior, if any, and/or react to the pre-identified behavior, if any, by the person.

The pre-identified behavior may include pre-identified addiction-related undesirable behavior, and the system may be configured to be operable for monitoring for, preempting, and/or mitigating the pre-identified addiction-related undesirable behavior. The system may be configured to determine, through the one or more communications networks, a location of an addict and/or a context of the addict at the location; predict and evaluate a risk of relapse by the addict in relation to the location and/or the context; and facilitate one or more actions and/or activities to mitigate the risk of relapse, if any, and/or react to the relapse, if any, by the addict. The system may be configured to determine whether one or more addiction triggers predetermined in the system are active or present based on the location and/or the context and/or biometric, environmental, and/or behavioral data for the person. The system may be configured to determine whether one or more addiction triggers predetermined in the system are active or present by comparing data from one or more of the plurality of devices and/or sensors with one or more settings for the person. The one or more settings for the person may include one or more of blood pressure, heart rate, skin temperature, body temperature, respiratory rate, perspiration, weight, exercise schedule, external temperature, noise loudness, and/or noise frequency. The plurality of devices and/or sensors may comprise one or more biometric, environmental, and/or behavioral sensors that provide the biometric, environmental, and/or behavioral data for the person usable by the system in determining whether one or more addiction triggers predetermined in the system are active or present. The system may be configured to receive and process feedback and to adjust the plurality of devices and/or sensors including increasing, decreasing, and/or otherwise modifying one or more of the settings and/or a frequency of data collection in response to the feedback including actions and behaviors of the person associated with the data.

The system may be configured to predict and evaluate a risk of the pre-identified behavior by the person in relation to the location and/or the context by using data from one or more of the plurality of devices and/or sensors. The one or more of the plurality of devices and/or sensors may comprise one or more biometric, environmental, and/or behavioral sensors. The one or more of the plurality of devices and/or sensors may comprise one or more of a blood pressure sensor, a breathalyzer, a blood alcohol content sensor, a thermometer, a skin temperature sensor, a breathing rate sensor, a heart rate sensor, a skin moisture sensor, an olfactory sensor, a vestibular sensor, a kinesthetic sensor, an optical sensor, a retinal scanner, a voice recognition sensor, a fingerprint sensor, a facial recognition sensor, a biogestation sensor, an acoustic sensor, a microphone, a weather sensor, a barometer, a precipitation sensor, a gyroscope, an accelerometer, and/or a compass.

The one or more communications networks comprise an Internet of Things network including one or more physical devices, items, vehicles, home appliances, and/or household items usable by the system for determining the location of the person and/or the context of the person at the location. The system may be configured to determine the location of the person via one or more of an Internet of Things network, a global positioning system, cell tower identification, cell tower triangulation, a beacon, radio frequency fingerprinting, real-time location services, Wi-Fi based location systems, radio frequency identification based location systems, a drone, crowdsourcing, and/or simultaneous localization and mapping.

The system may be configured to predict and evaluate a risk of the pre-identified behavior by the person by using the location and/or the context and one or more of biometric, environmental, and/or behavioral data of the person; voice data of the person and/or another person, including one or more of tone, inflection, cadence, tempo, and/or pre-identified words; and/or movement data, including the person's walking gate, stride, and/or direction of travel; and/or date and/or time of day; and/or historical visitation patterns of the person to predict and evaluate a risk of the pre-identified behavior by the person; and/or monitoring social media.

The system may be configured to detect and track behavior of the person via the plurality of devices and/or sensors to determine applicability and value of behavior and to provide a corresponding incentive or disincentive for the person. The system may be configured to facilitate avoidance of one or more predetermined locations by omitting the one or more predetermined locations from one or more navigation applications and/or by de-augmenting the one or more predetermined locations from one or more augmented reality applications. The system may be configured to establish one or more geo-fences for one or more predetermined locations and to provide one or more alerts when the person crosses a geo-fence to enter or exit the predetermined location corresponding to the geo-fence or otherwise violates the parameters associated with the geo-fence. The system may be configured to use the plurality of devices and/or sensors to assess a likelihood that the person is an alcoholic, drug addict, activity addict, and/or substance abuser.

The one or more communications networks may include one or more of a local network, a public network, a private network, the internet, the Internet of Things, a wireless network, a terrestrial network, a satellite network, and/or wireline network. The location of the person may be a physical location or a virtual location. The context may include a situation, an environment, and/or a state of mind of the person based on one or more of biometric, environmental, and/or behavioral data of the person.

The plurality of devices and/or sensors may include a plurality of sensors configured to monitor the location and/or the context of the person at the location. One or more of the plurality of sensors may be located in, on, and/or near the person. A plurality of interface devices may be configured to engage in interaction with the person, with one or more support persons for the person, and/or with one or more third parties in the event the system determines a relationship between the location and/or the context and one or more triggers predetermined in the system that indicates a risk of the pre-identified behavior by the person. The system may be configured to select the interaction based on the one or more triggers and the location and/or the context of the person at the location.

The system may be configured to develop and/or update a profile of the person including one or more predetermined actions to implement for the person depending on the prediction and evaluation of the risk of the pre-identified behavior by the person in relation to the location and/or the context. The person may be a parolee, and the one or more communications networks allow the system to monitor the location of the person both indoors and outdoors. The system may be configured to be usable by another one or more persons to voluntarily and/or involuntarily monitor the location of the person and/or the context of the person at the location.

The one or more actions and/or activities facilitated by the system may include one or more of requesting the person to attend a nearby addiction support meeting, visit another one or more persons in a support network, and/or travel to a predetermined location for a certain activity; and/or providing an alert to a family member, medical personnel, law enforcement, or other support person or persons; and/or disabling a vehicle of the person; and/or automatically changing operation of a vehicle of the person to driverless; and/or informing a community member or addiction sponsor of the person; and/or monitoring the location of the person and a location of one or more support network persons and determining one or more scenarios that allow one or more support persons to be dispatched to the person's location or vice versa; and/or automatically playing a voice of a family member or a friend; and/or linking and coordinating an ad hoc meeting between the person and another person, persons, or group; and/or providing a location-based alternative and/or a location-based advertisement to the person via a mobile phone; and/or provide linkages to a mobile phone that provide one or more personal and/or impersonal reminders to the person about addiction consequences.

The system may be configured to restrict and condition access to the system and/or to the person's data collected by one or more of the plurality of devices and/or sensors through the one or more communications networks based on selection of location-based data for the person from a plurality of options presented by the system for selection, the plurality of options including the location-based data and one or more other options. The system may be configured to use one or more interface devices for interfacing with the person and/or to disseminate information to/from the person and/or one or more support persons for the person. The one or more interface devices may comprise one or more of tangible and/or tactile interfaces including one or more of a display, illumination, sound, vibration, heat, and/or smell interface.

The system may be configured to detect a relationship between the location and/or the context and one or more triggers predetermined for the person as being related to the pre-identified behavior; and based on the detected relationship, use one or more interface devices, mechanisms, or techniques to interact with the person, with one or more support persons for the person, and/or with a third party.

In an exemplary embodiment, a method for monitoring for, preempting, and/or mitigating pre-identified behavior generally includes determining, via one or more devices and/or sensors across one or more communications networks, a location of a person and/or a context of the person at the location; predicting and evaluating a risk of a pre-identified behavior by the person in relation to the location and/or the context; and facilitating one or more actions and/or activities to mitigate the risk of the pie-identified behavior, if any, and/or react to the pre-identified behavior, if any, by the person.

The method may include detecting a relationship between the location and/or the context and one or more triggers predetermined for the person as being related to the pie-identified behavior, and based on the detected relationship, using one or more interface devices, mechanisms, or techniques to interact with the person, with one or more support persons for the person, and/or with a third party.

The method may include determining whether the location and/or the context correspond to a high-risk location and context, then identifying one or more potential actions and/or available support resources to mitigate the risk of the pie-identified behavior, selecting one or more actions and one or more interfaces for the person, and implementing the selected action(s) and interface(s) for the person; and/or selecting and implementing one or more actions and one or more interfaces for the person if the location and/or the context indicate an immediate high risk of the pie-identified behavior; and/or selecting and implementing one or more preventive actions for the person if the location and/or the context correspond to a trending risk of the pie-identified behavior or behaviors, and/or adjusting and continuing to monitor the person's location and context at the location.

The method may include determining, projecting, or predicting a current or future context of the person at the location by analyzing and linking real-time data and historical data for the person, the real-time and historical data including the location of the person, data from the one or more devices and/or sensors, historical context of the person at the location, behavior patterns, travel patterns, health data, and risk calculations; and/or monitoring the person's physical and mental condition via the one or more devices and/or sensors including one or more wearable sensors and/or embedded sensors.

Facilitating one or more actions and/or activities may comprise determining which one or more devices and/or sensors are in use; determining available interfaces on the one or more devices and/or sensors that are determined to be in use; determining an inventory of potential interfaces desired by selected actions and that satisfy a privacy requirement and/or live 2-way communication requirement; and selecting and implementing one or more interfaces from the inventory of potential interfaces.

The method may include determining, through the one or more communications networks, a location of an addict and/or a context of the addict at the location; predicting and evaluating a risk of relapse by the addict in relation to the location and/or the context; and facilitating one or more actions and/or activities to mitigate the risk of relapse, if any, and/or react to the relapse, if any, by the addict.

The one or more communications networks may include one or more of a local network, a public network, a private network, the internet, the Internet of Things, a wireless network, a terrestrial network, a satellite network, and/or wireline network. The location of the person may be a physical location or a virtual location. The determination of the context may be based on one or more of biometric, environmental, and/or behavioral data of the person. The pre-identified behavior may include pie-identified addiction-related undesirable behavior. The method may include monitoring for, preempting, and/or mitigating the pre-identified addiction-related undesirable behavior. The method may include determining whether one or more addiction triggers are active or present based on the location and/or the context and/or biometric, environmental, and/or behavioral data for the person.

In an exemplary embodiment, a non-transitory computer-readable storage media comprises computer-executable instructions for monitoring for, preempting, and/or mitigating pre-identified behavior, which when executed by at least one processor, cause the at least one processor to: determine, via one or more devices and/or sensors across one or more communications networks, a location of a person and/or a context of the person at the location: predict and evaluate a risk of a pre-identified behavior by the person in relation to the location and/or the context: and facilitate one or more actions and/or activities to mitigate the risk of the pre-identified behavior, if any, and/or react to the pre-identified behavior, if any, by the person.

The one or more communications networks may include one or more of a local network, a public network, a private network, the internet, and/or the Internet of Things. The location of the person may be a physical location or a virtual location. The determination of the context may be based on one or more of biometric, environmental, and/or behavioral data of the person. The pre-identified behavior may include pre-identified addiction-related undesirable behavior.

Also disclosed are exemplary embodiments of systems and methods for providing location-based security and privacy for restricting user access. In an exemplary embodiment, a system is configured to restrict and condition access to the system and/or data based on a user's selection of location-based data from a plurality of options presented by the system for selection by the user. The plurality of options include the location-based data and one or more other options that are selectable by the user.

The system may be configured to present one or more queries and/or qualifiers to prompt the user to select corresponding location-based data from the plurality of options in response to the one or more queries and/or qualifiers. The system may be configured to restrict the user's access to the system and/or data at least until the corresponding location-based data is selected that satisfies the one or more queries and/or qualifiers. The location-based data may comprise one or more images that satisfy the one or more queries and/or qualifiers. The one or more other options may comprise one or more other images that do not satisfy the one or more queries and/or qualifiers. The system may be configured to restrict the user's access to the system and/or data at least until the corresponding one or more images are selected that satisfy the one or more queries and/or qualifiers, or when the one or more other images are selected that do not satisfy the one or more queries and/or qualifiers. The system may be configured so as to not restrict the user's access to the system and/or data when the corresponding one or more images are selected that satisfy the one or more queries and/or qualifiers.

The location-based data may include a location of the user and/or a context of the user at the location as determined by the system using one or more of a plurality of user devices and/or sensors across one or more communications networks. The location-based data may comprise data obtained by the system via an Internet of Things network of physical devices, items, vehicles, home appliances, and/or household items usable by the system for determining a location of the user and/or a context of the user at the location. The location-based data may comprise one or more images based on a location and/or a context of the location to and/or known by the user, whereby the one or more images are usable by the system as one or more passwords or keys for permitting access to the user data.

The plurality of options may comprise a plurality of images presented by the system for selection by the user. The location-based data may comprise one or more images based on a location and/or a context of the location to and/or known by the user. The images may comprise one or more of a visual, audio, graphical, video-based, photographic, textual, and/or alphanumeric image: a sensor reading: a static image: a dynamic image: a multidimensional image: a past image: a present image: a future image: a live streaming image: an image of a vacation destination: an image of a family member, an image of a pet; an image of a vehicle; an image of a residence; an image of a location; and/or a virtual or augmented reality image; and/or; a drawing; a distorted image; a modified image; and/or an artificially rendered image.

The system may be configured to present a multidimensional (e.g., 2D, 3D, 4D, etch combination puzzle that includes one or more keys and that is successfully completed when corresponding location-based data is selected from the plurality of options for the one or more keys. The system may be configured to restrict the user's access to the system and/or data at least until the successful completion of the multidimensional combination puzzle. The system may be configured to present one or more queries and/or qualifiers to prompt the user to select, for the one or more keys, the corresponding location-based data from the plurality of options in response to the one or more queries and/or qualifiers. The system may be configured such that the multidimensional combination puzzle is successfully completed when the corresponding location-based data is selected for the one or more keys that satisfy the one or more queries and/or qualifiers. The location-based data may comprise one or more images that are based on a location and/or a context of the location to and/or known by the user and that satisfy the one or more queries and/or qualifiers. The one or more other options may comprise one or more other images that do not satisfy the one or more queries and/or qualifiers. The system may be configured such that the multidimensional combination puzzle is successfully completed when the corresponding one or more images are selected for the one or more keys that satisfy the one or more queries and/or qualifiers. The system may be configured such that the multidimensional combination puzzle comprises a three-dimensional cube that is successfully completed when the corresponding one or more images are selected for the one or more keys for at least one or more faces of the three-dimensional cube. The system may be configured to present the plurality of options to the user for selection as the one or more keys in a rotating, moving, and/or changing manner (e.g., zooming in/out, distorted, etch and/or for a predetermined amount of time. The system may be configured such that the multidimensional combination puzzle comprises a two-dimensional grid or a jigsaw puzzle that is successfully completed when the corresponding location-based data is selected from the plurality of options for the one or more keys in a predetermined order or sequence.

The system may be configured to present one or more queries and/or qualifiers to prompt the user to select corresponding location-based data from the plurality of options in response to the one or more queries and/or qualifiers. The location-based data may comprise one or more images that are based on a location and/or a context of the location to and/or known by the user and that satisfy the one or more queries and/or qualifiers. The one or more other options may comprise one or more other images that do not satisfy the one or more queries and/or qualifiers. The system may be configured to restrict the user's access to the system and/or data at least until the selection of the corresponding one or more images that satisfy the one or more queries and/or qualifiers and the corresponding one or more devices used to capture the corresponding one or more images.

The location-based data may comprise a plurality of different images of a location and/or context of the location to and/or known by the user. The one or more other options may comprise one or more other images. The system may be configured to present one or more queries and/or qualifiers to prompt the user to select the corresponding images of the location and/or context in response to the one or more queries and/or qualifiers. The system may be configured to restrict the user's access to the system and/or data at least until the corresponding images of the location and/or context are selected that satisfy the one or more queries and/or qualifiers. The system may be configured to present one or more queries and/or qualifiers to prompt the user to select corresponding location-based data from the plurality of options in response to the one or more queries and/or qualifiers. The location-based data may comprise one or more images that are based on a location and/or a context of the location to and/or known by the user and that satisfy the one or more queries and/or qualifiers. The one or more other options may comprise one or more other images that do not satisfy the one or more queries and/or qualifiers. The system may be configured to assign a numerical value to the one or more images and to the one or more other images. The system may be configured to use the numerical value(s) of the corresponding one or more images selected by the user that satisfy the one or more queries and/or qualifiers for generating a key or password for accessing the user data.

The location-based data may include recent and/or historical location and/or context information of the user. The system may be configured to use the recent and/or historical location and/or context information of the user for a password reset verification, to prove that a user is not a robot, and/or to verify a financial transaction.

The system may be configured to restrict and condition access to biometric data, environmental data, behavioral data, and/or location-based data for a person, obtained by the system via one or more of a plurality of devices and/or sensors through one or more communications networks, based on the user's selection of location-based data for the person from the plurality of options presented by the system for selection by the user. The user may be the person, another person, and/or an accessor.

The system may include a plurality of devices and/or sensors configured to determine, through one or more communications networks, a location of a person and/or a context of the person at the location; predict and evaluate a risk of a pre-identified behavior by the person in relation to the location and/or the context; and facilitate one or more actions and/or activities to mitigate the risk of the pre-identified behavior, if any, and/or react to the pre-identified behavior, if any, by the person. The system may be configured to restrict and condition access to data for the person, obtained via one or more of the plurality of devices and/or sensors through the one or more communications networks, based on a user's selection of location-based data for the person from the plurality of options presented by the system for selection by the user, whereby the user is the person, another person, and/or an accessor.

The system may be configured to restrict and condition access to a person's data based on the user's selection of location-based data for the person from the plurality of options presented by the system for selection by the user. The user may be the person, another person, and/or an accessor. The system may comprise a non-transitory computer-readable storage media including computer-executable instructions, which when executed by at least one processor, cause the at least one processor to present the plurality of options for selection by the user including the location-based data and the one or more other options; determine whether the user selected the location-based data from the plurality of options; and restrict access to the system and/or data at least until it is has been determined that the user selected the location-based data from the plurality of options.

In another exemplary embodiment, a method for providing security and/or privacy generally includes presenting a plurality of options for selection by a user, the plurality of options including location-based data and one or more other options; determining whether the user selected the location-based data from the plurality of options; and restricting the user's access to a system and/or data at least until it is has been determined that the user selected the location-based data from the plurality of options.

The method may include presenting one or more queries and/or qualifiers to prompt the user to select corresponding location-based data from the plurality of options in response to the one or more queries and/or qualifiers; determining whether the user selected the corresponding location-based data that satisfies the one or more queries and/or qualifiers;

and restricting the user's access to the system and/or data at least until it has been determined that the user selected the corresponding location-based data that satisfies the one or more queries and/or qualifiers.

The method may include presenting one or more images that are based on a location and/or a context of the location to and/or known by the user and that satisfy the one or more queries and/or qualifiers; presenting one or more other images that do not satisfy the one or more queries and/or qualifiers; and determining whether the user selected the corresponding one or more images that satisfy the one or more queries and/or qualifiers; restricting the user's access to the system and/or data at least until it has been determined that the user selected the corresponding one or more images that satisfy the one or more queries and/or qualifiers.

In an exemplary embodiment, a non-transitory computer-readable storage media comprises computer-executable instructions for providing security and/or privacy, which when executed by at least one processor, cause the at least one processor to restrict and condition access to a system and/or data based on a user's selection of location-based data from a plurality of options presented for selection by the user, the plurality of options including the location-based data and one or more other options that are selectable by the user.

The computer-executable instructions, when executed by the at least one processor, may cause the at least one processor to present the plurality of options for selection by the user including the location-based data and the one or more other options; determine whether the user selected the location-based data from the plurality of options; and restrict the user's access to the system and/or data at least until it is has been determined that the user selected the location-based data from the plurality of options.

The computer-executable instructions, when executed by the at least one processor, may cause the at least one processor to present one or more queries and/or qualifiers to prompt the user to select corresponding location-based data from the plurality of options in response to the one or more queries and/or qualifiers; determine whether the user selected the corresponding location-based data that satisfies the one or more queries and/or qualifiers; and restrict the user's access to the system and/or data at least until it has been determined that the user selected the corresponding location-based data that satisfies the one or more queries and/or qualifiers.

The computer-executable instructions, when executed by the at least one processor, may cause the at least one processor to present one or more images that are based on a location and/or a context of the location to and/or known by the user and that satisfy the one or more queries and/or qualifiers; present one or more other images that do not satisfy the one or more queries and/or qualifiers; determine whether the corresponding one or more images are selected that satisfy the one or more queries and/or qualifiers; and restrict the user's access to the system and/or data at least until it has been determined that the user selected the corresponding one or more images that satisfy the one or more queries and/or qualifiers.

Exemplary embodiments are disclosed of systems and methods for monitoring for and preempting pre-identified restriction violation-related behaviors) of persons under restriction. For example, disclosed are exemplary embodiments of systems and methods of preempting and modifying behavior via sensors and the Internet of Things (IoT) to expand and enhance sentencing, probation, and/or parolee monitoring, enforcement options, and capabilities.

Exemplary embodiments of the present disclosure include systems and methods for monitoring, tracking, obtaining/collecting, and analyzing location, context, behavior/behavior patterns, and/or behavior and context-based trigger information about parolee(s), prisoners), or person(s) on probation ("parolee") using sensors and/or sensor networks on, in and/or around one or more parolees and one or more communications networks connected to and/or associated with the parolee(s). The systems and methods may include providing in formation/feedback and support to those parolees or other persons and/or applications to help in the modification of the parolee's location, context, and/or behavior/triggers before a violation occurs, or, if need be, preemptively responding to violations about to occur or in progress with actions geared towards providing information about locations, contexts, and/or behaviors to the appropriate authorities or other interested persons to help in their recapture and overall limiting of damage to the public and themselves.

Exemplary embodiments disclosed herein may enable new ways of sentencing or assigning parole or probation conditions ("sentencing options"), which are otherwise not possible or available today. Examples include sentencing DUI or DWI offenders to no drinking of alcohol or even being near alcohol or near those who have been drinking; prohibiting driving a vehicle under certain conditions such as being angry, being in traffic, or having drank alcohol; prohibiting drug offenders from being near high-risk crime (drug dealing) areas as well as drug-dealing "friends"; or identifying when a parolee (such as a sex offender) uses the Internet, watches inappropriate programming, or plays (e.g., violent, etch games. There is no limit to the types of sentences, or parole/probation conditions that could be enabled that are not possible or available today. Some examples, while unusual, are indicative of new possibilities that could have a major and/or positive impact on the parolee depending on the crime/violation involved. Examples include prohibiting/restricting participation in certain hobbies; not allowing drinking and/or smoking; performing public service activities with very specific times/permissible activities and/or with particular people; not being allowed to get angry or frustrated under any conditions or under certain conditions, places, and/or times; being required to attend and participate in AA (alcoholics anonymous) meetings and confirming/verifying such attendance and participation via exemplary embodiments of the present disclosure not just relying upon paperwork signed for the AA meeting; getting at least eight hours of sleep a night and never watching anything rated more violent than PG; interacting personally with certain people at least once a day; not playing video (e.g., Xbox, PS4, etch games with certain persons at certain times of day over certain amounts of time; requiring a clean residence at all times; not viewing (in any form) any sports events; eating at least two balanced meals a day; not getting excited/angry/frustrated while performing a job; not listening to certain kinds of music (e.g., sexually violent rap music, etch; not engaging in any sort of activity that could be deemed sexually harassing; never yelling at your spouse, ex-spouse, and/or children, and so forth.

Beyond these types of new sentencing options, exemplary embodiments disclosed herein may enable new ways of monitoring, tracking, analyzing, interpreting, and acting upon behavior and context data ("trigger data") from and/or about those monitored person(s). It may include tailoring sensor and other data collection mechanisms specifically towards a parolee's trigger history and profile (and predicated to some degree on the violations/crimes involved)

including key vulnerabilities or other aspects that contributed to past crimes or may contribute to violations of sentencing in the future—and new ways of analyzing that data, as well as new ways of providing information/feedback about the monitored person(s) to third parties—not just to law enforcement-related such as parole officers, but also to support persons that can assist the parolees/prisoners, as well as to parolee/prisoners themselves to help them "self-correct" their behavior preemptively, before it reaches violation status.

Particularly important is monitoring/measuring/calculating key activity/behavior "triggers" that might cause a violation. Triggers can be defined as "situations, circumstances, activities, events, contexts, mental thought processes and/or frame-of-minds that tempt or cause a parolee to want to engage in an activity or behavior known or identified to be detrimental to the parolee and/or others."

Such behaviors and triggers that could potentially be monitored/measured/preempted/modified/subject to violation include anger levels (e.g., relevant to general anger-based crimes, etch, anxiety/pain-related issues (e.g., drug usage/theft, etch, frustration-related specific issues (e.g., road range, etch, excitement levels (e.g., thrill seekers, etch, hunger levels (e.g., theft, etch, money issues (e.g., theft, drug distribution, etch, associates/friends (e.g., peer pressure-related crimes, etch, relative issues (e.g., assault etch, sexual activity (e.g., sexual crimes, etc.). Indeed, to the extent that a parolee/prisoner argued in his/her trial(s) that a "certain thing" caused the crime to be committed, exemplary embodiments disclosed herein may thus enable monitoring (e.g., by the court, etch for that "certain thing" (e.g., behavior, activity, or even mindset or frame of mind, etch not possible or available today.

The feedback and information provided (e.g., real-time, etch to third parties such as support persons include descriptions of key locations, contexts, behaviors, incidents, and/or events such as parole violations or violations "in process", including historical information about such behaviors/triggers. More importantly, exemplary embodiments disclosed herein may provide pre-identified recommendations for, enablement of, and/or automatic execution of pre-identified actions and/or activities that would preemptively mitigate/change his/her location, context, and/or behavior before it reaches violation status. The feedback to the parolees, support persons, or law enforcement could include warnings about "in process" violations, disturbing trends, or other aspects of the monitored person(s) location, context, and/or behavior that have the potential of being reversed or corrected before it reaches violation status, along with specific actions based on the parolee's past or present behavior or anticipated future behavior.

In total, exemplary embodiments disclosed herein enable new sentencing options; preemptive tailored/personalized monitoring of behavior, context, and triggers; use of support resources; knowledge of a parolee's triggers and those actions that may preempt/prevent/mitigate negative triggers, and the developing of actions based on all of the above to prevent/mitigate recidivism/relapse of the parolee would provide great benefits to the public and to the parolees/offenders/violators themselves. In the unfortunate case that such violations do occur, exemplary embodiments disclosed herein may also provide new ways of preemptively aiding in apprehension of the violator and in general preventing/mitigating any additional damage to the public.

By way of background, the inventor hereof has recognized that previous inventions in the parolee/prisoner tracking field have focused on GPS-based centralized tracking, monitoring, and detection of location-based violations, such as violating home detention or being in proximity to forbidden areas such as schools, spouse, or businesses. The reliance on GPS, such as in a GPS ankle bracelet, which in itself is susceptible to tampering, in such prior inventions has been inherently limited, as GPS generally does not work well indoors, and even outdoors it is susceptible to a variety of factors that can result in inaccuracies of 50 meters or more, limiting applications and use cases and even potentially resulting in erroneous alarms. The reliance on centralized monitoring of the monitored person has also caused a variety of issues (e.g., if the parole officer is on vacation with no backup, etch, as has reliance on tamper-detection capability on a GPS ankle bracelet which can provide no benefits if the monitored person decides he/she doesn't care anymore and decides to go on a non-tracked crime spree.

By way of further background, the inventor hereof has also recognized that a focus on the location of a monitored person has resulted in limited attention being given to the least tangible aspects of the monitored person's life, particularly their mindset/frame-of-mind (such as being able to monitor their anger levels), as well as their broader activities and behavior while they are inside their home or other "confined" area (where GPS doesn't work). To the degree that such activities/behavior has been focused on, it has been for the hastening/accelerating of potential violations—not for purposes of preempting such a violation, or even proactively enlisting a support network to modify the parolee's/prisoner's behavior before it becomes a real or actual violation-worthy problem, finally, the security of parolee/prisoner information has generally been assumed to be secure and/or of little interest to anyone outside law enforcement; such an assumption today and going forward will likely be incorrect; in the future "stewards" of a parolee's data could be others such as support personnel keenly interested in preventing the parolee from having his sentence invoked or parole/probation revoked.

After recognizing the above issues, drawbacks, and obstacles with parolee monitoring and tracking, the inventor hereof has developed and disclosed herein exemplary embodiments that may address all of the above-noted parolee monitoring and tracking issues, drawbacks, or obstacles. As disclosed herein, exemplary embodiments may provide more comprehensive, more accurate, more preemptive, and more supportive monitoring and tracking, through one or more of the following elements:

Deploying and monitoring indoor and wearable sensors connected via an Internet-of-Things (IoT) network.

Use of the IoT network to decentralize or otherwise monitor "at-the-edge" potential rule breaking and other concerns.

Leveraging of other networks and environments (inside and outside, even ones without electronic or physical access by the parolee), for the purpose of behavior/activity assessment and analysis.

Connection to other sensor-based networks to provide broader, seamless, 24/7, anywhere/any time monitoring to prevent a violation at any time, in any circumstance.

Using pre-identified prevention/preempting behavior and context-based "triggers" to appropriate select and calibrate an appropriate subset of sensors (from a wide range of sensors, across all networks and environments), targeted at measuring and calculating/analyzing current behavior versus permitted "pre-identified" behavior and context, and, as needed relative to historical behavior and context. Examples of triggers include but are not limited to: Anger, Anxiety, Boredom, Change, Children, Conflict, Depression, Disorder, Embarrassment, Escape, Envy, Excitement, Fun, Frustration, Guilt, Health issues. Holidays Hunger, Insomnia, Job stress. Loneliness, Mid-life Crises, Money worries. Noise, Overconfidence, Pain, Peer Pressure, feeling Powerful or Powerless, Proximity (e.g., to the substance, etc.). Fear of Quitting (e.g., the substance or activity, etc.). Relationship issues. Relatives, Reminders, Sex, Shopping Situations, Social Situations, Special Occasions, Stress, Taste and Smell, Times of Day, being Tired, being "Unfun", being a Victim (e.g., of crime, abuse, etch, ex-spouses/partners, Yelling, even Season or Weather changes, and/or Music.

This term "context" as used herein may refer to the situation or circumstances in which a behavior, event, or activity occurs, e.g., the particular setting in which the behavior/event/activity occurs, etc. For example, when attempting to understand behavior, it is important to look at the situation or circumstances present at the time of the behavior. For example, the behavior Anger can be detected through measuring blood pressure, heart rate, skin temperature, and detection of yelling sounds, and for some people be considered a trigger by itself. But for some other people, in some circumstances, it is particularly valuable to know the context. For example, a person might be in the presence of his ex-spouse, and they may be in an argument. Or, for example, they could be having the argument in a public place on a hot day with no air conditioning. Having this understanding of context, in addition to behavior, helps to select the best preemptive or mitigating actions to cool down the Anger before a violation (e.g., a drinking relapse, etch occurs, such as getting the parolee physically away from the ex-spouse as soon as possible and to go cool down in an air conditioned, private place.

While there are potentially hundreds of possible addiction triggers (in the form of behaviors, contexts, or both behavior and context combinations), and many thousands of trigger combinations (such as Anger and Loneliness occurring at the same time), exemplary embodiments disclosed herein may emphasize the "pre-identification" of one or more of these behaviors and/or context-based triggers as a way to select, calibrate, and analyze various sensor and sensor network data collection of various pre-identified individuals, and to select and implement pre-identified actions based on those behaviors and/or context-based triggers to maximize the potential of preventing a violation or escalation of a violation.

Employ a risk-detection and action/activation system that provides an "early-warning-system" for early detection of adverse triggers such as "wrong or adverse" behavior, "wrong or adverse" contexts, and/or "wrong or adverse behavior and contexts", and implementing a set of actions with appropriate support resources to stop or "preempt" the parolee by pursuing actions and/or activity that address the triggers (behavior, context, or behavior/context pairings), before it reaches violation status, or if violations have already occurred, preempting any additional damage by the violator.

Use of big-data historical data collection and analytics combined with various learning protocols, artificial intelligence systems, neural learning networks, etc. to refine each individual's trigger profile and associated sensors/sensor settings, as well as continually improve actions and their effectiveness in preempting unwanted behavior. Such systems/methods can be used in designing and implementing more nuanced or "tiered" reward/punishment systems (e.g., states between being out on parole or back in prison, etch, and/or in gaining or losing points depending on the occurrence of performance of pre-identified (good and bad) behavior and/or activities.

There are many different embodiments of the present disclosure, but some of the more straightforward use an addiction-related crime, such as a DUI (Driving Under the Influence) arrest or a drug-trafficking charge. Such exemplary embodiments (generally, in increasing order of complexity and sophistication) may include:

1. A person on parole on DUI charges is prohibited from drinking or driving under the influence. A profile is setup flagging those activities, which in turn identifies key sensors to be activated to collect data on Blood Alcohol Content (e.g., breathalyzers included in various devices including the parolee's smartphone, required-wearing sensor bracelet, and in the parolee's home (by the parolee's bed and bathroom sink), etc.). All sensors are setup to collect any detection of alcohol data and immediately report to a central monitoring center (e.g., a rule violation is calculated locally), or the "raw" data is sent to the center for processing and rule violation checks. Any violation immediately results in a multi-media message to a parole officer that includes the rule violation information as well as supplemental information (e.g., where the violation occurred, where the violator is at presently, and BAC, etc.). Immediate steps are taken to "secure" the violator, including disabling all of the violator's cars, notifying anyone who has a restraining order against the violator, etc., as well as activating sensor networks outside the violator's immediate location to monitor the violator in case of attempted "escape". This includes GPS and/or various geofences (e.g., Mends' homes, etch to which the violator may attempt to escape on foot.

2. In an exemplary embodiment, an Internet of Things (IoT) network is established in the parolee's home, which besides connecting to (all) the breathalyzers, also connects to sensors on or near any alcohol (liquor cabinet, refrigerator, etc.). A proximity rule is established prohibiting physical contact with any alcohol-related container, such that not only liquor cabinets/wine storage are activated, but select refrigerator sensors on all alcohol beverages (e.g., a bar code reader that reads every bottle removed from the refrigerator, etch, and other bottles of alcohol-containing liquids (e.g., Listerine, etc.). If the IoT/sensor network detects immediate proximity to alcohol by the parolee or monitored person, or such products are moving (e.g., via bar codes, RFID, or motion sensors, etch, yet there is no indication (yet) of an immediate violation (e.g., BAC content, alcohol-sensitive "smell" detectors, etch, then a message is sent out to the person's "support network" that indicates that the person is (possibly) in imminent violation of parole/release conditions. The underlying logic machine may then analyze the location and other parameters of possible support personnel (such a familiarity with the person's present location) and directs them to immediately contact the person and/or go to that person's location to prevent/preempt the person from actually imbibing in alcohol and thus triggering a violation. If, once the support person visits the monitored person, the support person determines there was a potential violation, but it was stopped in time, then appropriate negative points/demerits are awarded to the monitored person. An accumulated points level of X may result in increased visits from a parole officer or some other punishment.

3. A parolee may be allowed outside the parolee's home for 2 hours from 2-4 pm but is not allowed within 100 meters of certain places, such as schools or liquor stores. (Note: Current GPS ankle bracelets often have variability in accuracy, up to over 50 meters or more in certain circumstances). Thus, "supplemental" readings are needed to collaborate a potential violation. Also, in some situations a GPS ankle bracelet battery life is a concern, thereby providing an incentive to conserve battery life if possible. A "wearable" (e.g., bracelet, clothes, hat, jewelry, etch with a specialized transmitter (that the parolee or monitored person is required to have on his/her person and active) transmits a signal at a certain frequency (and with an identifier) when the parolee leaves home (e.g., it is activated upon crossing a reverse geofence, along with the GPS capability, etc.). The being at-home assurance is done by the home's Internet of Things (IoT) sensor network that ensures that the parolee is at home by using sensor/sensor networks, such as motion sensors during daylight hours, and the use of to-the-outside door sensors that activate/deactivate the GPS bracelet when such an outdoor door is opened/closed.

Once outside, with the GPS activated and the proximity transmitter transmitting, the parolee runs a variety of errands. But if during the errands, the parolee or monitored person comes close to a (e.g., forbidden, impermissible, etch liquor store, a sensor at the store (which may be in a mall or otherwise indoors along with other stores and thus the GPS would not work well) detects/receives the signal, and records time, place, and identifier, including whether the parolee actually entered the store (e.g., via RFID or other precise egress-detection means, etc.). Alternatively, the bracelet or smartphone on/carried by the parolee detects and records the presence of several Wi-Fi networks (e.g., from the various stores, etch, along with signal strengths and (if possible) directional information of the signals. A logic program running real-time or after-the-fact does a real-time (local/edge) calculation or (possibly later) sends the data to a central processing server, where a precise location map and breadcrumb trail is developed and analyzed, and determines whether a violation occurred, and if so whether it was only a "technical" violation (e.g., the parolee was within 50 meters, but did not enter the store, etch or a "real" violation occurred (e.g., actually entering the forbidden or impermissible store, etc.). Because it is possible that the parolee had never entered the mall before, the parolee may have not realized there was a risk of the violation. Therefore, the system would perform a historical analysis to identify any instances of familiarity with the mall. If not, and a "technical" violation, then the parolee may be let off with a warning or some demerits. If a "real" violation did occur, the location of the parolee is reported and the parolee is taken into custody and the body of location evidence used to prove beyond a reasonable doubt that the violation indeed took place.

4. An exemplary embodiment addresses GPS ankle-bracelet tampering and related use cases. There have been numerous incidents of bracelet tampering (which can be difficult to prove that the tampering was deliberately done), or worse where the bracelet was removed and the parolee went on a crime spree, and where the parolee wasn't caught immediately because there was a delay between the tampering and it being detected and acted upon by the appropriate authorities. This exemplary embodiment may thus address these scenarios as follows.

A detection of (possible) tampering can be difficult to prove, as it historically relies on physical marks on the bracelet as the key evidence. An exemplary embodiment disclosed herein allows for increasing the body of evidence to prove (or disprove) the tampering, premised on the fact that tampering takes some time to successfully perform. In this exemplary embodiment, the parolee bracelet has a variety of additional sensors detect tampering (including matching pre-identified sounds and vibrations with measurements taken by the bracelet), as well as activating other sensors outside the bracelet upon first (local) detection of possible tampering. Other types of sensors could anticipate potential tampering, such as elevated heart rates or sweat levels.

The "matching" of sounds will result from internal bracelet recordings of sounds and other sound/vibration-based measurements taken when any sort of first indication of tampering occurs, such as a sudden bump of the bracelet (hitting it against something) or "clicking" (tampering with a screwdriver). With that initial detection, internal recordings of further sounds/vibrations are taken. In addition, any surrounding networks (particularly parolee's home network/IoT network) will be activated with a program to activate/wake up or otherwise increase the frequency of related readings (collectively "activating") that could prove (or disprove) the tampering. This includes activation of cameras, audio and vibration sensors, and any other indicators (such as sensors indicating prolonged stay in the garage and/or tool usage).

In the case that the parolee doesn't care if the parolee is detected, and cuts it off and takes off, another set of activations occurs, with speed of the essence as well as location precision (particularly for violent/sex offenders, stalkers, or grudge-based or psychotic offenders). Once any "full" tampering is conclusively (or with high degree of certainty) detected (such as tampering warnings followed by no motion by the bracelet yet other motion detected within the home confinement area), a variety of actions would be activated. The first set of activations would be focused on "preemption", e.g., preempting the possibility of escape as well as harm to the public. This kind of preemption includes disabling of any vehicles or automatic locking of doors (e.g., actions that could be controlled locally and activated real-time, etch, to alerting of nearby (as determined by other sensor networks) law enforcement or support personnel (who while not having apprehension authority, could help in finding and tracking the parolee manually). Alerts would also go out to known places and associates of the parolee, as well as Amber-Alert type notifications (e.g., broadcast, etch to the parolee's past victims and the general public, which could include photos and videos and other descriptors.

In addition, communications with the cell phone carrier and other communications providers of the parolee would be made, and real-time "pinging" of the parolee's device(s) started, as well as "activation" of any nearby (according to last position) sensor networks that could potentially help detect an on-the-run parolee. Real-time pinging allows use of device GPS to provide real-time, precise locations, in contrast with other methods that provide less accurate cell-tower based location estimates. In the event the parolee doesn't have such a device with the parolee, a continually updating ring of sensor networks would assist in obtaining at least a somewhat accurate location of the parolee. Real-time pinging currently requires a court order. Exemplary embodiments of the present disclosure envision a streamlined process for obtaining such an order in near-real time by packaging the evidence and presenting to a judge or judge equivalent for sign-off, then activating a pre-setup application interface to the carrier's systems to enable and report real-time GPS pinging.

Any responses to the alerts would be automatically compiled and analyzed, with a continually updated set of locations provided to appropriate humans and other tracking applications (particularly important if parolee is in a vehicle despite the preempting efforts).

In any tampering scenario, it would be beneficial for all concerned to preempt any tampering allegation, by immediately providing feedback to the parolee that tampering is being perceived, thus serving as a deterrent to further attempts. This preempting could be provided via a variety of scenarios, including alarms or vibrations from the bracelet, automated messages via the parolee's smart phone, etc. The interfaces could further include activating various alarm-type mechanisms within the environment where the parolee is at the time, such as the parolee's home (e.g., via an Internet of Things network, etch, such as a locking of doors or turning on of speakers or video to broadcast a message, etc. A key part is to anticipate the appropriate types of interface(s) to communicate with the parolee in order to maximize its speed and effectiveness, such as keeping "track" of what types of devices, mechanisms, and interfaces are currently (or most recently used) by the parolee, such as using the parolee's phone (immediately sending text/MMS messages, instant messaging, or phone calls; using the parolee's surfing the Internet (via desktop computer) (immediately enabling a Skype/Facetime session); watching TV (breaking in to the video feed with a pre-broadcast warning message); sending messages (even disorienting ones) to displays such as Google Glass; activating pain/discomfort-based "messages" in the form of shocks, intolerable noises, or even sedative drugs; displaying pre-recorded (or real-time) holographic images by doorways via projection mechanisms if the parolee is in the process of leaving the house, etc. The key is to identify and focus on the interfaces (and appropriate actions) that will preempt/deter the potential violator from making things any worse.

Once the parolee has been precisely located (either as a result of the preemptive actions or "reactive" locating efforts), the parolee may then be "followed" (e.g., continuing to report the location to law enforcement, etch, as well as continually calculating or anticipating possible "future" locations (e.g., based on past behavior stored by, obtained by, or accessed by this exemplary embodiment, etch and activating appropriate preemptive inhibitors to escape, such as if the parolee is approaching the home or residence of the parolee ex-spouse and may have the ex-spouse's car keys, in which the ex-spouse's car may then be disabled according to exemplary embodiments disclosed herein.

There are numerous other exemplary embodiments associated with this present disclosure. Some of the more common violations that could benefit from such exemplary embodiments include: possession, use, and/or intent to distribute (or arrange distribution of) controlled substances, theft. Driving under the Influence (DUI), aggravated assault (e.g., assault related to original/prior convictions, particularly sex/child-related, other forms of assault, etch, receiving stolen goods, etc.

Parolees and/or prisoners on some sort of controlled/temporary release are subject to significant rules that, if violated, will result in parole being revoked or modified, and/or privileges being revoked/modified. Such rules include but are not limited to: curfew violations, committing of (additional) misdemeanor/felonies, not reporting to a parole officer, crossing state lines or otherwise moving outside prescribed boundaries, substance usage/abuse, associating with specific person(s), violating court orders or other court mandated boundaries, off-limits, or non-interaction, use of vehicles, etc. Many of these rules/restrictions are location-oriented (and currently detectable), but behavioral violations are limited to rules that can only be detected by specific, controlled tests (such as drug testing, etc.). Exemplary embodiments disclosed herein provide the ability to detect a much greater range and types of behaviors/contexts (triggers), allowing more flexibility and/or precision in rule settings by law enforcement/judicial bodies, as well as the ability to monitor such behaviors to assist the parolee/prisoner in avoiding such behaviors before they reach violation status. Such triggers that could potentially be monitored, measured, preempted, modified, and/or subject to violation include anger levels (e.g., relevant to general anger-based crimes, etch, anxiety/pain-related issues (e.g., drug usage/theft, etch, frustration-related specific issues (e.g., road range, etch, excitement levels (e.g., thrill seekers, etch, hunger levels (e.g., theft, etch, money issues (e.g., theft, drug distribution, etch, associates/"friends" (e.g., peer pressure-related crimes, etch, relative issues (e.g., various, particularly assault, etch, sexual activity (e.g., sexual crimes, etch, etc. To the extent that a parolee/prisoner blamed a "certain thing" for causing the crime to be committed, exemplary embodiments disclosed herein enable monitoring (e.g., by the court, etch of such a "certain thing" that historically has not been otherwise detectable, measurable, or practical for some technological or other reason.

The collection and monitoring of such information, of course, has the potential of being "big brother" on steroids, measuring and monitoring the behavior of a person close to 24/7. To protect the rights and privacy of those persons, it is critical to provide the appropriate level of security to such information. Unfortunately, today's security mechanisms are vulnerable to hacking or other types of abuse. Thus, exemplary embodiments of the present disclosure may use a variety of individual and/or layers of security mechanisms and/or blockchain technology to record such transaction with the appropriate keys to "unlock" full data sets only to the appropriate persons and only for behavior/location/ context issues. Control of these keys/unlocking capabilities will have many forms depending on the parolee, crime, triggers, and other factors, but in general multiple types of humans (and even machines) may be such data "stewards" such as law enforcement, judicial members, support members, medical personnel, etc. An exemplary embodiment may include one or more systems and methods for providing location-based security and/or privacy for restricting user access as disclosed above.

One exemplary embodiment may include monitoring for, preempting, and/or mitigating pie-identified behavior, particularly substance use as disclosed herein. This exemplary embodiment may thus utilize methods and systems disclosed above to preempt (to the degree possible) a relapse by the parolee/prisoner, just as it would an addict, through various mechanisms such as use of support personnel, safe spaces, and identification and execution of actions as alternatives to drinking or using drugs. A further distinction may be that in the event of a relapse (e.g., usage, etch, various alarms may be triggered to appropriately inform law enforcement personnel, but ideally before this would happen utilizing the preemptive measures and support resources of the present disclosure to prevent the relapse from occurring or worsening.

An exemplary embodiment includes the detection and preemption of activities associated with associating with disreputable persons, potentially including an increased risk of performing a violation with those persons such as distributing drugs. This exemplary embodiment draws not only on the location of the parolee/prisoner, but extends that knowledge to anticipating the context (what they are doing, how they are doing it) in addition to the location (where, and when), to understand the why. This is supplemented with external data sources, such as social media postings and purchases, and (if available) similar information from those "associates" to compare the data sets to detect any potentially rule-breaking associations.

An exemplary embodiment includes the detection and preemption of driving under the influence (of drugs or alcohol), a major cause of parole violations. The sensors in, on, and/or associated with the person will enable detection of an "in progress" violation, not only by "traditional" methods (e.g., blood alcohol content or similar methods, etch, as well as detection of location, context, and/or behavior that "anticipates" such behavior, such as driving near/stopping by a liquor store or by known areas of drug dealing, as well as combining such information with locations of other persons known to be associated with the person's prior violations. The location of such $3^{rd}$ persons' could be determined by similar or other tracking mechanisms, as well as detection of such 3rd person's proximity "signatures" in the form of their device transmissions, attempts at peer-to-peer communications, monitoring of social media location postings, etc. Such "mashups" enable early detection of high risk situations that could avoid an actual violation (and associated potential damage). Support can take many forms, such as automatic facial recognition.

One form of unique identification is facial recognition. An exemplary embodiment may include the use of crowdsourcing image/video recognition/profile scanning to extend the reach of a victim's network. For example, the victim's device could connect to any devices within range of the victim's device and use their image/video/profile scan applications (obtaining distinct, even unique elements in a person's facial structure) to "scan" the environment around those devices. In turn, the images/videos/profile scans would be compared to data for the perpetrator to identify a match or probability of a match, and report this back to the victim. This concept can be extended to where the victim is going in the future, in order to obtain an "all clear" status. Such information (e.g., perpetrator in the vicinity of the victim despite the court order, etch is anticipated to be used to prove violations in court.

An exemplary embodiment includes the prevention/preemption of the parolee/prisoner from coming in contact with banned persons (e.g., court order, restraining order, etch or types/classes of people (e.g., minor children, etc.). This exemplary embodiment may enable more precise location determination via non-GPS technologies, allowing more specificity in court orders as well as evidence in violations. It also allows variations in behavior in court orders in addition to or instead of location, such as proscribing the non-allowance of Anger (with associated readings such as blood pressure and skin temperature levels combined with proximity to the spouse, for example), as well as early detection of "in progress" violations such as rising Anger that would trigger the intervention of support personnel to prevent Anger from passing certain thresholds and thus trigger a violation. Sexual parolees or those convicted but have served their time, but still have to register as a sex offender, could be monitored as part of their release. Sensors in this exemplary embodiment may be used to detect rising testosterone levels, or interfaces with mobile and/or fixed devices could monitor web activity to detect any porn or sexual content related to the original offense(s). Such sensor readings/activity could trigger support response to intervene before levels reach a point where the person reaches violation status (such as being tempted to get in proximity to a school). Alternatively, such "pre-crime" readings/activity could initiate a medical response such as automatic administering of testosterone-reducing drug, for example, or other medicine designed to reduce sexual desire. If such support/medical response(s) in response to a rising risk of "relapse" are not successful, then an alarm could be sent to the appropriate authority to apprehend the person for temporary "safe-keeping" until the risk has passed. The information sent would include the location of the person and the nearest "safekeeping" facility, which may or may not be a formal incarceration facility.

While the use of bracelets and other "wearable" technologies for the tracking of individual persons with specific location-related crime and/or parole-oriented limitations is known, there are many situations where the person involved has not actually been charged with a crime and/or the accused is not legally enforceable to include such an object on or near their person. The use of Restraining Orders to prevent stalking and other personal-interaction crimes and issues is an example. While victims of such personal violations can obtain such orders, generally the evidence of an actual crime is not egregious enough (or not criminal in nature) to warrant a judge ordering the stalker to wear such an object. This exemplary embodiment may enable the ability to track the "criminal" in a way that does not require such a wearable object. There are ways to do this via exemplary embodiments disclosed herein. A first way is for a court or other entity to order that an application be activated (associated with this disclosure), and to be put on the perpetuator's phone and other devices. The above instance may have a couple limitations, such as requiring access to (and permission of) the perpetuator's devices for such applications to be installed. The functionality of this part of the capabilities on the perpetuator would include monitoring the location, context, and/or behavior of the perpetuator as it relates specifically to the victim.

For example, in the case of ex-spouses/partners etc. it may be that the victim is most at risk in cases where the perpetuator becomes in an angry state, and/or when drinking. Other aspects described herein would seek to monitor/detect. While a court can do this, there are ways around it, notably obtaining other devices (e.g., replacement phones, etch, or to just not use or turn off devices with the application on it. While it is possible to detect such "active non-usage", it would be cumbersome to monitor and report said non-usage and to seek remedies. A better, if potentially less precise way of generating a "perpetuator alarm" is to use the sensors and other detection capabilities around the victim in order to detect the presence of the perpetuator. Specifically, the victim will "calibrate" the sensors and other controllable technologies to look for a "signature" of the perpetuator and use that to warn him/her of a rising risk situation. Such a signature could come in many forms. One form may include an identifier id or node address that uniquely identifies the perpetuator, either "truly unique" (such as a phone SSID or unique bracelet/wearable Identification Number, etch, or a "relative" unique address that enables clear identification within the context of the victim, such as the victim's network, peer-to-peer communications with the victim's device, a "victim network", a "perpetuator network", a "crime" network (e.g., theft in Missouri/Illinois, etch or some other network that in combination with a device identifier is able to uniquely identify the perpetuator. Various other limitations could be included such as time-based parameters that would both help to uniquely identify the perpetrator as well as provide a degree of privacy (e.g., the perpetuator would only be identifiable while the court order was in force, etc.). Because such unique ID's are either not broadcast or otherwise communicated outside a cellular network (such as a SSID), such a unique ID could be obtained in various other ways.

An exemplary embodiment may include the use of beacons. Historically, beacons have been used as one-way transmitters, typically attached to a wall in a room or other defined space, and used to trigger sensors in a phone or badge. Because beacons generally have limited range, a phone or device receiving a beacon transmission is by definition in the vicinity of the beacon, such as in a particular room, etc. The phone/device can then by itself or with other location determination systems infrastructure report the location to the infrastructure or other types of location services.

Exemplary embodiments may use the above type of real-time location service, but it is generally limited to a defined space, such as a hospital or campus, etc. As such, it has limited utility in terms of warning a victim if a perpetrator is anywhere else but that campus, hospital, or other defined space. Accordingly, exemplary embodiments disclosed herein may include a beacon on, in, or around the perpetuator's device, and will use that infrastructure to broadcast a signal uniquely identifying the perpetuators device. Once properly equipped, the perpetuator will be unable to silence the beacon (potentially even while off), and will likely have longer range than today's beacons. In fact, the beacon range could be set to a predetermined distance consistent with a court ruling, e.g., not within 1000 feet of the victim, etc. In turn, the victim's device(s) will be set to detect such beacons, as well as the individual perpetrator's' ID, which if "heard" by the victim's device means that the court order was violated. And, in turn, the victim's device can automatically inform law enforcement, which can then use its own methods for precisely locating the perpetrator. A refinement could be a 2-way beacon in the perpetrator's device, which could inform perpetrator that the perpetrator is violating the order (presumably it being done innocently/inadvertently), so that the perpetrator can quickly move away from the victim. For example, the perpetrator could perhaps be given a 2-minute lead time before the perpetrator is considered to be in violation.

An exemplary embodiment may utilize the "natural" tracking capabilities of wireless carriers. As part of their normal function, carriers need to keep constant track of where every subscriber is (that has their device(s) powered on), to be ready to connect at a call, text, or data session at any time, to be able to hand off to the nearest available tower when the subscriber is moving, and for billing purposes. The part of the process that tracks the subscriber (specifically, tracks the cell tower that the subscriber is connected to at any one time) is through the use of a Home Location Register (HLR) and a Visitor Location Register (VLR). As part of the call setup process, the HLR and VLR are checked and updates to reflect the device's location. An exemplary embodiment may modify this process in at least one of several ways. The first is once the carrier is informed that a subscriber has a court restraining order against the subscriber that has a location limit(s) to one or more location and/or other devices/subscribers, an indicator of such an order may be provided, in the form of a flag or other database table element, to indicate there is such an order. Additional information could also be included in the HLR/VLR, such as duration of the order, the locations/devices/subscribers they involve, and the respective location ranges. Every time a carrier "sees" a request to setup a call or terminate a call, if such a flag is set, the carrier will output the device's location to an external software interface, (possibly) along with the additional information such as devices/numbers/IMEI of persons who may need to be notified. A location lookup of the victim(s) phone current location may then be initiated, as well as other potentially applicable locations (e.g., victim's home or work, school, etch, and compare the locations and determine if the terms of the order are being violated, such as being within 1 mile of the victim or the victims/home or work. If so, appropriate action could be taken by the applicable law enforcement, but on an immediate basis the victim will know to move their own location immediately to stay out of harm's way.

One issue with this approach is while the victim's location can be precisely determined by the GPS in their device, the perpetuator's phone is being located by cell tower. There are several potential solutions to enhance the perpetuator's accuracy. The first is for the victim software to execute a "network initiated" request to the carrier for a more precise location. This could be done through location pinging capabilities already done for law enforcement purposes, or, alternatively, using an application similar to those used by family tracking applications. Another is utilizing the software and/or methods described earlier that resides on the perpetrator's phone. In this instance, the idea is that the HLR/VLR serves as an "early warning indicator" for the victim, and also as a legal initiating to a process to obtain a more precise location, through various means, e.g., Wi-Fi, RFID, beacon, RTLS, etc.

An exemplary embodiment may be configured to be involved with stalking or boundary sentences such as not leaving the state. The detection of absconding or otherwise leaving an area that a court has required a person to stay within is generally a straight forward process and system in the form of a geofence and a reporting of a violation of that geofence to the appropriate authorities. But preempting such a violation or anticipating it in the act (before crossing the geofence boundary) is another matter, one addressed by exemplary embodiments disclosed herein. Once a parolee/prisoner is anticipated to be at or above some level of absconding risk (generally at time of parole/release), tracking of movements and behavior begins using applications on the person's phone and potentially on wearables (e.g., bracelet, etch mandated to be worn. Such devices/wearables can generate a significant amount of data about movements/activities of the person, and over time can begin to detect/develop patterns as to how the person is living their lives. A material change in this activity can be an indicator of uncertainty or confusion on part of the person—a mindset that often precedes serious, non-common-sensical actions like fleeing the area (absconders are nearly always hit with a much worse penalty than they would have received if they had stayed for the original offense sentencing).

But "forcing" a person who has little desire to wear something or allow operation on their phone is a real problem, particularly if remedies require the victim constantly going back to court to enforce the terms of the restraining order. If the perpetuator can be monitored without active involvement on their part, this would be ideal. Exemplary embodiments disclose such capability, e.g., requiring broadcasting of a specific signature/signal, or requiring the cooperation of the wireless carriers involved.

An exemplary embodiment involves violations/crimes associated with the possession of a gun despite a court order. Detection of such a gun can be done by an exemplary embodiment directly or indirectly. Directly has to do with special locks/sensors attached to gun cases of guns in the possession of the person. An exemplary embodiment enables "tripping" of such sensors to send alarms to the appropriate support personnel (if such intermediate interventions are allowed in such cases) so that the support personnel can follow-up and see if there is a legitimate reason for the case to be opened/tampered with.

An indirect method includes detection of locations, sounds, or associated "damage" associated with guns and gun shots. Detecting the person's presence at a gun range is one such potential indicator as are noise detectors that register a gunshot sound (in terms of loudness or type of noise). Sensors tuned to hand residue could detect gunpowder. Any one or more or all of these could be utilized in detecting an "In progress" possible violation that can then utilize the support network to intervene, and failing that notifying the appropriate authorities or support personnel.

An exemplary embodiment involves bail jumping/bond violation and includes detection of and tracking down of bail jumpers (persons on bail that do not meet their court appearance). Such people generally are divided into 2 classes: 1) Accidental, or 2) Deliberate. Accidental are just that—they forgot about their court date. In these cases, the bounty hunter has to find the person and bring the person into court to get rebonded and rescheduled. An exemplary embodiment disclosed herein may be tuned to automatically detect such accidental violations and immediately inform bondsman (and hunters) of such violations, as well as the current location/context/behavior and likely locations/contexts/behavior during the next 24-48 hours, based on the person's history since the original bonding, which is tracked via an app on the bonder's phone as a condition of getting the bail. Thus, if the failed bonder usually is bowling Wednesday night, that is likely where the bonder will be the Wednesday after the missed hearing, and the bounty hunter can make appropriate arrangements based on that bowling context. For example, the bounty hunter may wait until after the bonder is finished bowling to avoid embarrassment in front of the bonder's bowling buddies, but before the bonder gets home and the associated embarrassment of arrest in front of the bonder's children.

Exemplary embodiments disclosed above are examples of previous violations/conviction-based location, contest and behavior monitoring, tracking, preempting/prevention, and relapse reporting. But there could also be numerous variations depending on a variety of factors including age (e.g., juvenile, senior, etch, type of conviction (e.g., felony vs misdemeanor, etch, level of crime, number of convictions, etc. History (of drug abuse, alcohol abuse, etch, sexual history/background, whether they are currently employed, degree of financial stability, how long since they last contacted high risk associates, whether they are in counseling and how long, have their own residence and how long (and with whom and associated stability of such persons, etch, have their own transportation, are in a stable relationship and how long, how long they've been paroled/under supervision, number of convictions, total years served, number of uneventful previous parole violations and problem-free parole years, number/types of previous parole violations, etc. Family and friends support structure and/or the type and degree of counseling/treatment are very important risk elements. For example, a DUI offender currently in closely (separately) monitored residential/inpatient rehab could be consider low risk, low frequency monitoring up to the time until leaving the treatment facility. At that point, their housing and family/friend support structure and employment/training prospects could keep the risk low (if those elements are all favorable) but shoot to high if the home life they are going (back) to is very unpleasant. In which case, it would immediate raise to high risk/high monitoring levels. Other treatment types such as Outpatient, Halfway Houses, and Day Reporting could also have associated risk elements.

Some or all of the above could be computed into a Risk Profile and/or a scoring system that could "calibrate" the sensitivity of monitoring/tracking/analysis algorithms and algorithms/methods for initiating support of the preemptive actions of possible high-risk violations. Behavior monitoring could even reach areas such as diet monitoring, in case for example low/high blood sugar has been demonstrated to be a high-risk factor of erratic behavior on part of the parolee/prisoner.

In exemplary embodiments, all of the above may be incorporated into different intensities of monitoring. A simple low/med/high intensity schema could serve as a non-limiting tiering.

Exemplary embodiments of the present disclosure can be implemented in numerous ways, including (without limitation) as method(s)/process(es), apparatus(es), system(s), composition(s) of matter, computer readable media, such as non-transitory computer readable storage media, and/or computer network(s) wherein program instructions may be sent, e.g., over optical, electronic, wireline, cloud-based, drone-based, Internet, wireless, peer-to-peer, machine-to-machine, and/or other communications link(s) and combination(s). At least some such implementations may be referred to, e.g., as techniques and/or mechanisms. In general, the order of the steps of disclosed processes may be altered within the scope of the present disclosure.

Exemplary embodiments are disclosed of systems and methods for monitoring for and preempting pre-identified restriction violation-related behaviors) of persons under restriction, such as a parolee, a prisoner, a person on probation, a person under house arrest, a person under a restraining order, a person under supervision and/or restriction(s) ordered by one or more of a criminal court, a civil court, a family court, and/or another justice entity, and/or a person under supervision and/or restriction(s) imposed by an association, an entity, and/or an organization, etc. In an exemplary embodiment, a system generally includes a plurality of different devices, sensors, sensor arrays, and/or communications networks. The system is configured to: determine, through a plurality of measurements/readings taken by the plurality of different devices, sensors, sensor arrays, and/or communications networks, behavior(s) of a person under restriction and context(s) associated with the behaviors) of the person under restriction: assess, evaluate, and predict a risk of a future occurrence(s) of a pre-identified restriction violation-related behavior(s) and associated context(s) by the person: and facilitate one or more pre-identified actions and/or activities to preempt and/or lower the risk of a future occurrence(s) of the pre-identified restriction violation-related behavior(s) by the person under restriction before a violation occurs.

The person under restriction may be one or more of a parolee, a prisoner, a person on probation, a person under house arrest, a person under a restraining order, a person under supervision and/or restrictions) ordered by one or more of a criminal court, a civil court, a family court, and/or another justice entity, and/or a person under supervision and/or restriction(s) imposed by an association, an entity, and/or an organization. By way of example, the person may be under supervision and/or restriction(s) imposed by Alcoholics Anonymous (AA), another organization disclosed herein, other non-governmental organization that is not associated with the government or justice system, etc.

When the person under restriction is a parolee, the system may be configured to: determine, through a plurality of measurements/readings taken by the plurality of different devices, sensors, sensor arrays, and/or communications networks, behavior(s) of the parolee and context(s) associated with the behavior(s) of the parolee: assess, evaluate, and predict a risk of a future occurrence(s) of a pre-identified parole violation-related behavior(s) and associated context(s) by the parolee: and facilitate one or more pre-identified actions and/or activities to preempt and/or lower the risk of a future occurrence(s) of the pre-identified parole violation-related behavior(s) by the parolee before a parole violation occurs.

The system may be configured to determine whether there is a variation from a defined set of conditions and/or allowed activities for the person under restriction based on the behavior(s) and associated context(s) of the person under restriction, whereby the variation indicates a risk of a future violation by the person under restriction. The defined set of conditions and/or allowed activities may comprise one or more of permitted travel, permitted location(s), permitted location dwell time, permitted travel path(s), proximity to a prohibited person(s), and/or proximity to a prohibited location(s).

The plurality of different devices, sensors, sensor arrays, and/or communications networks may be configured to collect and/or report different types of data for the person under restriction. The system may be configured to compare the data collected and/or reported by the plurality of different devices, sensors, sensor arrays, and/or communications networks with reference behavior data predefined for the person under restriction. The reference behavior data predefined for the person under restriction may comprise one or more of: criminal behavior data for the person under restriction: criminal history and criminal record data for the person under restriction: data relating to a number of different types of crimes: probability data that compares various crime types with various location types wherein a crime probability for each of the various crime types is determined and assigned for each of the various location types; and/or restraining order history and restraining order record data for the person under restriction.

The system may be configured to determine, project, or predict a current or future context of the person under restriction at a location by analyzing and linking real-time data and historical data for the person under restriction, the real-time and historical data including the location of the person under restriction, historical context of the person under restriction at the location, behavior patterns, travel patterns, health data, and risk calculations.

The plurality of different devices, sensors, sensor arrays, and/or communications networks may allow the system to monitor a location of the person under restriction both indoors and outdoors.

When the person under restriction is a parolee, the system may be configured to: determine, through the plurality of different devices, sensors, sensor arrays, and/or communications networks, a location of the parolee and the context of the parolee at the location; assess, evaluate, and predict a risk of a parole violation by the parolee in relation to the location and the context; and facilitate one or more pre-identified actions and/or activities to preempt and/or lower the risk of the future parole violation.

The system may be configured to determine whether one or more triggers indicative of a risk of a future violation by the person under restriction and predetermined in the system are active or present based on the behavior(s) of the person under restriction and the context(s) associated with the behavior(s) of the person under restriction, as determined through the plurality of different devices, sensors, sensor arrays, and/or communications networks. The system may be configured to determine whether any of the one or more triggers predetermined in the system are active or present by comparing data from one or more of the plurality of different devices, sensors, sensor arrays, and/or communications networks with one or more settings for the person under restriction. The one or more settings for the person under restriction may include one or more of blood pressure, heart rate, skin temperature, body temperature, respiratory rate, perspiration, weight, exercise schedule, external temperature, noise levels/loudness, and/or noise types/frequency(ies). The plurality of different devices, sensors, sensor arrays, and/or communications networks may comprise one or more biometric, environmental, and/or behavioral sensors that provide the biometric, environmental, and/or behavioral data for the person under restriction usable by the system in determining whether any of the one or more triggers predetermined in the system are active or present. The system may be configured to receive and process feedback and to adjust the plurality of different devices, sensors, sensor arrays, and/or communications networks including increasing, decreasing, and/or otherwise modifying one or more of the settings and/or a frequency of data collection in response to the feedback including actions, contexts, and behaviors of the person under restriction associated with the data.

The system may be configured to: determine, through the plurality of different devices, sensors, sensor arrays, and/or communications networks, a location of the person under restriction and the context of the person under restriction at the location; and determine whether one or more triggers indicative of a risk of a future violation by the person under restriction and predetermined in the system are active or present based on the location, the context, and one or more of biometric, environmental, activity, and/or behavioral data for the person under restriction.

The plurality of different devices, sensors, sensor arrays, and/or communications networks may include one or more of a local network, a public network, a private network, the internet, the Internet of Things, a wireless network, a terrestrial network, a cloud network, a Bluetooth network, a beacon network, a cloud network, a peer-to-peer network, a drone network, a Zigbee network, a satellite network, and/or wireline network. The context(s) include a situation, an environment, and/or a state of mind of the person under restriction based on one or more of biometric, environmental, activity, and/or behavioral data of the person under restriction.

The plurality of different devices, sensors, sensor arrays, and/or communications networks may include: a plurality of sensors configured to monitor a location and/or the context(s) of the person under restriction at the location, one or more of the plurality of sensors being located in, on, and/or near the person under restriction; and a plurality of interface devices configured to engage in interaction with the person under restriction, with one or more support persons for the person under restriction, and/or with one or more third parties in the event the system determines a relationship between the location and/or the context(s) and one or more triggers predetermined in the system that indicates a risk of a future occurrence(s) of the pie-identified restriction violation-related behavior(s) by the person under restriction. The system may be configured to select the interaction based on the one or more triggers and the location and/or the context(s) of the person under restriction at the location.

The system may be configured to develop and/or update a profile of the person under restriction including one or more predetermined actions to implement for the person under restriction depending on the prediction and evaluation of the risk of an occurrence(s) of the pie-identified restriction violation-related behavior(s) by the person under restriction. The system may be configured to be usable by another one or more persons to voluntarily and/or involuntarily monitor a location of the person under restriction, the behavior(s) of the person under restriction, and the context(s) of the person under restriction at the location. The one or more pre-identified actions and/or activities facilitated by the system may include one or more of disabling a vehicle of the person under restriction and/or providing an alert to one or more of law enforcement, a support person, or other person.

The system may be configured to assess, evaluate, and predict, a risk of a future occurrence(s) of a pre-identified restriction violation-related behavior(s) and associated context(s) by the person under restriction based on historical location-based data for the person under restriction.

The pre-identified restriction violation-related behavior(s) may include one or more pre-identified behavior patterns, one or more pie-identified behavior trends, one or more pie-identified contextual patterns, one or more pie-identified contextual trends, and/or one or more pre-identified triggers. The system may be configured for monitoring for and preempting the one or more pre-identified behavior patterns, the one or more pre-identified behavior trends, the one or more pre-identified contextual patterns, the one or more pre-identified contextual trends, and/or the one or more pie-identified triggers of the person under restriction.

The context(s) associated with the behavior(s) of the person under restriction may comprise at least one or more interrelated conditions including situations, circumstances, events, environment, activities, and/or actions being done by, associated with, and/or around the person under restriction, time, and/or location(s) of the person under restriction as determined through the plurality of different devices, sensors, sensor arrays, and/or communications networks.

The plurality of different devices, sensors, sensor arrays, and/or communications networks may be configured to collect and/or report different types of data for the person under restriction including biometric, environmental, activity, and/or behavioral data. The system may be configured to use the data collected and/or reported by the plurality of different devices, sensors, sensor arrays, and/or communications networks that meets one or more pie-identified criteria.

The system may be configured to determine behavior(s) of the person under restriction and context(s) associated with the behavior(s) of the person under restriction by a comparison of data from the plurality of different devices, sensors, sensor arrays, and/or communications networks with one or more settings for the person under restriction.

The system may be configured to allow a user to modify an identity of the person under restriction, the pre-identified restriction violation-related behavior(s) and the associated context(s), the pre-identified actions and/or activities, and/or the plurality of different devices, sensors, sensor arrays, and/or communications networks.

The plurality of different devices, sensors, sensor arrays, and/or communications networks may comprise at least one sensor array including a plurality of different types of sensors operable for taking a plurality of different types of measurements/readings usable by the system to determine the behavior(s) of the person under restriction and the context(s) associated with the behavior(s) of the person under restriction. The plurality of different devices, sensors, sensor arrays, and/or communications networks may include one or more social networks. The plurality of different devices, sensors, sensor arrays, and/or communications networks may include one or more devices, sensors, and/or sensor arrays remote from the person under restriction.

The system may be configured to use, in combination, the plurality of measurements/readings taken by the plurality of different devices, sensors, sensor arrays, and/or communications networks to determine when a violation trigger is being activated and/or when a potential violation is in progress through a pre-identification process and an iterative machine learning/artificial intelligence process incorporating human input of high risk chance of violation situations, to thereby enable the system to proactively and preemptively detect high-risk violation situations for the person under restriction.

The system may be configured to: determine whether a location and the context(s) correspond to a high-risk location and context(s) and/or correspond to a trending risk of the pre-identified restriction violation-related behaviors); identify one or more potential actions and/or available support resources to preempt and/or lower the risk of a future occurrence(s) of the pre-identified restriction violation-related behavior(s); select one or more actions and one or more interfaces for the person under restriction: and implement the selected action(s) and interface(s) for the person under restriction.

The system may be configured to restrict and condition access to data for the person under restriction collected by the plurality of different devices, sensors, sensor arrays, and/or communications networks based on a user's selection of location-based data for the person under restriction from a plurality of options presented by the system for selection.

The plurality of options may include the location-based data and one or more other options that are selectable by the user.

The system may be configured to determine at least one historical location of the user and at least one historical context of the user at the at least one determined historical location. The system may be configured to, in connection with the determining the at least one historical location and the at least one historical context: determine the at least one historical location based on data obtained through at least one location sensor: and determine the at least one historical context based on data obtained through the at least one location sensor and at least one different sensor. The system may be further configured to: receive a request for access by the user to data for the person under restriction obtained through the plurality of different devices, sensors, sensor arrays, and/or communications network: present one or more queries or qualifiers to prompt the user to select at least one of the plurality of options in response to the one or more queries or qualifiers: and present the plurality of options for selection by the user. The plurality of options may include location-based data for the user and the one or more other options. The location-based data for the user may include data based on the determined at least one historical location of the user and the determined at least one historical context of the user. The system may be configured to include the location-based data for the user in the at least one of the plurality of options based on a consistency between (a) the one or more queries or qualifiers and (b) the determined at least one historical location for the user and the determined at least one historical context for the user. The system may be configured to allow the requested access by the user to the data for the person under restriction based on the user's selection of at least one of the plurality of options including the location-based data for the user, whereby the user is the person under restriction, another person, and/or an accessor.

The system may be configured to determine the at least one historical context of the user at the determined at least one historical location based, at least in part, on data obtained through at least one biometric sensor. The system may be configured to present the one or more queries or qualifiers to prompt the user to select at least one of a plurality of options in response to the one or more queries or qualifiers, based on a memory profile for the user. The memory profile may include one or more user-specific preferences for a query or qualifier.

The system may be configured to select one or more sensors through which to obtain the data to determine the at least one historical location of the user and the at least one historical context of the user, based on a memory profile for the user. The memory profile may include one or more user-specific preferences defining one or more types of sensors through which the data used for determining the at least one historical location and the at least one historical context of the user at the at least one determined historical location is obtained.

The system may be configured to: predict, based on the determined at least one historical location of the user and the determined at least one historical context of the user at the determined at least one historical location, at least one future location of the user and at least one future context of the user at the predicted at least one future location: and present the plurality of options for selection by the user. The plurality of options may include the location-based data for the user, the location-based data for the user based on the predicted at least one future location of the user and the predicted at least one future context of the user at the predicted at least one future location.

The person under restriction may comprise a group of at least two persons under restriction. The system may be configured for monitoring for and preempting pre-identified restriction violation-related behavior(s) of the group of at least two persons under restriction. In this example, a violation by any one person of the group may be deemed to be a violation for the entire group.

The group of at least persons under restriction may comprise a group of at least two children under restriction. In this example, the children in the group may be related (e.g., siblings, cousins, etch or not related. And, the system may be configured for monitoring for and preempting pre-identified restriction violation-related behavior(s) of the entire group of children instead of a single child.

The group of persons under restriction may comprise a group of at least two persons living together (e.g., a married couple, unmarried persons cohabitating. Mends living together, etch who are under restriction (e.g., on parole for the crime, under the same restrictions, etc.). The system may be configured for monitoring for and preempting pre-identified restriction violation-related behavior(s) of the group of at least two persons living together.

The group of at least two persons under restriction may comprise a cell block of prisoners outside on work detail. In this example, a violation by a single prisoner of the cell block of prisoners may be treated as or deemed to be a violation for the entire cell block of prisoners, which, in turn, may then have repercussions for the entire cell block of prisoners. For example, a violation by a single prisoner may result in the revocation or loss of outside work detail for the entire cell block of prisoners. An exemplary embodiment may include a cell-block-only network and sensor array configured to monitor for pre-identified restriction violation-related behavior(s) of the cell block of prisoners, e.g., monitor for predetermined action(s) targeted at the cell block of prisoners, etc.

Also disclosed are exemplary methods for monitoring for and preempting pre-identified restriction violation-related behavior(s) of persons under restriction. The method generally includes determining, through a plurality of measurements/readings taken by a plurality of different devices, sensors, sensor arrays, and/or communications networks, behavior(s) of the person under restriction and context(s) associated with the behavior(s) of the person under restriction; assessing, evaluating, and predicting a risk of a future occurrence(s) of a pre-identified restriction violation-related behavior(s) and associated context(s) by the person: and facilitating one or more pre-identified actions and/or activities to preempt and/or lower the risk of a future occurrence(s) of the pre-identified restriction violation-related behavior(s) by the person under restriction before a violation occurs.

In an exemplary embodiment, a non-transitory computer-readable storage media comprises computer-executable instructions for monitoring for and preempting pre-identified restriction violation-related behavior(s) of a person under restriction, which when executed by at least one processor, cause the at least one processor to: determine, through a plurality of measurements/readings taken by a plurality of different devices, sensors, sensor arrays, and/or communications networks, behavior(s) of the person under restriction and context(s) associated with the behavior(s) of the person under restriction; assess, evaluate, and predict a risk of a future occurrence(s) of a pre-identified restriction violation-related behavior(s) and associated context(s) by the person: and facilitate one or more pre-identified actions and/or activities to preempt and/or lower the risk of a future occurrence(s) of the pre-identified restriction violation-related behavior(s) by the person under restriction before a violation occurs.

Exemplary embodiments include systems and methods for developing, monitoring, and enforcing legal, technical, and social agreements, understandings, and/or contracts (e.g., legal, common law, or "handshake-like" agreements, etch, such as by using behaviors and/or actions (e.g., pre-identified behaviors, preemptive actions, etch determined via one or more different devices, sensors, sensor arrays, and/or communications networks (e.g., the Internet of Things (IOT), social networks, etc.). As disclosed herein, behaviors and contexts may be monitored by sensors, sensor arrays, devices, and/or communications networks including wireless, wireline, social networks, and/or The Internet of Things (IoT) and can include physical conditions, activities, and mental thought processes of pre-identified individuals in a variety of situations or circumstances ("contexts"). Current behaviors and, as applicable, contexts of pre-identified individuals are compared to pre-identified behaviors and, as applicable, contexts and associated acceptable variances to determine whether or not current behaviors/contexts as well as behavior/context trends conform within accepted boundaries of the behaviors/contexts. Based on if/degree of conformity, inclusiveness, fit, or other determinations, actions are initiated to either (1) "approve" the behavior in the form of some sort of contract, agreement, or understanding along with associated follow-up, measurement, and/or monitoring to ensure compliance/adherence to the agreement(s), or (2) alternatively, initiate pre-identified actions or artificial intelligence (AI) developed or other machine-determined actions to deter, stop, improve, or mitigate the behavior/contexts from continuing in their present ("unapproved") form.

In exemplary embodiments disclosed herein, a trigger may be generally defined as or include behavior and (optionally) context. Behavior may be generally defined as or include the way or manner that someone conducts themselves or behaves (whether in public or private). Context may be generally defined as or include the interrelated conditions in which behavior occurs, exists, or takes place, such as situations, circumstances, events, activities, actions, location, and/or time (year/month/day and hour/minute).

As recognized herein, detection or determination of behavior(s) can be difficult. This is particularly true when a behavior can have physical "symptoms" that are similar or even common to other very different behaviors. One example is Anger for which physical symptoms may include raised blood pressure, increased body/skin temperature, and/or raising of a person's voice. But such measures may also apply to other conditions or behaviors, such as having too much caffeine (e.g., elevated blood pressure), being in a very warm environment (e.g., hot body/skin temperature), talking to someone who is hard-of-hearing (e.g., raised voice), or talking in a loud environment (e.g., a bar). As a result, such measures and in particular the associated interpretations of those measures can vary greatly from person to person.

In order to confirm (or at least increase the likelihood of a correct diagnosis of) a behavior, exemplary embodiments disclosed herein include a pre-identification of data, measurements, and/or metrics, and in turn the sensors or other devices that collect(s) and develop(s) such data, measurement(s), and/or metric(s) as they relate to triggers, behaviors, and contexts. Such data, measurements, and/or metrics are taken, measured, and/or detected via sensors, sensor arrays, devices, and/or communications networks, including the Internet of Things (IoT) and social media networks. Generally (but not a requirement for all embodiments), more than one measurement may be taken, and such measurements may include a combination of one or more physical readings and one or more "non-physical" readings geared towards fully and accurately assessing the physical state of a person and even more importantly, assessing a person's state of mind and/or mental viewpoint. For example, exemplary embodiments may focus on (loud) word selection (e.g., curse words, etch besides or in addition to blood pressure as a way of indicating Anger. Other measures might be taken to "calibrate" such readings, such as a sensor that determines if/how much caffeine is in the person's system. Such indicators would be personalized to each individual as part of a the "pre-identification" process. For example. Person A may only curse when they are very Angry, whereas Person B may curse as a normal matter of course (and perhaps only doesn't curse when Angry).

Even these person-oriented measures (e.g. measures focused on a person's physical and/or mental state) may not be enough to accurately determine a person's behavior, such that the person's context may also need to be determined via a context identification/determination process. For example, being in the context of an outdoor ball game could explain elevated blood pressure (e.g., from excitement), hot body/skin temperature (e.g., outside seating on a hot day in the sun), and even some (e.g., good natured) cursing (e.g., "you struck out, you jerk!"). Without the context of the hot ball game, the person could easily be misidentified as being Angry. Thus, identifying behavior accurately often requires a plurality of different types of measurements, e.g., measurement(s) of the person being monitored and measurement(s) as to the context the person is in at the time of measurement. In turn, determining the correct course of action to mitigate a (mis)behavior is not only dependent on an accurate behavior "diagnosis", it is often also critical to have a full (and accurate) understanding of the person's context as well. For example, the same behavior of the same person but with different contexts will very often have very different preemptive/risk-mitigating actions. Actions that may be taken will vary depending on the person, behaviors detected, and context, as well as the actions possible depending on support networks, nearby locations, and other factors. Such actions as well as exemplary ways of detecting and interpreting behavior, context, triggers, and/or actions are addressed and disclosed herein. Exemplary ways of protecting the privacy of that information is also disclosed herein.

Exemplary embodiments may focus on certain kinds of behaviors, contexts, triggers, and actions that enable heretofore new ways of detecting certain kinds of human interaction (e.g., roman tic/sex/sexual-related interaction, fidelity, infidelity, interpersonal relationship, etch and enforcing agreements in some form with a variety of pre-identified information capture, documentation, measurements, compliance metrics, "punishments" or other actions for enforcing such behaviors and associated agreements.

For example, an exemplary embodiment may be configured to address a situation in which a person (Person A) who wants to ensure that she or he ("she") does not undertake sexual activity (e.g., say with Person B ("he") or any person within type C such as a "just-met" person) when she is not behaving "normally" (e.g., such as being drunk) and/or when doing so in an unusual context(s) (e.g., anywhere outside her bedroom and when there is the potential for her roommates coming home within the next 4 hours). Person B may have generally similar concerns, but also specific concerns about engaging in sexual activity with someone who may later claim to "not be responsible for their actions" because of drinking or other factors, exposing Person B to potential accusations of harassment or worse. Exemplary embodiments disclosed herein enable both Persons to be comfortable that their sexual encounter "requirements" are being met. Further, exemplary embodiments disclosed herein enable Person A to "certify" or otherwise legally or at least objectively and verifiably agree that Person A is of sound mind and body and fully agreeing to participate in the sexual encounter. Note "sexual encounter" does not necessarily mean intercourse. Rather, it could pertain to any type of interaction between two or more parties, such that some element with respect to sex is involved, including touching kissing, or other behaviors short of intercourse. It would also apply to all forms and variations of such "romantic activity." Such agreement(s) would be stored in a form of social agreement and/or potentially even legal document, using a variety of secure, and if needed, independently verifiable transaction mechanisms including but not limited to secure cloud storage, escrow-type data lockboxes, and/or blockchain transactions. Indeed, such privacy and security mechanisms are important due to the nature of the data collected as disclosed herein being highly sensitive or even among the most sensitive possible. Example privacy/security mechanisms are disclosed herein. A security/privacy mechanism employed in exemplary embodiments may have a requirement requiring both/all parties involved to agree to disclose the information associated with an agreement or dispute, and be precluded technically and/or legally from being disclosed without all parties' consent. In other exemplary embodiments, a single person's agreement or consent may or may not be all that is needed before disclosure depending on the nature of the agreement.

Furthermore, ensuring the security of the collected data may also help to avoid disputes with respect to the data collection, including key measurements/metrics, places and times, and any interpretations of the data. Towards that end, the use of blockchain technology (e.g., the use of distributed ledger technologies and methods) may be used in exemplary embodiments to store collected data in a completely secure, agree-by-all manner. Accordingly, exemplary embodiments disclosed herein may include blockchain-based designs for capturing/storing all romantic/sexual "transaction" data as well as ensuring that the data remains private until/unless it is needed. This may include concepts disclosed herein.

The inventor hereof has recognized a need for a way for one or both person(s) (or more than two person(s) depending on the situation) to protect themselves from false, misleading, or after-the-fact regret-based accusations of sexual misconduct through a behavior monitoring and social/legal contract mechanism.

This is not to paint a picture of reverse power roles with the only concern being for the male and possible false accusations. Both males and females (biologically or self-identified) will continue to be presented with situations and circumstances that may tempt or accidently stumble into types of (sexual) behavior that they are uncomfortable with upon a moment's reflection. But females are physically different than men; for example, studies show that women may be more vulnerable to alcohol (such as a 2:1 per drink multiple in terms of impact) even with equal body weight. There are many anecdotes indicating alcohol use by one or both parties in a disputed sexual situation was involved. Studies have shown or suggest that after drinking alcohol, males may become more aggressive sexually after drinking alcohol, while women may become more susceptible to "agreeing" (or at least not disagreeing in the drunken male's view) to sex, including in situations where if the woman was sober she would not have "agreed" to the sexual encounter in anyone's definition of the term. A similar situation from a male perspective would be someone who recognizes that he gets aggressive when he drinks, and is afraid that he may cross a behavioral and/or socially acceptable line when interacting with others (particularly women). In one University of Minnesota study, as much as 70% of certain violent crimes (particularly rape) occur when the (male) criminal has been drinking, thus preempting/preventing unacceptable behavior (which clearly rape is, but so are many other behaviors short of rape) by males when drinking is a major objective of this invention, in addition to the obvious benefits to the (potential) victims of such unacceptable behavior, male or female.

The inventor hereof has also recognized a need for a way for a person (particularly those vulnerable to making bad decisions in certain behavior/context combinations, such as having been drinking with a person they find attractive) to protect themselves—and others—from making a bad decision (or multiple bad decisions). An example bad decision may include drunkenly agreeing to have sex to which agreement would not have occurred if the person was sober. Another example bad decision may be tending to behave inappropriately when drinking that puts the person at risk of embarrassment or worse sexually or otherwise harassing people while under the influence. In today's environment in particular, such behavior could have life-long lasting implications in terms of societal shunning, loss of job, or even incarceration.

The inventor hereof has further recognized the benefit from early detection of "trends" towards (presumably "bad" even if intentions are good) behavior, such as having more than one drink in a defined timeframe when the person knows that having more in such a time frame has historically led to drunkenness. In which case (e.g., bad behavior either having been "achieved" or is going in that direction), exemplary embodiments disclosed herein have pre-identified actions at their disposal to prevent/mitigate potential bad decisions. This could, for example, include automatically initiating a messaging series (e.g., text, messaging, voice calls, social media posts) to the person's best friend(s) (via preferred interfaces and mechanisms) alerting them to the (impending) bad behavior and providing response(s) as pre-identified by the person and/or friend(s), along with appropriate methods and interfaces, pre-identified and selected according the best fit with the person's behavior, triggers and context. Escalation actions are also possible, such that if the friend's "intervention" is not successful, a text or call to the person's mother is automatically placed or threatened to take place if the person does not alter his/her behavior direction.

After recognizing the above, the inventor hereof discloses herein exemplary embodiments of systems and methods that may address one or more or all of the above needs by using and/or including one or more or all of the following.

- Pre-identify behavior (physical and mental actions) and frame-of-mind of concern to the person (or others), potentially along with location(s), timeframe(s), situation(s), and circumstance(s) (context) within or associated with the particular concerned behavior.
- Monitoring that behavior(s) through sensors, sensor arrays, communications networks (e.g., social networks, etch, devices, and/or other mechanisms, such as with sensors pre-configured or otherwise tuned, calibrated, set to, or otherwise focused on detecting those behavior(s) and (as needed) contexts. Collectively, behavior (and as appropriate, contexts) may be referred to herein as "triggers."

After one or more concerned triggers (behavior and if needed context) is detected (including "trending" behavior/context, e.g. behavior/context that has not yet reached a certain state but is moving in that direction), then the system initiates and manages one or more pre-identified actions to preempt, mitigate, or (if applicable) "approve" the behavior according to exemplary embodiments disclosed herein.

When preempting/mitigating "bad" triggers is needed, one or more pre-identified action(s) are initiated and managed by the system according to exemplary embodiments disclosed herein. For example, in the case of drunkenness, an alert may be sent to someone in the person's support network with information about what is going on and specific (pre-identified) actions to be undertake by that support network according to exemplary embodiments disclosed herein.

In the case of an "approved" behavior or behavior/context, exemplary embodiments of this invention may initiate and manage a process to execute a social/legal contract or otherwise independent record of consensual agreement between the parties.

Various examples are described below that help to illustrate, elaborate, and describe aspects, elements, and features according to exemplary embodiments of this disclosure.

Example 1—Person Afraid of Drunken "Yes" to Having Sex

In this first example, a "safety net" may be provided for a person who knows they are vulnerable to doing, saying, and/or agreeing to some activity or other "thing" while under the influence of some substance, e.g., give consent that would not otherwise be given while sober or had only been indulging below a certain point. A particular example of this that can cause great social, legal, and even criminal difficulties is agreeing to having sex or otherwise putting oneself in a vulnerable position via behavior or activity that may lead to such an end result, such as going bar-hopping with or going home with a person just met, or becoming (often at the spur-of-the-moment) involved in an activity with the other person, such as traveling with them, possibly to a unsafe part of town, that may put them in a context that may result in such difficulties (e.g. you shouldn't go out in this part of town by yourself—let me give you a ride home). Having (or not) sexual activity (or other romantic activity) under circumstances that could later be involved in some sort of dispute after-the-fact is at the core of this exemplary embodiment.

Pre-identification of acceptable behavior(s) and/or context(s) is included as part of this exemplary embodiment (though one-time, multiple, and ongoing adjustment/modification of these behavior(s) and context(s) is also enabled herein). For example, a person may want to never be involved in sexual activity in the following scenarios: A) with someone just met: B) with anyone when any alcoholic drink has been consumed or other mind-altering substance taken (perhaps with an exception for a "special" someone, discussed more shortly): C) with anyone with whom the person works (with special actions if a possible sexual partner is a boss, supervisor, other coworker to which the person is subordinate, etch; D) at certain locations (such as at a parent's house), or E) with an ex-boyfriend/girlfriend.

For Scenario B, there may be an exception for a specific person, who is a "friend with benefits." In which case, that specific person may then be placed on a list subject to the other scenario conditions, such as restrictions on time and place for such "benefits" to take place. For Scenario C, the possible Action Tree (discussed shortly) may have a special branch of possible actions (and associated supplemental data collection) to both "gently" discourage the boss, supervisor, or co-worker and also to collect data for a possible sexual harassment charge.

To pre-identify this behavior, the person may have one or more sensors enabled that are nearby, on, or around the person, such as a bracelet (e.g., see FIG. 2, etch, a breathalyzer built into their phone that measures blood alcohol content (BAC), and/or other sensors/sensor combinations on the person (e.g., devices carried by the person, wearables, bracelets, glasses, etch, in the person (e.g., implants, etch, and/or near the person (e.g., sensors in the room the person is, on/in the furnishings, etch that may indicate a high risk of (potential) drunkenness, such as location in a bar for more than a certain period of time, being in the company of someone that frequently or always drinks with the person, the person starts to talk rapidly (as compared to the particular person's typical talking speed), slurring of words, etc. The sensor or other device readings may initially be pre-identified/tailored to the person with subsequent modification possible as behavior data is collected and additions/deletions/modifications/enhancements are determined through Machine Learning, Artificial Intelligence (AI), Adaptive Learning, Affective Learning, Big Data Analysis, Support Personnel suggestions, pie-identified actions and adjustments, and other mechanisms and methods for parameter/configuration adjustments identified. Such technologies are also used in exemplary embodiments in identifying/implementing key actions that need to occur/not occur in relation to behaviors and/or contexts.

The sensors or other devices may be pie-identified and pie-configured to detect the existence of alcohol and/or to detect what degree might the person have a high intolerance, for example hard liquor. Thus, any detection of the proximity of hard liquor (e.g., within 2 feet of the person based on smell, visual evidence, etch may be considered as cause for alarm and initiation of preemptive/preventative action(s).

This behavior(s), as indicated by one or more indicators (e.g., badly trending Blood Alcohol Content (BAC) levels, drinking "friends" present, etch, and as measured by the one or more sensors that may indicate drunkenness or an imminent trend towards such, may be pie-identified, and the appropriate settings on the sensor(s) pre-identified and then pie-configured, such as detecting (and reporting) any BAC of over 0.04% (e.g., the person's view of what the limit is and still retaining full control of behavior), and/or allowing oneself only to drink at certain establishments and/or only with certain friends (or definitely not with certain drinking "friends"). Certain such friends add a non-location element to the context setting (along with location), as well as implicitly introducing the need to sense the particular identities of certain (pie-identified) people.

Aspects of this invention enable modification and/or adjustment of pie-selection and/or pie-configuration of sensors and sensor-settings based on accumulation and analysis of historical data and/or observations of the monitored persons or others. For example, the person's friends may point out that person starts acting different after only 2 drinks, whereas the initial BAC level settings are calibrated for 3 drinks. Analysis of the person's drinking data may confirm this, by for example, walking at a slower, uneven, and/or erratic pace (e.g., data collected by walking/fitness-type sensors) and/or analysis of speech patterns. This may include recording samples of the person's voice, of which samples are collected when drinking is detected and compared to non-drinking recorded samples of the person's voice that were pie-collected for such analysis purposes. Modification of sensors can refer to the adding of or deleting of various types of sensors, for example, adding a blood pressure monitoring capability to an initial sensor set (that did not include monitoring blood pressure monitoring sensor(s)) identified for detecting the Anger trigger, and adjustment of sensors refers to adjusting the parameters for a given (pre-identified or later added) sensor regarding what type/level of data is collected and when, for example changing the frequency of a periodic measuring of BAC from 0.04% to 0.05%, and/or changing the frequency of measurement depending on the BAC level, e.g. once an hour up to 0.04%, once every 15 minutes at a BAC level of 0.05%, and continually/near continually once BAC level reaches 0.06%.

When a certain pie-identified drinking threshold is passed (e.g., 04%), or a disturbing trend is detected (e.g., going from 0% to 0.03% in 15 minutes), this exemplary embodiment may analyze the possible (pie-identified) actions for that person's behavior and (as applicable) context. Besides the context elements discussed above (e.g., which bar, where located, with what persons), action-related context elements may be measured and compared to pie-identified concerns. For example, possible actions may vary depending on whether the person drove a car to the bar or came some other way (e.g. with a friend or an Uber driver). Because this kind of data would not be able to be collected while the person was in the bar, this exemplary embodiment includes some level of "pre-behavior" data collection of various elements (e.g., driving a car) that may come into play when a behavior concern is activated. Actions can vary widely and can be individually or in combination. For example, while a certain BAC level may initiate a disabling of the person's care and a call to Uber, the invention may take actions to stop or slow the degree/volume of drinking, such as sending reminders to stop drinking or playing drunk-driving-related videos on the person's phone, to contacting friends, relatives, or other support persons to get them to take actions on behalf of the original person, such as calling them or stopping by the bar that they currently are at. The invention would also include functionality for the support person they need to respond to the original person's situation, such as the person's location and information on how much they've been drinking, who they are with, how long they have been drinking/at the location, etc.

Although the potential actions may vary, possible actions are pre-identified based on the behaviors (and as applicable, contexts), e.g. "triggers", and other actions generated by artificial intelligence (AI), "if/then"-type decision trees and/or other machine-based technologies described above. Example actions include sending out message(s) to trusted friends or family members; automatically calling an Uber driver (while disabling the person's own car from being driven); essentially forcing the person to leave the bar; and/or sending a message to the bar/bartender to cut the person off and stop providing any alcoholic beverages to the person. A particular impactful action might be a pre-recorded video of that person warning oneself that "YOU ARE NOT SOBER—GO HOME!", perhaps even connecting to Bluetooth speakers near the person to add a public self-"shaming" element. Other actions could involve bringing in $3^{rd}$ parties to the "stopping" action, such as causing one or both of the parties' mothers to call or be called and put on speaker, creating a Skype/Facetime link, or even transmitting real-time audio/video of the current situation or a virtual reality/augmented reality simulation of the "direction" that the situation/context is trending towards. In such circumstances, the support network and interfaces chosen to facilitate the actions, particularly communication-intensive actions, are a part of the overall action selection/generation process as is the action itself.

Determining which interfaces will be most effective in delivering these actions is important, both pre-identifying and AI-generated interfaces, as will be determining in what context is involved in "delivering" those actions (particularly message-based actions). This determining is an important element of exemplary embodiments disclosed herein, as are methods and mechanisms for determining and implementing ongoing updates to those action/messaging pairing as behaviors, actions, and sensors that enable monitoring/delivering them are refined and as new technologies become available. For example, instead of or in addition to an audio (or even video) recording of the person's self-yelling at oneself, there may be a holographic image instead. Or as implants become more widespread, a shock may be delivered to the person in some behavior/context pairings to avoid public humiliation yet achieving the goal: to get the person out of the predicament the person is about to get into before it is too late. By way of example, an exemplary embodiment may use an electrode-based vibration-inducing smartphone-controlled system, such as Quell, etc. An aspect of the invention will be deciding which kind(s) of interface (s) will be most effective given the person's profile as well as location and context. For example, the interface used if the person is driving will be different than if in a quiet place and different than if the person is in a loud bar or a crowded ball game.

Example 2—Person Afraid of Drunken/Inappropriate Behavior

This second example is the converse of the first example described immediately above. This second example addresses the scenario in which a person is afraid of being accused of inappropriate behavior, such as drunken sexual assault, and understandably wanting to prevent that from happening before it happens. The challenge, in today's society in particular, is that one person's well-meaning but "forward" or aggressive behavior may be another person's sexual harassment or worse.

There are two main windows of concern addressed by this exemplary embodiment. The first is while the "harassment" is actually happening, e.g. Person A (sometimes under the influence) tries to convince Person B (also possibly under the influence) to have sex. Person A may be too forward, such as by putting hands in inappropriate places, saying inappropriate things, or talking too suggestively, to make this happen. Or, Person A might only say a few things to gauge Person B's interest in an encounter, none of them particularly objectionable, at least to Person A. Regardless, Person B may become offended (which may be visible or not), and who finally says no and leaves whatever context/setting at which they were together.

Historically, that might have been the end of a dud date perhaps a bit of an unpleasant encounter, and that would be that. But more recently, social media allows for this unpleasant encounter to be "reported to" dozens even thousands of followers, who can quickly start gunning for Person A's reputation, job, etc. Often found in newspapers are stories in which Person A is fired from their job and/or their reputation is ruined without any due process or even proof other than the accuser's accusatory words. This exemplary embodiment may provide such proof to protect oneself by capturing by various types of sensor measurements or other data collection mechanisms (e.g. audio, video) at key times in various forms, e.g., key "snapshots" of the evening that can be used to refute (or confirm) the behavior that took place.

An even more problematic scenario is when Person A is "successful" with Person B. For example. Person A convinces Person B to (seemingly willingly) go to an apartment and (seemingly willingly) have sex. Person B then leaves or sleeps over and returns home in the morning. Historically, when this would happen, if either party has regrets about what they did the night before, they chock it up to people blinded by the throws of passion and perhaps alcohol, and resolve not to do it again. But current society has introduced new variations in this Monday-morning quarterbacking. Instead of writing the evening off by saying "I'll never drink that much again", or "I have to stop doing this", the "aggrieved" person may feel that someone has to "pay" for "making" Person B have sex now that Person B is having the morning-after regrets. Another scenario might be that there is no "true" issue involved, but Person B, who lives at home, is caught by the parents. In a panic. Person B makes up a cover story that implicates or accuses Person A in harassing behavior or worse. In either such examples. Person B may talk to Mends, take to social media, and/or even call the police. Person B (or his/her parents or Mends) may contend that since Person B was not fully under control of their own faculties (e.g., because Person B was drinking), then what happened was sexual harassment or rape because Person A took advantage of Person B. As noted, sometimes this is "crime" is "caused" by a $3^{rd}$ party finding out about the encounter, such as a parent or supposedly close Mend who blabs to the world, embarrassing Person B and "forcing" Person B to manufacture a "defense" by claiming that Person B was taken advantage of even if it was mutually and con sensually agreed to and no matter the consequences to the other party.

Person A in this situation often has no evidence other than their word, and perhaps a few Mends or acquaintances at the bar who could testify a "subjective" opinion as to how drunk/control of their faculties Person B really was at the time. Seemingly, this type of accusation in recent times has the accused as guilty until proven innocent and sometimes not even then when it comes to Person A's job and reputation in society.

Accordingly, the inventor hereof has recognized a need for and discloses herein exemplary embodiments of systems and methods to monitor behavior (by both parties); and preempt the sexual "transaction" from going too far if various warning signs/risks are detected. If the transaction proceeds anyway, the collection of data as disclosed herein may protect both parties from an after-the-fact accusation of harassment, rape, etc.

Example 3—Woman and Man Want to Ensure Genuine "Yes"

This third example address a scenario different from the first and second examples described immediately above. In this exemplary embodiment. Person A wants to say "Yes" and is in the right state-of-mind (e.g., behavior) and context (e.g., safe place). Person B also wants to say "Yes" and is in the right state of mind (e.g., behavior) by being mentally genuine about a Yes (e.g., not being drunk) and in the right context (e.g., also a safe place).

This exemplary embodiment includes monitoring both parties' behavior and context and comparing the monitored behavior and context to a list of rules/preconditions. If those rules/preconditions are met and there are no major red flags in terms of "executing" (such as Person B having no money to get a ride home in the morning), then alerts may be provided to both of them that the "coast is clear" regarding getting together. At that point, a social contract (e.g., legally and/or binding contract and/or mutually acceptable social agreement, etch is presented to both parties to attest that they are both in the right frame of mind and body. The parties may then click the appropriate button, or in some other form (e.g. body language, etch accept and agree to the social contract. Accordingly, the parties have now insulated themselves from any sort of morning-after regret and, worse, actions that could wrongfully accuse one or the other party of taking advantage of the other.

Example 4A—A Full Agreement to Have Sex and the Nature of the Sex

If there are no conditions, exceptions, or other identified inhibitors regarding the participants having sex, then a contract (social and/or legal) or some other type of formalized agreement is provided for the parties. This fourth example 4A includes not just information about the consensus of "yes", but if needed agreement on time, place, duration, and range and/or type(s) of sexual activity. The latter may be somewhat problematic both in terms of diminishing the spontaneity of the moment, but also not knowing what types of sex both parties are mutually interested in. That said, some sort of documentation or other recorded proof may be provided—even if only a brief yes/no to prompted questions from one party or even a prompting from the system regarding different types of and ranges of sex encouraged, allowed, off limits, areas of the body that can be touched and how, any safety words, etc. If agreed to by both parties (through a verbal, video, or other affirmation mechanism), a record of the sexual occurrence will be taken. This can also be done by various means, utilizing both parties' devices and/or other sensors in the room/area/bed etc. where the occurrence occurs, particularly (but not limited to) video and/or audio recordings.

If a forbidden act or act not explicitly agreed to is detected (typically verbal or physical cues or through predefined recognition algorithms), the device (of one or both of the parties) or other alert-capable sensors may then document the "termination" of the act as well as the aftermath. If the act continues or continues in a non-approved way, appropriate alerts or other actions are then taken to discontinue the actions.

Example 4B—Retraction of a Yes

There are circumstances where after an agreement has been made and sex has commenced, one of the parties may retract or revoke consent and change their mind about the sexual encounter. This can be very problematic as cues given to indicate the revoked consent may not be obvious (e.g. "STOP!") and/or the other party may be wrapped up in the activity and be oblivious to the change of mind, incapable of correctly interpreting the cues, or just plain refuses to listen or doesn't believe it (e.g., No doesn't really mean NO). The technology of this exemplary embodiment 4B can be helpful in such situations as pre-identification of cues may be captured by the system according to this exemplary embodiment. "Safety words" or sounds (e.g., clapping of hands three times) may be used to trigger the system to take action(s). The system action(s) may be tiered, such as warnings to Person B: "Person B—Stop Please" escalating to Loud Alarms, calling 911 in extreme situations, etc.

Example 5—Woman/Man Afraid of Post-Sex Accusations

This fifth example is a variation of the above examples and is applicable to "morning-after" regrets. Unfortunately, it can be devastating on a person who thought everything was consensual the night before to find out the next day that the other party believes otherwise, e.g., the other part is not content to chalk up their consent at the time to foolishness or other reasons they alone are responsible for, decides to blame the other party, etc. Or, the person involved is a celebrity and wants to make sure they are not being used. This exemplary embodiment looks to preempt this by "documenting" the consent and subsequent actions (potentially even the romantic encounter itself with consent) in the form of a contract (e.g., verbally "signed" legal contract, etch, e.g., an immediate post-romantic encounter "agreement" (e.g., verbally, video, etch that the encounter was consensual along with readings of the physical state of both parties if possible (e.g. sound mind and body). The combination of the pre-encounter agreement record and the post-romantic encounter agreement should dissuade the other party from a next day "revision" of the consensual encounter to a non-consensual encounter and/or provide the accused with irrefutable proof regarding the consensual nature of the encounter.

This exemplary embodiment may also include monitoring of the potential reviser/revisionist/accuser's social media and other communications network accounts that would potentially signal a change of heart if it occurs over time (particularly if the romantic encounter does not extend a relationship or itself was unpleasant in some way). It could also provide non-testing proof of paternity (e.g., a "timestamp") of the encounter if needed at a later date. Various mechanisms (e.g., machine-based, etch focused on key words may be used to monitor the social media accounts of the other person (and possibly his/her friend(s)), with alerts or other actions triggered when a change-of-heart is detected or trending towards a change-of-heart.

Example 6—Post Interaction Behavior Monitoring (Both Parties)—Including Social Media This sixth example includes a variation of part of the fifth example described immediately above. This embodiment provides a trolling/bot review and analysis function of all of the parties' social media accounts to detect/determine if unpleasant posts are appearing or if such posts are "trending downwards." This exemplary embodiment includes a "scoring" of sorts regarding each post and provides an alert if a post goes below a certain predetermined negativity threshold regarding one of the parties or if trending downwards.

Example 7—Falsehood Monitoring

This seventh example is a variation of the fifth and sixth examples described immediately above. This exemplary embodiment includes social media monitoring capability specifically looking for falsehoods, particularly with respect to the romantic encounter. Upon identification of potential falsehoods (e.g., libel, slander, etch, notifications are sent to the victim (e.g., directly to the victim and/or to the victim's legal representation, etch along with a cease-and-desist order (e.g., via social media and/or legal form, etc.).

Example 8—Underage—Adult Inappropriate Interactions

This eighth example may address inappropriate and illegal sexual liaisons between persons under legal age and those of legal age. A variation of this is when both persons are of legal age but given the legal structure of the relationship (e.g. teacher-student), a sexual relationship is prohibited.

Upon a physical or virtual interaction commencing between two such persons, and a concern is raised by one (for example, the adult has concern about the other party's age, but the underage party says they are of legal age), exemplary embodiment 8A will "activate" a data collection process to collect as much information as possible on both parties. This includes taking "measurements" of the persons such as photographs, voice recordings (including assertions of legal age by the possible underage person), etc. and essentially performing a real-time private investigation of that person. A voice recording giving permission may be captured. Various databases may be scrutinized with a focus on detecting age-specific information, including birthdate, school attendance (with associated extrapolation of birthdate), etc. If such access is blocked due to minor privacy restrictions, this exemplary embodiment considers that as an indicator of being underage. Any such indicators may then be reported to the adult person and with additional data capture (e.g. voice recordings, video, etch that will provide a record of the adult being informed of the situation along with (presumably) a record of the social interaction being terminated.

A variation of the recording of the interaction between the adult and underage person will take place with some differences in another exemplary embodiment 8B. Because a pre-existing relationship (e.g. student-teacher) is already acknowledged in this example, this exemplary embodiment focuses on detecting unusual or "out-of-bounds" behavior on either participant. For example, a sensor may be activated when both persons are within proximity of each other and another "keyword" sensor may be calibrated to detect any untoward interaction, such as words "sex", "come back later", "meet me at", and so forth. If such key words are detected, additional sensors are activated (e.g. video, full-time recording, etch to capture a complete record of the interaction with forwarding of the interaction later or in real-time to the appropriate person (e.g. parents, school administrators, authorities, etc.). Actions may also be triggered such as messages telling the underage person to come home or otherwise remove oneself from the situation. If the "aggressive action" is by the underage person (e.g. a high school senior male, etch, additional action(s) may be taken to protect the teacher or other party, such as a real-time alert to a school principal or other school personnel to come immediately to the classroom or location where the interaction is taking place.

Example 9—Sexual Harassment "Scoring"

Many forms of possible sexual harassment are not well defined and may be to a degree in the eye of the beholder, cf. how an alleged harasser interprets a comment, gesture, or action versus a recipient's interpretation. Historically, verbal-only differences have not consistently been considered a major deal at least for individual occurrences and do not lend themselves to requiring a solution.

But any accusation of harassment in any form (even if unfounded or without any specifics) may be sufficient to damage and even end a career and/or ostracize a person in society. This exemplary embodiment includes pre-identification of behavior(s) and context(s) that may lead to inappropriate content generation or other types of posts with the same outcome; includes (e.g., puts in place, etch sensors and other mechanisms to detect as soon as possible a trend (hence, a scoring mechanism) towards such behavior, context, and associated social media action; and takes action(s) to stop the posting of the content, modify the content, and/or redirect the content to other platforms where it will have less impact.

For example. Person A may have an issue with what Person A considers hypocritical political postings on Twitter. Person A's "problem" may get considerably worse when Person A knows or has met people with those postings, and furthermore if those postings have to do with sexual-related disparities and perceived "wrongs" done by Person A's "culture" (such as being a white male) against Person B's culture (being a minority female). Person A may recognize this propensity to get Angry when faced with what Person A views as unfair, biased, or unreasonable posts, and would appreciate a form of "safety net" provided by the system to protect Person A against oneself, and thus prevent or limit the types of responses Person A does when exposed to such provocative postings. Person A may also want to keep a record of the transactions involved such that if there is any after-the-fact question of whether harassment or other inappropriate behavior took place between Person A and Person B, then there is a record that can be consulted, thus avoiding a he-said/she-said situation; one that may be skewed harshly against the one accused of harassment to the extent that they can lose their jobs and livelihood without any sort of due process.

The above examples 1-9 are generally or specifically addressed at romantic/sexual embodiments in some form. The following examples also utilize technology/methods described in previous embodiments but are less romantic/sexual in nature.

Example 10—Social Media Self-Protection

It has become relatively easy to literally ruin one's life with an off-color, politically incorrect, inflammatory, and/or otherwise stupid comment or post on any number of apps such as Facebook, Instagram, Twitter, other social media, etc. This exemplary embodiment looks to preempt such unwise remarks/postings by pie-identifying those types of remarks/postings that a person is susceptible towards (e.g., political postings, etch, and in particularly pie-identifying the behavioral conditions and context that are at the greatest risk for posting inappropriate content and then monitoring the person and their communications/communications channels.

This exemplary embodiment focuses on proactively identifying the Triggers, Behaviors and/or Contexts when such communications/posting occur and proactively/preempting such communications/postings through one or more actions. For example, when such conditions occurred, this exemplary embodiment may enact a variety of actions ranging from temporarily disabling a Twitter account, enacting a social media "overlay" that will allow a post to be written, yet delaying its actual posting (e.g., similar to live TV seven-second delay) to immediately addressing the triggers) such as "soothing" the triggers(s) (such as Anger) that make the person more susceptible to posting inappropriate content in the first place.

A variation on the above is a preempting of communications regarding certain topic(s), such as topics that fall under the old adage of never talk "sex, politics, and religion in polite company". With a heightened focus on "micro-aggressions", a proactive form of self-censorship may help to avoid antagonizing one of many identity groups. This exemplary embodiment facilitates that by detecting Trigger, Behavior, and/or Context(s) that a person might be susceptible to saying (posting or otherwise communicating to the outside world) such antagonizing statements. Once pre-identified (again, with Anger a high potential trigger), one or more actions may take place focused on preventing or delaying such postings/communications and/or mitigating the damage by soothing or otherwise addressing the Trigger. Post-communications action(s) may also take place, such as automatic deletions of postings to prevent or at least reduce the number of persons viewing the postings.

Example 11—Bullying

This eleventh example is a variation of several above examples and in particular the previous tenth example described immediately above. This exemplary embodiment is focused on both preventing bullying of a particular person by pre-identifying triggers, behaviors, and/or contexts when he/she is susceptible to performing bullying (and preempting/preventing it), as well as detecting bullying by others and preventing a response (likely in reaction to a trigger being activated by the bullying). Besides the monitoring for and detecting/determining pre-identified triggers, behaviors and as applicable contexts as disclosed herein, these exemplary embodiments also includes pie-identification of known likely bullies/persons to be bullied and monitoring their locations (physical and virtual). When proximity is detected (e.g., in a social media context in which they are online or actively posting, etch, this exemplary embodiment includes taking steps/actions to essentially prevent the parties from being aware of their respective social media or other activity, and thereby preventing a response.

Example 12—Domestic Violence Accusation: Restraining Order

This twelfth example focuses on prisoner/parolee/probation situations and with domestic violence-related embodiments focused on preventing physical contact. This exemplary embodiment elaborates on the capability and extends it to "virtual" contact, which may or may not be construed by the court as a violation of a restraining order. But virtual activity by an accused/criminal may be considered a threat by the victim, and thus should be prevented. In this exemplary embodiment, an accused/criminal's behavior, trigger, and/or context(s) are monitored to detect those that might "cause" the criminal/accused to post threatening or otherwise uncomfortable communication, social media posting, etc. that may be construed negatively by the court. When such triggers/contexts/behaviors are detected, then similar to exemplary embodiments disclosed above, this exemplary embodiment may initiate, implement, or take actions) to relatively immediately preempt/prevent/mitigate such communications/postings. Upon the detection of such triggers or high risk of such triggers, action(s) may be initiated to the accused/criminal's support network to immediately address the "near-miss" and provide support to prevent any such trigger/behavior/context from happening again, if possible.

Example 13—Workplace/Co-Worker Behavior "Compliance"

There is some anecdotal evidence that suggests that men are becoming reluctant to meet singly with a woman whether on work premises or offsite and/or even communicate with a woman when there is no way of verifying the integrity/accuracy of the communications. Evidence has started to indicate a reluctance of even hiring women under a fear of a "guilty until proven innocent" atmosphere where even a single, uncorroborated accusation may be enough to destroy a man's reputation, lose a job, and/or lose prospects of future employment.

To prevent (or at least reduce the occurrence) of such situations, and more positively possibly help in restoring trust in the workplace, this exemplary embodiment seeks to capture relevant information about workplace interactions particularly those involving one-on-one interactions between a man and a woman and more broadly a person having authority or power over another person in a subordinate position. As such, this exemplary embodiment will detect or otherwise initiate monitoring of behavior when "high-risk" situations appear, such as a one-on-one meeting between a boss and a subordinate in the boss' private office (e.g. detection of a high-risk context). Upon such detection, monitoring/data collection of various types as described above commences with a focus on monitoring and, if needed, documenting the behavior of the boss or other person of power/authority, as well as the circumstances leading up to a determination of the high-risk situation, such as suggestive comments and/or body language of one or both parties. Upon such detection, actions may then be initiated to prevent or at least reduce the possibility of a potentially uncomfortable (or worse) situation from progressing, such as initiating alerts, requesting other parties to "intrude" on the situation, and/or other explicit actions deemed to interrupt or otherwise "correct" the situation.

Example 14—Adultery/Suspicion of Adultery/Proof of No-Adultery

A variation of several of the above examples utilizes aspects to "prove" adultery or no adultery through monitoring of and behavior detection of suspected party(s) involved. In this exemplary embodiment, the monitoring may be performed on a voluntary or involuntary basis (or both). This exemplary embodiment focuses on beginning the monitoring when "suspicious" behavior begins, such as being in strange location/contexts at unusual times and/or exhibiting certain behaviors/Triggers outside the norm (for that person(s)). Detection of such context/behaviors/triggers activate certain action(s) that may range from "discouraging" adultery-leading behavior to intense monitoring of locations/activities/behaviors, which may include capturing data of any romantic/sexual liaisons that could be used in subsequent divorce proceedings.

Other related embodiments are not restricted to permissions/permissible behavior as it is related directly to sex or other forms of "commercial" harassment. There are other permissible behaviors that may be deemed monitorable and turn actionable such as job interviews, education interactions, private investigations, etc.

Exemplary embodiments disclosed herein may advantageously provide individuals with a way to ensure there is no misunderstanding about what activity(ies) each party is agreeing to that is accessible, timely, and flexible. As disclosed herein, exemplary embodiments may advantageously provide a way to capture consent as well as a lack of consent. The technologies disclosed herein enable or provide guardrails for ongoing consent. By way of example, an exemplary embodiment includes an app (e.g., Apple iOS app, Android app, etch that includes features such as email login, a customized icon, ability to create a personal profile, etc. The app also includes expanded capabilities, such as connection to a server (e.g., a company or third-party server, etch to store consent details, ability to set permissions to integrate with wearables and to access to a smartphone microphone and camera that are delivered in an interface. Continuing with this example, two versions of the app may be available. The first app version may be free with functionality for an in-app purchase to capture a one-time "yes" or "no" choice for an activity, e.g., yes for consent or no for lack of consent to intercourse, oral sex, anal sex, other activity, etc. Space for displaying ads via the app may be available to provide additional revenue. The second app version may be a subscription version that includes expanded capabilities for monitoring ongoing consent.

Some exemplary embodiments disclosed herein may be generally divided into three main aspects or parts: (1) preemption, (2) agreement/contract formation, and (3) ongoing monitoring and ongoing validation to ensure compliance or detect violation(s).

According to the first preemption aspect, a preemption mechanism is geared to making sure that the participants really want to progress to some level of interaction or activity such as by meeting predetermined conditions (e.g., via comparing to acceptable/nonacceptable conditions/triggers/contexts/behaviors) listed in their profiles. To the extent that the profile does not seem to capture the user's desires on a particular condition, etc., the system may be configured to dynamically create such a condition, etc. based on the specific situational data. The system may also be configured to include or issue a warning or alert for the user indicating that this an unanticipated condition, etc., and that the system-created condition is a system recommendation only for which acceptance, rejection, or revisions is needed from the user.

For example, a person may meet another person at a mutual friend's wedding at which alcohol is involved. While his/her profile may include the condition or stipulation about not meeting people when drinking alcohol, this may be varied depending on the situation. Or, it may be a blanket no-alcohol restriction, but there may be a separate "meet people my friends also know" parameter. In which case, these 2 profile elements "conflict" to some extent relative to the wedding scenario. Thus, the system may then make recommendations for Terms and Conditions for that particular interaction. For example, the system may be configured to weight and compare individual parameters and make a recommendation based on highest weight parameter. In this example, if he/she has no alcohol as Very High in importance and "meet people my friends know" as just a Medium importance, then the system recommendation would be "No." But the user may want to override the system recommendation. In which case, the system may not allow the user override without first requiring that a friend "vouch" (e.g., a third-party voucher) for the potential mate, which vouching may be a general default requirement in some cases. This vouching requirement may be implemented via an online vouching signature capability within an App (e.g., Apple iOS app, Android app), via a voice recording, or via another method that would confirm the friend's vouching for the "transaction."

Continuing with the preemption aspect for this wedding example, a list of actions may be provided to help the user avoid or dodge an evolving, and perhaps confusing, situation. For example, the list of actions may include texting a friend of the user that is pre-identified and listed as a support person to the user. The friend may be known to also be at the wedding if the friend's location is being individually monitored and tracked and/or if all of the user's pre-identified support persons are pinged for their respective locations to determine which support person(s) are at the wedding if it becomes known that a situation requiring a friend vouching has arisen. Thus, this action functionality to preempt/avoid a situation from going further is an important aspect of the overall preemption functionality in exemplary embodiments.

According to the second aspect, this assumes that above hurdles have been cleared, and it's time for agreement/contract formation. This would involve the parties (e.g., two or more persons, etch to agree that some sort of romantic/sexual/interpersonal interaction or activity is acceptable for the parties involved. In exemplary embodiments, an App may be used that is on just one person's smartphone or other device or the App may be on the smart phone or device of each party or participant to be involved with the interaction or activity. In some exemplary embodiments, the friend or other third-party voucher may be provided by an App on the smartphone or other device of the vouching person or one of the parties to the agreement/contract.

The agreement/contract include terms and conditions, and importantly agreement on the ability for monitoring behavior of the parties after completion and execution of the agreement/contract to ensure compliance and non-violation. The agreement/contract may include static terms and conditions that are the same in every case (e.g., boilerplate legalese, etc.). The agreement/contract also includes dynamic data about the persons involved and the situation/context involved. The agreement/contract would include information about how far an interaction is allowed to progress and in what form. This may include identification of behavior(s) that are acceptable and behavior(s) that are not acceptable, and information about how the acceptability of behavior(s) might vary by time and other circumstance(s).

For example, it may be the (somewhat drunken) user is ok (with a friend vouching, either overall or perhaps even by specific behavior-by-behavior) to allow the other party to only progress to a certain limited level of sex-related behavior as defined in the terms and conditions the first encounter/date and the next two encounters/dates, if any, occur. This would thus include ongoing tracking of both parties. And if there is a fourth encounter/date, then the user may allow sexual intercourse or higher level of sexual relations, e.g., perhaps without conditions and/or overriding the user profile, according to the general conditions or a "custom" set of conditions (e.g., depending on location, etc.). The terms and conditions may have "custom" conditions related to monitoring/contact verification as explained below for the third aspect. This may include the ability to monitor one or both/all party(ies) social media account(s) to ensure, for example, that there is no disclosure of their relationship in any way unless explicitly agreed to (later) by the parties. Or if disclosure of the relationship is allowed, this may include the ability to monitor one or both/all party(ies) social media account(s) to ensure there is no disparaging comments or other disclosures about either party as defined in the terms and conditions.

The imminent interaction of the parties and the ongoing monitoring/validating may occur dynamically in exemplary embodiments. Because the preemption aspect described above may also be dynamic (e.g., creation of custom, on-the-fly conditions because of conflicting profile parameters, etch, exemplary embodiments may therefore include features that function, operate, and/or change dynamically in relation to the context and other parameters of the situation, such as anticipating, reacting, recommending, monitoring, and alerting with respect to (un)desired behavior(s). The contracting functionality disclosed herein may include custom/dynamic evaluation/creation of modified acceptable/not-acceptable situations, etc., third party/friend vouching components, customization by-type-of-romantic-behavior (e.g., $3^{rd}$ base, type of sexual activity, etch allowed and dynamically inserted into the agreement/contract.

According to the third aspect, ongoing monitoring and ongoing validation is performed to determine whether the agreement/contract has or has not been violated, including detecting violation(s) and initiating action(s) to address the detected violation(s). Accordingly, this third aspect relates to functionality that happens after the agreement/contract formation. This includes tracking behavior of the parties (two or more individuals) relative to each other and relative to the contracted/agreed upon behavior. This behavior may practically be anything but will be customized based on the contract/agreement. This may start with monitoring immediate "intimate" behavior using one or more devices or sensors as needed (e.g., video, audio, heart rate, etc.). For example, two or more sensors may be used to confirm the occurrence of a given behavior. A plurality of sensors may be used to monitor location and related context at the location (e.g., only at my apartment, only on a weekend when I haven't had more than three beers, only if we just got home from a baseball game, etch and related behavior (e.g., only to 3rd base for the 1st interaction/date, etc.). The sensors for monitoring the location, context, and behavior may include social media monitoring. The type of behaviors and limitations associated with each behavior should requirement agreement by both/all parties, e.g., if initially proposed by only one party/user and negotiated thereafter by the parties/users. Based on the sensor output (e.g., detection of safety word(s), gestures, other detectable actions by a person, etch, alert(s) may be provided and/or other action(s) initiated, e.g., a set of actions initiated such as loudspeaker warnings, texts to friends, contacting police, etc.

The ongoing (post-interaction) monitoring may be focused on different types of behaviors at different times, cf., monitoring during the interaction). The post-type behaviors may focus on mutual behavior monitoring of both/all parties. For example, if Person 1 had fully consented (with verification/legal agreement), then Person 2 may want to ensure that Person 1 does not disparage Person 2, e.g., by social media posting damaging to Person's 2 reputation. For example, monitoring tools may be implemented and integrated with an App to warn Person 2 of detected disparaging social media posting(s) by Person 1. Conversely, if Person 2 discloses the relationship with Person 1 in violation of Person's 1 demand that there be no disclosure of their relationship, then Person 1 may be alerted and provided with the details of a detection that Person 2 has disclosed the relationship. The system may be configured to provide recommend action(s) for one or both/all parties to take in either of these above example scenarios, such as notifying the violator about violating the terms of their agreement and to cease-and-desist.

Exemplary embodiments disclosed herein may be used for the preemption and/or detection of an extra-relationship affair or cheating, e.g., extramarital cheating/affairs by spouses, boyfriend/girl friend extra-relationship affair/cheating, etc. In addition, exemplary embodiments disclosed herein may also be used to detect "upstream" behavior or indicators that are likely to indicate a future occurrence(s) of an extra-relationship affair or cheating. Such exemplary embodiments are not limited to detection of the actual occurrence of the extra-relationship affair or cheating, but may also include monitoring, tracking, and/or detecting behavior(s) that might lead to and/or that may be predictive of a future occurrence of an extra-relationship affair or cheating.

Regarding detection of an extra-relationship affair/cheating and/or detection of breaking or violating an agreement in a romantic encounter contract, exemplary embodiments are not exclusively focused on direct/obvious indicators of misbehaving, cheating, agreement/contract violations, etc. as such exemplary embodiments also focus on early indicators) predictive of such behavior. For example, in the case of extra-relationship affairs/cheating, an early indicator may include creation of a user account on a website that facilitates finding a willing participant for an extramarital affair, etc. As another example, an early indicator may include tracking of a spouse to a location (e.g., bar after work, etch more frequently than historically. In addition, other example early indicators of an extra-relationship affair/cheating may include triggers as disclosed herein, such as the triggers associated with loneliness, depression, unhappiness with a spouse or other partner, etc.

Accordingly, exemplary embodiments may detect possible/trending-in-the-direction-of an extra-relationship affair/cheating and then initiate preemptive action(s) to attempt to prevent or reduce the likelihood of the occurrence of the extra-relationship affair/cheating. For example, an alert may be provided to a husband in that process of setting up a user account on a website that facilitates finding a willing participant for an extramarital affair that his wife will be notified (but has not yet been notified) if the process continues and the husband's user account is fully set up and activated. Exemplary embodiments may allow a person in a relationship for which the other person is suspicious (but yet unfounded in reality) to willingly signup for monitoring in order to appease that other person. Example preemptive actions may also include suggest marriage or relationship counseling or some other activity that will help the spouse or other partner come home from work in a much better mood.

With exemplary embodiments disclosed herein, an affair may possibly be stopped before it started. Or, exemplary embodiments disclosed herein may allow for an agreement to be created between persons that stipulated that they were having an affair and stipulated what kind of activity(ies) is permissible and what kind of activity(ies) is prohibited (e.g., different types of intimacy, sexual activity(ies), etc.). The existence of such an agreement, the parties would then provide protection against unfounded allegations of prohibited activity(ies) (e.g., different type(s) that are set forth in the agreement as permissible. Accordingly, exemplary embodiments may allow for (a) avoiding misunderstandings as to which activity(ies) are prohibited and which are permissible, (b) preempting or stopping a prohibited activity(ies) before it proceeds to far, and/or c) provide one side (or the other) with definitive legal and/or behavior tracking support for what did (or did not) actually happen.

Exemplary embodiments disclosed herein may also prove useful for control freaks, overly jealous persons, etc. For example, a person being controlling and becoming a control freak does not happen instantaneously but instead involves a process that happens incrementally over time. Thus, exemplary embodiments disclosed herein may provide the ability to detect controlling behavior relatively early. This early detection and implemented remedial action(s) thereafter may help the controllee as well as informing someone who might not be self aware that he/she is engaging in or exhibiting controlling-type behavior(s), which if left unchecked/unabated may ruin a relationship. This avoidance of the controlling/jealous-type behavior may be implemented at various stages or processes in exemplary embodiments, such as in someone's profile, in "screening" a person before moving into dating/intimacy mode, to detecting controlling/jealous-type behavior "the morning after" as well as in established relationships including marriage, etc.

Like other undesirable behavior, there are a variety of actions that may implemented or initiated, including action(s) that are upstream of and taken before the undesirable behavior after early detection of issue(s). For example, the early detection may include early detection of trends either in frequency of controlling/jealous-type behavior(s) and/or severity of the behavior and/or types of behaviors. The actions, in turn, may include notifying both or all parties of the detected trend and suggesting actions to reduce or preempt the frequency, severity, and/or type(s) of the controlling/jealous-type behavior(s) in the future.

For example, if there is an increase in money arguments between spouses, an exemplary embodiment may include recommending that parties to agree on a discretionary budget such as a discretionary budget based on an AI analysis of the financial and purchasing habit parts of their profiles and/or to modify/build a person's financial/purchasing profiles and habits based on a plurality of sensors' observations, readings, measurements, etc. taken over time. A recommended budget may include a monthly dollar value limit to spend on clothes each month where spending is monitored to detect when that limit is being approached. Such a spending limit would not necessarily be an outright victory for the controller, as the controller may have been demanding that no money is spend and instead of a budgetary limit for clothing purchases each month. For just-met or other early-dating couples, such demands/arguments about money may be more troubling as it spending habits may be too sensitive or private at the start of a relationship. In which case, more emphasis may be placed on "extracting" the person from the relationship or at least informing person(s) within the controllee's support network (e.g., alerting loved ones of the controlled person with the controlled person's permission, etch about the troubling control freak tendencies emerging in the new relationship according to an exemplary embodiment. The controlling-type person/control freak in an early stage of a relationship may be alerted about the undesirable behavior, e.g., advised to stop the behavior and seek counseling, etc. according to an exemplary embodiment. Accordingly, this exemplary embodiment may be operable as a virtual counselor for both parties when dealing with incremental behavior (e.g., indicators of controlling or jealous behavior(s), etch that if left unchecked/unabated may escalate from being a minor nuisance(s) to a major issue(s) and/or relationship trigger point(s) in the future.

Embodiments disclosed above involve parolee or persons-under-re strict ions and include novel and inventive capabilities as do the exemplary embodiments disclosed hereinafter that involve a person(s) under quarantine. The example discussed next involves a person(s) under quarantine being allowed (under certain conditions) to go to a grocery store, which may be considered similarly to, essentially the same as, or substantially no different than the concept or details from, for example, a parolee under house arrest who might be allowed (under very controlled conditions) to leave his home to see his doctor (or go the grocery store or similar necessary/benign purpose).

The term "quarantine" has a number of definitions. As a noun, quarantine may be defined as a state, period, or place of isolation in which people or animals that have arrived from elsewhere or been exposed to infectious or contagious disease are placed. As a verb, quarantine may be defined as impose isolation on (a person, animal, or place); put in quarantine. Exemplary embodiments may utilize these definitions and other definitions including "self" isolation or quarantine, such as a person having been exposed to a virus/illness and takes the precaution of self-imposing on themselves a predetermined quarantine/isolation period (e.g., a 14-day quarantine/isolation period, etc.). It could also apply to embodiments involving refugee containment/management, animal control (e.g., not relegated to humans only, particularly given that many diseases have their "start" in non-humans, etch, military applications (e.g., locked on base, confined to quarters, etch, conflict management (e.g., riot containment, enforcement of curfew, or "hybrid" embodiments involving military containment of biological warfare with associated deployment of troops/command and control in managing/controlling the biological warfare agent, etc.). The persons/other entities do not even have to be living—control/management of deceased entities related to the reason for quarantine/re strict ion could be addressed by the invention, as deceased entities can pose as much (or even greater) risk to other entities when deceased. In other words, quarantine should not be restricted to quarantine that is involuntary, "imposed", or "placed" on an individual, such as by a governmental authority(ies), etc. Aspects of the present disclosure may also apply to by-necessity monitoring/control of a person or other entity (who for their own good, if not others) that needs to be closely monitored to prevent "involuntary" breaking of "quarantine" (such as Dementia or Alzheimer's patients).

A quarantine-related exemplary embodiment may be configured to "allow" a person under quarantine to go to the grocery store (including proscribing when, where, with who, how, and why) based on a variety of contextual factors, such as the current state of the person's household's pantry/refrigerator and "deployed" supplies (such as toilet paper) all of which may be determined by using IoT sensors for example; the number of people in the household (based on any number of factors, including number of beds in the house, credit cards with that address, facial recognition "keys" enabled for the doors, etc.—all determinable by sensors, or via a pre-identified profile determined at startup); patterns of usage (individually or collectively) within the household, and associated trends/predictions/projections of low inventories of a good/supply (based on daily/weekly consumption patterns detected by sensors, historical trends (e.g. rate of usage based on historical buying patterns of a given good, etch; the last time someone in the household went to the grocery store (based on integration with navigation or social media apps, or integration/interface integration with credit card systems or grocery store databases), why they went (e.g. was it to shop, or see his cashier girlfriend—determinable based on credit card statements, changes in household goods "inventory" relative to grocery store visits by IoT-type sensors, etch, how long he was in the immediate proximity of his girlfriend's smartphone while he was at the store-based on standard personal geofence determination (possibly assisted by in store location beacons); what was bought (e.g. using historical location/contextual/other sensor data cross-referenced to household "inventory management" systems utilizing IoT and other sensor arrays and/or cross referenced to detailed electronic grocery store receipts); what are the household's dietary and/or health needs (e.g. diabetics, heart disease, allergies, genetic susceptibility, obtained through Integration/interfaces to medical databases and/or pre-identified risk profiles as part of quarantine setup) and key demographics (e.g. elderly, babies, also part of quarantine profile setup); and even considering the work that person(s) in the household does (e.g. if they are EMTs or nurses (obtained by quarantine profile setup or by access to employer records (with the employee's permission), or perhaps a special essential-employee electronic certificate or flag in a $3^{rd}$ party database)—a circumstance/demographic that can add to the risk-of-running-out-of-food risk by them consuming (and needing to consume) food at a faster rate versus someone working at home (increased rates of consumption obtained by access to calorie-consumption tables based on age, gender, occupation, etc.).

The use of integration or interfaces (except where otherwise noted, particularly with respect to user-interaction type interfaces such as text, email, phone calls, holograms, heads up displays, etch generally are interchangeable when in the context of an exemplary embodiment. From a technical standpoint, there are some distinctions. For example, systems integration—the kind generally used in exemplary embodiments disclosed herein—refers to the electronic-tying together of one or more computer systems, sub-systems, applications, communications networks, and/or databases through various methods and mechanisms. Often these computer systems et al. are owned/operated by different entities and/or have different functions and capabilities such that integration may include combining the respective functions and capabilities or even creating new capabilities, e.g., 1+1=3, etc. An interface (not an personal or human user interface), such as in API (Application Program Interface) may also involve combining/integrating otherwise separate/disparate systems, but does so by providing special capabilities to facilitate doing so, such as providing standards and specialized software to make it easier to integrate multiple systems, instead of "customizing" all the electronic links system-by-system, data-element-by-data-element, and so on.

Risks are also detectable in exemplary embodiments disclosed herein. For example, a much higher rate-of-consumption of food may be indicative of "stress eating"-a risk that, left unaddressed, could lead to the household running out of food (or certain foods) earlier rather than later. It could even result in "downstream" issues (e.g., gastrointestinal (GI) tract issues, etc.). As indicated by the possibility of "stress-eating," mental/mentally-based risks are detectable in exemplary embodiments. Mental/mental-based triggers such as Anxiety or Fear (e.g., of getting sick, infecting others, or dying). Excitement (e.g., the desire to/excitement about something, or even getting out of the house). Boredom (e.g., the "need" to get out of the house), and so forth, could by themselves or in conjunction with other physical/environmental aspects as described above could trigger—at least in the person(s) mind—a "need" to break quarantine, which may, or may not, meet the requirements of breaking quarantine. Certainly, being able to detect the existence of various forms of Anxiety, Depression, or other "cabin fever" mental conditions, where the person(s) is growing increasingly unstable, may be a "valid" quarantine-breaking condition (possibly if verified by an appropriate medical authority, who has access to the sensors et. al. readings), because left unchecked could result in some sort of psychotic-episode. Or, perhaps, detection of such about-to-explode-cabin-fever conditions could cause doctors/authorities to prescribe (without normal seeing-in-person protocols) Anxiety etc.—reducing medications and/or other actions (such as allowing the person out of the house once a day for local-based running under appropriate control conditions). As such, the detection and preemption of risks are an example of the dynamic risk detection capabilities achievable herein, with appropriate machine learning, artificial intelligence, and/or other mechanism-based updating of pre-identified risk profile and employment of new or modification of existing sensors et al., as well as creation of new risk calculations, risk preemption/mitigation actions, resources, and interfaces to prevent/preempt the risk(s). Demographic elements, such as ethnicity could also be incorporated, particularly if there are ethnicity-based risk factors associated with an illness/virus. Such special risk factors, such as ethnicity and age, could feed into considerations of these factors on a macro or micro-basis. Various validation mechanisms could be employed to verify demographic risks linking to databases and also/instead to sensor et. al. readings for measuring, verifying, and/or validating physical (and mental) demographic risks.

For example, local authorities could create special ethnicity and/or age-based group exemptions, allowing for example senior-only grocery store visit date/time blocks such that only seniors/age blocks into a store for a given time period. Various validation (of their exemption "qualifications") mechanisms could be employed to ensure only those meeting the qualifications would indeed be allowed to enter the store. In addition to validating that a person can leave his house before leaving the house, exemplary embodiments may also be configured to provide levels or controls as to what-he-is-going-to-do level, in this case wanting to enter the grocery store. This further supports the notion that quarantines will be implemented at multiple levels in exemplary embodiments, e.g., at home, at intended destination, for intended purpose (e.g., location-less context), etc.

An exemplary embodiment may include a health-related example/extension including a certification or other indicator of immunity for person(s) already infected/recovered from the illness (and thus having immunity) or having "natural" immunity. Such certification, validation, or other verification indicator may be provided in various forms, such as an "immunity card" (with a RFID chip or other sensors that could be "read" before allowing access to a space, like a store), an encrypted file loaded on a "standard" device (e.g. phone, apple watch, etch that could be also "read" by readers and compared to other personal data via other application integration/interfaces, e.g. a facial recognition program (adjusted for mask wearing, if applicable) to scan the person holding (electronically) the "immunity card" (in whatever form) and then comparing the embedded data (including facial profile) with a person's actual (live) image real-time, and so forth. "Remote" mechanisms may also be used, such as QR codes (individualized to a person, including whether the person has immunity) that can be scanned at key checkpoints. Embedded chips/sensors with appropriate certification/validation could also be used. However, some of these "close quarters" mechanisms may be problematic and thus avoided when conditions require social distancing. In such instances, the use of technology-based extenders and/or readers not requiring human involvement could be utilized.

Figure 4:
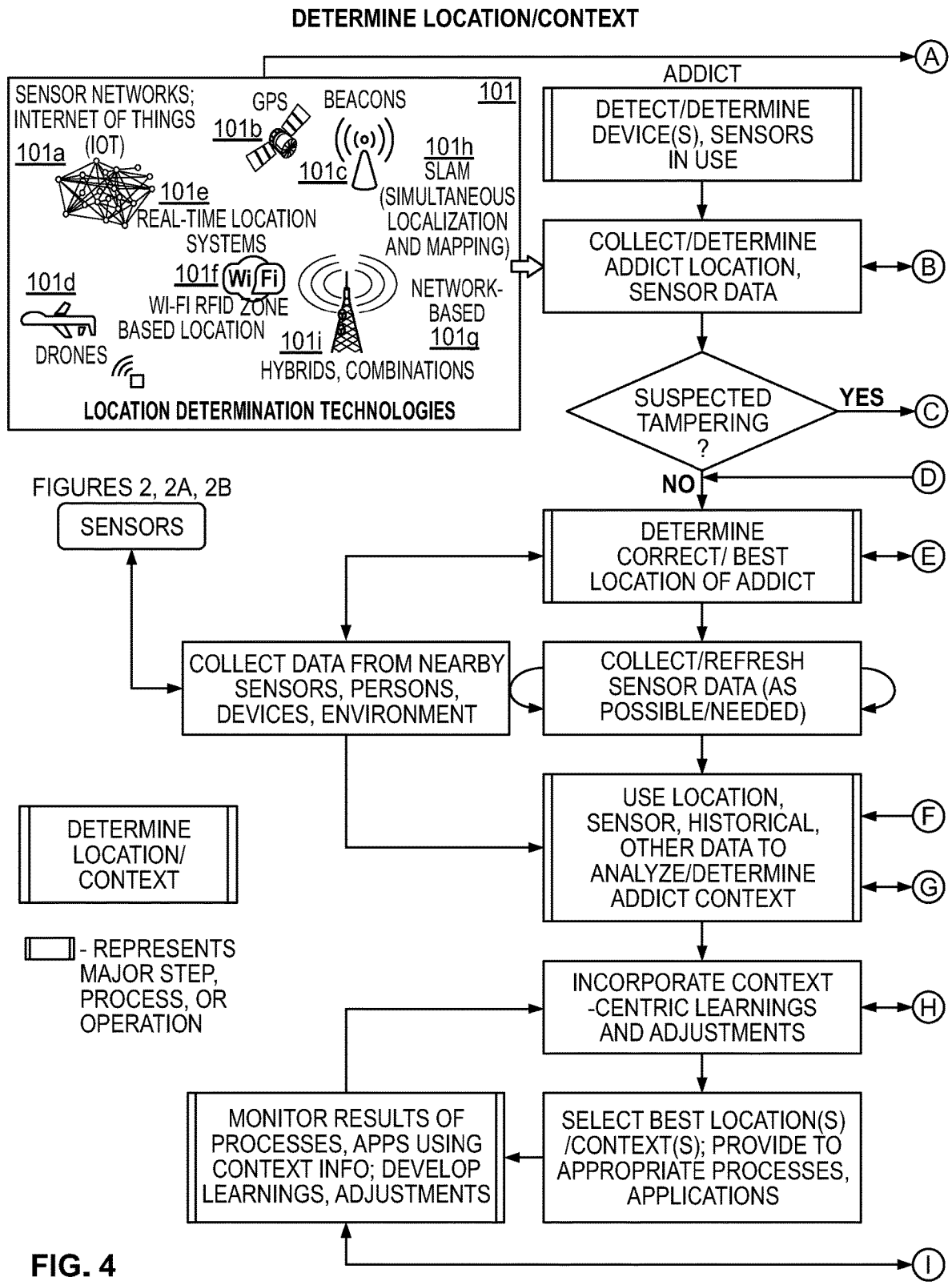
Figure 4:
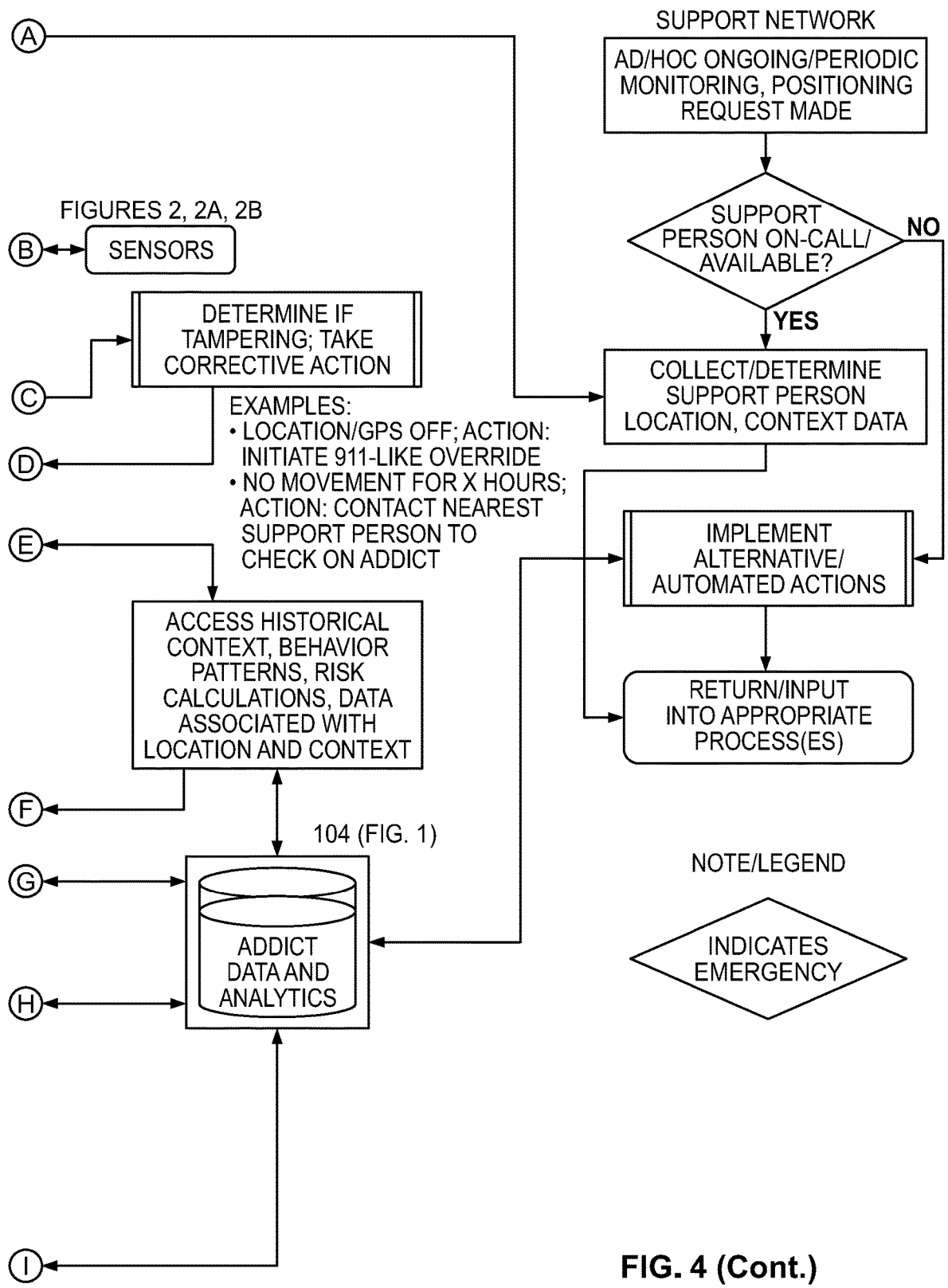

Both privacy and security may be provided to protect against tampering (e.g. trying to electronically "fake" immunity, certifications, etc.) and electronic identity theft. Such privacy/security aspects are disclosed herein including tampering mechanisms (e.g., FIG. 4, etc.).

Other considerations addressed by the present disclosure include environmental factors such as the conditions of the building the household lives in (with influencing factors ranging from whether tap water can be drunk, if there is air-conditioning in hot weather, or what floor the household lives on and if there are elevators)—accessed by integration/interfaces to building records or included as part of the pre-identified profile setup; the nature and conditions of the neighborhood (e.g. crime rates, level of and proximity to public transportation—readily identified by access to various $3^{rd}$ party databases), including likely routes (if any) between the household and the grocery store (computed/obtained via integration/interfaces to various navigation apps). In "big city" scenarios where the household has no car and ride-hailing services (e.g., Uber service, taxis, etch are constrained/prohibited by the quarantine, additional focus will be put on pedestrian-oriented mapping programs (and underlying map data) identifying additional risk factors such as open dumpsters (with possible contaminated waste), and other contextual factors such as the weather (rain or snow prohibiting/inhibiting walking—easily accessible by integration/interfaces to weather apps or even real-time, extremely localized weather sensors deployed along the route or in its vicinity) or air quality (poor air quality prohibiting elderly or people with asthma from going to the store during poor quality days—obtainable via integration with local air quality apps/databases) and how they impact the ability to travel safely to the store in inclement conditions on any given day/time (part of an invention "travel safely" risk assessment algorithm based on any/many/all of the above factors). Regional/local conditions could also be incorporated into the risk factors/algorithms, such as the need for certain seeds in time for planting (in home vegetable gardens), particularly given (current or predicted) contextual factors such as weather patterns, soil conditions, dietary needs of household members, and so forth. Regional etc. variations could also (greatly) influence needs, supplies etc. by how restrictive regional/state/local controls are on essential businesses, control of key goods, etc., as well as determining the priority/weighting/conditions of who/when/why/how/where a person in quarantine is allowed an exemption, and/or even who has to be in quarantine in the first place (e.g., persons over 60 regardless of health, persons under 60 with certain health conditions or comorbidity, etc.). Even the contextual nature of the physical household could be considered, as highlighted by someone in a rural setting with say ¼ acre of plan table land versus a high-risk urban apartment, or the "mental context" of the household, detectable by monitoring various mental metrics of individual household members to determine their individual and collective "happiness" or stress quotient and how that quotient individually/collectively impacts the risk of breaking quarantine.

In various contextual/demographic examples (for example, households that have a sufficient amount of arable land), the household could—and perhaps should—be encouraged to plant a house garden or even a small farm. In the rural example, the household could—and perhaps should—be encouraged to plant a house garden. In such a context, what is deemed essential—or even recommended (an action that could be recommended by an exemplary embodiment(s) disclosed herein based on the household context and other factors, such as time of year, availability of seeds and planting supplies, etch-could vary (e.g. seeds would be useless in a high-rise apartment context, but (long-term) essential to a household with arable land, particularly a rural household without ready access to other food sources), and could also influence quarantine exemptions—and type(s) of exemption(s). Recommendations (e.g. actions) by an exemplary embodiment(s) disclosed herein for preempting a risk are a key part of exemplary embodiment(s) of this invention, whether for example it includes recommendations for rationing/slowing down rate of consumption of a certain product (based on supplies and rate of consumption, prospects for replenishment, and mental "state" of the household and/or individuals therein), or providing proactive recommendations and specific steps for planting and nurturing a garden, or even in recommending the household apply for a "specialty" exemption that would enable the household to go hunting.

In a further example/extension of the above, it would be recognized that the high-riser has little or no resources other than a local grocery store or similar for food (with availability or not of readily available online-ordered food/supplies also possibly taken into consideration), (likely) has very limited stockpiles of goods, and would have few/no viable "specialty" exemptions that could possibly increase its stockpile outside of a local grocery store. In a rural setting, this might not be as true, but other/different consideration for rural variations could be incorporated in exemplary embodiment(s). For example, it might take an hour or more to drive to a grocery store, placing practical limitations on access to a car, gas, etc., as well as recognition that the rural household would be logistically limited to fewer exemptions, but perhaps with a broader scope, e.g. trips to multiple stores, even visits to elderly parents (to make sure they are ok, e.g. through the window). As mentioned earlier, other variations on exemptions could include allowing such rural households to go hunting to supplement their food supply. Indeed, it can be argued that in certain epidemics and quarantines, the ability to self-source food could become very important to the extent possible. As an illustration an immediate need to accurately setup—or modify after setup—upon the imposition of a quarantine, one of the key profile elements relative to the risk of violating such quarantine would of course be the type of—and amounts of—various supplies, as well as other associated factors such as perishability, expiration dates, vulnerability (e.g. from going bad depending on contexts such as weather and storage conditions), etc. The ability to establish such pre-identified supply "baseline" profiles, or updating the household's profile, via sensors, predictive estimates based on historical data, or even manual input is reflected in the scope of this invention. The quarantine exemptions acknowledge, account for, and enable such all the above variations in exemplary embodiment(s), as they are heavily context-based and reflective of its ability to dynamically (e.g., via automation) detect such contexts and create/modify actions accordingly.

Exemplary embodiments may not rely on an unchanging or fixed pre-identified profile of risks, etc., but are configured for continually modifying/updating the profile and associated risks through a closed loop, machine-learning intensive, context-based, dynamic methods and mechanisms. There are various ways to perform the updates/modifications to the profile, e.g., including manually through prompting, etc. Exemplary embodiments are configured for dynamically (and both manually but particularly via automation) updating the profile and/or include system and process integration. As disclosed herein, exemplary embodiments are directed to preemption—preemption of risks, preemptions of behaviors that might lead to violations, preemption of other things that could result in an "official" or otherwise punitive warning/punishment. Exemplary embodiments may be configured to help or be on the side of the person, not the authorities-even to the extent of not alerting the authorities until it is absolutely necessary as a last resort without any other choice or option Government regulations in a quarantine situation play an outsized role, potentially controlling every aspect of life from personal mobility to civil liberties to supply chains. Such re strict ions/regulations could change often—even daily—and as such the appropriate $3^{rd}$ party data sources describing those restrictions et al. would need to be fed into the system according to exemplary embodiment(s) via the varied architectural capabilities disclosed herein, e.g. communication links, directly to a client app, via $3^{rd}$ party servers, via distributed nodes, etc., as appropriate. All of the factors/considerations could be used to establish—or update—the pre-identified profile in exemplary embodiment(s) through a variety of means: manually, periodical (electronic) updates, and/or real-time updates to the profile via systems integration as disclosed herein and appropriate $3^{rd}$ party sources.

The use of predictive analytics may be used in the exemplary embodiments disclosed herein. For quarantines, this is important as its not necessarily the current supply of, say, toilet paper, it is when it is likely to run out. Thus, predictive analytics including the use of context (e.g., people in the household, their conditions (e.g., GI problems, etc.), rate of consumption, number of bathrooms, type of toilet paper (e.g. 2 ply versus 1 ply, etch, etch and dynamic monitoring (e.g., not just frequently checking the usage, but recognizing that changing (re: dynamic) conditions/context (e.g. grandma is now sheltering-in-place with us, Janie's increased level of Fear is causing her gastral distress, Tom's PTSD is getting worse as confinement continues, etch is very important. For example, this is important when predicting necessary supplies (on an absolute basis, on a relative basis compared to needs and/or certain circumstances or assumptions, and/or given/relative to a specific time period(s)), and particularly when an exemption is needed to preempt someone being tempted to break quarantine (and what and how that is measured, e.g. rising Anxiety as measured by heart palpitations, monitoring of household conversations, types of web sites visited, content of messages sent, etc.).

In exemplary embodiment, the above may be utilized to identify when there is a "valid" need to go the grocery store, and identifying it early enough that there is minimal (or at least reduced) risk of someone in the household being tempted to risk breaking quarantine unlawfully in order to obtain supplies. Minimizing or at least reducing this risk could include identifying "special" goods needed by individuals such that if they begin to get low, there is a noticeable rise in Agitation, Anxiety, or Fear levels as indicated by (personalized) values. Such values—determined via various sensors as disclosed herein—include certain amounts or percentages of raising of (in relation to normal, pre-identified levels) blood pressure, average pulse levels, and/or increase in average decibel-based average speaking volumes, possibly measured in conjunction with immediate usage of a fear-of-running-out product, such as the use of toilet paper, for those persons who have a major need for that product (such as people with no colon-which require very frequent restroom visits); or the fear/agitation is "just" identified as a major fear-of-running-out product based on other, less logical reasons. A "need" to stockpile— perhaps as mandated by local authorities', or based on a variety of factors such as a baby-on-the-way in the household, exacerbated by lack of room, money, or fear of new sources of noise—could also be included in both consideration of the household's "necessary" supplies (type and quantity), as well as predicting when an exemption would be needed. Part of the risk calculations in exemplary embodiment(s) is to anticipate/predict the risk of unauthorized quarantine violation(s)—well before the person(s) in the household become aware of the possibility of those risk(s) themselves.

Two additional aspects address the identification of risks. One aspect is in the identification of pre-identified risks and associated behaviors, activities, triggers, and contexts. The second aspect is the various methods and mechanisms for adding to/deleting/modifying any or all of those risks and associated behaviors/activities/triggers/contexts. In exemplary embodiments disclosed herein, the invention allows for many diverse ways of adding to/deleting/modifying the profile, and in turn what data dimensions are tracked, how they are tracked (e.g. what sensors/sensor arrays/networks et al. are used), how they are configured, values/levels/ranges/tracked, how the risk/compliance algorithms are calculated/configured/calibrated, and in turn what actions/resources/integration/interfaces are employed, how the results of those actions/resources/integration/interfaces are measured, and how (via various techniques such as Artificial Intelligence/Machine Learning are "fed back" into the integrated/overall system to further add to/delete/modify the profile, and thus ripple through/add to/delete/modify the risks, risk measurement systems, and soon in iterative/continuous loops.

Exemplary embodiments include highly technological closed loop or feedback control system that doesn't rely solely on technologies, e.g., "low-tech" mechanisms can be used to update the profile on which risks et al. are captured. For example, a person in the household could notice on their own that a) they are getting low on a supply, and/or b) that they are getting increasingly concerned, fearful, depressed, stressed, or anxious about individual triggers, behaviors, activities, and/or contexts (in a way not originally anticipated when the original pre-identified profile was setup). Various techniques/filters could be used to incorporate (e.g., unfiltered/filtered, modified, etch the concern of the member household into the profile, including direct (manual) input/updating process, via an application that filters/assesses the input on a variety of dimensions (including viability, as well as assessing the risk/possibility of the person inputting data to "game" or otherwise tamper the system to try and obtain an exemption when it is not needed, etc.). In exemplary embodiments, the system could also, for example via a Siri or Alexa-type interface, ask the user/household member—"Hi Sally, are you running low on anything, or concerned," or "what is on your mind?" "What are you concerned about?"—a kind of mechanism-based therapy that also serves to assess risks related to the quarantine. The responses can be analyzed, crosschecked, assessed (or simply indulged), through adding the responses to the risk of quarantine violation risk algorithm, actions, etc., including "just" automatically ordering it (what is deemed to be likely to alleviate the risk(s)) via Amazon or other source, to the extent possible. In exemplary embodiments, this kind of mechanism and interface could be used-even if the supply request/quarantine exemption is not "approved"—to mitigate another real risk of quarantine: mental distress associated with mental (triggers (or mental/physical combination triggers) of including but not limited to Agitation, Anger, Anxiety, Boredom, Change, Children concerns. Depression, Escape, Excitement, Fear, Frustration, Fun (or lack thereof). Guilt, Health concerns, (missing of) Holidays, Insomnia, Irritability, Job worries. Loneliness, Money concerns, building intolerance to Noise, Overconfidence (in a solution being found quickly). Peer Pressure (to break the quarantine). Power (feelings of ability to break quarantine with impunity). Powerlessness (to do anything about the quarantine). Relationship problems. Sexual problems, various forms of Stress, upsets associated with Times of Days/Habit/Routine disruptions, increased feelings of Victimhood, and fear of Yelling or conflict. For example, a loneliness/boredom risk may be measured/detected by various methods and mechanisms as disclosed herein including context and being dynamic, e.g., why and how/what in particular in contrast to location-only. So even if not approved, by just the mechanism of asking the person, through Alexa, Siri, a "voice call" on her phone or even texts or emails generate by bots, could be very helpful. Such a loneliness/boredom risk (measured/detected by various methods and mechanisms as disclosed herein), if beginning to elevate, could result in dynamic, context-based actions/interfaces/resources such as automatically placing (or causing to be placed) a call to a "quarantine hot-line" to discuss—specifically—the household's supply situation and talk about ways to conserve them, with information about the household's situation preceding the call to be sent to the (human) hotline person receiving/placing the call. If not deliverable (in that sense), it could even be added (subject to the appropriate controls, qualifications, etch to a neighbor's shopping list—one who has already been granted an exemption, or seems likely to be granted one before the household is. In fact, such a "shopping representative" type of situation could be employed in contexts/situations where a person needs supplies but cannot—or is afraid to—go out to get them, and they can't be ordered and delivered automatically.

Exemplary embodiments may also be configured for uses involving the grouping or pooling of people under quarantine and/or include one or more groupings or pooling of risks (e.g., everyone in the household, or even everybody in an old building with lead pipes that need bottled water) detection/monitoring of elements underlying those risks, and how they manifest throughout the invention, e.g., everybody or some plurality of individuals is at risk of breaking quarantine because of a common denominator—i.e., water: and all the way through the actions, resources, etc., e.g., someone(s) go and get water for the whole building. The pooling could manifest itself everywhere, even influencing when and what kind of exemptions are granted (and to whom) to reflect the common/pooled risk and the logic of addressed that pooled risk with pooled actions, e.g., delivering a truck-load of water to the building and then employing specialized/pooled distribution methods and mechanisms, e.g., everybody come down to the shipping dock in scheduled/staggered times; designated residents (based on relevant criteria, such as those in the best health, the youngest adults, the physically strongest, etc.); delivering certain numbers of water bottles on each floor, or in front of each door, depending on need, etc.

In exemplary embodiments, actions/interfaces may include peer-to-peer (P2P) communications between the person and resources. For example, in the grocery store examples, walkie-talkies or smart watches (e.g., Dick Tracy-like) could be used to make it much easier to communicate from a (local) distance, without using a phone. Plus, touch-screens of smartphones are not usable while wearing most gloves. Walkie-talkies (that use a manual push button) could be "standard issue" (sanitized of course) as a person walks into a store, to communicate with store personnel, once the person is verified to be wearing the appropriate protective gloves, or, better yet, voice-activated communicators that require minimal physical interaction. Such P2P communications could also be employed with home deliveries, and/or assistance with deliveries, and/or "pooling" of resources, among other uses.

In exemplary embodiments, a core capability of the invention is to identify the "triggers"/certain behaviors/activities/states (mental, physical, or both) of a person by which, if left unaddressed, could lead to undesirable behavior—in this case, violation of quarantine. This risk of quarantine violation, however it is defined for the circumstances, could be a major input into an "application"/submission to the appropriate "authority(ies)" for a (temporary) quarantine exemption certificate. Here again would be where various privacy/security protocols/mechanisms would be employed to prevent a household from "gaming" the system to generate an "inflated" risk of quarantine violation by manipulating various risk factors and so forth. In turn, the exemption authority could incorporate the household's individual risk assessment along with other considerations, including, but not limited to, the number of other requests/submissions; their geographical distribution to each other and to local grocery stores or other needed supply source(s); the timing of the risk (e.g. who is most imminent at risk of breaking quarantine); the goods listed in the submissions of being most at need; the "priority" of those goods (e.g. toilet paper and protein products would be much higher than ice cream for example); the supply of those goods at those grocery stores; the expected traffic (and routes) if exemptions were issued (e.g. tailoring which submissions would be approved, and when, in order to manage pedestrian/road/store traffic). Similar elements would be involved in the obtaining of services, such as needing a plumber for plumbing problems, with additional considerations/precautions required given the need for a plumber (in this example) to be specially screened relative to quarantine requirements and the individual household needs and situation, such as requiring full haz-mat suits if there is an elderly person in residence. This submission evaluation/approval process might be a multi-step process; first, a tentative approval might be made, and then second, once additional analysis (e.g. selection of household member, preparations have been made) then a second-much more time/store/route-specific exemption would be issued, along with associated systemic verification mechanisms (e.g. disabling any alarms that might be set on the household's door, updates to police databases to make sure that the specific exemption is set up in their enforce men t/tracking databases, etc.).

Supplies may also be delivered to the house through delivery services, e.g., Amazon, etc. In such a case, the details associated with a household member leaving quarantine to shop would not be applicable. But that doesn't eliminate the risk of exposure to the illness even if delivery is allowed. Further, the nature of the illness-causing entity would be very important in terms of precautions that would be required to take place before any shopping or even the person being allowed to leave the household. For example, air-transmitted viruses may require extreme attention to face/nose coverings and social distancing, whereas surface-spreading diseases would require gloves, and extreme attention to minimizing any sort of contact to any surface, human, even pets, elevator buttons, etc. The aspects employed in this invention can be dependent upon the full range of details involved: the nature of the disease/situation; the requirements of the quarantine and quarantine exemption, both overall and locally; the demographics and other individual characteristics of the household; the context/characteristics of the environment and household; the needs of the household (and of course individuals within the household); the availability and sourcing of the goods and services needed to fulfill those needs; the logistics involved in fulfilling those needs; various timing/time frames involved (e.g., how long the quarantine/current quarantine level is expected to go on; the nature of and/or priority of the goods and services involved, such as perishability of goods, priority of service needed, etch; the macro availability and logistical complexity of the relevant goods and services (e.g., is rationing needed), the ability to deliver—in whatever form—the goods or services to the household, and so on.

As noted before, a key goal of this invention is not only pre-empt/prevent quarantine violations, but to pre-empt/prevent the "upstream" behaviors/triggers/associated risks that may, if left unchecked/unmodified, lead to a possible violation. For instance, example embodiment above have to do with possible violations caused by running out of toilet paper, or plumbing problems (perhaps caused by using too much toilet paper). An objective of exemplary embodiments of this invention would not be focused on the running out of toilet paper per se, or detection of a clogged toilet, but to identify and pre-empt the behaviors that might in turn be causing a high consumption of toilet paper. It may be that a certain person(s) in the household has a gastric-related medical condition, with confinement exacerbating that condition because of his/her Anxiety, Fear and/or Stress trigger's impact on gastric irritation (and, in turn, increasing the amount of bathroom trips and amount of toilet paper consumed). Exemplary embodiments of this invention would be able to detect these triggers (either their existence or levels that are deemed as elevated/high) as early as possible in quarantine (perhaps benchmarked with pre-quarantine toilet paper consumption data), and proscribe actions to pre-empt high toilet paper usage, proactively, instead of reactively trying to order higher volumes of toilet paper once the trigger/health condition is fully "active." Towards that end, exemplary embodiments of the invention may proscribe the need for virtual mental therapy to address the Anxiety etc. triggers), and/or perhaps recognizing that therapy may not work or only be partially successful, proscribe (and even automatically ordering) a bidet that will cut down on toilet paper usage.

The above example is indicative that triggers may be either or both mental and/or physical. As disclosed herein, triggers may encapsulate various forms of mental thoughts, mental and/or physical behaviors, mental and/or physical states, and/or mental and/or physical activities. For example, a mental trigger may be Fear, a mental/physical combination trigger may be Anxiety and Health, etc. In particular for quarantine, mental triggers Anxiety, Depression, Fear, Frustration, Insomnia, Loneliness, and Power less ness may be major triggers at issue with physical elements being secondary. Health may also be a primarily mental trigger, such as when a person is not sick, it may be the fear of getting sick (e.g., hypochondria) that is the issue, or if the person is actually sick or shows symptoms of being sick, it may be the fear of dying or infecting others that is the issue. Accordingly, mental/mentally-based triggers may also be in conjunction with physical triggers.

There are many more detailed exemplary embodiments that are enabled by this invention. For example, through its "support resources" integration, the invention would also be able to access the profiles of any potential delivery or service persons, including their immunity (or not), familiarity with and/or access to the household (e.g. could they be allowed to bring in groceries without the need for a household member to open the door for them or otherwise get anywhere close to a household member, and so forth).

A variation on the above embodiment enabled by this invention is the use of "flash" delivery points to allow delivery person(s) and recipients to meet in an area/controlled environment to deliver and pickup goods somewhere else other than, for example, a household or store. Such meeting places in addition to being "fixed" (e.g., post office boxes, etch could be dynamic in nature (e.g. short-lived, even setup purely for that particular date, time, and context, specific package type, persons needing to be involved, location otherwise used for other purposes, etc.). Such meeting places may be similar to the "flash meetings" as disclosed herein, e.g., FIG. 10 illustrating example ways in which Real-Time Location System (RTLS) technologies can be used to enable ad hoc, spontaneous, unscheduled, or flash addict meetings between people with similar addiction issues. Such meeting places may be based on identifying meeting places and appropriate related contexts (e.g. sterilized, secure/exception-qualified credentials, meeting places appropriate for/accompanied by other resources for safe handling, middlemen-type services, etch to allow for the safe "transfer" of the package from the delivery person to the recipient (in real-time, scheduled, or asynchronous delivery) dynamically (e.g. the location/context being short-lived, and potentially established purely for this package only or perhaps similar packages or contexts (e.g. people with similar issues and contexts also using the "flash" delivery point. Further, exemplary embodiments of the invention enable "context-based" delivery, e.g. given the constraints of a household (e.g. an elderly woman who can't pick up anything more than 5 pounds), the size/weight of the package (e.g. a pack of 48 water bottles), and the capabilities of (e.g. weight-lifting capabilities being up to 50 pounds-less than the pack of water bottles) and "health-certification" of the delivery driver (e.g. has been certified immune), that when delivering an over-weight-limit package to that weight-constrained, particularly-virus-sensitive-and-thus-requiring-extended (12 feet instead of 6 feet social distancing)-social-distancing-household, that the delivery/delivery driver would be allowed special delivery "exemption and context-based instructions (action) to allow in-home delivery of the package (even allowing electronic access to the home while the household member practices social distancing) and even "setup," such as bringing into the house, wiping down the package, and "putting away" the package (such as a shipment of 48 water bottles) in the house.

A specific sub-embodiment of the water bottle scenario is further illustrative of the novel and inventive aspects of the invention, and how it contrasts with existing, location-only prior art. For example, consider an elderly gentleman who lives alone in a $3^{rd}$ floor apartment in a 100-year old building with no elevators or air conditioning, nor does he have a car. The nature of the disease causing his quarantine dictates that he has to drink bottled water, as his building has lead pipes and the nature of the virus and his health conditions means drinking tap water is hazardous. According to exemplary embodiments, the invention (e.g., systems and methods, etch is configurable to know or have knowledge of the last time he went grocery store shopping, which store, and what he bought, particularly how many water bottles he bought. Internet of Things sensors (IoT-type sensors) may track his consumption, and predictive algorithms based on his consumption patterns, adjusted for weather predictions (e.g. how hot it will be and how his consumption will increase) may predict when he is likely to run out of water. Since a key goal is to preempt/prevent the risk of the man violating quarantine to get water (or, alternatively, risk his health by drinking tap water), the next part is to determine the best set actions, resources and integration/interfaces for him to obtain that water, before the risk of running out of water/ having to drink tap water becomes too high, or he is tempted to violate quarantine to the risk (of infection) to himself or others (in the event he is an asymptomatic carrier). In this sub-embodiment, support resources (including the delivery driver example) would become critically important. As illustrative throughout the disclosed exemplary embodiments, the dynamic determination and deployment of actions and support resources, via context-based interfaces—including creation of new actions et al. to address unforeseen contexts, utilizing AI, machine learning, and/or drawing from similar contexts beyond the individual history of the person(s) involved—are key elements in exemplary embodiments. As disclosed herein, dynamic, context, machine learning, multiple support resources, and closed loop aspects are also important in exemplary embodiments.

Picking up with a household-needing-to-go-to-the-store embodiment, there are numerous context, location, and dynamic sensor/network based elements that factor into identifying what store to go to (presuming delivery is not available in this scenario), when (day/time) to go, who else will be involved (in helping him shop/bring stuff home), how he will get to the store (walking and subway, and what route is best to take), what to buy (given his water requirements, what he's able to get home, and up to his apartment).

The above described exemplary embodiments and its variations are enabled by aspects of this invention, though some exemplary embodiments are focused on preempting the core risk of violating a quarantine and/or a valid quarantine exemption, exemption, through focus on various "upstream" behaviors/activities/states/triggers/risks.

A particular concern, and highly important in calculating the risk of quarantine violation—not just risk of a violation itself, but the risk to public health—is in the case of a household member having an active (e.g. contagious) case of the sickness. To the extent that tests are available to determine contagiousness or not, they would be employed, and taking a test and obtaining the results would be a prerequisite to obtain a restriction. Variations of risk could be considered based on the type of test(s) employed, e.g. antibody tests, micro blood testing stations, small micro needles sampling blood and rapidly scanning for infection. Other tests might include a thermal camera or infrared (IR) contactless thermometer, just doing temporary scans, any or all of which could impact the type and/or duration of any exemption.

The test results could result in an immediate update of an "immunity card" (physical or virtual) or equivalent, and/or be sent to the various endpoints (e.g. grocery stores) or other in-route/possible-route nodes, as needed. In the early days of a pandemic, tests may not be available. In such circumstances, it is to the benefit of all—not just "forcing" a sick person to go out for (possibly desperately) needed supplies, but for the sake of anyone that they would interact with in the process—to do everything to prevent a situation. In such a situation, not only could the person's priority be dramatically escalated (particularly if they are a single-person household, but also even multi-person households where non-sick persons may be asymptomatic and thus for all practical purposes be as dangerous as the obviously sick symptomatic person), and, instead of applying a household exemption, instead employing (probably scarce) support resources to do the shopping for them and to deliver them to the household. In this scenario, the support resource(s) would need to have an equivalent exemption made for them, but with varying conditions such that they are not as subject to as strict routing or time windows, do not have their own personal future exemptions somehow impacted, and indeed to the contrary those "do-gooders" (even if paid), are providing future exemption "credits" or other rewards, including but not limited to those disclosed herein, e.g., FIG. 9 describing an example addict re ward s/de merits system based on an addict's behaviors and actions, which may include rewarding (or punishing) an addict based on behavior via tracking and data analytics and various reward mechanisms, etc.

Embodiments/sub-embodiments disclosed herein are/can be applicable to Parolee/Persons Under Restriction as well as being useful in related forensics applications. For example, the information/data generated may be used to actually forensically prove related crimes, for example, proving that an "alibi" that a person dies from a virus was instead actually murdered, and so forth. In this exemplary forensic application, the risk avoided or preempted by the system/method in this example would be in allowing someone to literally get away with murder. All sorts of data that is collected as part of the quarantine risk of violation preemption as disclosed herein could be also used in reverse-engineering crimes, including murder, etc. For example, if there is evidence that the wife disappeared 10 days ago, but the husband maintains she disappeared two days ago, various data could prove/disprove that, such as how the rate-of-consumption of toilet paper changed 10 days ago, not 2 days ago.

It is worth reiterating that a core purpose of exemplary embodiments disclosed herein is to preempt a behavioral/activity/trigger-based violation from ever occurring (e.g., breaking quarantine, etch, by monitoring/tracking/assessing and preempting risks of behaviors/activities/states that, left unchecked, might lead to actual violations, long before there is imminent risk of such actual violations. Another core purpose is to preempt/prevent the person going to the store from being tempted to (or accidentally) violate restrictions associated with how he/she goes to the store. In all these examples, this may be implemented (more) for the purpose of protecting individuals in the traumatic event of a quarantine, rather than implementation for use a tool for government to monitor individuals and impose penalties on violators.

If it is determined that a trip to the grocery store is needed to prevent serious risk of violating quarantine, exemplary embodiment(s) would enable several other activities and monitor associated behavior(s)/activity(ies)/state(s)/trigger(s) that, if they occur (or, show signs of starting to occur, or being a risk of occurring), could lead to violations (e.g. revocation of current quarantine exemption, lowering the possibility of future exemptions, public shaming, arrest, etc.). As noted before, the invention could for example integrate/integration/interface with quarantine exception systems/app(s) (perhaps run by the local government) to request an electronic exemption certificate, providing some of the key information described above and below. Once—in general—an exemption is approved (pending details, as supported by the 2-step local government process discussed above), the details must be determined, such as person(s) who will be the designated shopper, which store(s) will be allowed to be shopped at, what route(s) is/are allowed, what time(s) has been allotted for that specific shopping visit(s), what variations in the above are acceptable (e.g. if it is raining, more time might be allowed). Or if a critical item is out-of-stock by the time the person gets to the store, an extra allotment of time (along with new computation of routes and associated restrictions) may be allowed to enable him to get to a "secondary" store, etc. These details could be stored on a device/mechanism on/in/in the vicinity of the person, or they could be stored elsewhere and retrieved in conjunction with various personal identifiers on/in/associated with the person, and/or stored in various distributed network nodes (potentially with distribution of details according to what a node "needs to know, and be known" relative to when the person is in the "coverage area" (logically or physically) of the node).

All these details may be important, as for a quarantine exception to function, it has to be relatively limited (or at least well defined), including a start time window, the start (e.g. home) and particularly the destination (the specific grocery store allowed), the ending time window, and what variances/flexibility (if any) is allowed in route travelled, destination(s), method of travel, etc., as well as environmental and other factors associated with all the above (e.g. weather, crime, garbage dumpsters, etc.). These details would depend on a variety of considerations, which considerations are anticipated by and addressed by the exemplary embodiments. Various variations in geofence techniques may be included as well as the context-related capabilities disclosed herein.

If a risk of someone possibly being tempted to break quarantine is identified (in the form of an absolute score, a relative score in comparison to other households of similar composition/characteristics, a relative score in comparison to pre-quarantine metrics/"benchmarks, and/or risk categories or even specific qualitative/quantitative examples of specific risk manifestations), and/or a recognition of the household's need (by local authorities, for example) has been acknowledged by the authority(ies), a next step (in a multi-person household) would be to "select" the household member (or this selection may be made by the exemplary embodiment(s) via assessment/computation, and in turn enforcing its selection) to go on the grocery store run (assuming only 1 person per household was allowed out). The selection—if not left to the household—could in turn depend on any number of risk factors, including but not limited to health and mobility factors (determined by pre-identified profiles and/or various sensors and/or access to various databases, as described before), such as age (e.g. not being too old or too young, for reasons such as being able to physically perform the shopping), whether he/she has positive or negative health factors such as virus antibodies (e.g. was already sick, as discussed earlier), pre-existing health conditions (putting him/her in extra danger if the virus was caught while they were out shopping), and/or genetic susceptibility (to catching the illness and/or the illness will be extra detrimental given their genetic conditions). Any/all of the above could also be evaluated against local contextual factors such as weather, crime, etc.

Further, mobility factors could be considered, e.g. does the person have access to a car/safe transportation, or whether the person if he/she has to walk has demonstrated a past ability to walk the required distance and shop, have the ability to carry/push a certain weight and bulk of groceries, and return in the allotted time; and/or other risk factors such as the possibility or propensity to get "distracted" on or near the route needed to go to the selected grocery store (such as, for example, him having friends/a girlfriend that live along/near the route). Note that "safe transportation" by itself would require a risk assessment calibrated for the day/time that the person will be traveling. Certainly not all public transportation options will be equal in terms of safety relative to the person's specific requirements, and even private transportation options (e.g., bikes) may have practical obstacles that prevent their usage, in the specific context for which the person would need it (e.g., it is impractical to carry heavy water bottles on a bike). All these factors could be pre-identified as part of the profile setup process of the invention, and/or various sensors, and/or could be computed by the exemplary embodiment(s), such as combining various personal characteristics into a "ability to shop while walking X distance with Y pounds" score). In exemplary embodiments, the invention may also incorporate the use of "Support Resources," such as the availability of (immune) nearby strong young persons to help elderly in carrying groceries from the store back to their apartment on the $3^{rd}$ floor. Requesting/needing the support of additional resources (inside the household but especially outside the household) may be part of the exemption request process, and may include requiring access to many of that support person(s) personal and/or household data as part of the exemption request risk assessment and evaluation/approval processes.

In the shopper selection (or preparation) phase, exemplary embodiment(s) could also incorporate current local and/or demographic-oriented official guidance regarding movement/shopping and associated conditions (e.g. use of masks and gloves, and considering the household inventory of such). If masks and gloves are required, for example, then that requirement could be included in the exemption "certificate" (or equivalent), a potential source of a violation. Towards that end, if the household/shopper does not have a mask and/or gloves (e.g., medically approved, not just winter gloves, etch, then an expedited acquisition process could be initiated, interfacing with Amazon or other online store, or perhaps local government stock, to get them expedited shipped to the household. This latter step would ideally not happen. Instead, one of the immediate tasks upon implementation would be to ensure that each household had all the medically-necessary "pre-requisites" necessary for not only surviving the quarantine, but also have what is necessary when it is necessary (and allowed) to venture outside their individual quarantine area.

A precursor, concurrent, or next step at this point is determination of a complete—and verifiable—shopping list (virtual and/or physical). This list would be predicated on (but not necessarily limited to) the high-risk item(s) (that is/are causing the risk of quarantine violation). This list could be open ended, e.g. whatever household wanted (as long as it included the high-risk items); or it could be partially restricted (say, to total estimated weight); or it could be restricted to specific, individually approved items and quantities by the authorities. And/or it could be adjusted/restricted depending on supplies/anticipated supplies in the store(s) that the household member has access to, based on geography and other factors, discussed next.

Turning to the "destination" of the quarantine, exemplary embodiment(s) could also incorporate current availability of certain foods at the nearest grocery store versus what the household is getting low on and/or needs/desires, and even selecting the grocery store(s) based on current (or projected) traffic in the store. For example, if there is less foot traffic/people in store A versus store B perhaps measured on a square foot basis, or number of active cashier lanes at that time or projected for when the person will be there. Store A would be selected even if Store B is closer. The exemplary embodiment(s) could even incorporate information like pedestrian traffic (current or projected), if the person would need to walk to a store, and designing a route that minimizes interaction/maximizes the possibility of 6 feet or more social distancing, at various possible specific dates/times that are under consideration to be assigned/al located to the person. Such assign men t/al location of permissible go-to-the-grocery-store times could even extend to integration with, and coordination with, scheduling programs, e.g., a person is allotted a coveted spot at 5 pm Friday because the person is a high priority go-to-the-store person based on the above, and the person is not scheduled to be at work at that time. A potential key part in the grocery store selection would be current and projected inventory of all items in order to make sure that an exemption and selection of a specific store does not go for naught by the person showing up to a store that is out-of-stock. This risk could be preempted by ties to the store's inventory management system, e.g. timing the store visit with expected delivery times (and stocking) of the high-risk items; use of an electronic ration-book control system; and/or a pre-allocation of stock by the store to a specific person (or exemption certificate), essentially setting aside the inventory for that person (or certificate) only. This would include re-introducing the stock into inventory, or allocating it to another person, if the item(s) are not picked up by the exemption certificate expires.

The exemplary embodiment(s)—at any point in the process—could also incorporate the household financial situation (based on pre-identified profile in the setup process, and/or access to credit score, etch, e.g., income levels, whether the household is on food stamps that are awarded at the beginning of the month (thus being slotted at the beginning of the month is better than the end of the month), or even take into considerations when scarce supplies (e.g., toilet paper) that the household needs (or has been allocated a monthly "ration") will be available in Store A, and if that is one of the household's pressing needs given the rate of consumption in the household (projected consumption based on household demographics, or even actual consumption as measured by IoT-type sensors). The financial situation of the stores in the area of the household could also be incorporated into the algorithms involved in choosing the store(s) that could best serve the needs of the household at that time.

In addition, an electronic "certificate"—with an embedded duration and where-can-be-used embedded, could be issued to the person authorized to go to the store, that could be monitored by various sensors in the street, and actions and/or alerts of various content, Integration/interfaces, and intent, sent to various enforcement entities if the certificate is missing or not valid at that time, place, location, and purpose. A core purpose of the invention is to preempt any actual violation. As such, the invention's primary—and first priority—purpose and associated actions, etc. is to inform/influence/mitigate a person's behavior before an actual violation occurs. Thus, warnings/alerts etc. would be sent to the person (supposed to be) shopping or on the way to/from shopping, to get them to address "inappropriate" behavior well before an actual violation occurs and in turn triggering all manner of unpleasant actions by law enforcement etc. being visited on the person.

For example, any deviation from the authorized routes by the person from their home to the selected grocery store could be analyzed and predictive analytics employed to determine if the person is accidentally (or within acceptable parameters) deviating from its authorized destination of the grocery store, or warnings/alerts sent to the person if their departure time or rate of progress is too slow relative to expected shopping time (estimated based on shopping list, traffic, and average through-put times of the store as historically indicated for that date/time or projected/predicted). If for example, the person using the "authorization" seems to instead go (or start to) to a nearby friend's place, in violation of official gathering guidelines, could be detected. In keeping with the invention's emphasis on extra-early early warning, and the preemption/prevention of an actual violation, indicators that indicate such misuse of the authorization could be monitored via a variety of sensors/networks et al., ranging from not taking a wallet (e.g. not taking any money to buy something), text(s) to a friend that says (be there soon) to dressing up "inappropriately" (e.g. getting all decked out in a way unlikely to a grocery store visit) to not taking a mask and gloves (prerequisites for being allowed to entering the grocery store), and so forth. Even checking that the person's primary device(s) has a sufficient amount of power for the trip could be part of the risk preemption mechanisms (e.g. if the phone dies in route, this would create all sorts of problems—mostly unmitigable). Again, the emphasis of the invention would be on actions to pre-empt a violation, through extra-early detection (particularly using behavior(s), activity(ies), state(s), triggers), and/or context(s)) and focus on actions, alerts, etc. to the person, versus prior art that focuses on location-centric, imminent or already-in-progress violations that are focused on involving law enforcement or other authorities.

Once a person has been designated to go to the store, and the conditions under which he can go have been defined (e.g. what store(s) and where, under what date/time window(s), with what support resource(s), what route(s), by what mechanisms (e.g. car, walking, Uber, taxi, bus, etch, and what can be purchased, to address the overall underlying risk of breaking quarantine and what individual risks making up that broader risk (e.g. the elements of where, when, who, how, what, and why), then the "processes" of actually going to the store, doing the shopping, and returning need to take place. This includes the management of a series of related risks, including but not limited to: violating any of the related who/what/when/where/why/how aspects such as leaving too late or too early; going without appropriate personal protective equipment (PPE); going with unapproved resources: deviating from the approved route(s) (or taking routes that could jeopardize being able to complete the shopping in the window allowed): going to the wrong stores (or unapproved stores): interacting with person(s) not deemed essential to the shopping (for example, stopping at a friend's house along the way): not purchasing the supplies that underlaid the reason(s) for the shopping in the first place: purchasing goods that might jeopardize being able to complete the shopping in the time allowed (for example, buying a 50 gallon container of water that could not be carried without assistance up the 3 flights of stairs up to the household apartment), for example. All the above can be tracked/monitored via some aspects of the exemplary embodiment(s). To enable at least some of this in-route, while shopping, and/or getting goods home sub-embodiments, it will be necessary to have Integration/interface/integrate with various deployed sensors, networks, systems, et al. along the way and/or in the store. Accordingly, this exemplary embodiment may rely upon context including Where, When, Who, but also What, How, and perhaps most important of all Why. This use of context is considerably different than prior art that relies upon location only (Where When Who without any context and with Why).

There are numerous—and perhaps an unlimited or countless number of—ways for "validating" that a person outside their home is doing so "legally" or otherwise in an approved fashion. For example, just leaving the household could be validated with a geofence-based validation that the person leaving (or about to leave, or having just left) a geofence (defined by any number of methods, such as the property footprint for a single-family home, the actual footprint of the home, going out of the range of a beacon placed within an apartment or on the door(s), etc.). Upon detection of a (possible) violation, various devices associated with the household could be checked for an exemption certificate or equivalent, and local, EDGE-type IoT computing could prevent any further escalation of possible violation checking, at least with respect to immediacy of household leaving risks. Or, such possible violation behaviors could be communicated electronically to central server and/or decentralized nodes in the vicinity of the household to confirm a valid exemption. Such geofence-type checking is addressed in the prior art, or could be considered obvious, even if the mechanisms (e.g. EDGE-computing and validation via decentralized nodes) were not.

But a device leaving the geofenced area or crossing a geofence is not the end of the exemption checking. See, for example, the tampering mechanisms disclosed herein (e.g., FIG. 4, etc.). The tampering mechanism(s) may be used to make sure that the person leaving the household (with the device with the approved exemption) is the one who should be leaving. Although verification mechanisms may be known, the quarantine exemption—with a stated destination, allocated time, etc.—can also be context dependent. For example, various sensors (in the household, in/on the person, etch could detect the existence of—and proper usage—of masks and gloves, if for example those are required or recommended by various authorities (the existence of determined via systems integration with appropriate $3^{rd}$ party systems/data sources). The exemplary embodiments may focus on determining this as soon as possible prior to leaving the vicinity of the household (or even before leaving the household), generating certain alerts/actions if the masks or gloves are deemed to be missing (e.g. go to pantry #3, they are on the bottom shelf) or not being used properly (e.g. the mask is around the neck, not over the mouth and nose, in proper orientation and coverage). Even non-required elements could be detected, such as bringing reusable bags in an environment is discouraging (but not prohibiting) use of such bags (due to their retention of germs), or, alternatively, since part of the shopping list may include heavy items (that would cause plastic bags to tear), ensuring (via the alerts/actions and subsequent results measurement) that the reusable bags being brought have been appropriately disinfected before leaving the household.

As an example of the dynamic, context-based actions/alerts of the exemplary embodiment(s)—and a distinction between geofence (e.g. location or location/context)—only based alerts—can be seen in the selection of interfaces in the above leaving-the-house example. The interface could vary for example both with respect to where the person is relative to the geofence boundary as well as the specifics of what the risk is. For example, if the person is still in the house, but not having opened the door, without having yet picked up masks and gloves, an audible alarm from in-house speakers could be generated with a message of "don't forget your mask and gloves!" Once he crosses the boundary (e.g. opens the door and steps out), then a buzzing or beeping on his phone could be activated (without an audible voice, to prevent panicked listening by neighbors). If he still hasn't turned around and gone back to his house, various automated calls and/or texts could be sent to all his devices, escalating if he continues to ignore them, such as sending messages to any support personnel (accompanying them, or being planned on being met) to try and contact the person/get their attention. If in a different context (e.g. he left carrying reusable bags), then the nature of the actions/alerts, and their content, might be dramatically different, reflecting the difference in severity between an "essential" risk of violation (e.g. leaving quarantine without proper PPE versus an "optional" risk of having discouraged (but not prohibited) reusable bags). Further, to the extent the various actions and/or interfaces (and or additional resources employed, if any) were not effective in changing the person's behavior (and thereby increasing the risk of an actual violation), then these (non) results would be fed back into the system/method embodiment(s) of the invention (via mechanisms including AI and machine learning) to modify (or even create new) actions/ interfaces/resources to be employed instead of the those used in the current actions/interfaces/resources, the next time a similar risk, behavior, and/or context was detected, so that preemption of the behavior(s) that might lead to an actual violation could be done better/earlier/in a more effective manner.

The above leaving-the-house example helps to demonstrate (novel and inventive) context-based extensions of "traditional" geofence-based restrictions, not only in what is tracked/measured, but how various context-based risks are identified (e.g. masks, reusable bags, etch, and dynamic, context-based generation of actions are employed, even within a context-type (e.g. instead of the context-based possible risk of violation being not having a mask, it is one about how the person not wearing the mask properly, with variations of actions and interfaces within even that same context-type, even before he reaches the door)—all examples of dynamically detecting, and preempting, various risks, via various behavior/activity/trigger/risk/context-based methods and mechanisms, before they can become actual violations.

As the household member (and potentially, support resource(s)) travels to the grocery store, his progress will be tracked. There are a variety of ways to do this, e.g. by traditional GPS, or via Wi-Fi Real-Time Location Systems (RTLS), or beacon-based tracking, or other such systems. While such this tracking may be known per se, what is done with the tracking information in embodiments disclosed here in non-conventional and less traditional. Given this invention's focus on preempting violations, the invention's primary—and initial focus, at least—is in detecting behaviors that might lead to violations, and initiating context-based action, using context-based interfaces and resources, to "course-correct" the person before an actual violation can occur and/or be reported. Exemplary embodiment(s) would go to great lengths to prevent a violation from being reported, including (under certain circumstances/contexts), not reporting actual violations to authorities if there is any chance of the person (quickly) correcting their behavior. For example, if a person is deviating from their "approved" course-even to the extent of exceeding a "tolerance," buffer zone, or other approved range of variance (measured in distance, time, or other metrics), the exemplary embodiment(s) would implement an increasingly strident series of actions and interfaces and/or resources to "encourage" the person to correct their behavior, potentially ending with a kind of "last warning" message (via ALL possible interfaces), after which actions/alerts/messages to the appropriate authorities would be implemented. In this set of tiered or progressive actions, et al. the context(s) of the person will be critical in determining the tiering/progression, as well as to what degree of "leeway" or flexibility in the tiered/ progressive actions will be implemented.

For example, if the context is that the person has a broken bike (a transportation alternative somewhere between a car and walking, and a context detectable by sensors on the person's devices, on the bike, or even self-reported) and the person appears to be seeking repair assistance somewhere off the approved route, then the invention would not only not report the deviation to authorities, it would recognize the circumstances and try to help by contacting other (non-infectious) resources in the vicinity with the necessary skills and/or directing the person to the nearest bike shop that is allowed (in emergency circumstances) to repair bikes. Even if such a specific context cannot be detected, then the exemplary embodiment(s) could make differing tiered/progressive decisions and associated actions et al. based on not only where he is, but how he is moving (e.g., running, getting in a car, etch, and using that information along with historical data on his movements and contexts as to where he is likely to be going. That predicted "final" destination would then likely have dramatic impact on the actions et al. employed by the exemplary embodiment(s). If it looks like he is going to a hidden, prohibited party for example, the actions et al. could be quite different than if he appears to be wanting to quickly visit his mother.

Once at the store, a new round of sensor usage is employed, some traditional and some via this invention. To start, just entering the store will require validation of the person's "credentials," e.g. having a valid exemption, and validation that the person trying to enter is indeed the one on the exemption (checked locally, centrally, via distributed "smart" nodes, etc.). This may include various techniques, including facial recognition (adjusted for mask-wearing). Context could come into play, however, for example, if the store has different entrances for different needs, than those contextual needs (e.g. the shopping list of the person/ household, or at least their critical needs) could further modify the validation "protocol" or equivalent of the store. It could also vary for example by the age and (non-virus) health conditions of the person (e.g. a separate section for senior citizens who are otherwise healthy). A further variation could be if the person is accompanied by support resource(s) or needs support resources within the store.

As the person traverses the store (practicing enforced social distancing using for example, personal geofences, or beacons that permit only 1 person at a time to be within range), the person's shopping list is compared to the goods on the shelves (using various tags/beacons per item). For example, persons with the store may be require to wear wristbands that vibrate when someone in the store comes within a predetermined distance (e.g., six feet, etch of another person in the store, whereby the wristbands would thus provide personal geofences for each person (e.g., shopper, cashier, Stocker, other store employee, etch in the store. If the person passes by a needed (e.g., required/essential item that was a factor in their getting an exemption in the first place), then various alerts could be enacted. These could be delivered via a "standard" interface (or even specialized app automatically loaded on his device of choice when he entered the store), with alerts escalating if he continues to pass by the item without picking it up (in other words, enforced shopping of a sort). The nature of these actions could also be tiered, generally localized to the person, support person, and/or store management, e.g. not such as to disturb the other shoppers. Exemplary embodiment(s) could even enable "assisted" shopping in a sense that if a person "misses" as certain item, store employees will "pick" the item(s) (in the allowed quantities) and have it ready for the shopper when they get to the register. Indeed, at checkout (preferably via contactless mechanisms), the shopping list of the person could be automatically checked against the "required" items. Any omission would result in the total (including the item) to include the missing item(s), and then requiring the person to wait (probably outside) while the items are picked and "delivered" to the person (preferably without human interaction). In exemplary embodiments, other considerations may include a comparison of (A) how much time the person has left, ability to carry items, distance involved, how travelling (e.g., subway, car, bike, etch with (B) whether a (missing) item should be (involuntarily) enforced via perhaps a dynamic (context) calculation of total "allowed" purchases" (e.g., by weight if the person has to carry the purchases and/or other transportation alternatives, etc.). A predictive algorithm may be used to determine if the person cannot get home before the exemption expires, and if so, then a "forced" replacement of non-essential items may be made with essential items.

Leaving the store to return home could be tracked just like going to the store. But here again, the different context (e.g. going home, with a load of groceries versus going to the grocery store with none) could result in significantly different actions/interfaces/resources being employed. For example, any deviations from the route could be cause for different actions et al. to be taken than a similar deviation in the going-to-the-store context. A bike breakdown, for example, would make going to a bike store with a bunch of groceries impractical, if not impossible. As such, (approved) bike resources would need to come to the person. Such a situation would very likely result in an exemption time-expiration if left unaltered. Thus, a dynamic, rapid-approval extension and update to various certificate mechanisms would also need to be employed. Another, less forgiving, example might be a detection of a route deviation to a party. Going to a party, with an arm/basket load of groceries might be considered especially problematic (e.g., a risk of not only the person being exposed, but the groceries intended for the rest of the household being exposed), and thus the actions employed may have a much shorter/limited set of actions trying to rectify the person's course before law enforcement or other authorities are alerted. Or, other more "harmful" yet not-quite-as-bad-as-alerting-authorities might be employed, such as social credit score negative hits or even public shaming on social media. As an example of the use of interfaces, as the person follows an "approved" route, the navigation system might use one standard pleasant voice. But upon a deviation of the route, the voice changes, for example, from a woman to a man's voice that gets progressively angrier and/or louder as the deviation continues/gets farther from the approved route.

Upon entering a building (e.g., for apartment dwellers, etch, specific conditions of the building and context of the person could come into play. For example, a problem in many older buildings is that the main door out of the elevator must be opened by hand, and apparently it is against the fire code to put an automatic opener. Anyone going in or out of the building must touch that door handle and pull. This is obviously problematic in many respects, so as the person nears the building, an appropriate resource must be employed to operate the elevator appropriately, both to prevent the person from having to touch it (e.g., have less people touching anything on the elevator) as well as in the process assist the person with the groceries. Exemplary embodiment(s) would ensure that this took place appropriately, particularly from a timing and social distancing standpoint. This "narrow" assistance could also take into account making sure the steps up to the building were cleared of ice and snow under a presumption that such regular maintenance of such would be discouraged and thus need to be done for exemption travel only in a just-in-time basis.

Upon returning home, a variety of sensors and actions would then be employed. Based on individual goods, sensors in storage spaces, the shopping list, the shopping list receipt (e.g. actual goods), and/or all of the above, the household inventory of goods would be updated to be used in future risk of violating quarantine calculations. Tracking of any support resources who entered the household would be noted, and the exemption certificate "closed" or otherwise updated to show that the exemption was successfully used and within the allotted conditions.

In addition to (or an expansion on) the capabilities exemplified by the virus/grocery store examples above, another overall distinction between the exemplary embodiments disclosed herein and prior art, is that while some prior art may be considered a "warning system," or, at best, even an "early warning system," exemplary embodiments disclosed herein are an "extra early-early warning system." In the virus/grocery store examples disclosed herein, all sorts of risks may be assessed and incorporated into the broader purposes disclosed for exemplary embodiments. For example, the risk(s) of running out of food or key supplies, to individual health needs, that might lead to a temptation to violate the quarantine could be assessed and preempted. On the other end, a deviation from a route (in consideration of other factors, such as likely destinations, time left over before the authorization expired, how much he was carrying, etch could be assessed for its likelihood of the deviation to be accidental versus deliberate, with context-based, even dynamically created actions (and resources and Integration/interfaces, as applicable) being implemented to prevent an actual violation from occurring, well before it could occur, thus (hopefully) avoiding all manner of actual violation-induced punitive penalties and enforcement actions. Thus, the distinction between "early warning" (at best) of various prior art, and "extra-early" early warning system as disclosed herein is not just a question of semantics; instead, it is a major difference that is reflected in exemplary embodiments disclosed herein that are greatly distinct from prior art, and the associated emphasis in exemplary embodiments on preventing (e.g., doing essentially everything possible to prevent, etch an actual violation from occurring, through extensive use of dynamic, context-based, utilization of sensors, risk evaluation mechanisms, dynamic use of actions, resources, and interfaces, and the use of and feedback into the invention of actions et al. learnings via Artificial Intelligence, machine learning, and other learning mechanisms.

Exemplary embodiments may also be configured for monitoring for and/detecting possible illness(es) based on changes in behavior. While this would include monitoring/detecting changes in temperature-fevers, sluggishness, etc., exemplary embodiments may be further configured to monitor for and detect unusual and/or non-medical behavior, such as, for example, changes in voice frequency, changes in sleeping habits, or perhaps decreased "productivity" from everything from how fast they can prepare a meal to how fast they type, as compared with historical (contextual) norms. The above in particular would be context-based, such as work typing (in Word) vs. doing personal texts. Advantageously, such exemplary embodiments may thus be able to detect illness in persons who are otherwise asymptomatic by detecting changes in behavior even if the persons otherwise "feel fine." This would involves detecting (possible) "extra early" early warning signs of an (eventual) medical situation of asymptomatic cases and/or cases where eventually the persons get sick and have symptoms.

Exemplary embodiments may also be configured for monitoring behaviors within the home environment. For example, this may include monitoring to determine whether school-age student(s) are studying (or not), along the lines of monitoring rates-of-consumption, etc. This may include tracking at-home schooling with the risk of the student avoiding required school activities, starting with logging in to the school's daily classwork, etc. This may include monitoring computer time to distinguish between playing video games versus school-related activities. The "risk" of violating quarantine associated with this would be that to the extent the child is falling behind at school, the parent might be concerned enough to violate quarantine in some way to "break" it for some reasons—particularly if schools are in session for those "immune" children, and the parents get panicked enough about the student so poorly with online learning that they want to break quarantine and send him to school, even though the student is not eligible.

Exemplary embodiments may include the concept of "tiered" quarantine areas. Thus, for certain locations, people, and/or context, there may be differently defined quarantine areas (and/or contexts). Thus, for a given household, there may be multiple quarantines: some people, (possibly, even likely) further qualified by context, might be constrained to the house or apartment (like seniors): other (people)/contexts to the yard (or for apartment dwellers—floor or building): others let outside the home and lot/building but constrained to the neighborhood or city limits.

Beyond this location-based geofence-type quarantine, these tiered quarantines could depend on context, e.g., a home dweller allowed outside for chores (but not socializing), or the apartment dweller allowed to go to the basement where the washer/dryers are to clean their clothes (in this the "tiered" exemption may be "micro" in nature, e.g., making sure than only one person goes down to the basement at any given time). Again, this may all be geared to avoiding the risk of violating quarantine. For example, if someone has a sewer problem that he thinks has to be unclogged via the outside access, he will violate a house-only quarantine.

Exemplary embodiments may include location-less context-based "fence(s)" without any location element. For example, if a hurricane is approaching, and a household is in need of plywood, certain foods, etc., then a shopping-for-hurricane exemption can be granted, that doesn't have any restriction on WHERE he can go, just WHY he is going, and WHAT he is getting, and perhaps how (e.g. has to go by car). A building dweller might have an exemption to walk her dog—not specifying exactly where or how (or maybe not even where): just that she's got a window to take her dog out, and perhaps being back by a certain time. Another example is the clogged sewer in that it may be considered an emergency, and he (and the system of the exemplary embodiment) doesn't have time to figure out where he needs to go to get what he needs, therefore he is given an emergency "sewer-unclogging" exemption that allows him to go anywhere (within a certain time limit perhaps), as long as it is for the purpose of getting what he needs to fix his sewer problem.

In addition, the pooled resources aspects disclosed herein may be extended to other exemplary embodiments. For example, a building may have a specific common issue (risk) that needs to be addressed in a pooled-related set of ways of detecting/monitoring it, evaluating the risk, and via pooled/common actions/resources/interfaces. This aspect of pooled resources may be extended to location-less context-based fence(s). For example, if the whole building has a sewer, water, or electricity problem, and time is of the essence, then a common purpose-based exemption could be given to multiple people in the same timeframe, without a number of restrictions that would typically accompany an exemption (e.g. destinations, routes, etc.)

Regarding the interfaces, exemplary embodiments may preferably use interfaces that (a) are contactless or those that at least minimize contact with surfaces and/or nearness with other persons, and/or (b) do not require persons to remove their PPE, particularly gloves and masks. This would also include at key points, such as checking out at a store, e.g. avoiding all contact with anything through the use of wireless-enabled mobile payment mechanism, as well as maintaining social distancing (e.g., air "contact").

Exemplary embodiments may include the use of robotics/automation. For example, home delivery/delivery assistance via the use of (sanitized) robots, including interfacing with support resources/delivery drivers, with the goal of a) minimizing human contact, both with the groceries as well as each other), and b) providing key support (instead of human support) to, for example, get the groceries from the front of the building to inside the household unit. It would be pointless, for example, to go to great extremes to buy the groceries only to later contaminate the groceries getting them into the building, up the stairs/elevator, to and into the front door. This may also include robotic bagging of groceries, or the "picking" of goods off shelves, e.g., instead of touching a good (and thus contaminating it, particularly if you put it back), the shopper could speak the good and a robotic arm would take it off the shelf and put it in the shopper's cart. Another option is to have the shopping list used as the picking mechanism, e.g. the list is communicated to the (distributed or server-based) shelf "intelligence," and as the shopper approaches the good a robotic arm has the good ready to put into the shopper's cart (which the shopper could reject via voice command, want 2 of them instead of 1, etc.). Also, once this is done, then there may be an automatic updating of the shopping list, which could be used as another mechanism for making sure the shopper does not leave the store without having bought everything that is needed (e.g. the reason the shopper was granted an exception in the first place).

Accordingly, disclosed herein are exemplary embodiments of systems and methods for monitoring for and preempting the risk of a future occurrence of a quarantine violation which may include one or more (or all) of the follow major innovations not present in the prior art:
- use of systems and process integration to preempt the risk of a future occurrence of a quarantine violation
- using context and being dynamic as compared to prior art systems that are location-only, using "fixed" or static sensors, risk algorithms, and actions. In contrast, aspects of the present invention use context in some way as well as emphasizing "dynamisms," e.g., emphasizing rapidly changing risks, behaviors, etc.
- use of closed/partially closed loop and/or learning systems and methods. For example, the system may continually learn and improve without manual input the longer it goes on. The system/may start with a pre-identified risk profile, associated initial set of sensors et al., and initially identified risk assessment algorithms (which, it should be noted, is not just a score, range of values, etc., but can be in other forms, such software code (this might be new). Qualitative descriptions etch, and initial set of actions, resources and interfaces.

Then, as the RESULTS of the actions/resources/interfaces are measured, the results, via various methods and mechanisms including AI, machine learning, etc. are then "fed back" (via the "closed loop") into the exemplary embodiment(s), and/or new elements (e.g., sensors, actions, data sources) are determined to need to be added (e.g., partially closed loop), including updating the profile and/or also changing (possibly) the risks measured: what sensors et al. are used and/or what configurations/values are used/measured; what risk assessment formulas/algorithms are used; and/or what actions, resources, and/or interfaces are employed to address the (possibly now modified) risks-particularly the context. Then, these results are fed back again in an ongoing process of continual improvement/modification/learning.

As disclosed herein and shown by the table below, triggers may encapsulate various forms of mental thoughts, mental and/or physical behaviors, mental and/or physical states, and/or mental and/or physical activities. Generally, triggers are predicated on, or a description of, behaviors/activities/states which may be either or both physical and/or mental. By way of example only, the table below categorizes various examples of triggers in which "X" and "m" respectively indicate major and minor applicability.

| TRIGGER | MENTAL | PHYSICAL | BOTH/Occurring Together |
|---|---|---|---|
| Anger | X | | |
| Anxiety | X | | |
| Boredom | X | | |
| Change | X | X | X (e.g., moving to new city) |
| Depression | X | | |
| Escape | X (e.g., feeling physically closed in) | m (e.g., getting out of house) | m (e.g., getting away from "everything") |
| Excitement | X | | |
| Fear | X | | |
| Fun | X | | |
| Frustration | X | | |
| Guilt | X | | |
| Health | X | X | X (e.g., physical health problems caused by mental conditions) |
| Insomnia | X | m (e.g., too much caffeine) | |
| Job | X | m (e.g., job may be physically exhausting) | m |
| Kids | X | X | X |
| Loneliness | X | m (e.g., Loneliness can occur even when other persons are around) | Could be both - mental loneliness caused by lack of physical interaction) |
| Money | X | X | |
| Mid-Life | X | | |
| Overconfidence | X | | |
| Peer Pressure | X | | |
| Power | X | | |
| Powerlessness | X | | |
| Proximity | | X | |
| Fear of Quitting | X | | |
| Relationships | X | X | X |
| Relatives | X (e.g., Political differences w/ relatives may be huge, even if you haven't seen them in years) | m | m |
| Sex | X (desire) | X (actual) | X |
| Smell | | X | |
| Stress | X | m | m |
| Taste | | X | |
| Times of Day/ Holidays | X | | |
| UnFun | X | | |
| Victim | X | | |

-continued

| TRIGGER | MENTAL | PHYSICAL | BOTH/Occurring Together |
|---|---|---|---|
| Weather | m (e.g., Possibility of being snowed-in before snow even starts is mental) | X | Fear of storms is both mental and physical |
| ex-relationship partner | X - problems with ex-spouse, significant other, or other relationship partner doesn't necessarily require physical interaction | X | X |
| Yelling/conflict | X (e.g.. fear of conflict is mental) | X (e.g., Physical yelling) | X |

As shown by the table above. Proximity may be considered a physical only trigger, whereas Anxiety and Boredom may be considered mental only triggers. Some may considered as both physical and mental triggers, such as money or relationships. In addition, a mental trigger (e.g., Fear, etch may be caused by any sort of context, including mental (e.g., an imminent important deadline), physical (e.g., a physical examination that could determine whether I pass and can get the job), or both physical and mental and physical (upcoming physical interview with a prospective boss). In addition, physical environmental factors disclosed herein (e.g., nature of lead pipes in a residential building, etch may be characterized differently than simply running out of an item. Such environmental factors may be characterized as contributory contextual factors (both physical and mental) that could be combined with triggers, e.g., mental/mentally-related triggers. Accordingly, triggers may thus be mental, physical, or a combination of both, while context may also be physical, mental, or a combination of both (e.g., being in a pressure-packed meeting at a physical workplace versus a pressure-packed zoom meeting or upcoming deadline).

In addition, physical triggers may also be caused by and/or are interrelated with mental triggers. For example, a person being hot (physical trigger) may be caused by elevated blood pressure (physical), which elevated blood pressure may have been caused by Anxiety/Worry (mental). As another example, a person feeling thirsty (physical trigger) may be caused by the person being hot (a both mental and physical state), which, in turn, may have been caused by Anxiety/Worry (mental state/behavior/trigger). As yet a further example, a person being short-of-breath (physical trigger) may be caused by Anxiety or Excitement (mental). In addition to these examples, another example includes mental and physical triggers that have a more clear/major cause-and-effect connection, such as a person having mental issue/trigger/state caused by a vitamin D deficiency and the household is running out of vitamin D supplements/food.

Exemplary embodiments may include one or more computing devices, such as one or more servers, workstations, personal computers, laptops, tablets, smartphones, person digital assistants (PDAs), etc. In addition, the computing device may include a single computing device, or it may include multiple computing devices located in close proximity or distributed over a geographic region, so long as the computing devices are specifically configured to function as described herein. Further, different components and/or arrangements of components than illustrated herein may be used in the computing device and/or in other computing device embodiments.

Exemplary embodiments may include one or more processors and memory coupled to (and in communication with) the one or more processors. A processor may include one or more processing units (e.g., in a multi-core configuration, etch such as, and without limitation, a central processing unit (CPU), a microcontroller, a reduced instruction set computer (RISC) processor, an application specific integrated circuit (ASIC), a programmable logic device (PLD), a gate array, and/or any other circuit or processor capable of the functions described herein.

In exemplary embodiments, a memory may be one or more devices that permit data, instructions, etc., to be stored therein and retrieved therefrom. The memory may include one or more computer-readable storage media, such as, without limitation, dynamic random access memory (DRAM), static random access memory (SRAM), read only memory (ROM), erasable programmable read only memory (EPROM), solid state devices, flash drives, CD-ROMs, thumb drives, and/or any other type of volatile or nonvolatile physical or tangible computer-readable media.

In exemplary embodiments, computer-executable instructions may be stored in the memory for execution by a processor to particularly cause the processor to perform one or more of the functions described herein, such that the memory is a physical, tangible, and non-transitory computer readable storage media. Such instructions often improve the efficiencies and/or performance of the processor that is performing one or more of the various operations herein. It should be appreciated that the memory may include a variety of different memories, each implemented in one or more of the functions or processes described herein.

In exemplary embodiments, a network interface may be coupled to (and in communication with) the processor and the memory. The network interface may include, without limitation, a wired network adapter, a wireless network adapter, a mobile network adapter, or other device capable of communicating to one or more different networks. In some exemplary embodiments, one or more network interfaces may be incorporated into or with the processor.

It should be appreciated that the functions described herein, in some embodiments, may be described in computer executable instructions stored on a computer readable media, and executable by one or more processors. The computer readable media is a non-transitory computer readable storage medium. By way of example, and not limitation, such computer-readable media can include RAM, ROM, EEPROM, CD-ROM or other optical disk storage, magnetic disk storage or other magnetic storage devices, or any other medium that can be used to carry or store desired program code in the form of instructions or databases and that can be accessed by a computer. Combinations of the above should also be included within the scope of computer-readable media.

It should also be appreciated that one or more aspects of the present disclosure transform a general-purpose computing device into a special-purpose computing device when configured to perform the functions, methods, and/or processes described herein.

Example embodiments are provided so that the present disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the present disclosure. In some example embodiments, well-known processes, well-known device structures, and well-known technologies are not described in detail. For example, technical material that is known in the technical fields related to the present disclosure has not been described in detail so that the present disclosure is not unnecessarily obscured. This includes, but is not limited, to technology utilized in determining the location of mobile devices via a variety of means. In addition, advantages and improvements that may be achieved with one or more exemplary embodiments of the present disclosure are provided for purposes of illustration only and do not limit the scope of the present disclosure, as exemplary embodiments disclosed herein may provide all or none of the above mentioned advantages and improvements and still fall within the scope of the present disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. In addition, as used herein, the term "or" is an inclusive "or" operator, and is equivalent to the term "and/or," unless the context clearly dictates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The term "based on" is not exclusive and allows for being based on additional factors not described, unless the context clearly dictates otherwise. The term "network" is used in multiple contexts within the present disclosure, and its use generally (but not necessarily) falls into one of two categories. The first is in the form of a (generally human) support "network" including one or more individuals/entities that provide the addict or other person with some sort of support or assistance. The second is in a technical context, such as a communications network that transmits, receives, and/or otherwise provides technical connectivity between various technical components disclosed herein.

As used herein, the terms "support network" and "support community" refer to a concept that an individual's or groups of individuals' personal network of Mends, family colleagues, coworkers, medical/mental health/addiction professionals, members of their social network (e.g. Face book, Twitter, Snapchat, etch, etc. and the subsequent connections within those networks can be utilized to find more relevant connections for a variety of activities, including, but not limited to dating, job networking, service referrals, content sharing, like-minded individuals, activity partners, or the like. Such social network may be created based on a variety of criteria, including, for example, an address book, a social event, an online community, or the like. As used herein, the term "member" refers to a user who is included in a support network. The term "group" or "community" refers to a collection of members.

Although the terms first, second, third, etc. may be used herein to describe various elements, components, or features, these elements, components, or features should not be limited by these terms. These terms may be only used to distinguish one element, component, or feature from another element, component, or feature. Terms such as "first," "second," and other numerical terms when used herein do not imply a sequence or order unless clearly indicated by the context. Thus, a first element, component, or feature could be termed a second element, component, or feature without departing from the teachings of the example embodiments.

None of the elements recited in the claims are intended to be a means-plus-function element within the meaning of 35 U.S.C. $112(f) unless an element is expressly recited using the phrase "means for," or in the case of a method claim using the phrases "operation for" or "step for."

The foregoing description of the embodiments has been provided for purposes of illustration and description. It is not intended to be exhaustive or to limit the present disclosure. Individual elements, intended or stated uses, or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the present disclosure, and all such modifications are intended to be included within the scope of the present disclosure.

What is claimed is:

1. A system comprising a plurality of different devices, sensors, sensor arrays, and/or communications networks, the system configured to:
   determine, through a plurality of measurements/readings taken by the plurality of different devices, sensors, sensor arrays, and/or communications networks, behavior(s) of at least one person under quarantine and:
      (a) context(s) associated with the behavior(s) of the at least one person under quarantine; or
      (b) location and the context(s) associated with the behavior(s) of the at least one person under quarantine;
   assess, evaluate, and predict a risk of a future quarantine violation by the at least one person under quarantine in relation to the behavior(s) of the at least one person under quarantine and the context(s) associated with the behavior(s) of the at least one person under quarantine; and facilitate one or more actions and/or activities to preempt and/or lower the risk of a future quarantine violation by the at least one person under quarantine before a quarantine violation occurs;

wherein:
the system is configured to define at least first and second different and/or tiered quarantine areas;
the first quarantine area defines one or more first permissible activity(ies) and/or one or more first prohibited activity(ies) for a first group of one or more persons under quarantine;
the second quarantine area defines one or more second permissible activity(ies) and/or one or more second prohibited activity(ies) for a second group of one or more persons under quarantine; and
at least one of the first permissible activity(ies) and/or at least one of the first prohibited activity(ies) defined by the first quarantine area is different than the corresponding second permissible activity(ies) and/or second prohibited activity(ies) defined by the second quarantine area.

2. The system of claim 1, wherein:
the first group of one or more persons under quarantine and the second group of one or more persons under quarantine reside in a common residence and/or at a common location; and
the first and second quarantine areas define permissible activity(ies) and/or prohibited activity(ies) respectively for the first and second groups relative to the common residence and/or common location at which they reside.

3. The system of claim 1, wherein the system is configured to define at least one context-based exemption that allows a person under quarantine to perform a prohibited activity without violating quarantine.

4. The system of claim 1, wherein the system is configured to define at least one purpose-based exemption that allows a person under quarantine to perform a prohibited activity without violating quarantine for fulfilling a purpose defined by the purpose-based exemption without restricting location.

5. The system of claim 1, wherein:
the system is configured such that the plurality of measurements/readings are taken by the plurality of different devices, sensors, sensor arrays, and/or communications networks proactively without requiring the at least one person under quarantine to take the plurality of measurements/readings; and/or
the system is configured to predict the risk of a future quarantine violation by the at least one person under quarantine proactively without requiring the at least one person under quarantine to actively participate in predicting the risk.

6. A system comprising a plurality of different devices, sensors, sensor arrays, and/or communications networks, the system configured to:
determine, through a plurality of measurements/readings taken by the plurality of different devices, sensors, sensor arrays, and/or communications networks, behavior(s) of at least one person and:
(a) context(s) associated with the behavior(s) of the at least one person; or
(b) location and the context(s) associated with the behavior(s) of the at least one person;
assess, evaluate, and predict a risk of a future occurrence(s) of a behavior(s) and associated context(s) by the at least one person; and
facilitate one or more actions and/or activities to preempt and/or lower the risk of a future occurrence(s) of the behavior(s) by the at least one person before the behavior(s) occurs;

wherein the system is configured to restrict and condition access to data for the at least one person collected by the plurality of different devices, sensors, sensor arrays, and/or communications networks based on a user's selection of location-based and/or context-based data from a plurality of options presented by the system for selection by the user, the plurality of options including the location-based and/or context-based data and one or more other options that are selectable by the user;

wherein the system is configured to:
in response to a receipt of a request for access by the user to data for the at least one person, present the plurality of options for selection by the user and one or more queries or qualifiers to prompt the user to select at least one of the plurality of options in response to the one or more queries or qualifiers;
determine whether the user selected the location-based and/or context-based data from the plurality of options that satisfies the one or more queries and/or qualifiers;
restrict the user's requested access to the data for the at least one person if it is determined that the user did not select the location-based and/or context-based data that satisfies the one or more queries and/or qualifiers; and
allow the requested access by the user to the data for the at least one person if it is determined that the user selected the location-based and/or context-based data that satisfies the one or more queries and/or qualifiers;
whereby the user is the at least one person, another person, and/or an accessor.

7. The system of claim 6, wherein the at least one person includes at least one person under quarantine, and wherein the system is configured to:
dynamically determine, through the plurality of measurements/readings taken by the plurality of different devices, sensors, sensor arrays, and/or communications networks, behavior(s) of the at least one person under quarantine and:
(a) the context(s) associated with the behavior(s) of the at least one person under quarantine; or
(b) the location and the context(s) associated with the behavior(s) of the at least one person under quarantine;
dynamically assess, evaluate, and predict the risk of the future quarantine violation by the at least one person under quarantine in relation to the behavior(s) of the at least one person under quarantine and the context(s) associated with the behavior(s) of the at least one person under quarantine; and
dynamically facilitate the one or more actions and/or activities to preempt and/or lower the risk of the future quarantine violation by the at least one person under quarantine before a quarantine violation occurs.

8. The system of claim 7, wherein:
the at least one person under quarantine comprises at least two persons under quarantine; and
the system is configured for monitoring for and preempting quarantine violation-related behavior(s) of the at least two persons under quarantine.

9. The system of claim 6, wherein the at least one person includes at least one person under restriction, and wherein the system is configured to:
dynamically determine, through the plurality of measurements/readings taken by the plurality of different devices, sensors, sensor arrays, and/or communications networks, behavior(s) of the at least one person under restriction and:
(a) context(s) associated with the behavior(s) of the at least one person under restriction; or
(b) location and the context(s) associated with the behavior(s) of the at least one person under restriction;
dynamically assess, evaluate, and predict a risk of a future occurrence(s) of a restriction violation-related behavior(s) by the at least one person under restriction in relation to the behavior(s) of the at least one person under restriction and the context(s) associated with the behavior(s) of the at least one person under restriction; and
dynamically facilitate one or more actions and/or activities to preempt and/or lower the risk of a future occurrence(s) of a restriction violation-related behavior(s) by the at least one person under restriction before a violation occurs.

10. The system of claim 9, wherein the person under restriction comprises one or more of a person under quarantine, a parolee, a prisoner, a person on probation, a person under house arrest, a person under a restraining order, a person under supervision and/or restriction(s) ordered by one or more of a criminal court, a civil court, a family court, and/or another justice entity, and/or a person under supervision and/or restriction(s) imposed by an association, an entity, and/or an organization.

11. The system of claim 6, wherein the location-based and/or context-based data includes a location of the user and a context of the user at the location.

12. The system of claim 6, wherein the at least one person includes at least one person under an agreement defining one or more permissible activity(ies) and/or one or more prohibited activity(ies), and wherein the system is configured to:
dynamically determine, through the plurality of measurements/readings taken by the plurality of different devices, sensors, sensor arrays, and/or communications networks, behavior(s) of the at least one person under the agreement and:
(a) context(s) associated with the behavior(s) of the at least one person under the agreement; or
(b) location and the context(s) associated with the behavior(s) of the at least one person under the agreement;
dynamically assess, evaluate, and predict a risk of a future occurrence(s) of an agreement violation-related behavior(s) and associated context(s) by the at least one person under the agreement; and
dynamically facilitate one or more actions and/or activities to preempt and/or lower the risk of a future occurrence(s) of the agreement violation-related behavior(s) by the at least one person under the agreement before a violation of the agreement occurs.

13. The system of claim 6, wherein the system is configured to determine, project, or predict a current or future context of the at least one person at a location by analyzing and linking real-time data and historical data for the at least one person, the real-time and historical data including the location of the at least one person, context of the at least one person at the location, behavior patterns, travel patterns, health data, and risk calculations.

14. The system of claim 6, wherein the system is configured to determine whether at least one mental trigger indicative of a risk of a future occurrence(s) of the behavior(s) by the at least one person is active, present, or in danger of becoming active or present based on the behavior(s) of the at least one person and: (a) the context(s) associated with the behavior(s) of the at least one person or (b) the location and the context(s) associated with the behavior(s) of the at least one person at the location, as determined through the plurality of different devices, sensors, sensor arrays, and/or communications networks.

15. The system of claim 6, wherein the system is configured to determine whether at least one or more of an Anger trigger, an Anxiety trigger, a Boredom trigger, a Depression trigger, a Fear trigger, and a Frustration trigger that are indicative of a risk of a future occurrence(s) of the behavior(s) by the at least one person is active or present based on the behavior(s) of the at least one person and: (a) the context(s) associated with the behavior(s) of the at least one person or (b) the location and the context(s) associated with the behavior(s) of the at least one person at the location, as determined through the plurality of different devices, sensors, sensor arrays, and/or communications networks.

16. The system of claim 6, wherein the system is configured for monitoring for and detecting illness of one or more persons including persons that are otherwise asymptomatic by detecting changes in behavior as determined through the plurality of different devices, sensors, sensor arrays, and/or communications networks.

17. A system comprising a plurality of different devices, sensors, sensor arrays, and/or communications networks, the system configured to:
determine, through a plurality of measurements/readings taken by the plurality of different devices, sensors, sensor arrays, and/or communications networks, behavior(s) of at least one person and:
(a) context(s) associated with the behavior(s) of the at least one person; or
(b) location and the context(s) associated with the behavior(s) of the at least one person;
assess, evaluate, and predict a risk of a future occurrence(s) of a behavior(s) and associated context(s) by the at least one person; and
facilitate one or more actions and/or activities to preempt and/or lower the risk of a future occurrence(s) of the behavior(s) by the at least one person before the behavior(s) occurs;
wherein:
the system is configured to automatically and/or dynamically create a condition based on specific situational data when a profile of the at least one person does not adequately address a particular condition or when profile elements conflict, and thereafter provide an alert to the at least one person indicating that the system created the condition for which acceptance, rejection, or revision is required from the at least one person; and/or
the system is configured to weight individual parameters within a profile of the at least one person and make a recommendation based on a highest weighted parameter, set of parameters, or combination of various weighted parameters, and wherein the system is configured to allow the at least one person to override the system recommendation with an online, verbal, written, or other authorized voucher from a third party.

18. A method comprising:

determining, via a plurality of measurements/readings taken by a plurality of different devices, sensors, sensor arrays, and/or communications networks, behavior(s) of at least one person under quarantine and:
  (a) context(s) associated with the behavior(s) of the at least one person under quarantine; or
  (b) location and the context(s) associated with the behavior(s) of the at least one person under quarantine;

assessing, evaluating, and predicting a risk of a future quarantine violation by the at least one person under quarantine in relation to the behavior(s) of the at least one person under quarantine and the context(s) associated with the behavior(s) of the at least one person under quarantine;

facilitating one or more actions and/or activities to preempt and/or lower the risk of a future quarantine violation by the at least one person under quarantine before a quarantine violation occurs;

in response to a receipt of a request for access by a user to data for the at least one person collected by the plurality of different devices, sensors, sensor arrays, and/or communications networks, presenting a plurality of options for selection by the user and one or more queries or qualifiers to prompt the user to select at least one of the plurality of options in response to the one or more queries or qualifiers, the plurality of options including the location-based and/or context-based data and one or more other options that are selectable by the user;

determining whether the user selected the location-based and/or context-based data from the plurality of options that satisfies the one or more queries and/or qualifiers;

restricting the user's requested access to the data for the at least one person if it is determined that the user did not select the location-based and/or context-based data that satisfies the one or more queries and/or qualifiers; and allowing the requested access by the user to the data for the at least one person if it is determined that the user selected the location-based and/or context-based data that satisfies the one or more queries and/or qualifiers;

whereby the user is the at least one person, another person, and/or an accessor.

19. A non-transitory computer-readable storage media comprising computer-executable instructions, which when executed by at least one processor, cause the at least one processor to:

determine, through a plurality of measurements/readings taken by a plurality of different devices, sensors, sensor arrays, and/or communications networks, behavior(s) of the at least one person under quarantine and:
  (a) context(s) associated with the behavior(s) of the at least one person under quarantine; or
  (b) location and the context(s) associated with the behavior(s) of the at least one person under quarantine;

assess, evaluate, and predict a risk of a future quarantine violation by the at least one person under quarantine in relation to the behavior(s) of the at least one person under quarantine and the context(s) associated with the behavior(s) of the at least one person under quarantine;

facilitate one or more actions and/or activities to preempt and/or lower the risk of a future quarantine violation by the at least one person under quarantine before a quarantine violation occurs;

restrict and condition access to data for the at least one person collected by the plurality of different devices, sensors, sensor arrays, and/or communications networks based on a user's selection of location-based and/or context-based data from a plurality of options presented by the system for selection by the user, the plurality of options including the location-based and/or context-based data and one or more other options that are selectable by the user;

in response to a receipt of a request for access by the user to data for the at least one person, present the plurality of options for selection by the user and one or more queries or qualifiers to prompt the user to select at least one of the plurality of options in response to the one or more queries or qualifiers;

determine whether the user selected the location-based and/or context-based data from the plurality of options that satisfies the one or more queries and/or qualifiers;

restrict the user's requested access to the data for the at least one person if it is determined that the user did not select the location-based and/or context-based data that satisfies the one or more queries and/or qualifiers; and allow the requested access by the user to the data for the at least one person if it is determined that the user selected the location-based and/or context-based data that satisfies the one or more queries and/or qualifiers;

whereby the user is the at least one person, another person, and/or an accessor.

* * * * *